United States Patent
Chiu et al.

(10) Patent No.: US 9,593,164 B2
(45) Date of Patent: Mar. 14, 2017

(54) BISPECIFIC EGFR/C-MET ANTIBODIES

(71) Applicant: Janssen Biotech, Inc., Horsham, PA (US)

(72) Inventors: Mark Chiu, Spring House, PA (US); Sheri Moores, Spring House, PA (US); Joost Neijssen, Ultrecht (NL); Paul Parren, Ultrecht (NL); Janine Schuurman, Ultrecht (NL)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 14/086,588

(22) Filed: Nov. 21, 2013

(65) Prior Publication Data

US 2014/0141000 A1 May 22, 2014

Related U.S. Application Data

(60) Provisional application No. 61/728,912, filed on Nov. 21, 2012, provisional application No. 61/782,550, filed on Mar. 14, 2013, provisional application No. 61/809,541, filed on Apr. 8, 2013, provisional application No. 61/864,717, filed on Aug. 12, 2013, provisional application No. 61/892,797, filed on Oct. 18, 2013.

(51) Int. Cl.
| | |
|---|---|
| *C07K 16/28* | (2006.01) |
| *A61K 39/395* | (2006.01) |
| *A61K 31/517* | (2006.01) |
| *A61K 45/06* | (2006.01) |
| *A61K 31/4545* | (2006.01) |
| *A61K 31/437* | (2006.01) |
| *A61K 31/5377* | (2006.01) |
| *A61K 33/24* | (2006.01) |
| *A61K 39/00* | (2006.01) |

(52) U.S. Cl.
CPC ........ *C07K 16/2863* (2013.01); *A61K 31/437* (2013.01); *A61K 31/4545* (2013.01); *A61K 31/517* (2013.01); *A61K 31/5377* (2013.01); *A61K 33/24* (2013.01); *A61K 39/395* (2013.01); *A61K 39/3955* (2013.01); *A61K 45/06* (2013.01); *A61K 2039/505* (2013.01); *C07K 2317/31* (2013.01); *C07K 2317/73* (2013.01); *C07K 2317/76* (2013.01); *C07K 2318/20* (2013.01)

(58) Field of Classification Search
None
See application file for complete search history.

(56) References Cited

U.S. PATENT DOCUMENTS

| | | |
|---|---|---|
| 5,212,290 A | 5/1993 | Vogelstein et al. |
| 5,223,409 A | 6/1993 | Ladner et al. |
| 5,403,484 A | 4/1995 | Ladner et al. |
| 5,427,908 A | 6/1995 | Dower et al. |
| 5,558,864 A | 9/1996 | Bendig et al. |
| 5,571,698 A | 11/1996 | Ladner et al. |
| 5,580,717 A | 12/1996 | Dower et al. |
| 5,885,793 A | 3/1999 | Griffiths et al. |
| 5,891,996 A | 4/1999 | Mateo de Acosta del Rio et al. |
| 5,969,108 A | 10/1999 | McCafferty et al. |
| 6,172,197 B1 | 1/2001 | McCafferty et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Grigg et al. |
| 6,737,056 B1 | 5/2004 | Presta |
| 7,247,301 B2 * | 7/2007 | van de Winkel et al. . 424/130.1 |
| 7,589,180 B2 | 9/2009 | Old et al. |
| 7,595,378 B2 | 9/2009 | van de Winkel et al. |
| 2004/0166544 A1 | 8/2004 | Morton et al. |
| 2004/0197332 A1 | 10/2004 | Ullrich et al. |
| 2005/0118643 A1 | 6/2005 | Burgess et al. |
| 2005/0272083 A1 | 12/2005 | Seshagiri |
| 2009/0042906 A1 | 2/2009 | Huang et al. |
| 2009/0182127 A1 | 7/2009 | Kjaergaard et al. |
| 2010/0015133 A1 | 1/2010 | Igawa et al. |
| 2010/0028637 A1 | 2/2010 | Tavsanli et al. |
| 2010/0254989 A1* | 10/2010 | Bossenmaier et al. .... 424/136.1 |
| 2011/0091372 A1 | 4/2011 | Ghayur et al. |
| 2011/0097262 A1 | 4/2011 | Goetsch et al. |
| 2011/0123532 A1 | 5/2011 | Gurney et al. |
| 2011/0256142 A1 | 10/2011 | Van De Winkel et al. |
| 2012/0149876 A1 | 6/2012 | Von Kreudenstein et al. |
| 2013/0195849 A1 | 8/2013 | Spreter Von Kreudenstein et al. |

FOREIGN PATENT DOCUMENTS

| | | |
|---|---|---|
| WO | WO 02/100348 A2 | 12/2002 |
| WO | WO 2005/016382 A1 | 2/2005 |
| WO | WO 2006/015371 A2 | 2/2006 |
| WO | WO 2006/028936 A2 | 3/2006 |

(Continued)

OTHER PUBLICATIONS

Adjei, et al., "Early Clinical Development of ARQ 197, a Selective, Non-ATP-Competitive Inhibitor Targeting MET Tyrosine Kinase for the Treatment of Advanced Cancers," the Oncologist, 16: 788-799 (2011).

Amado, et al., "Wild-Type KRAS Is Required for Panitumumab Efficacy in Patients With Metastatic Colorectal Cancer," Journal of Clinical Oncology, 26(10): 1626-1634 (2008).

Baselga, et al., "Critical Update and Emerging Trends in Epidermal Growth Factor Receptor Targeting in Cancer," Journal of Clinical Oncology, 23(11): 2445-2459 (2005).

Batley, et al., "Inhibition of FGF-1 Receptor Tyrosine Kinase Activity by PD 161570, a New Protein-Tyrosine Kinase Inhibitor," Life Sciences, 62(2): 143-150 (1998).

Bean, et al., "MET amplification occurs with or without T790M mutations in EGFR mutant lung tumors with acquired resistance to gefitinib or erlotinib," Proceedings of the National Academy of Science, 104(52): 20932-20937 (2007).

(Continued)

*Primary Examiner* — Ruixiang Li
(74) *Attorney, Agent, or Firm* — Kirk Baumeister

(57) ABSTRACT

Bispecific EGFR/c-Met antibodies and methods of making and using the molecules.

2 Claims, 18 Drawing Sheets

(56) References Cited

FOREIGN PATENT DOCUMENTS

| WO | WO 2008/077546 A1 | 7/2008 |
| --- | --- | --- |
| WO | WO 2008/127710 A2 | 10/2008 |
| WO | WO 2009/030239 A1 | 3/2009 |
| WO | WO 2009/085462 A1 | 7/2009 |
| WO | WO 2009/111691 A2 | 9/2009 |
| WO | WO 2009/126834 A2 | 10/2009 |
| WO | WO 2010/039248 A1 | 4/2010 |
| WO | WO 2010/115551 A1 | 10/2010 |
| WO | WO 2011/110642 A2 | 9/2011 |
| WO | WO 2011110642 A2 * | 9/2011 |
| WO | WO 2011/131746 A2 | 10/2011 |
| WO | WO 2012/042026 A1 | 4/2012 |
| WO | WO 2014/081944 A2 | 5/2014 |

OTHER PUBLICATIONS

Cappuzzo, et al., "Epidermal Growth Factor Receptor Gene and Protein and Gefitinib Sensitivity in Non-small-Cell Lung Cancer," Journal of the National Cancer Institute, 97: 643-655 (2005).

Christensen, et al., "c-Met as a target for human cancer and characterization of inhibitors for therapeutic intervention," Cancer Letters, 225: 1-26 (2005).

Cooper, et al., "Molecular cloning of a new transforming gene from a chemically transformed human cell line," Nature, 311: 29-33 (1984).

Dall'Acqua, et al., "Properties of Human IgGls Engineered for Enhanced Binding to the Neonatal Fc Receptor (RcRN)," The Journal of Biological Chemistry, 281(33): 23514-23524 (2006).

DeRoock, et al., "Effects of KRAS, BRAF, NRAS, and PIK3 CA mutations on the efficacy of cetuximab plus chemotherapy in chemotherapy-refractory metastatic colorectal cancer: a retrospective consortium analysis," Lancet Oncology, 11: 753-762 (2010).

Downward, et al., "Autophospholylation sites on the epidermal growth factor receptor," Nature, 311: 483-485 (1984).

Engelman, et al., "MET Amplification Leads to Gefitinib Resistance in Lung Cancer by Activating ERBB3 Signaling," Science, 316: 1039-1043 (2007).

Kathryn M. Ferguson, "Structure-Based View of Epidermal Growth Factor Receptor Regulation," Annual Review of Biophysics, 37: 535-373 (2008).

Ferrara, et al., "Modulation of Therapeutic Antibody Effector Functions by Glycosylation Engineering: Influence of Golgi Enzyme Localization Domain and co-Expression of Heterologous β1, 4-N-acetylglucosaminyltransferase III and Golgi α-mannosidase II," Biotechnology and Bioengineering, 93(5): 851-861 (2006).

Ferrara, et al., "The Carbohydrate at FcγRIIIa Asn-162," The Journal of Biological Chemistry, 281(8): 5032-5036 (2006).

GenBank Accession No. NP_005219.

GenBank Accession No. NP_001120972.

Gill, et al., "Monoclonal Anti-epidermal Growth Factor Receptor Antibodies Which Are Inhibitors of Epidermal Growth Factor Binding and Antagonists of Epidermal Growth Factor-stimulated tyrosine Protein Kinase Activity," The Journal of Biological Chemistry, 259(12): 7755-7760 (1984).

Goldstein, et al., "Biological efficacy of a chimeric antibody to the epidermal growth factor receptor in a human tumor xenograft model," Clinical Cancer Research, 1: 1311-1318 (1995).

Viktor Grunwald, et al., "Developing Inhibitors of the Epidermal Growth Factor Receptor for Cancer Treatment," Journal of the National Cancer Institute, 95(12): 851-867 (2003).

Hirsch, et al., "Combination of EGFR gene copy number and protein expression predicts outcome for advanced non-small-cell lung cancer patients treated with gefitinib," annals of Oncology, 18: 752-760 (2007).

Hoogenboom, et al., "By-passing Immunisation Human Antibodies from Synthetic Repertoires of Germline $V_H$ Gene Segments Rearranged in Vitro," Journal of Molecular Biology, 277: 381-388 (1992).

Hynes, et al., "ERBB Receptors and Cancer: the Complexity of Targeted Inhibitors," Nature Reviews, 5: 341-356 (2005).

Ichimura, et al., "Expression of c-met/HGF Receptor in Human Non-small Cell Lung Carcinomas in vitro and in vivo and Its Prognostic Significance," Japan Journal of Cancer Research, 87: 1063-1069 (1996).

Jänne, et al., "Effect of Epidermal Growth Factor Receptor Tyrosine Kinase Domain Mutations on the Outcome of Patients with Non-small Cell Lung Cancer Treated with Epidermal Growth Factor Receptor Tyrosine Kinase Inhibitors," Clinical Cancer Research, 12(14 Suppl): 4416s-4420s (2006).

Knappik, et al., "Fully Snythetic Human Combinatorial Antibody Libraries (HuCAL) Based on Modular Consensus Frameworks and CDRs Randomized with Trinucleotides," Journal of Molecular Biology, 296: 57-86 (2000).

Konno, et al., "Fucose content of monoclonal antibodies can be controlled by culture medium osmolality for high antibody-dependent cellular cytotoxicity," Cytotechnology, 64: 249-265 (2012).

Krebs, et al., "High-throughput generation and engineering of recombinant human antibodies," Journal of Immunological Methods, 254: 67-84 (2001).

Lièvre, et al., "KRAS Mutations As an Independent Prognostic Factor in Patients with Advanced Colorectal Cancer Treated with Cetuximab," Journal of Clinical Oncology, 26(3): 374-379 (2008).

Linardou, et al., "Somatic EGFR mutations and efficacy of tyrosine kinase inhibitors in NSCLC," National Review of Clinical Oncology, 6: 352-366 (2009).

Li, et al., "Skin toxicities associated with epidermal growth factor receptor inhibitors," Target Oncology, 4: 107-119 (2009).

Livingston et al., NIEHS-SNPs, environmental genome project, NIEHS ES15478, http://egp.gs.washington.edu.

Määttä, et al., "Proteolytic Cleavage and Phosphorylation of a Tumor-associated EfbB4 Isoform Promote Ligand-independent Survival and cancer Cell Growth," Molecular Biology, 17: 67-79 (2006).

Ma, et al., "c-Met: Structure, functions and potential for therapeutic inhibition," Cancer and Metastasis Reviews, 22: 309-325 (2003).

Marks, et al., "By-passing Immunization Human Antibodies from V-gene Libraries Displayed on Phage," Journal of Molecular Biology, 222: 581-597 (1991).

Mendelsohn, et al., "Epidermal Growth Factor Receptor Targeting in Cancer," Seminars in Oncology, 33: 369-385 (2006).

Mendelsohn, et al., "The EGF receptor family as targets for cancer therapy," Oncogene, 19: 6550-6565 (2000).

Mori, et al., "Engineering Chinese Hamster Ovary Cells to Maximize Effector Function of Produced Antibodies Using FUT8 siRNA," Biotechnology and Bioengineering, 88(7): 901-908 (2004).

Nakata, et al., "Recent understanding of the molecular mechanisms for the efficacy and resistance of EGF receptor-specific tyrosine kinase inhibitors in non-small cell lung cancer," Expert Opinions in Therapeutic Targets, 16(8): 771-781 (2012).

Oliver, et al., "EB66 cell line, a ducky embryonic stem cell-derived substrate for the industrial production of therapeutic monoclonal antibodies with enhanced ADCC activity," mAbs, 2(4): 405-415 (2010).

Panek, et al.,"In Vitro Pharmacological Characterization of PD 166285, a New Nanomolar Potent and Broadly Active Protein Tyrosine Kinase Inhibitor," The Journal of Pharmacology and Experimental Therapeutics, 283(3): 1433-1444 (1997).

Peters, et al., "MET: a promising anticancer therapeutic target," National Review of Clinical Oncology, 9: 314-326 (2012).

Prewett, et al., "Mouse-Human chimeric Anti-Epidermal Growth Factor Receptor Antibody C225 Inhibits the Growth of Human Renal Cell Carcinoma Xenografts in Nude Mice," Clinical Cancer Research, 4: 2957-2966 (1998).

Riely, et al., "Clinical Course of Patients with Non-Small Cell Lung Cancer and Epidermal Growth Factor Receptor Exon 19 and Exon 21 Mutations Treated with Gefitinib or Erlotinib," Clinical Cancer Research, 12(3): 839-844 (2006).

Sakakura, et al., "Gains, Losses, and amplifications of Genomic Materials in Primary Gastric Cancers Analyzed by Comparative Genomic Hybridization," Genes, Chromosomes & Cancer, 24: 299-305 (1999).

(56) References Cited

OTHER PUBLICATIONS

Schmidt, et al., "Novel mutations of the MET proto-oncogene in papillary renal carcinomas," Oncogene, 18: 2343-2350 (1999).
Sheets, et al., "Efficient construction of a large nonimmune phage antibody library: The production of high-affinity human single-chain antibodies to protein antigens," Proceedings of the National Academy of Science USA, 95: 6157-6162 (1998).
Shi, et al., "De Novo Selection of High Affinity Antibodies from Synthetic Fab Libraries Displayed on Phage as pIX Fusion Proteins," Journal of Molecular Biology, 397: 385-396 (2010).
Shields, et al., "Lack of Fucose on Human IgG1 N-Linked Oligosaccharide Improves Binding to Human FcγRIII and Antibody-dependent Cellular Toxicity," The Journal of Biological Chemistry, 277(30): 26733-26740 (2002).
Shimamura, et al., "Epidermal Growth Factor Receptors Harboring Kinase Domain Mutations Associate with the Heat Shock Protein 90 Chaperone and Are Destabilized following Exposure to Geldanamycins," Cancer Research, 65(14): 6401-6408 (2005).
Shinkawa, et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," The Journal of Biological Chemistry, 278(5): 3466-3473 (2003).
Siegfried, et al., "The Clinical Significance of Hepatocyte Growth Factor for Non-Small Cell Lung Cancer," Annals of Thoracic Surgeons, 66: 1915-1918 (1998).
Sierra, et al., "c-MET as a potential therapeutic target and biomarker in cancer," Therapeutic Advances in Medical Oncology, 3(S1): S21-S25 (2011).
Spiess, et al., "Bispecific antibodies with natural architecture produced by co-culture of bacteria expressing two distinct half-antibodies," Nature Biotechnolgy, 31: 753-759 (2013).
Spigel, et al., "Final efficacy results from OAM4558g, a randomized phase II study evaluating MetMAbor placebo in combination with erlotinib in advanced NSCLS," Journal of Clinical Oncology, 29(15): 7505 (2011). Abstract Only.
Stamos, et al., "Crystal structure of the HGF β-chain in complex with the Sema domain of the Met receptor," The EMBO Journal, 23: 2325-2335 (2004).
SwissProt Accession No. P00533.
William R Strohl, "Optimization of Fc-mediated effector functions of monoclonal antibodies," Current Opinion in Biotechnology, 20: 685-691 (2009).
Tracy, et al., "Gefitinib Induces Apoptosis in the EGFR$^{L858R}$ Non-Small-Cell Lung Cancer Cell Line H3255," Cancer Research, 64: 7241-7244 (2004).
Turke, et al., "Preexistence and Clonal Selection of MET Amplification in EGFR Mutant NSCLC," Cancer Cell, 17: 77-88 (2010).
Ullrich, et al., "Human epidermal growth factor receptor cDNA sequence and aberrant expression of the amplified gene in A431 epidermoid carcinoma cells," Nature, 309: 418-425 (1984).
Van Cutsem, et al., "Cetuximab and Chemotherapy as Initial Treatment for Metastatic Colorectal Cancer," The New England Journal of Medicine, 360: 1408-1417 (2009).
Vaughan, et al., "Human Antibodies with Sub-nanomolar Affinities Isolated from a Large Non-immunized Phage Display Library," Nature Biotechnolgy, 14: 309-314 (1996).
Zhou, et al., "Development of A Simple and Rapid Method for Producing Non-Fucosylated Oligonammose Containing Antibodies with Increased EffectorFunction," Biotechnology and Bioengineering, 99(3): 652-665(2008).
Kathryn M. Ferguson, "Structure-Based View of Epidermal Growth Factor Receptor Regulation," Annual Review of Biophysics, 37: 353-373 (2008).
Tang, et al., "dual MET-EGFR combinatorial inhibition against T790M-EGFR-mediated erlotinib-resistant lung cancer," British Journal of Cancer, 99: 911-922 (2008).

* cited by examiner

Figure 1A.

| SEQ ID NO: | | |
|---|---|---|
| 18 | LPAPKNLVVSEVTEDSLRLSWADP-HGFYDSFLIQYQESEKVGEAINLTVPGSERSYDLTG | (60) |
| 19 | LPAPKNLVVSEVTEDSLRLSWTYD-RDGYDSFLIQYQESEKVGEAINLTVPGSERSYDLTG | |
| 20 | LPAPKNLVVSEVTEDSLRLSWGYN-GDHFDSFLIQYQESEKVGEAINLTVPGSERSYDLTG | |
| 21 | LPAPKNLVVSEVTEDSLRLSWDDP-RGFYESFLIQYQESEKVGEAINLTVPGSERSYDLTG | |
| 22 | LPAPKNLVVSEVTEDSLRLSWTWP-YADLDSFLIQYQESEKVGEAINLTVPGSERSYDLTG | |
| 23 | LPAPKNLVVSEVTEDSLRLSWGYN-GDHFDSFLIQYQESEKVGEAINLTVPGSERSYDLTG | |
| 24 | LPAPKNLVVSEVTEDSLRLSWDYDLGDHFDSFLIQYQESEKVGEAINLTVPGSERSYDLTG | |
| 25 | LPAPKNLVVSEVTEDSLRLSWDDP-WAFYESFLIQYQESEKVGEAIVLTVPGSERSYDLTG | |
| 27 | LPAPKNLVVSEVTEDSARLSWDDP-WAFYESFLIQYQESEKVGEAIVLTVPGSERSYDLTG | |
| 29 | LPAPKNLVVSEVTEDSLRLSWTWP-YADLDSFLIQYQESEKVGEAIVLTVPGSERSYDLTG | |
| 107 | LPAPKNLVVSEVTEDSARLSWADP-HGFYDSFLIQYQESEKVGEAIVLTVPGSERSYDLTG | |
| 108 | LPAPKNLVVSEVTEDSARLSWDDP-WAFYESFLIQYQESEKVGEAIVLTVPGSERSYDLTG | |
| 109 | LPAPKNLVVSEVTEDSARLSWDDP-HAFYESFLIQYQESEKVGEAIVLTVPGSERSYDLTG | |
| 110 | LPAPKNLVVSEVTEDSARLSWADP-HGFYDSFLIQYQESEKVGEAIVLTVPGSERSYDLTG | |
|   | ******************  ****  :: ********************* ******** | |

| 18 | LKPGTEYTVSIYGVHNVYKDTNMRGIPLSAEFTT | (94) |
|---|---|---|
| 19 | LKPGTEYTVSIYGVHNVYKDTNMRGIPLSAEFTT | |
| 20 | LKPGTEYTVSIYGVHNVYKDTNMRGIPLSAEFTT | |
| 21 | LKPGTEYTVSIYGVHNVYKDTNMRGIPLSAEFTT | |
| 22 | LKPGTEYTVSIYGVHNVYKDTNMRGIPLSAEFTT | |
| 23 | LKPGTEYTVSIYGVHNVYKDTNMRGIPLSAEFTT | |
| 24 | LKPGTEYTVSIYGVHNVYKDTNMRGIPLSAEFTT | |
| 25 | LKPGTEYTVSIYGVHNVYKDTNMRGIPLSAEFTT | |
| 27 | LKPGTEYTVSIYGVHNVYKDTNMRGIPLSAEFTT | |
| 29 | LKPGTEYTVSIYGVHNVYKDTNMRGIPLSAIFTT | |
| 107 | LKPGTEYTVSIYGVHNVYKDTNMRGIPLSAIFTT | |
| 108 | LKPGTEYTVSIYGVHNVYKDTNMRGIPLSAIFTT | |
| 109 | LKPGTEYTVSIYGVHNVYKDTNIRGIPLSAIFTT | |
| 110 | LKPGTEYTVSIYGVHNVYKDTNIRGIPLSAIFTT | |
|   | ********************** ****** *** | |

Figure 1B

| SEQ ID NO: | | |
|---|---|---|
| 26 | LPAPKNLVVSEVTEDSLRLSWTAP-DAAFDSFLIQYQESEKVGEAINLTVPGSERSYDLTG | (60) |
| 28 | LPAPKNLVVSEVTEDSARLSWTAP-DAAFDSFLIQYQESEKVGEAIVLTVPGSERSYDLTG | |
|    | ********************  *********************************** | |
| 26 | LKPGTEYTVSIYGVLGSYVFEHDVMLPLSAEFTT | (94) |
| 28 | LKPGTEYTVSIYGVLGSYVFEHDVMLPLSAIFTT | |
|    | ****************************** *** | |

Figure 2.

```
                    A        AB      B          BC
TENCON27  (1)  LPAPKNLVVSRV TEDS ARLSW TAPDAAF DS    (30)
TCL14     (1)  LPAPKNLVVSRVTEDSARLSWTAPDAAFDS        (30)

C      CD     D           DE     E
TENCON27 (31)  FLIQYQE SEKVGE AIVLTV P GSER SYDLT G  (60)
TCL14    (31)  FXIXYXEXXXXGEAIVLTVPGSERSYDLTG        (60)

EF        F      FG       G
TENCON27 (61)  LKPG TEYTVSIYGV KGGHRSN PLSAIFTT      (89)
TCL14    (61)  LKPGTEYXVXIXGVKGGXXSXPLSAIFTT         (89)
```

Figure 3A.

| SEQ ID NO: | Sequence |
|---|---|
| 32 | LPAPKNLVVSRVTEDSARLSWTAPDAAEDSFWIRYDEVVGGEAIVLTVPGSERSYDLTG (60) |
| 33 | LPAPKNLVVSRVTEDSARLSWTAPDAAEDSFFIRYDEFLRSGEAIVLTVPGSERSYDLTG |
| 34 | LPAPKNLVVSRVTEDSARLSWTAPDAAEDSFWIRYFEFLGSGEAIVLTVPGSERSYDLTG |
| 35 | LPAPKNLVVSRVTEDSARLSWTAPDAAEDSFWIRYFEFLGSGEAIVLTVPGSERSYDLTG |
| 36 | LPAPKNLVVSRVTEDSARLSWTAPDAAEDSFVIRYFEFLGSGEAIVLTVPGSERSYDLTG |
| 37 | LPAPKNLVVSRVTEDSARLSWTAPDAAEDSFWIRYLEFLLGGEAIVLTVPGSERSYDLTG |
| 38 | LPAPKNLVVSRVTEDSARLSWTAPDAAEDSFWIRYFEFLGSGEAIVLTVPGSERSYDLTG |
| 39 | LPAPKNLVVSRVTEDSARLSWTAPDAAEDSFWIRYFEFLGSGEAIVLTVPGSERSYDLTD |
| 40 | LPAPKNLVVSRVTEDSARLSWTAPDAAEDSFWIRYFEFLGSGEAIVLTVPGSERSYDLTG |
| 41 | LPAPKNLVVSRVTEDSARLSWTAPDAAEDSFWIRYFEFLGSGEAIVLTVPGSERSYDLTG |
| 42 | LPAPKNLVVSRVTEDSARLSWTAPDAAEDSFWIRYFEFLGSGEAIVLTVPGSERSYDLTG |
| 43 | LPAPKNLVVSRVTEDSARLSWTAPDAAEDSFWIRYFEFLGSGEAIVLTVPGSERSYDLTG |
| 44 | LPAPKNLVVSRVTEDSARLSWTAPDAAEDSFWIRYFEFLGSGEAIVLTVPGSERSYDLTG |
| 45 | LPAPKNLVVSRVTEDSARLSWTAPDAAEDSFWIRYFEFLGSGEAIVLTVPGSERSYDLTG |
| 46 | LPAPKNLVVSRVTEDSARLSWTAPDAAEDSFWIRYFEFTAGEAIVLTVPGSERSYDLTG |
| 47 | LPAPKNLVVSRVTEDSARLSWTAPDAAEDSFWIRYFEFTTAGEAIVLTVPGSERSYDLTG |
| 48 | LPAPKNLVVSRVTEDSARLSWTAPDAAEDSFWIRYFELLSTGEAIVLTVPGSERSYDLTG |
| 49 | LPAPKNLVVSRVTEDSARLSWTAPDAAEDSFWIRYFEFVSKGEAIVLTVPGSERSYDLTG |
| 111 | LPAPKNLVVSRVTEDSARLSWTAPDAAEDSFWIRYFEFLGSGEAIVLTVPGSERSYDLTG |
| 112 | LPAPKNLVVSRVTEDSARLSWTAPDAAEDSFWIRYFEFVGSGEAIVLTVPGSERSYDLTG |
| 113 | LPAPKNLVVSRVTEDSARLSWTAPDAAEDSFWIRYFEFVSKDAIVLTVPGSERSYDLTG |
| 114 | LPAPKNLVVSRVTEDSARLSWTAPDAAEDSFWIRYFEFVSKGDAIVLTVPGSERSYDLTG |

Figure 3B.

| SEQ ID NO: | |
|---|---|
| 32 | LKPGTEYYVNILGVKGGSISVPLSAIFTT |
| 33 | LKPGTEYWTILGVKGGLVSTPLSAIFTT |
| 34 | LKPGTEYIVNIMGVKGGSISHPLSAIFTT |
| 35 | LKPGTEYVVNILGVKGGGLSVPLSAIFTT |
| 36 | LKPGTEYVVQILGVKGGYISIPLSAIFTT |
| 37 | LKPGTEYVVQIMGVKGGTVSPPLSAIFTT |
| 38 | LKPGTEYVVGINGVKGGYISYPLSAIFTT |
| 39 | LKPGTEYGVTINGVKGGRVSTPLSAIFTT |
| 40 | LKPGTEYVVQILGVKGGHISLPLSAIFTT |
| 41 | LKPGTEYVVNIMGVKGGKISPPLSAIFTT |
| 42 | LKPGTEYAVNIMGVKGGRVSVPLSAIFTT |
| 43 | LKPGTEYVVQILGVKGGSISVPLSAIFTT |
| 44 | LKPGTEYVVNIMGVKGGSISYPLSAIFTT |
| 45 | LKPGTEYVVQILGVKGGYISIPLSAIFTT |
| 46 | LKPGTEYVVQIMGVKGGTVSPPLSAIFTT |
| 47 | LKPGTEYVVNIMGVKGGSISPPLSAIFTT |
| 48 | LKPGTEYVVNIMGVKGGSISPPLSAIFTT |
| 49 | LKPGTEYVVNIMGVKGGSISPPLSAIFTT |
| 111 | LKPGTEYVVNILGVKGGKISPPLSAIFTT |
| 112 | LKPGTEYVVNILGVKGGSISPPLSAIFTT |
| 113 | LKPGTEYVVNILGVKGGSISPPLSAIFTT |
| 114 | LKPGTEYVVNILSVKGGSISPPLSAIFTT |
|  | ****  **  *:*****  **  . :***** |

(89)

BISPECIFIC EGFR/C-MET ANTIBODIES

CROSS REFERENCE TO RELATED APPLICATIONS

This application claims the benefit of U.S. Provisional Application No. 61/728,912, filed 21 Nov., 2012, U.S. Provisional Application No. 61/782,550, filed 14 Mar., 2013, U.S. Provisional Application No. 61/809,541, filed 8 Apr., 2013, U.S. Provisional Application No. 61/864,717 filed 12 Aug., 2013, and U.S. Provisional Application No. 61/892,797, filed 18 Oct., 2013, the entire contents of which are incorporated herein by reference.

FIELD OF THE INVENTION

The present invention relates to bispecific EGFR/c-Met antibodies and methods of making and using the molecules.

BACKGROUND OF THE INVENTION

Epidermal growth factor receptor (EGFR, ErbB1 or HER1) is a Type I transmembrane glycoprotein of 170 kDa that is encoded by the c-erbB1 proto-oncogene. EGFR is a member of the human epidermal growth factor receptor (HER) family of receptor tyrosine kinases (RTK) which includes HER2 (ErbB2), HER3 (ErbB3) and HER4 (ErbB4). EGFR signaling is initiated by ligand binding followed by induction of conformational change, homodimerization or heterodimerization of the receptor with other ErbB family members, and trans-autophosphorylation of the receptor (Ferguson et al., Annu Rev Biophys, 37: 353-73, 2008), which initiates signal transduction cascades that ultimately affect a wide variety of cellular functions, including cell proliferation and survival. Increases in expression or kinase activity of EGFR have been linked with a range of human cancers, making EGFR an attractive target for therapeutic intervention (Mendelsohn et al., Oncogene 19: 6550-6565, 2000; Grünwald et al., J Natl Cancer Inst 95: 851-67, 2003; Mendelsohn et al., Semin Oncol 33: 369-85, 2006). Increases in both the EGFR gene copy number and protein expression have been associated with favorable responses to the EGFR tyrosine kinase inhibitor, IRESSA™ (gefitinib), in non-small cell lung cancer (Hirsch et al., Ann Oncol 18:752-60, 2007).

EGFR therapies include both small molecules and anti-EGFR antibodies, approved for treatment of colorectal cancer, pancreatic cancer, head and neck cancer, and non-small cell lung cancer (NSCLC) (Baselga and Arteaga, J Clin Oncol 23:2445-2459 (20005; Gill et al., J Biol Chem, 259:7755-7760, 1984; Goldstein et al., Clin Cancer Res, 1:1311-1318; 1995; Prewett et al., Clin Cancer Res, 4:2957-2966, 1998).

Efficacy of anti-EGFR therapies may depend on tumor type and EGFR mutation/amplification status in the tumor. Side effects of current therapeutics may include skin toxicity (De Roock et al., Lancet Oncol 11:753-762, 2010; Linardou et al., Nat Rev Clin Oncol, 6: 352-366, 2009; Li and Perez-Soler, Targ Oncol 4: 107-119, 2009). EGFR tyrosine kinase inhibitors (TKI) are commonly used as $2^{nd}$ line therapies for non small cell lung cancer (NSCLC), but often stop working within twelve months due to resistance pathways (Riely et al., Clin Cancer Res 12: 839-44, 2006).

c-Met encodes a transmembrane tyrosine kinase receptor. It was first identified as a proto-oncogene in 1984 after it was found that treatment with a carcinogen resulted in a constitutively active fusion protein TPR-MET (Cooper et al., Nature 311:29-33, 1984). Activation of c-Met by its ligand hepatocyte growth factor (HGF) stimulates a plethora of cell processes including growth, motility, invasion, metastasis, epithelial-mesenchymal transition, angiogenesis/wound healing, and tissue regeneration (Christensen et al., Cancer Lett 225:1-26, 2005; Peters and Adjei, Nat Rev Clin Oncol 9:314-26, 2012). c-Met is synthesized as a single chain protein that is proteolytically cleaved into a 50 kDa alpha- and 140 kDa beta-subunits that are linked by a disulphide bond (Ma et al., Cancer and Metastasis Reviews, 22: 309-325, 2003). c-Met is structurally similar to other membrane receptors such as RON and Sea. The exact stoichiometry of HGF:c-Met binding is unclear, but it is generally believed that two HGF molecules bind to two c-Met molecules leading to receptor dimerization and autophosphorylation at tyrosines 1230, 1234, and 1235 (Stamos et al., The EMBO Journal 23: 2325-2335, 2004). Ligand-independent c-Met autophosphorylation can also occur due to gene amplification, mutation or receptor over-expression.

c-Met is frequently amplified, mutated or over-expressed in many types of cancer including gastric, lung, colon, breast, bladder, head and neck, ovarian, prostate, thyroid, pancreatic, and CNS cancers. Missense mutations typically localized to the kinase domain are commonly found in hereditary papillary renal cell carcinomas (PRCC) and in 13% of sporadic PRCCs (Schmidt et al., Oncogene 18: 2343-2350, 1999). c-Met mutations localized to the semaphorin or juxtamembrane domains of c-Met are frequently found in gastric, head and neck, liver, ovarian, NSCLC and thyroid cancers (Ma et al., Cancer and Metastasis Reviews, 22: 309-325, 2003; Sakakura et al., Chromosomes and Cancer, 1999. 24:299-305). c-Met amplification has been detected in brain, colorectal, gastric, and lung cancers, often correlating with disease progression (Ma et al., Cancer and Metastasis Reviews, 22: 309-325, 2003). Up to 4% and 20% of non-small cell lung cancer (NSCLC) and gastric cancers, respectively, exhibit c-Met amplification (Sakakura et al., Chromosomes and Cancer, 1999. 24:299-305: Sierra and Tsao, Therapeutic Advances in Medical Oncology, 3:S21-35, 2011). Even in the absence of gene amplification, c-Met overexpression is frequently observed in lung cancer (Ichimura et al., Jpn J Cancer Res, 87:1063-9, 1996). Moreover, in clinical samples, nearly half of lung adenocarcinomas exhibited high levels of c-Met and HGF, both of which correlated with enhanced tumor growth rate, metastasis and poor prognosis (Sierra and Tsao, Therapeutic Advances in Medical Oncology, 3:S21-35, 2011; Siegfried et al., Ann Thorac Surg 66: 1915-8, 1998).

Nearly 60% of all tumors that become resistant to EGFR tyrosine kinase inhibitors increase c-Met expression, amplify c-Met, or increase c-Met only known ligand, HGF (Turke et al., Cancer Cell, 17:77-88, 2010), suggesting the existence of a compensatory pathway for EGFR through c-Met. c-Met amplification was first identified in cultured cells that became resistant to gefitinib, an EGFR kinase inhibitor, and exhibited enhanced survival through the Her3 pathway (Engelman et al., Science, 316:1039-43, 2007). This was further validated in clinical samples where nine of 43 patients with acquired resistance to either erlotinib or gefitinib exhibited c-Met amplification, compared to only two of 62 untreated patients. Four of the nine treated patients also acquired the EGFR activating mutation, T790M, demonstrating simultaneous resistance pathways (Beat et al., Proc Natl Acad Sci USA, 104:20932-7, 2007).

The individual roles of both EGFR and c-Met in cancer is well established, making these targets attractive for combination therapy. Both receptors signal through the same survival and anti-apoptotic pathways (ERK and AKT); thus, inhibiting the pair in combination may limit the potential for compensatory pathway activation thereby improving overall efficacy. Combination therapies targeting EGFR and c-Met are tested in clinical trials with Tarceva® (erlotinib) in combination with anti-c-Met monovalent antibody for NSCLC (Spigel et al., 2011 ASCO Annual Meeting Proceedings 2011, Journal of Clinical Oncology: Chicago, Ill. p. 7505) and Tarceva (erlotinib) in combination with ARQ-197, a small molecule inhibitor of c-Met (Adjei et al., Oncologist, 16:788-99, 2011). Combination therapies or bispecific anti-EGFR/c-Met molecules have been disclosed for example in: Intl. Pat. Publ. Nos. WO2008/127710, WO2009/111691, WO2009/126834, WO2010/039248, WO2010/115551 and U.S. Pat. Publ. No. US2009/0042906.

Current small molecule and large molecule therapeutic approaches to antagonize EGFR and/or c-Met signaling pathways for therapy may be sub-optimal due to possible lack of specificity, potential off-target activity and dose-limiting toxicity that may be encountered with small molecule inhibitors. Typical monospecific bivalent antibodies may result in clustering of membrane bound receptors and unwanted activation of the downstream signaling pathways. Monovalent antibodies having full length heavy chains (half arms) pose significant complexity and cost to the manufacturing process.

Accordingly, the need exists for additional monospecific and bispecific EGFR and/or c-Met inhibitors for both therapeutic and diagnostic purpose.

SUMMARY OF THE INVENTION

One embodiment of the invention is an isolated bispecific epidermal growth factor receptor (EGFR)/hepatocyte growth factor receptor (c-Met) antibody, comprising:
  a first heavy chain (HC1) comprising a HC1 constant domain 3 (HC1 CH3) and a HC1 variable region 1 (VH1);
  a second heavy chain (HC2) comprising a HC2 constant domain 3 (HC2 CH3) and a HC2 variable region 2 (VH2);
  a first light chain (LC1) comprising a light chain variable region 1 (VL1); and
  a second light chain (LC2) comprising a light chain variable region 2 (VL2), wherein the VH1 and the VL1 pair to form a first antigen-binding site that specifically binds EGFR, the VH2 and the VL2 pair to form a second antigen-binding site that specifically binds c-Met, the HC1 comprises at least one substitution in the HC1 CH3 and the HC2 comprises at least one substitution in the HC2 CH3, and the substitution in the HC1 CH3 and the substitution in the HC2 CH3 occur at different amino acid residue positions, when residue numbering is according to the EU index.

In other embodiments, the invention provides for bispecific EGFR/c-Met antibodies, wherein the antibody inhibits phosphorylation of extracellular signal-related kinases 1 and 2 (ERK1/2) in NCI-H292, NCI-H1975 or SKMES-1 cell line with an $IC_{50}$ value that is at least about 10-fold less, at least about 20-fold less, at least about 30-fold less, at least about 40-fold less, at least about 50-fold less or at least about 60-fold less when compared to the $IC_{50}$ value of inhibition of phosphorylation of ERK1/2 in NCI-H292, NCI-H1975 or SKMES-1 cell lines with a mixture of a control monovalent EGFR antibody comprising a heavy chain 3 (HC3) and a light chain 3 (LC3) and a control monovalent c-Met antibody comprising a heavy chain 4 (HC4) and a light chain 4 (LC4), wherein the HC3 and the HC1, the LC3 and the LC1, the HC4 and the HC2, and the LC4 and the LC2 have identical amino acid sequences, respectively, wherein the phosphorylation of ERK1/2 is measured in whole cell lysates using a sandwich immunoassay using an anti-phosphoERK1/2 antibody as a capture antibody and an antibody binding to unphosphorylated and phosphorylated ERK1/2 conjugated with an electrochemiluminescent compound as a detection antibody.

In other embodiments, the invention provides for bispecific EGFR/c-Met antibodies, wherein the antibody inhibits phosphorylation of protein kinase B (AKT) at Ser473 in NCI-H1975 cell line with an $IC_{50}$ value that is at least about 70-fold less when compared to the $IC_{50}$ value of inhibition of phosphorylation of AKT at Ser473 in NCI-H1975 cell line with the mixture of the control monovalent EGFR antibody comprising the HC3 and the LC3 and the control monovalent c-Met antibody comprising the HC4 and the LC4, wherein the HC3 and the HC1, the LC3 and the LC1, the HC4 and the HC2, and the LC4 and the LC2 have identical amino acid sequences, respectively, wherein the phosphorylation of AKT at Ser473 is measured in whole cell lysates using a sandwich immunoassay using an antibody binding to unphosphorylated and phosphorylated AKT as a capture antibody and an anti-phosphoAKT Ser473 antibody conjugated to an electrochemiluminescent compound as a detection antibody.

In other embodiments, the invention provides for bispecific EGFR/c-Met antibodies that bind EGFR of SEQ ID NO: 73 at EGFR residues K489, 1491, K467 and S492 and c-Met at residues PEFRDSYPIKYVHAF (SEQ ID NO: 238) and FAQSKPDSAEPMDRSA (SEQ ID NO: 239).

In other embodiments, the invention provides for bispecific EGFR/c-Met antibodies that inhibit growth of NCI-H292 or NCI-H1975 cells with an $IC_{50}$ value that is at least about 300-fold less, at least about 400-fold less, at least about 500-fold less, at least about 600-fold less, at least about 700-fold less or at least about 800-fold less when compared to the $IC_{50}$ value of inhibition of growth of NCI-H292 or NCI-H1975 cells with cetuximab, when NCI-H292 or NCI-H1975 cells are grown in low attachment conditions.

In other embodiments, the invention provides for bispecific EGFR/c-Met antibodies that inhibit growth of HGF-expressing SKMES-1 cell tumor in SCID Beige mice with percentage (%) T/C value of at least 500-fold less on day 36 when compared to cetuximab, when the bispecific antibody and cetuximab are administered at 20 mg/kg dose.

In other embodiments, the invention provides for bispecific EGFR/c-Met antibodies wherein the HC1 CH3 comprises a K409R or a F405L substitution and the HC2 CH3 comprises a K409R or F405L substitution, wherein residue numbering is according to the EU index.

In other embodiments, the invention provides for bispecific EGFR/c-Met antibodies comprising certain heavy and light chain CDR, VH1, VL1, VH2, VL2, HC1, LC1, HC2 and LC2 sequences.

Another embodiment of the invention is an isolated synthetic polynucleotide encoding the HC1, the HC2, the LC1 or the LC2 of the invention.

Another embodiment of the invention is a vector comprising the polynucleotide of the invention.

Another embodiment of the invention is a host cell comprising the vector of the invention.

Another embodiment of the invention is a method of producing the isolated bispecific EGFR/c-Met antibody, comprising:

combining an isolated monospecific bivalent anti-EGFR antibody comprising two heavy chains of SEQ ID NO: 199 and two light chains of SEQ ID NO: 200 and an isolated monospecific bivalent anti-c-Met antibody comprising two heavy chains of SEQ ID NO: 201 and two light chains of SEQ ID NO: 202 in a mixture of about 1:1 molar ratio;

introducing a reducing agent into the mixture;

incubating the mixture about ninety minutes to about six hours;

removing the reducing agent; and purifying the bispecific EGFR/c-Met antibody that comprises a first heavy chain of SEQ ID NO: 199 and a second heavy chain of SEQ ID NO: 201, a first light chain of SEQ ID NO: 200 and a second light chain of SEQ ID NO: 202, wherein the first heavy chain of SEQ ID NO: 199 pairs with the first light chain of SEQ ID NO: 200 to form the first binding domain that specifically binds EGFR, and the second heavy chain of SEQ ID NO: 201 pairs with the second light chain of SEQ ID NO: 202 to form the second binding domain that specifically binds c-Met.

Another embodiment of the invention is a pharmaceutical composition comprising the bispecific antibody of the invention and a pharmaceutically acceptable carrier.

Another embodiment of the invention is method of treating a subject having cancer, comprising administering a therapeutically effective amount of the bispecific EGFR/c-Met antibody of the invention to a patient in need thereof for a time sufficient to treat the cancer.

Another embodiment of the invention is method of inhibiting growth or proliferation of cells that express EGFR and/or c-Met, comprising contacting the cells with the bispecific antibody of the invention.

Another embodiment of the invention is method of inhibiting growth or metastasis of EGFR and/or c-Met expressing tumor or cancer cells in a subject comprising administering to the subject an effective amount of the bispecific antibody of the invention to inhibit the growth or metastasis of EGFR and/or c-Met expressing tumor or cancer cells.

BRIEF DESCRIPTION OF THE DRAWINGS

FIGS. 1A and 1B. Amino acid alignment of the EGFR-binding FN3 domains. The BC and FG loops are boxed at residues 22-28 and 75-86 of SEQ ID NO: 18. Some variants include thermal stability improving L17A, N46K and E86I substitutions (residue numbering according to Tencon SEQ ID NO: 1).

FIG. 2. Sequence alignment of the Tencon27 scaffold (SEQ ID NO: 99) and a TCL14 library (SEQ ID NO: 100) having randomized C-CD-F-FG alternative surface. The loop residues are boxed. Loops and strands are indicated above the sequences.

FIG. 3. Sequence alignment of the c-Met-binding FN3 domains. The C loop and the CD strand and the F loop and the FG strand are boxed and span residues 29-43 and 65-81.

Figure 10:
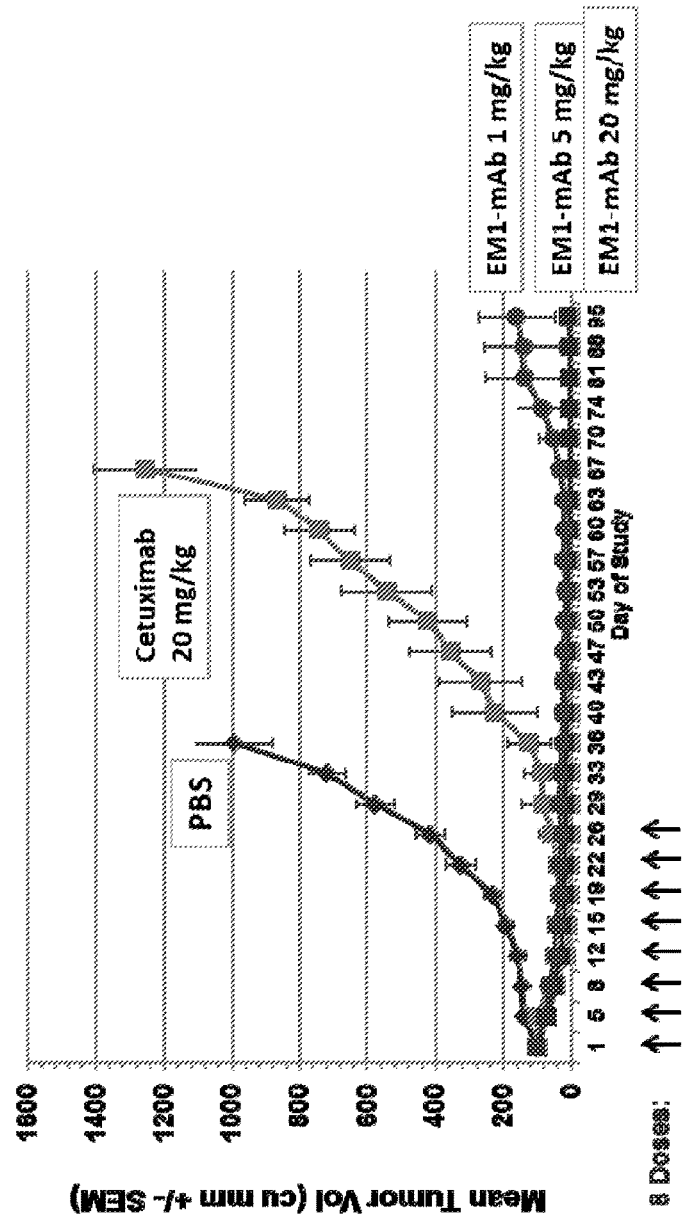

FIG. 10. SKMES-HGF tumor xenografts were implanted into SCID Beige mice and the mice were treated with 5 different therapies. The anti-tumor activity of the therapies is shown as change in tumor size (mm$^3$) over time. The bispecific EGFR/c-Met antibody EM1-mAb was dosed intraperitoneally (i.p.) twice a week at either 20 mg/kg, 5 mg/kg, or 1 mg/kg; cetuximab was dosed i.p. twice a week at 20 mg/kg. Arrows in the figure show the administration days. Numbers after the antibodies indicated the administered dose.

Figure 11:
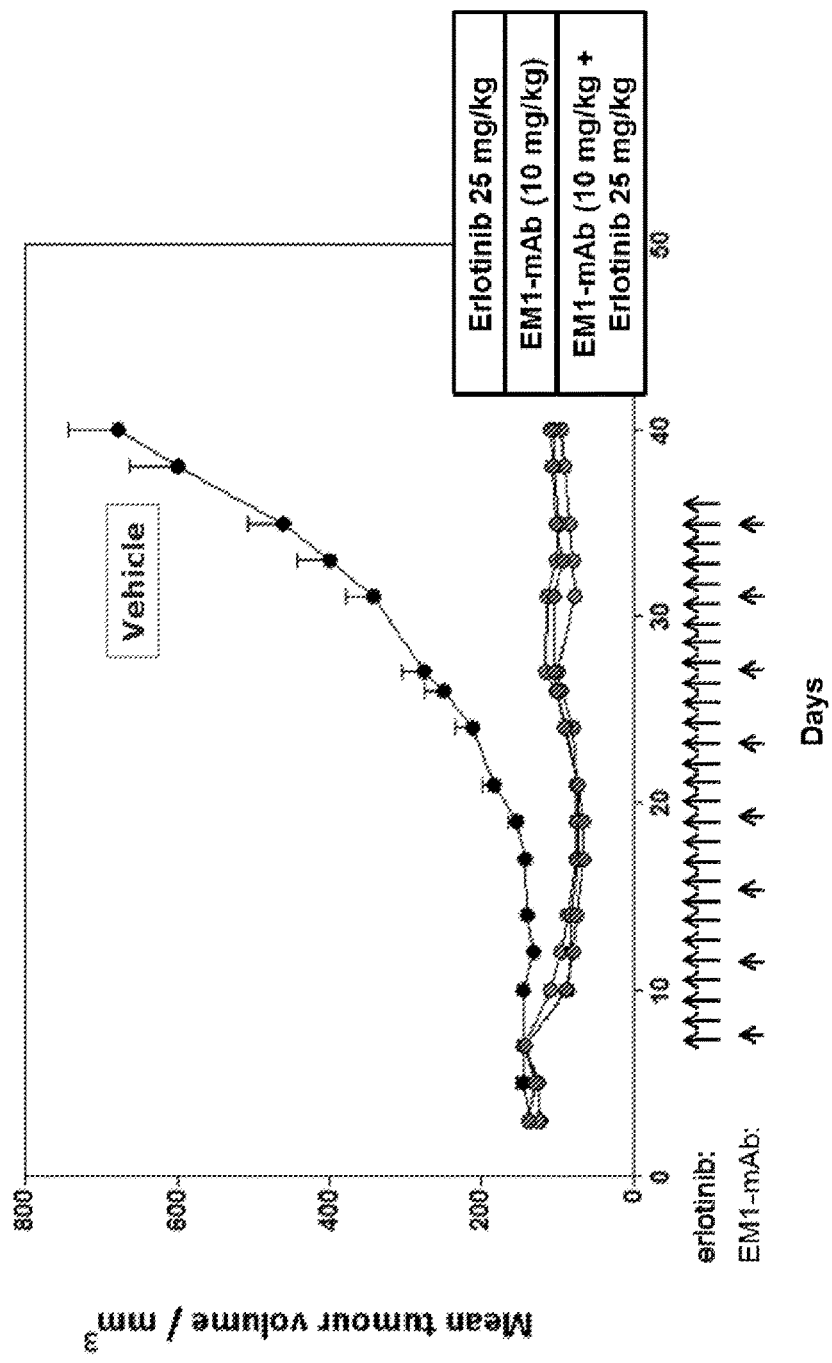

FIG. 11. HCC827 tumor xenografts were implanted into nude mice and the mice were treated with erlotinib or EM1-mAb at indicated doses. EM1-mAb was dosed biweekly and erlotinib once a day for four weeks. Arrows in the figure show the administration days. The anti-tumor activity of the therapies is shown as change in tumor size (mm$^3$) over time.

Figure 12:
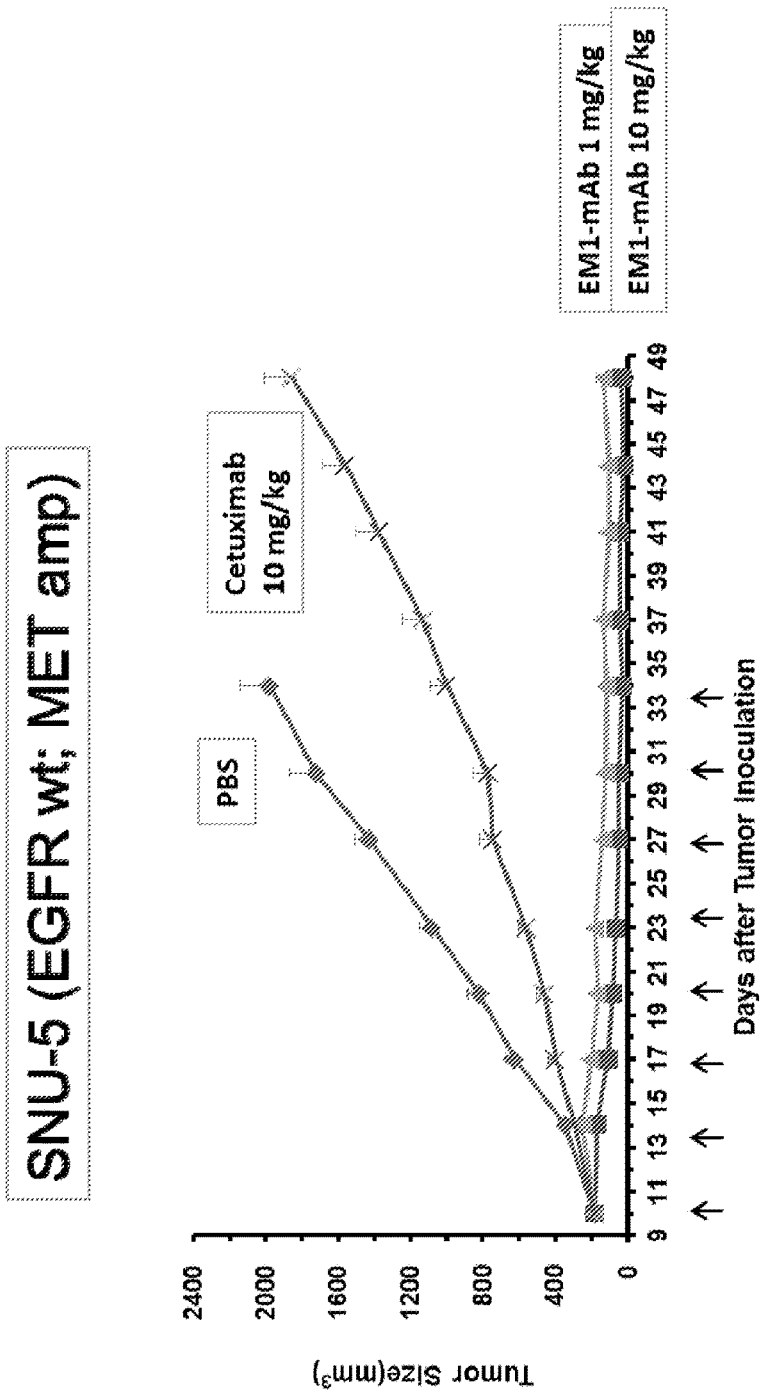

FIG. 12. SNU-5 tumor xenografts were implanted into CB17/SCID mice and the mice were treated with 10 mg/kg cetuximab or 10 mg/kg or 1 mg/kg EM1-mAb. Antibodies were dosed biweekly for four weeks. Arrows in the figure show the administration days. The anti-tumor activity of the therapies is shown as change in tumor size (mm$^3$) over time.

Figure 13:
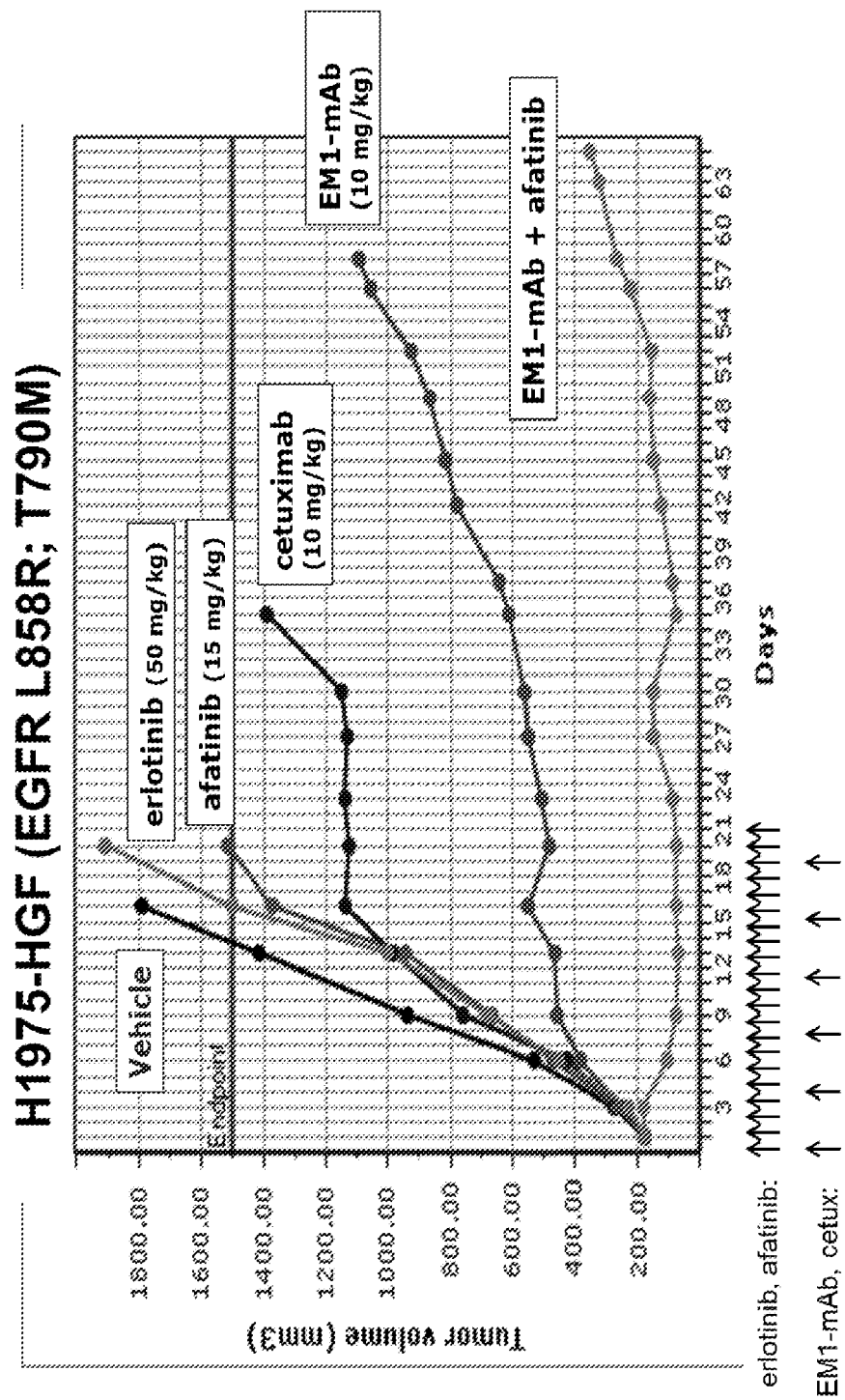

FIG. 13. H1975-HGF tumor xenografts were implanted into nude mice and the mice were treated with 10 mg/kg cetuximab, 10 mg/kg EM1-mAb, 50 mg/kg erlotinib, 15 mg/kg afatinib, or a combination of 10 mg/kg EM1-mAb and 15 mg/kg afatinib. Antibodies were dosed biweekly and the small molecules once a day for three weeks. Arrows in the figure show the administration days. The anti-tumor activity of the therapies is shown as change in tumor size (mm$^3$) over time.

Figure 14:
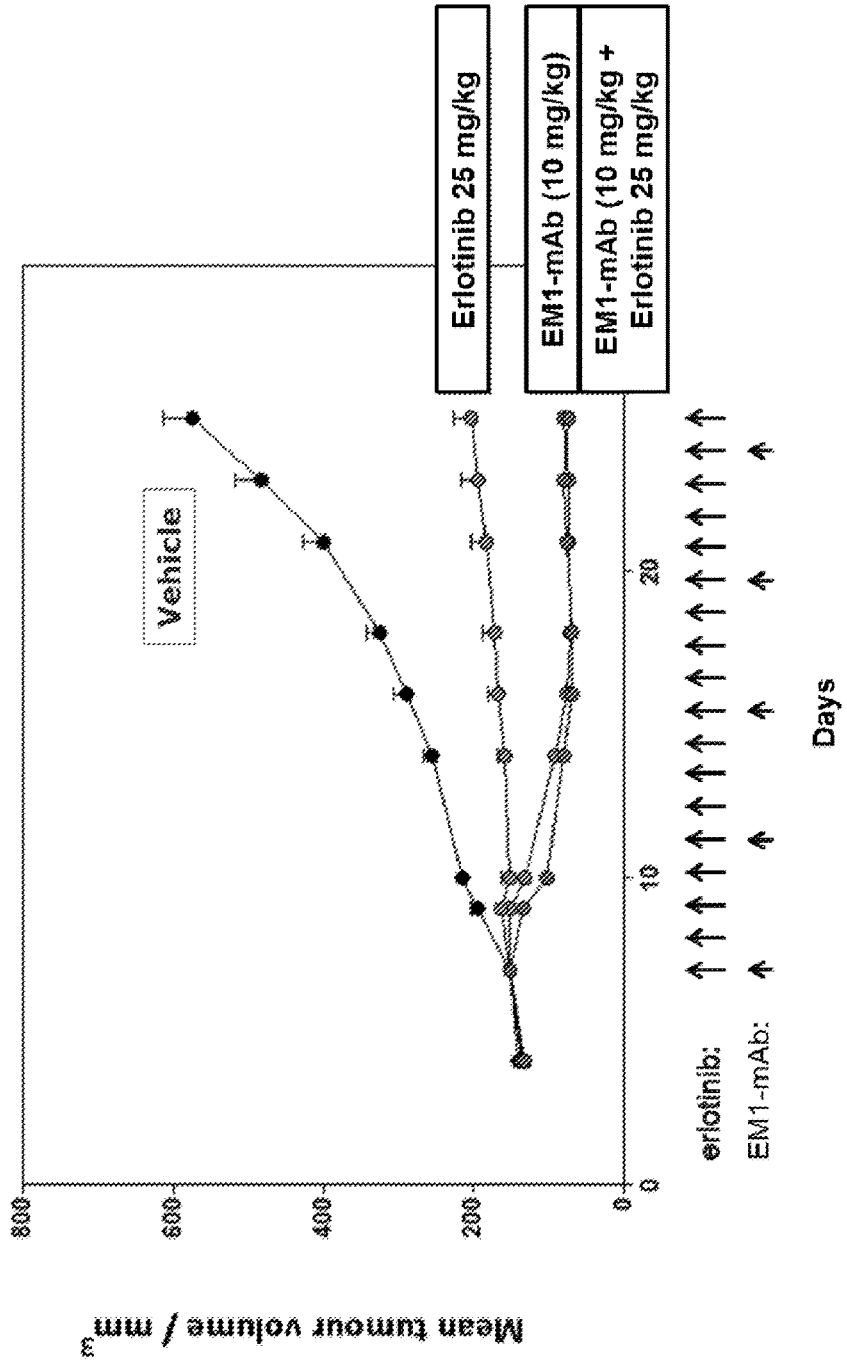

FIG. 14. HCC827-ER1 tumor xenografts were implanted into nude mice and the mice were treated with 10 mg/kg EM1-mAb, 25 mg/kg erlotinib, or a combination of the two. EM1-mAb was dosed biweekly and erlotinib once a day for 19 days. Arrows in the figure show the administration days. The anti-tumor activity of the therapies is shown as change in tumor size (mm$^3$) over time.

Figure 15:
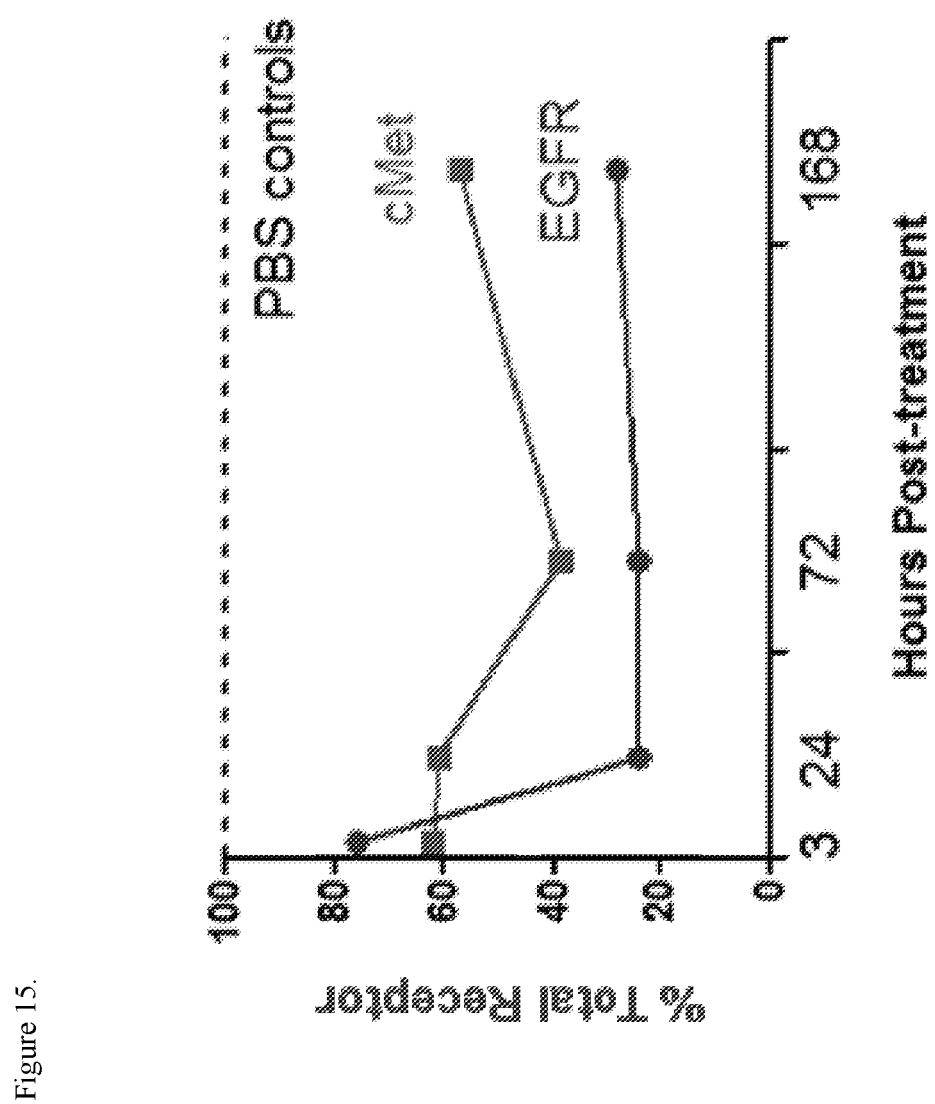

FIG. 15. Average EGFR and c-Met levels in tumor lysates isolated from H1975 HGF tumor xenografts implanted into SCID Beige mice after administration of a single dose of 20 mg/kg EM1-mAb. Receptor levels are shown as % of PBS control at indicated times post-treatment.

Figure 16:
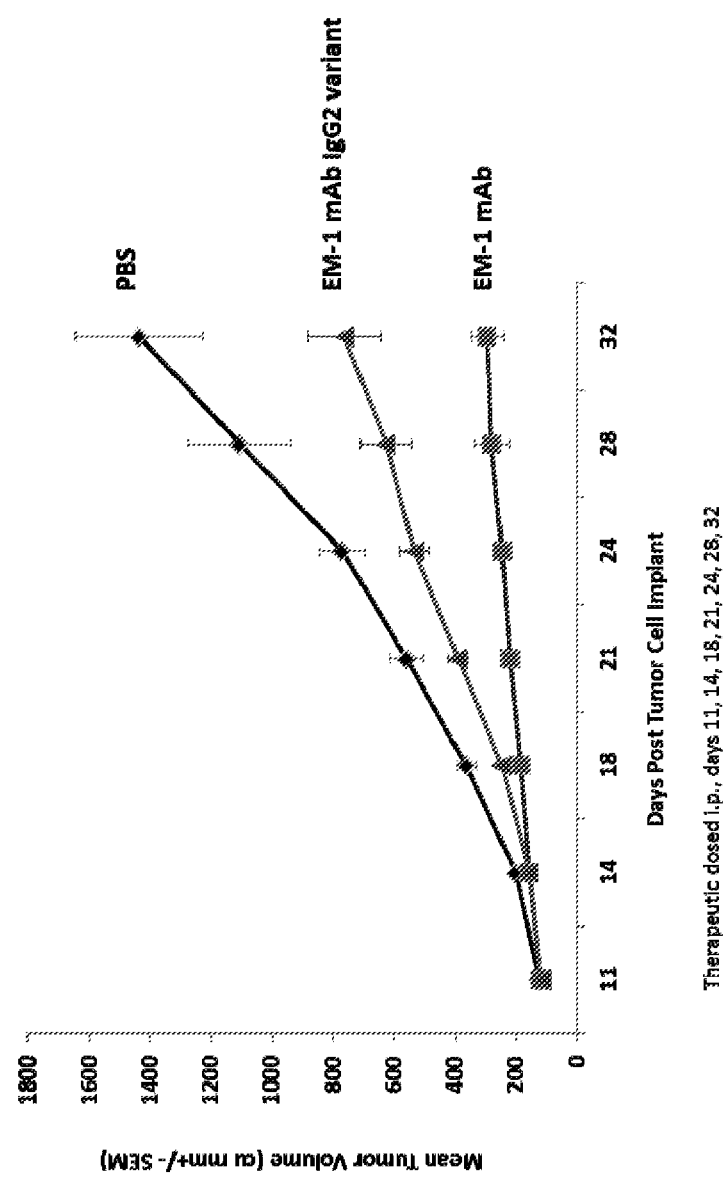

FIG. 16. H1975-HGF tumor xenografts were implanted into nude mice and the mice were treated with 10 mg/kg EM1-mAb or 10 mg/kg EM1-mAb variant IgG2 V234A/G237A/P238S/H268A/V309L/A330S/P331S having no Fc receptor binding and lacking effector functions. Antibodies were dosed biweekly at indicated days. The anti-tumor activity of the therapies is shown as change in tumor size (mm$^3$) over time.

DETAILED DESCRIPTION OF THE INVENTION

The term "fibronectin type III (FN3) domain" (FN3 domain) as used herein refers to a domain occurring frequently in proteins including fibronectins, tenascin, intracellular cytoskeletal proteins, cytokine receptors and prokaryotic enzymes (Bork and Doolittle, Proc Nat Acad Sci USA 89:8990-8994, 1992; Meinke et al., J Bacteriol 175:1910-1918, 1993; Watanabe et al., J Biol Chem 265:15659-15665, 1990). Exemplary FN3 domains are the 15 different FN3 domains present in human tenascin C, the 15 different FN3 domains present in human fibronectin (FN), and non-natural synthetic FN3 domains as described for example in U.S. Pat. Publ. No. 2010/0216708. Individual FN3 domains are referred to by domain number and protein name, e.g., the 3$^{rd}$ FN3 domain of tenascin (TN3), or the 10$^{th}$ FN3 domain of fibronectin (FN10).

The term "substituting" or "substituted" or "mutating" or "mutated" as used herein refers to altering, deleting or inserting one or more amino acids or nucleotides in a polypeptide or polynucleotide sequence to generate a variant of that sequence.

The term "randomizing" or "randomized" or "diversified" or "diversifying" as used herein refers to making at least one substitution, insertion or deletion in a polynucleotide or polypeptide sequence.

"Variant" as used herein refers to a polypeptide or a polynucleotide that differs from a reference polypeptide or a reference polynucleotide by one or more modifications for example, substitutions, insertions or deletions.

The term "specifically binds" or "specific binding" as used herein refers to the ability of an FN3 domain, a bispecific agent that specifically binds EGFR and c-Met, or a bispecific EGFR/c-Met antibody of the invention to bind to a predetermined antigen with a dissociation constant ($K_D$) of about $1 \times 10^{-6}$ M or less, for example about $1 \times 10^{-7}$ M or less, about $1 \times 10^{-8}$ M or less, about $1 \times 10^{-9}$ M or less, about $1 \times 10^{-10}$ M or less, about $1 \times 10^{-11}$ M or less, about $1 \times 10^{-12}$ M or less, or about $1 \times 10^{-13}$ M or less. Typically the FN3 domain, the bispecific agent that specifically binds EGFR and c-Met or the bispecific EGFR/c-Met antibody of the invention binds to a predetermined antigen (i.e. EGFR or c-Met) with a $K_D$ that is at least ten fold less than its $K_D$ for a nonspecific antigen (for example BSA or casein) as measured by surface plasmon resonance using for example a Proteon Instrument (BioRad). Thus, the bispecific EGFR/c-Met FN3 domain containing molecule, the bispecific agent that specifically binds EGFR and c-Met or the bispecific EGFR/c-Met antibody of the invention specifically binds to each EGFR and c-Met with a binding affinity ($K_D$) of at least about $1 \times 10^{-6}$ M or less, for example about $1 \times 10^{-7}$ M or less, about $1 \times 10^{-8}$ M or less, about $1 \times 10^{-9}$ M or less, about $1 \times 10^{-10}$ M or less, about $1 \times 10^{-11}$ M or less, about $1 \times 10^{-12}$ M or less, or about $1 \times 10^{-13}$ M or less. The bispecific EGFR/c-Met FN3 domain containing molecule, the bispecific agent that specifically binds EGFR and c-Met or the bispecific EGFR/c-Met antibody of the invention that specifically binds to a predetermined antigen may, however, have cross-reactivity to other related antigens, for example to the same predetermined antigen from other species (homologs).

The term "library" refers to a collection of variants. The library may be composed of polypeptide or polynucleotide variants.

The term "stability" as used herein refers to the ability of a molecule to maintain a folded state under physiological conditions such that it retains at least one of its normal functional activities, for example, binding to a predetermined antigen such as EGFR or c-Met.

"Epidermal growth factor receptor" or "EGFR" as used here refers to the human EGFR (also known as HER1 or ErbB1 (Ullrich et al., Nature 309:418-425, 1984) having the amino acid sequence shown in SEQ ID NO: 73 and in GenBank accession number NP_005219, as well as naturally-occurring variants thereof. Such variants include the well known EGFRvIII and other alternatively spliced variants (e.g., as identified by SwissProt Accession numbers P00533-1 (wild type; identical to SEQ ID NO: 73 and NP_005219), P00533-2 (F404L/L4055), P00533-3 (628-705: CTGPGLEGCP . . . GEAPNQALLR→PGNESLKAML . . . SVIITASSCH and 706-1210 deleted), P00533-4 (C628S and 629-1210 deleted), variants G1nQ98, R266, K521, 1674, G962, and P988 (Livingston et al., NIEHS-SNPs, environmental genome project, NIEHS ES15478), T790M, L858R/T790M and del(E746, A750).

"EGFR ligand" as used herein encompasses all (e.g., physiological) ligands for EGFR, including EGF, TGFα, heparin binding EGF (HB-EGF), amphiregulin (AR), and epiregulin (EPI).

"Epidermal growth factor" (EGF) as used herein refers to the well known 53 amino acid human EGF having the amino acid sequence shown in SEQ ID NO: 74.

"Hepatocyte growth factor receptor" or "c-Met" as used herein refers to the human c-Met having the amino acid sequence shown in SEQ ID NO: 101 or in GenBank Accession No: $NP_{13}$ 001120972 and natural variants thereof.

"Hepatocyte growth factor" (HGF) as used herein refers to the well known human HGF having the amino acid sequence shown in SEQ ID NO: 102 which is cleaved to form a dimer of an alpha and beta chain linked by a disulfide bond.

"Blocks binding" or "inhibits binding", as used herein interchangeably refers to the ability of the FN3 domains, the bispecific EGFR/c-Met FN3 domain containing molecule, the bispecific agent that specifically binds EGFR and c-Met or the bispecific EGFR/c-Met antibody of the invention to block or inhibit binding of the EGFR ligand such as EGF to EGFR and/or HGF to c-Met, and encompass both partial and complete blocking/inhibition. The blocking/inhibition of EGFR ligand such as EGF to EGFR and/or HGF to c-Met by the FN3 domains, the bispecific EGFR/c-Met FN3 domain containing molecule, the bispecific agent that specifically binds EGFR and c-Met or the bispecific EGFR/c-Met antibody of the invention reduces partially or completely the normal level of EGFR signaling and/or c-Met signaling when compared to the EGFR ligand binding to EGFR and/or HGF binding to c-Met without blocking or inhibition. The FN3 domains, the bispecific EGFR/c-Met FN3 domain containing molecule, the bispecific agent that specifically binds EGFR and c-Met or the bispecific EGFR/c-Met antibody of the invention "blocks binding" of the EGFR ligand such as EGF to EGFR and/or HGF to c-Met when the inhibition is at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100%. Inhibition of binding can be measured using well known methods, for example by measuring inhibition of binding of biotinylated EGF on EGFR expressing A431 cells exposed to the FN3 domain, the bispecific EGFR/c-Met FN3 domain containing molecule, the bispecific agent that specifically binds EGFR and c-Met or the bispecific EGFR/c-Met antibody of the invention using FACS, and using methods described herein, or measuring inhibition of binding of biotinylated HGF on c-Met extracellular domain using well known methods and methods described herein.

The term "EGFR signaling" refers to signal transduction induced by EGFR ligand binding to EGFR resulting in autophosphorylation of at least one tyrosine residue in the EGFR. An exemplary EGFR ligand is EGF.

"Neutralizes EGFR signaling" as used herein refers to the ability of the FN3 domains, the bispecific EGFR/c-Met FN3 domain containing molecule, the bispecific agent that specifically binds EGFR and c-Met or the bispecific EGFR/c-Met antibody of the invention to inhibit EGFR signaling induced by EGFR ligand such as EGF by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100%.

The term "c-Met signaling" refers to signal transduction induced by HGF binding to c-Met resulting in autophosphorylation of at least one tyrosine residue in the c-Met. Typically at least one tyrosine residue at positions 1230, 1234, 1235 or 1349 is autophosphorylated upon HGF binding.

"Neutralizes c-Met signaling" as used herein refers to the ability of the FN3 domain, the bispecific EGFR/c-Met FN3 domain containing molecule, the bispecific agent that specifically binds EGFR and c-Met or the bispecific EGFR/c-Met antibody of the invention to inhibit c-Met signaling induced by HGF by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100%.

"Overexpress", "overexpressed" and "overexpressing" as used herein interchangeably refer to a cancer or malignant cell that has measurably higher levels of EGFR and/or c-Met on the surface compared to a normal cell of the same tissue type. Such overexpression may be caused by gene amplification or by increased transcription or translation. EGFR and/or c-Met expression and overexpression can be measured using well know assays using for example ELISA, immunofluorescence, flow cytometry or radioimmunoassay on live or lysed cells. Alternatively, or additionally, levels of EGFR and/or c-Met-encoding nucleic acid molecules may be measured in the cell for example using fluorescent in situ hybridization, Southern blotting, or PCR techniques. EGFR and/or c-Met is overexpressed when the level of EGFR and/or c-Met on the surface of the cell is at least 1.5-fold higher when compared to the normal cell.

"Tencon" as used herein refers to the synthetic fibronectin type III (FN3) domain having the sequence shown in SEQ ID NO: 1 and described in U.S. Pat. Publ. No. US2010/0216708.

A "cancer cell" or a "tumor cell" as used herein refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is exemplified by, e.g., morphological changes, immortalization of cells, aberrant growth control, foci formation, proliferation, malignancy, tumor specific marker levels, invasiveness, tumor growth or suppression in suitable animal hosts such as nude mice, and the like, in vitro, in vivo, and ex vivo (Freshney, Culture of Animal Cells: A Manual of Basic Technique (3rd ed. 1994)).

The term "vector" means a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

The term "expression vector" means a vector that can be utilized in a biological system or in a reconstituted biological system to direct the translation of a polypeptide encoded by a polynucleotide sequence present in the expression vector.

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

"Complementary DNA" or "cDNA" refers to a well known synthetic polynucleotide that shares the arrangement of sequence elements found in native mature mRNA species with contiguous exons, with the intervening introns present in genomic DNA are removed. The codons encoding the initiator methionine may or may not be present in cDNA. cDNA may be synthesized for example by reverse transcription or synthetic gene assembly.

"Synthetic" or "non-natural" or "artificial" as used herein refers to a polynucleotide or a polypeptide molecule not present in nature.

The term "polypeptide" or "protein" means a molecule that comprises at least two amino acid residues linked by a peptide bond to form a polypeptide. Small polypeptides of less than about 50 amino acids may be referred to as "peptides".

The term "bispecific EGFR/c-Met molecule" or "bispecific EGFR/c-Met FN3 domain containing molecule" as used herein refers to a molecule comprising an EGFR binding FN3 domain and a distinct c-Met binding FN3 domain that are covalently linked together either directly or via a linker. An exemplary bispecific EGFR/c-Met binding molecule comprises a first FN3 domain specifically binding EGFR and a second FN3 domain specifically binding c-Met.

"Valent" as used herein refers to the presence of a specified number of binding sites specific for an antigen in a molecule. As such, the terms "monovalent", "bivalent", "tetravalent", and "hexavalent" refer to the presence of one, two, four and six binding sites, respectively, specific for an antigen in a molecule.

"Mixture" as used herein refers to a sample or preparation of two or more FN3 domains not covalently linked together. A mixture may consist of two or more identical FN3 domains or distinct FN3 domains. Mixture as used herein also refers to a sample or preparation of two or more monovalent antibodies that are monovalent towards EGFR and/or monovalent towards c-Met.

The term "bispecific agent that specifically binds EGFR and c-Met" as used herein refers to a molecule comprising a first domain that specifically binds EGFR and a second domain that specifically binds c-Met. An exemplary agent that specifically binds EGFR and c-Met is a bispecific antibody. Another exemplary bispecific agent that specifically binds EGFR and c-Met is a molecule comprising an EGFR binding FN3 domain and a distinct c-Met binding FN3 domain. The bispecific agent that specifically binds EGFR and c-Met may be composed of a single polypeptide or more than one polypeptide.

The term "bispecific anti-EGFR/c-Met antibody" or "bispecific EGFR/c-Met antibody" as used herein refers to a bispecific antibody having a first domain that specifically binds EGFR and a second domain that specifically binds c-Met. The domains specifically binding EGFR and c-Met are typically VH/VL pairs, and the bispecific anti-EGFR/c-Met antibody is monovalent in terms of binding to EGFR and c-Met.

The term "antibodies" as used herein is meant in a broad sense and includes immunoglobulin molecules including polyclonal antibodies, monoclonal antibodies including murine, human, human-adapted, humanized and chimeric monoclonal antibodies, antibody fragments, bispecific or multispecific antibodies, dimeric, tetrameric or multimeric antibodies, and single chain antibodies.

Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$. Antibody light chains of any vertebrate species can be assigned to one of two clearly distinct types, namely kappa (κ) and lambda (λ), based on the amino acid sequences of their constant domains.

The term "antibody fragments" refers to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region (VH), or a light chain variable region (VL). Antibody fragments include a Fab fragment, a monovalent fragment consisting of the VL, VH, CL and CHI domains; a F(ab)$_2$ fragment, a bivalent fragment comprising two Fab fragments linked by a disulfide bridge at the hinge region; a Fd fragment consisting of the VH and CHI domains; a Fv fragment consisting of the VL and VH domains of a single arm of an antibody; a domain antibody (dAb) fragment (Ward et al (1989) Nature 341:544-546), which consists of a VH domain. VH and VL domains can be engineered and linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody; described for example in PCT Intl. Publ. Nos. WO1998/44001, WO1988/01649, WO1994/13804, and WO1992/01047. These antibody fragments are obtained using well known techniques known to those of skill in the art, and the fragments are screened for utility in the same manner as are full length antibodies.

The phrase "isolated antibody" refers to an antibody or antibody fragment that is substantially free of other antibodies having different antigenic specificities (e.g., an isolated bispecific antibody specifically binding EGFR and c-Met is substantially free of antibodies that specifically bind antigens other than human EGFR and c-Met). An isolated antibody that specifically binds EGFR and c-Met, however, can have cross-reactivity to other antigens, such as orthologs of human EGFR and/or c-Met, such as *Macaca fascicularis* (cynomolgus) EGFR and/or c-Met. Moreover, an isolated antibody may be substantially free of other cellular material and/or chemicals.

An antibody variable region consists of a "framework" region interrupted by three "antigen binding sites". The antigen binding sites are defined using various terms: (i) Complementarity Determining Regions (CDRs), three in the VH (HCDR1, HCDR2, HCDR3), and three in the VL (LCDR1, LCDR2, LCDR3), are based on sequence variability (Wu and Kabat J Exp Med 132:211-50, 1970; Kabat et al Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3), refer to the regions of an antibody variable domains which are hypervariable in structure as defined by Chothia and Lesk (Chothia and Lesk Mol Biol 196:901-17, 1987). Other terms include "IMGT-CDRs" (Lefranc et al., Dev Comparat Immunol 27:55-77, 2003) and "Specificity Determining Residue Usage" (SDRU) (Almagro Mol Recognit 17:132-43, 2004). The International ImMunoGeneTics (IMGT) database (http://www_mgt_org) provides a standardized numbering and definition of antigen-binding sites. The correspondence between CDRs, HVs and IMGT delineations is described in Lefranc et al., Dev Comparat Immunol 27:55-77, 2003.

"Chothia residues" as used herein are the antibody VL and VH residues numbered according to Al-Lazikani (Al-Lazikani et al., J Mol Biol 273:927-48, 1997).

"Framework" or "framework sequences" are the remaining sequences of a variable region other than those defined to be antigen binding sites. Because the antigen binding sites can be defined by various terms as described above, the exact amino acid sequence of a framework depends on how the antigen-binding site was defined.

"Humanized antibody" refers to an antibody in which the antigen binding sites are derived from non-human species and the variable region frameworks are derived from human immunoglobulin sequences. Humanized antibodies may include substitutions in the framework regions so that the framework may not be an exact copy of expressed human immunoglobulin or germline gene sequences.

"Human-adapted" antibodies or "human framework adapted (HFA)" antibodies refers to humanized antibodies adapted according to methods described in U.S. Pat. Publ. No. US2009/0118127. Human-adapted antibodies are humanized by selecting the acceptor human frameworks based on the maximum CDR and FR similarities, length compatibilities and sequence similarities of CDR1 and CDR2 loops and a portion of light chain CDR3 loops.

"Human antibody" refers to an antibody having heavy and light chain variable regions in which both the framework and the antigen binding sites are derived from sequences of human origin. If the antibody contains a constant region, the constant region also is derived from sequences of human origin.

Human antibody comprises heavy or light chain variable regions that are "derived from" sequences of human origin if the variable regions of the antibody are obtained from a system that uses human germline immunoglobulin or rearranged immunoglobulin genes. Such systems include human immunoglobulin gene libraries displayed on phage, and transgenic non-human animals such as mice carrying human immunoglobulin loci as described herein. "Human antibody" may contain amino acid differences when compared to the human germline or rearranged immunoglobulin sequences due to for example naturally occurring somatic mutations or intentional introduction of substitutions in the framework or antigen binding sites. Typically, "human antibody" is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by a human germline or rearranged immunoglobulin gene. In some cases, "human antibody" may contain consensus framework sequences derived from human framework sequence analyses, for example as described in Knappik et al., J Mol Biol 296:57-86, 2000), or synthetic HCDR3 incorporated into human immunoglobulin gene libraries displayed on phage, for example as described in Shi et al., J Mol Biol 397:385-96, 2010 and Intl. Pat. Publ. No. WO2009/085462). Antibodies in which antigen binding sites are derived from a non-human species are not included in the definition of "human antibody".

Isolated humanized antibodies may be synthetic. Human antibodies, while derived from human immunoglobulin sequences, may be generated using systems such as phage display incorporating synthetic CDRs and/or synthetic frameworks, or can be subjected to in vitro mutagenesis to improve antibody properties, resulting in antibodies that do not naturally exist within the human antibody germline repertoire in vivo.

The term "recombinant antibody" as used herein, includes all antibodies that are prepared, expressed, created or isolated by recombinant means, such as antibodies isolated from an animal (e.g., a mouse) that is transgenic or transchromosomal for human immunoglobulin genes or a hybridoma prepared therefrom (described further below), antibodies isolated from a host cell transformed to express the antibody, antibodies isolated from a recombinant, combinatorial antibody library, and antibodies prepared, expressed, created or isolated by any other means that involve splicing of human immunoglobulin gene sequences to other DNA sequences, or antibodies that are generated in vitro using Fab arm exchange.

The term "monoclonal antibody" as used herein refers to a preparation of antibody molecules of single molecular composition. A monoclonal antibody composition displays a single binding specificity and affinity for a particular epitope, or in a case of a bispecific monoclonal antibody, a dual binding specificity to two distinct epitopes.

The term "substantially identical" as used herein means that the two antibody variable region amino acid sequences being compared are identical or have "insubstantial differences". Insubstantial differences are substitutions of 1, 2, 3, 4, 5, 6, 7, 8, 9, 10, 11, 12, 13, 14, or 15 amino acids in an antibody variable region sequence that do not adversely affect antibody properties Amino acid sequences substantially identical to the variable region sequences disclosed herein are within the scope of the invention. In some embodiments, the sequence identity can be about 90%, 91%, 92%, 93%, 94%, 95%, 96%, 97%, 98%, 99% or higher. Percent identity can be determined for example by pairwise alignment using the default settings of the AlignX module of Vector NTI v.9.0.0 (Invitrogen, Carlsbad, Calif.). The protein sequences of the present invention can be used as a query sequence to perform a search against public or patent databases to, for example, identify related sequences. Exemplary programs used to perform such searches are the XBLAST or BLASTP programs (http_//www_ncbi_nlm/nih_gov), or the GenomeQuest™ (GenomeQuest, Westborough, Mass.) suite using the default settings.

The term "epitope" as used herein means a portion of an antigen to which an antibody specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. An epitope can be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

The term "in combination with" as used herein means that two or more therapeutics can be administered to a subject together in a mixture, concurrently as single agents or sequentially as single agents in any order.

The numbering of amino acid residues in the antibody constant region throughout the specification is performed according to the EU index as described in Kabat et al., Sequences of Proteins of Immunological Interest, 5th Ed. Public Health Service, National Institutes of Health, Bethesda, Md. (1991), unless otherwise explicitly stated.

Compositions of Matter

The present invention provides bispecific agents that specifically bind EGFR and c-Met. The present invention provides polypeptides and polynucleotides encoding the bispecific agents of the invention or complementary nucleic acids thereof, vectors, host cells, and methods of making and using them.

Monospecific and Bispecific EGFR and/or c-Met FN3 Domain Containing Binding Molecules Monospecific EGFR FN3 Domain Containing Binding Molecules The present invention provides fibronectin type III (FN3) domains that bind specifically to epidermal growth factor receptor (EGFR) and block binding of epidermal growth factor (EGF) to EGFR, and thus can be widely used in therapeutic and diagnostic applications. The present invention provides polynucleotides encoding the FN3 domains of the invention or complementary nucleic acids thereof, vectors, host cells, and methods of making and using them.

The FN3 domains of the invention bind EGFR with high affinity and inhibit EGFR signaling, and may provide a benefit in terms of specificity and reduced off-target toxicity when compared to small molecule EGFR inhibitors, and improved tissue penetration when compared to conventional antibody therapeutics.

One embodiment of the invention is an isolated fibronectin type III (FN3) domain that specifically binds epidermal growth factor receptor (EGFR) and blocks binding of epidermal growth factor (EGF) to EGFR.

The FN3 domains of the invention may block EGF binding to the EGFR with an $IC_{50}$ value of less than about $1\times10^{-7}$ M, less than about $1\times10^{-8}$ M, less than about $1\times10^{-9}$ M, less than about $1\times10^{-10}$ M, less than about $1\times10^{-11}$ M, or less than about $1\times10^{-12}$ M in a competition assay employing A431 cells and detecting amount of fluorescence from bound biotinylated EGF using streptavidin-phycoerythrin conjugate at 600 nM on A431 cells incubated with or without the FN3 domains of the invention. Exemplary FN3 domains may block EGF binding to the EGFR with an $IC_{50}$ value between about $1\times10^{-9}$ M to about $1\times10^{-7}$ M, such as EGFR binding FN3 domains having the amino acid sequence of SEQ ID NOs: 18-29, 107-110, or 122-137. The FN3 domains of the invention may block EGF binding to the EGFR by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to binding of EGF to the EGFR in the absence of the FN3 domains of the invention using the same assay conditions.

The FN3 domain of the invention may inhibit EGFR signaling by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to the level of signaling in the absence of the FN3 domains of the invention using the same assay conditions.

Binding of a ligand such as EGF to EGFR stimulates receptor dimerization, autophosphorylation, activation of the receptor's internal, cytoplasmic tyrosine kinase domain, and initiation of multiple signal transduction and transactivation pathways involved in regulation of DNA synthesis (gene activation) and cell cycle progression or division. Inhibition of EGFR signaling may result in inhibition in one or more EGFR downstream signaling pathways and therefore neutralizing EGFR may have various effects, including inhibition of cell proliferation and differentiation, angiogenesis, cell motility and metastasis.

EGFR signaling may be measured using various well know methods, for example measuring the autophosphorylation of the receptor at any of the tyrosines Y1068, Y1148, and Y1173 (Downward et al., Nature 311:483-5, 1984) and/or phosphorylation of natural or synthetic substrates. Phosphorylation can be detected using well known methods such as an ELISA assay or a western plot using a phosphotyrosine specific antibody. Exemplary assays can be found in Panek et al., J Pharmacol Exp Thera 283:1433-44, 1997 and Batley et al., Life Sci 62:143-50, 1998, and assays described herein.

In one embodiment, the FN3 domain of the invention inhibits EGF-induced EGFR phosphorylation at EGFR residue position Tyrosine 1173 with an $IC_{50}$ value of less than about $2.5\times10^{-6}$ M, for example less than about $1\times10^{-6}$ M, less than about $1\times10^{-7}$ M, less than about $1\times10^{-8}$ M, less than about $1\times10^{-9}$ M, less than about $1\times10^{-10}$ M, less than about $1\times10^{-11}$ M, or less than about $1\times10^{-12}$ M when measured in A431 cells using 50 ng/mL human EGF.

In one embodiment, the FN3 domain of the invention inhibits EGF-induced EGFR phosphorylation at EGFR residue position Tyrosine 1173 with an $IC_{50}$ value between about $1.8\times10^{-8}$ M to about $2.5\times10^{-6}$ M when measured in A431 cells using 50 ng/mL human EGF. Such exemplary FN3 domains are those having the amino acid sequence of SEQ ID NOs: 18-29, 107-110, or 122-137.

In one embodiment, the FN3 domain of the invention binds human EGFR with a dissociation constant ($K_D$) of less than about $1\times10^{-8}$ M, for example less than about $1\times10^{-9}$ M, less than about $1\times10^{-10}$ M, less than about $1\times10^{-11}$ M, less than about $1\times10^{-12}$ M, or less than about $1\times10^{-13}$ M as determined by surface plasmon resonance or the Kinexa method, as practiced by those of skill in the art. In some embodiments, the FN3 domain of the invention binds human EGFR with a $K_D$ of between about $2\times10^{-10}$ to about $1\times10^{-8}$ M. The affinity of a FN3 domain for EGFR can be determined experimentally using any suitable method. (See, for example, Berzofsky, et al., "Antibody-Antigen Interactions," In Fundamental Immunology, Paul, W. E., Ed., Raven Press: New York, N.Y. (1984); Kuby, Janis Immunology, W.H. Freeman and Company: New York, N.Y. (1992); and methods described herein). The measured affinity of a particular FN3 domain-antigen interaction can vary if measured under different conditions (e.g., osmolarity, pH). Thus, measurements of affinity and other antigen-binding parameters (e.g., $K_D$, $K_{on}$, $K_{off}$) are preferably made with standardized solutions of protein scaffold and antigen, and a standardized buffer, such as the buffer described herein.

Exemplary FN3 domains of the invention that bind EGFR include FN3 domains of SEQ ID NOs: 18-29, 107-110, or 122-137.

In one embodiment, the FN3 domain that specifically binds EGFR comprises an amino acid sequence at least 87% identical to the amino acid sequence of SEQ ID NO: 27.

In one embodiment, the FN3 domain that specifically binds EGFR comprises an FG loop comprising the sequence HNVYKDTNX$_9$RGL (SEQ ID NO: 179) or the sequence LGSYVFEHDVML (SEQ ID NO: 180), wherein X$_9$ is M or I; and a BC loop comprising the sequence $X_1X_2X_3X_4X_5X_6X_7X_8$ (SEQ ID NO: 181);

wherein
$X_1$ is A, T, G or D;
$X_2$ is A, D, Y or W;
$X_3$ is P, D or N;
$X_4$ is L or absent;
$X_5$ is D, H, R, G, Y or W;
$X_6$ is G, D or A;
$X_7$ is A, F, G, H or D; and
$X_8$ is Y, F or L.

The FN3 domains of the invention that specifically bind EGFR and inhibit autophosphorylation of EGFR may comprise as a structural feature an FG loop comprising the sequence HNVYKDTNX$_9$RGL (SEQ ID NO: 179) or the sequence LGSYVFEHDVML (SEQ ID NO: 180), wherein $X_9$ is M or I. Such FN3 domains may further comprise a BC loop of 8 or 9 amino acids in length and defined by the sequence $X_1X_2X_3X_4X_5X_6X_7X_8$ (SEQ ID NO: 181), and inhibit EGFR autophosphorylation with an IC$_{50}$ value of less than about $2.5\times10^{-6}$ M, or with an IC$_{50}$ value of between about $1.8\times10^{-8}$ M to about $2.5\times10^{-6}$ M when measured in A431 cells using 50 ng/mL human EGF.

The FN3 domains of the invention that specifically bind EGFR and inhibit autophosphorylation of EGFR further comprise the sequence of LPAPKNLVVSEVTEDSLRLSWX$_1$X$_2$X$_3$X$_4$X$_5$X$_6$X$_7$X$_8$DSFLIQ-
YQESEKVGEAINLTVP GSERSYDLTGLK-
PGTEYTVSIYGVHNVYKD-
TNX$_9$RGLPLSAEFTT (SEQ ID NO: 182), or the sequence LPAPKNLVVSEVTEDSLRLSWX$_1$X$_2$X$_3$X$_4$X$_5$X$_6$X$_7$X$_8$DSF-
LIQYQESEKVGEAINLTVP GSERSYDLT-
GLKPGTEYTVSIYGVLGSYVFEHDVMLPL-
SAEFTT (SEQ ID NO: 183), wherein
$X_1$ is A, T, G or D;
$X_2$ is A, D, Y or W;
$X_3$ is P, D or N;
$X_4$ is L or absent;
$X_5$ is D, H, R, G, Y or W;
$X_6$ is G, D or A;
$X_7$ is A, F, G, H or D;
$X_8$ is Y, F or L; and
$X_9$ is M or I The EGFR binding FN3 domains can be generated and tested for their ability to inhibit EGFR autophosphorylation using well known methods and methods described herein.

Another embodiment of the invention is an isolated FN3 domain that specifically binds EGFR, wherein the FN3 domain comprises the sequence shown in SEQ ID NOs: 18-29, 107-110, or 122-137.

In some embodiments, the EGFR binding FN3 domains comprise an initiator methionine (Met) linked to the N-terminus or a cysteine (Cys) linked to a C-terminus of a particular FN3 domain, for example to facilitate expression and/or conjugation of half-life extending molecules.

Another embodiment of the invention is an isolated fibronectin type III (FN3) domain that specifically binds EGFR and blocks binding of EGF to the EGFR, wherein the FN3 domain is isolated from a library designed based on Tencon sequence of SEQ ID NO: 1.

Monospecific c-Met FN3 Domain Containing Binding Molecules

The present invention provides fibronectin type III (FN3) domains that bind specifically to hepatocyte growth factor receptor (c-Met) and block binding of hepatocyte growth factor (HGF) to c-Met, and thus can be widely used in therapeutic and diagnostic applications. The present invention provides polynucleotides encoding the FN3 domains of the invention or complementary nucleic acids thereof, vectors, host cells, and methods of making and using them.

The FN3 domains of the invention bind c-Met with high affinity and inhibit c-Met signaling, and may provide a benefit in terms of specificity and reduced off-target toxicity when compared to small molecule c-Met inhibitors, and improved tissue penetration when compared to conventional antibody therapeutics. The FN3 domains of the invention are monovalent, therefore preventing unwanted receptor clustering and activation that may occur with other bivalent molecules.

One embodiment of the invention is an isolated fibronectin type III (FN3) domain that specifically binds hepatocyte growth factor receptor (c-Met) and blocks binding of hepatocyte growth factor (HGF) to c-Met.

The FN3 domains of the invention may block HGF binding to c-Met with an IC$_{50}$ value of less than about $1\times10^{-7}$ M, less than about $1\times10^{-8}$ M, less than about $1\times10^{-9}$ M, less than about $1\times10^{-10}$ M, less than about $1\times10^{-11}$ M, or less than about $1\times10^{-12}$ M in an assay detecting inhibition of binding of biotinylated HGF to c-Met-Fc fusion protein in the presence of the FN3 domains of the invention. Exemplary FN3 domains may block HGF binding to the c-Met with an IC$_{50}$ value between about $2\times10^{-10}$ M to about $6\times10^{-8}$ M. The FN3 domains of the invention may block HGF binding to c-Met by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to binding of HGF to c-Met in the absence of the FN3 domains of the invention using the same assay conditions.

The FN3 domain of the invention may inhibit c-Met signaling by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to the level of signaling in the absence of FN3 domains of the invention using the same assay conditions.

Binding of HGF to c-Met stimulates receptor dimerization, autophosphorylation, activation of the receptor's internal, cytoplasmic tyrosine kinase domain, and initiation of multiple signal transduction and transactivation pathways involved in regulation of DNA synthesis (gene activation) and cell cycle progression or division. Inhibition of c-Met signaling may result in inhibition of one or more c-Met downstream signaling pathways and therefore neutralizing c-Met may have various effects, including inhibition of cell proliferation and differentiation, angiogenesis, cell motility and metastasis.

c-Met signaling may be measured using various well know methods, for example measuring the autophosphorylation of the receptor on at least one tyrosine residues Y1230, Y1234, Y1235 or Y1349 and/or phosphorylation of natural or synthetic substrates. Phosphorylation may be detected, for example, using an antibody specific for phosphotyrosine in an ELISA assay or on a western blot. Assays for tyrosine kinase activity are described for example in: Panek et al., J Pharmacol Exp Thera 283:1433-44, 1997 and Batley et al., Life Sci 62:143-50, 1998, and assays described herein.

In one embodiment, the FN3 domain of the invention inhibits HGF-induced c-Met phosphorylation at c-Met residue position 1349 with an IC$_{50}$ value of less than about $1\times10^{-6}$ M, less than about $1\times10^{-7}$ M, less than about $1\times10^{-8}$ M, less than about $1\times10^{-9}$ M, less than about $1\times10^{-10}$ M, less than about $1\times10^{-11}$ M, or less than about $1\times10^{-12}$ M when measured in NCI-H441 cells using 100 ng/mL recombinant human HGF.

In one embodiment, the FN3 domain of the invention inhibits HGF-induced c-Met phosphorylation at c-Met tyrosine Y1349 with an $IC_{50}$ value between about $4\times10^{-9}$ M to about $1\times10^{-6}$ M when measured in NCI-H441 cells using 100 ng/mL recombinant human HGF.

In one embodiment, the FN3 domain of the invention binds human c-Met with an dissociation constant ($K_D$) of equal to or less than about $1\times10^{-7}$ M, $1\times10^{-8}$ M, $1\times10^{-9}$ M, $1\times10^{-10}$ M, $1\times10^{-11}$ M, $1\times10^{-12}$ M, $1\times10^{-13}$ M, $1\times10^{-14}$ M, or $1\times10^{-15}$ M as determined by surface plasmon resonance or the Kinexa method, as practiced by those of skill in the art. In some embodiments, the FN3 domain of the invention binds human c-Met with a $K_D$ of between about $3\times10^{-10}$ M to about $5\times10^{-8}$ M. The affinity of a FN3 domain for c-Met may be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W.H. Freeman and Company: New York, N.Y. (1992); and methods described herein). The measured affinity of a particular FN3 domain-antigen interaction can vary if measured under different conditions (e.g., osmolarity, pH). Thus, measurements of affinity and other antigen-binding parameters (e.g., $K_D$, $K_{on}$, $K_{off}$) are preferably made with standardized solutions of protein scaffold and antigen, and a standardized buffer, such as the buffer described herein.

Exemplary FN3 domains of the invention that bind c-Met include FN3 domains having the amino acid sequence of SEQ ID NOs: 32-49 or 111-114.

In one embodiment, the FN3 domain that specifically binds c-Met comprises an amino acid sequence at least 83% identical to the amino acid sequence of SEQ ID NO: 41.

In one embodiment, the FN3 domain that specifically binds c-Met comprises a C strand and a CD loop comprising the sequence DSFX$_{10}$IRYX$_{11}$E
X$_{12}$X$_{13}$X$_{14}$X$_{15}$GX$_{16}$ (SEQ ID NO: 184), wherein
X$_{10}$ is W, F or V;
X$_{11}$ is D, F or L;
X$_{12}$ is V, F or L;
X$_{13}$ is V, L or T;
X$_{14}$ is V, R, G, L, T or S;
X$_{15}$ is G, S, A, T or K; and
X$_{16}$ is E or D; and a F strand and a FG loop comprising the sequence TEYX$_{17}$VX$_{18}$IX$_{19}$X$_{20}$V KGGX$_{21}$X$_{22}$SX$_{23}$ (SEQ ID NO: 185), wherein
X$_{17}$ is Y, W, I, V, G or A;
X$_{18}$ is N, T, Q or G;
X$_{19}$ is L, M, N or I;
X$_{20}$ is G or S;
X$_{21}$ is S, L, G, Y, T, R, H or K;
X$_{22}$ is I, V or L; and
X$_{23}$ is V, T, H, I, P, Y or L.

The FN3 domains of the invention that specifically bind c-Met and inhibit autophosphorylation of c-Met further comprises the sequence:

LPAPKNLVVSRVTEDSARLSWTAPDAAFDSFX$_{10}$IRYX$_{11}$E
X$_{12}$X$_{13}$X$_{14}$X$_{15}$GX$_{16}$AIVLTVPGSERSYDLTGLKPGT-
EYX$_{17}$VX$_{18}$IX$_{19}$X$_{20}$VKGGX$_{21}$X$_{22}$SX$_{23}$PLSAEFTT
(SEQ ID NO: 186), wherein
X$_{10}$ is W, F or V; and
X$_{11}$ is D, F or L;
X$_{12}$ is V, F or L;
X$_{13}$ is V, L or T;
X$_{14}$ is V, R, G, L, T or S;
X$_{15}$ is G, S, A, T or K;
X$_{16}$ is E or D;
X$_{17}$ is Y, W, I, V, G or A;
X$_{18}$ is N, T, Q or G;
X$_{19}$ is L, M, N or I;
X$_{20}$ is G or S;
X$_{21}$ is S, L, G, Y, T, R, H or K;
X$_{22}$ is I, V or L; and
X$_{23}$ is V, T, H, I, P, Y or L.

Another embodiment of the invention is an isolated FN3 domain that specifically binds c-Met, wherein the FN3 domain comprises the sequence shown in SEQ ID NOs: 32-49 or 111-114.

Another embodiment of the invention is an isolated fibronectin type III (FN3) domain that specifically binds c-Met and blocks binding of HGF to the c-Met, wherein the FN3 domain is isolated from a library designed based on Tencon sequence of SEQ ID NO: 1.

Isolation of EGFR or c-Met FN3 Domains from a Library Based on Tencon Sequence

Tencon (SEQ ID NO: 1) is a non-naturally occurring fibronectin type III (FN3) domain designed from a consensus sequence of fifteen FN3 domains from human tenascin-C (Jacobs et al., Protein Engineering, Design, and Selection, 25:107-117, 2012; U.S. Pat. Publ. No. 2010/0216708). The crystal structure of Tencon shows six surface-exposed loops that connect seven beta-strands as is characteristic to the FN3 domains, the beta-strands referred to as A, B, C, D, E, F and G, and the loops referred to as AB, BC, CD, DE, EF, and FG loops (Bork and Doolittle, Proc Natl Acad Sci USA 89:8990-8992, 1992; U.S. Pat. No. 6,673,901). These loops, or selected residues within each loop, can be randomized in order to construct libraries of fibronectin type III (FN3) domains that can be used to select novel molecules that bind EGFR or c-Met. Table 1 shows positions and sequences of each loop and beta-strand in Tencon (SEQ ID NO: 1).

Library designed based on Tencon sequence may thus have randomized FG loop, or randomized BC and FG loops, such as libraries TCL1 or TCL2 as described below. The Tencon BC loop is 7 amino acids long, thus 1, 2, 3, 4, 5, 6 or 7 amino acids may be randomized in the library diversified at the BC loop and designed based on Tencon sequence. The Tencon FG loop is 7 amino acids long, thus 1, 2, 3, 4, 5, 6 or 7 amino acids may be randomized in the library diversified at the FG loop and designed based on Tencon sequence. Further diversity at loops in the Tencon libraries may be achieved by insertion and/or deletions of residues at loops. For example, the FG and/or BC loops may be extended by 1-22 amino acids, or decreased by 1-3 amino acids. The FG loop in Tencon is 7 amino acids long, whereas the corresponding loop in antibody heavy chains ranges from 4-28 residues. To provide maximum diversity, the FG loop may be diversified in sequence as well as in length to correspond to the antibody CDR3 length range of 4-28 residues. For example, the FG loop can further be diversified in length by extending the loop by additional 1, 2, 3, 4 or 5 amino acids.

Library designed based on Tencon sequence may also have randomized alternative surfaces that form on a side of the FN3 domain and comprise two or more beta strands, and at least one loop. One such alternative surface is formed by amino acids in the C and the F beta-strands and the CD and the FG loops (a C-CD-F-FG surface). A library design based on Tencon alternative C-CD-F-FG surface and is shown in FIG. 1 and detailed generation of such libraries is described in U.S. Pat. Publ. No. US2013/0226834.

Library designed based on Tencon sequence also includes libraries designed based on Tencon variants, such as Tencon variants having substitutions at residues positions 11, 14, 17, 37, 46, 73, or 86 (residue numbering corresponding to SEQ ID NO: 1), and which variants display improved thermal stability. Exemplary Tencon variants are described in US Pat. Publ. No. 2011/0274623, and include Tencon27 (SEQ ID NO: 99) having substitutions E11R, L17A, N46V and E86I when compared to Tencon of SEQ ID NO: 1.

TABLE 1

| FN3 domain | Tencon (SEQ ID NO: 1) |
|---|---|
| A strand | 1-12 |
| AB loop | 13-16 |
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Tencon and other FN3 sequence based libraries can be randomized at chosen residue positions using a random or defined set of amino acids. For example, variants in the library having random substitutions can be generated using NNK codons, which encode all 20 naturally occurring amino acids. In other diversification schemes, DVK codons can be used to encode amino acids Ala, Trp, Tyr, Lys, Thr, Asn, Lys, Ser, Arg, Asp, Glu, Gly, and Cys. Alternatively, NNS codons can be used to give rise to all 20 amino acid residues and simultaneously reducing the frequency of stop codons. Libraries of FN3 domains with biased amino acid distribution at positions to be diversified can be synthesized for example using Slonomics® technology (http:_//www_s-loning_com). This technology uses a library of pre-made double stranded triplets that act as universal building blocks sufficient for thousands of gene synthesis processes. The triplet library represents all possible sequence combinations necessary to build any desired DNA molecule. The codon designations are according to the well known IUB code.

The FN3 domains specifically binding EGFR or c-Met of the invention can be isolated by producing the FN3 library such as the Tencon library using cis display to ligate DNA fragments encoding the scaffold proteins to a DNA fragment encoding RepA to generate a pool of protein-DNA complexes formed after in vitro translation wherein each protein is stably associated with the DNA that encodes it (U.S. Pat. No. 7,842,476; Odegrip et al., Proc Natl Acad Sci USA 101, 2806-2810, 2004), and assaying the library for specific binding to EGFR and/or c-Met by any method known in the art and described in the Example. Exemplary well known methods which can be used are ELISA, sandwich immunoassays, and competitive and non-competitive assays (see, e.g., Ausubel et al., eds, 1994, Current Protocols in Molecular Biology, Vol. 1, John Wiley & Sons, Inc., New York). The identified FN3 domains specifically binding EGFR or c-Met are further characterized for their ability to block EGFR ligand such as EGF binding to EGFR, or HGF binding to c-Met, and for their ability to inhibit EGFR and/or c-Met signaling using methods described herein.

The FN3 domains specifically binding to EGFR or c-Met of the invention can be generated using any FN3 domain as a template to generate a library and screening the library for molecules specifically binding EGFR or c-Met using methods provided within. Exemplar FN3 domains that can be used are the 3rd FN3 domain of tenascin C (TN3) (SEQ ID NO: 75), Fibcon (SEQ ID NO: 76), and the 10$^{th}$ FN3 domain of fibronectin (FN10) (SEQ ID NO: 77). Standard cloning and expression techniques are used to clone the libraries into a vector or synthesize double stranded cDNA cassettes of the library, to express, or to translate the libraries in vitro. For example ribosome display (Hanes and Pluckthun, Proc Natl Acad Sci USA, 94, 4937-4942, 1997), mRNA display (Roberts and Szostak, Proc Natl Acad Sci USA, 94, 12297-12302, 1997), or other cell-free systems (U.S. Pat. No. 5,643,768) can be used. The libraries of the FN3 domain variants may be expressed as fusion proteins displayed on the surface for example of any suitable bacteriophage. Methods for displaying fusion polypeptides on the surface of a bacteriophage are well known (U.S. Pat. Publ. No. 2011/0118144; Int. Pat. Publ. No. WO2009/085462; U.S. Pat. Nos. 6,969,108; 6,172,197; 5,223,409; 6,582,915; 6,472,147).

The FN3 domains specifically binding EGFR or c-Met of the invention can be modified to improve their properties such as improve thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, Curr Opin Biotechnol, 12, 371-375, 2001). High thermal stability may increase the yield of the expressed protein, improve solubility or activity, decrease immunogenicity, and minimize the need of a cold chain in manufacturing. Residues that can be substituted to improve thermal stability of Tencon (SEQ ID NO: 1) are residue positions 11, 14, 17, 37, 46, 73, or 86, and are described in US Pat. Publ. No. 2011/0274623. Substitutions corresponding to these residues can be incorporated to the FN3 domains or the bispecific FN3 domain containing molecules of the invention.

Another embodiment of the invention is an isolated FN3 domain that specifically binds EGFR and blocks binding of EGF to EGFR, comprising the sequence shown in SEQ ID NOs: 18-29, 107-110, 122-137, further comprising substitutions at one or more residue positions corresponding to positions 11, 14, 17, 37, 46, 73, and 86 in Tencon (SEQ ID NO: 1).

Another embodiment of the invention is an isolated FN3 domain that specifically binds c-Met and blocks binding of HGF to c-Met, comprising the sequence shown in SEQ ID NOs: 32-49 or 111-114, further comprising substitutions at one or more residue positions corresponding to positions 11, 14, 17, 37, 46, 73, and 86 in Tencon (SEQ ID NO: 1).

Exemplary substitutions are substitutions E11N, E14P, L17A, E37P, N46V, G73Y and E86I (numbering according to SEQ ID NO: 1).

In some embodiments, the FN3 domains of the invention comprise substitutions corresponding to substitutions L17A, N46V, and E86I in Tencon (SEQ ID NO: 1).

The FN3 domains specifically binding EGFR (FIG. 1) have an extended FG loop when compared to Tencon (SEQ ID NO: 1). Therefore, the residues corresponding to residues 11, 14, 17, 37, 46, 73, and 86 in Tencon (SEQ ID NO: 1) are residues 11, 14, 17, 37, 46, 73 and 91 in EGFR FN3 domains shown in FIG. 1A and 1B except for the FN3 domain of SEQ ID NO: 24, wherein the corresponding residues are residues 11, 14, 17, 38, 74, and 92 due to an insertion of one amino acid in the BC loop.

Another embodiment of the invention is an isolated FN3 domain that specifically binds EGFR and blocks binding of EGF to EGFR comprising the amino acid sequence shown in SEQ ID NOs: 18-29, 107-110, or 122-137, optionally having substitutions corresponding to substitutions L17A, N46V, and E86I in Tencon (SEQ ID NO: 1).

Another embodiment of the invention is an isolated FN3 domain that specifically binds c-Met and blocks binding of HGF to c-Met comprising the amino acid sequence shown in SEQ ID NOs: 32-49 or 111-114, optionally having substitutions corresponding to substitutions L17A, N46V, and E86I in Tencon (SEQ ID NO: 1).

Measurement of protein stability and protein lability can be viewed as the same or different aspects of protein integrity. Proteins are sensitive or "labile" to denaturation caused by heat, by ultraviolet or ionizing radiation, changes in the ambient osmolarity and pH if in liquid solution, mechanical shear force imposed by small pore-size filtration, ultraviolet radiation, ionizing radiation, such as by gamma irradiation, chemical or heat dehydration, or any other action or force that may cause protein structure disruption. The stability of the molecule can be determined using standard methods. For example, the stability of a molecule can be determined by measuring the thermal melting ("TM") temperature, the temperature in ° Celsius (° C.) at which half of the molecules become unfolded, using standard methods. Typically, the higher the TM, the more stable the molecule. In addition to heat, the chemical environment also changes the ability of the protein to maintain a particular three dimensional structure.

In one embodiment, the FN3 domains binding EGFR or c-Met of the invention exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same domain prior to engineering measured by the increase in the TM.

Chemical denaturation can likewise be measured by a variety of methods. Chemical denaturants include guanidinium hydrochloride, guanidinium thiocyanate, urea, acetone, organic solvents (DMF, benzene, acetonitrile), salts (ammonium sulfate, lithium bromide, lithium chloride, sodium bromide, calcium chloride, sodium chloride); reducing agents (e.g. dithiothreitol, beta-mercaptoethanol, dinitrothiobenzene, and hydrides, such as sodium borohydride), non-ionic and ionic detergents, acids (e.g. hydrochloric acid (HCl), acetic acid ($CH_3COOH$), halogenated acetic acids), hydrophobic molecules (e.g. phosopholipids), and targeted denaturants. Quantitation of the extent of denaturation can rely on loss of a functional property, such as ability to bind a target molecule, or by physiochemical properties, such as tendency to aggregation, exposure of formerly solvent inaccessible residues, or disruption or formation of disulfide bonds.

In one embodiment, the FN3 domain of the invention binding EGFR or c-Met exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same scaffold prior to engineering, measured by using guanidinium hydrochloride as a chemical denaturant. Increased stability can be measured as a function of decreased tryptophan fluorescence upon treatment with increasing concentrations of guanidine hydrochloride using well known methods.

The FN3 domains of the invention may be generated as monomers, dimers, or multimers, for example, as a means to increase the valency and thus the avidity of target molecule binding, or to generate bi- or multispecific scaffolds simultaneously binding two or more different target molecules. The dimers and multimers may be generated by linking monospecific, bi- or multispecific protein scaffolds, for example, by the inclusion of an amino acid linker, for example a linker containing poly-glycine, glycine and serine, or alanine and proline. Exemplary linker include $(GS)_2$, (SEQ ID NO: 78), $(GGGGS)_5$ (SEQ ID NO: 79), $(AP)_2$ (SEQ ID NO: 80), $(AP)_5$ (SEQ ID NO: 81), $(AP)_{10}$ (SEQ ID NO: 82), $(AP)_{20}$ (SEQ ID NO: 83) and $A(EAAAK)_5AAA$ (SEQ ID NO: 84), linkers. The dimers and multimers may be linked to each other in an N- to C-direction. The use of naturally occurring as well as artificial peptide linkers to connect polypeptides into novel linked fusion polypeptides is well known in the literature (Hallewell et al., *J Biol Chem* 264, 5260-5268, 1989; Alfthan et al., *Protein Eng.* 8, 725-731, 1995; Robinson & Sauer, *Biochemistry* 35, 109-116, 1996; U.S. Pat. No. 5,856,456).

Bispecific Agents Specifically Binding EGFR and c-Met

The bispecific agents that specifically bind EGFR and c-Met of the invention may provide a benefit in terms of specificity and reduced off-target toxicity when compared to small molecule EGFR and/or c-Met inhibitors. The present invention is based at least in part on the surprising finding that the bispecific agents specifically binding EGFR and c-Met provide a significantly improved synergistic inhibitory effect when compared to a mixture of EGFR-binding and c-Met-binding monospecific agents. The molecules may be tailored to specific affinity towards both EGFR and c-Met to maximize tumor penetration and retention. The bispecific agents that specifically bind EGFR and c-Met provide more efficient inhibition of EGFR and/or c-Met signaling pathways and inhibit tumor growth more efficiently than cetuximab (Erbitux®).

The bispecific agents specifically binding EGFR and c-Met may be formed by any polypeptide or a multimeric polypeptide that comprises an EGFR binding domain and a c-Met binding domain. The EGFR and the c-Met binding domains may be an antigen binding sites of an antibody, a VH/VL pair of an antibody, or another type of binding molecule such as a domain based on fibronectin type III (FN3) domain, a fibronectin type IX (FN9) domain, or any combination thereof.

The EGFR and c-Met binding polypeptides may be derived from existing monospecific EGFR and c-Met binding polypeptides or may be isolated de novo.

Bispecific EGFR/c-Met FN3 Domain Containing Molecules

One embodiment of the invention is an isolated bispecific FN3 domain containing molecule comprising a first fibronectin type III (FN3) domain and a second FN3 domain, wherein the first FN3 domain specifically binds epidermal growth factor receptor (EGFR) and blocks binding of epidermal growth factor (EGF) to EGFR, and the second FN3 domain specifically binds hepatocyte growth factor receptor (c-Met) and blocks binding of hepatocyte growth factor (HGF) to c-Met.

The bispecific EGFR/c-Met FN3 domain containing molecules of the invention may be generated by covalently linking any EGFR-binding FN3 domain and any c-Met-binding FN3 domain of the invention directly or via a linker. Therefore, the first FN3 domain of the bispecific molecule may have characteristics as described above for the EGFR-binding FN3 domains, and the second FN3 domain of the bispecific molecule may have characteristics as described above for the c-Met-binding FN3 domains.

In one embodiment, the first FN3 domain of the bispecific EGFR/c-Met FN3 domain containing molecule inhibits EGF-induced EGFR phosphorylation at EGFR residue Tyrosine 1173 with an $IC_{50}$ value of less than about $2.5 \times 10^{-6}$ M when measured in A431 cells using 50 ng/mL human EGF, and the second FN3 domain of the bispecific EGFR/c-Met FN3 domain containing molecule inhibits HGF-induced c-Met phosphorylation at c-Met residue Tyrosine 1349 with an $IC_{50}$ value of less than about $1.5 \times 10^{-6}$ M when measured in NCI-H441 cells using 100 ng/mL human HGF.

In another embodiment, the first FN3 domain of the bispecific EGFR/c-Met FN3 domain containing molecule inhibits EGF-induced EGFR phosphorylation at EGFR residue Tyrosine 1173 with an $IC_{50}$ value of between about $1.8 \times 10^{-8}$ M to about $2.5 \times 10^{-6}$ M when measured in A431 cells using 50 ng/mL human EGF, and the second FN3 domain of the bispecific EGFR/c-Met FN3 domain containing molecule inhibits HGF-induced c-Met phosphorylation at c-Met residue Tyrosine 1349 with an $IC_{50}$ value between about $4 \times 10^{-9}$ M to about $1.5 \times 10^{-6}$ M when measured in NCI-H441 cells using 100 ng/mL human HGF.

In another embodiment, the first FN3 domain of the bispecific EGFR/c-Met FN3 domain containing molecule binds human EGFR with a dissociation constant ($K_D$) of less than about $1 \times 10^{-8}$ M, and the second FN3 domain of the bispecific EGFR/c-Met FN3 domain containing molecule binds human c-Met with a $K_D$ of less than about $5 \times 10^{-8}$ M.

In the bispecific molecule binding both EGFR and c-Met, the first FN3 domain binds human EGFR with a $K_D$ of between about $2 \times 10^{-10}$ to about $1 \times 10^{-8}$ M, and the second FN3 domain binds human c-Met with a $K_D$ of between about $3 \times 10^{-10}$ to about $5 \times 10^{-8}$ M.

The affinity of the bispecific EGFR/c-Met molecule for EGFR and c-Met can be determined as described above for the monospecific molecules.

The first FN3 domain in the bispecific EGFR/c-Met molecule of the invention may block EGF binding to EGFR with an $IC_{50}$ value of between about $1 \times 10^{-9}$ M to about $1.5 \times 10^{-7}$ M in an assay employing A431 cells and detecting the amount of fluorescence from bound biotinylated EGF using streptavidin-phycoerythrin conjugate at 600 nM on A431 cells incubated with or without the first FN3 domain. The first FN3 domain in the bispecific EGFR/c-Met molecule of the invention may block EGF binding to the EGFR by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to binding of EGF to EGFR in the absence of the first FN3 domains using the same assay conditions.

The second FN3 domain in the bispecific EGFR/c-Met molecule of the invention may block HGF binding to c-Met with an $IC_{50}$ value of between about $2 \times 10^{-10}$ M to about $6 \times 10^{-8}$ M in an assay detecting inhibition of binding of biotinylated HGF to c-Met-Fc fusion protein in the presence of the second FN3 domain. The second FN3 domain in the bispecific EGFR/c-Met molecule may block HGF binding to c-Met by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to binding of HGF to c-Met in the absence of the second FN3 domain using the same assay conditions.

The bispecific EGFR/c-Met molecule of the invention may inhibit EGFR and/or c-Met signaling by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to the level of signaling in the absence of the bispecific EGFR/c-Met molecule of the invention using the same assay conditions.

EGFR and c-Met signaling may be measured using various well know methods as described above for the monospecific molecules.

The bispecific EGFR/c-Met molecules of the invention comprising the first FN3 domain specifically binding EGFR and the second FN3 domain specifically binding c-Met provide a significantly increased synergistic inhibition of EGFR and c-Met signaling and tumor cell proliferation when compared to the synergistic inhibition observed by a mixture of the first and the second FN3 domain. Synergistic inhibition can be assessed for example by measuring inhibition of ERK phosphorylation by the bispecific EGFR/c-Met FN3 domain containing molecules and by a mixture of two monospecific molecules, one binding EGFR and the other c-Met. The bispecific EGFR/c-Met molecules of the invention may inhibit ERK phosphorylation with an at least about 100 fold smaller, for example at least 500, 1000, 5000 or 10,000 fold smaller $IC_{50}$ value when compared to the $IC_{50}$ value for a mixture of two monospecific FN3 domains, indicating at least 100 fold increased potency for the bispecific EGFR/c-Met FN3 domain containing molecules when compared to the mixture of two monospecific FN3 domains. Exemplary bispecific EGFR-c-Met FN3 domain containing molecules may inhibit ERK phosphorylation with and $IC_{50}$ value of about $5 \times 10^{-9}$ M or less. ERK phosphorylation may be measured using standard methods and methods described herein.

The bispecific EGFR/c-Met FN3 domain containing molecule of the invention may inhibit NCI-H292 cell proliferation with an $IC_{50}$ value that is at least 30-fold less when compared to the $IC_{50}$ value of inhibition of NCI-H292 cell growth with a mixture of the first FN3 domain and the second FN3, wherein the cell proliferation is induced with medium containing 10% FBS supplemented with 7.5 ng/mL HGF. The bispecific molecule of the invention may inhibit tumor cell proliferation with an $IC_{50}$ value that is about 30, 40, 50, 60, 70, 80, 90, 100, 150, 200, 300, 400, 500, 600, 700, 800, or about 1000 fold less when compared to the $IC_{50}$ value of inhibition of tumor cell proliferation with a mixture of the first FN3 domain and the second FN3 domain Inhibition of tumor cell proliferation may be measured using standard methods and methods described herein.

Another embodiment of the invention is a bispecific FN3 domain containing molecule comprising a first fibronectin type III (FN3) domain and a second FN3 domain, wherein the first FN3 domain specifically binds epidermal growth factor receptor (EGFR) and blocks binding of epidermal growth factor (EGF) to EGFR, and the second FN3 domain specifically binds hepatocyte growth factor receptor (c-Met), and blocks binding of hepatocyte growth factor (HGF) to c-Met, wherein the first FN3 domain comprises
   an FG loop comprising the sequence HNVYKDTNX$_9$RGL (SEQ ID NO: 179) or the sequence LGSYVFEHDVML (SEQ ID NO: 180), wherein X$_9$ is M or I; and
   a BC loop comprising the sequence $X_1X_2X_3X_4X_5X_6X_7X_8$ (SEQ ID NO: 181), wherein
     $X_1$ is A, T, G or D;
     $X_2$ is A, D, Y or W;
     $X_3$ is P, D or N;
     $X_4$ is L or absent;

$X_5$ is D, H, R, G, Y or W;
$X_6$ is G, D or A;
$X_7$ is A, F, G, H or D; and
$X_8$ is Y, F or L;
the second FN3 domain comprises
a C strand and a CD loop comprising the sequence DSFX$_{10}$IRYX$_{11}$E X$_{12}$X$_{13}$X$_{14}$X$_{15}$GX$_{16}$ (SEQ ID NO: 184), wherein
$X_{10}$ is W, F or V;
$X_{11}$ is D, F or L;
$X_{12}$ is V, F or L;
$X_{13}$ is V, L or T;
$X_{14}$ is V, R, G, L, T or S;
$X_{15}$ is G, S, A, T or K; and
$X_{16}$ is E or D; and
a F strand and a FG loop comprising the sequence TEYX$_{17}$VX$_{18}$IX$_{19}$X$_{20}$V KGGX$_{21}$X$_{22}$SX$_{23}$ (SEQ ID NO: 185), wherein
$X_{17}$ is Y, W, I, V, G or A;
$X_{18}$ is N, T, Q or G;
$X_{19}$ is L, M, N or I;
$X_{20}$ is G or S;
$X_{21}$ is S, L, G, Y, T, R, H or K;
$X_{22}$ is I, V or L; and
$X_{23}$ is V, T, H, I, P, Y or L.
In another embodiment, the bispecific molecule comprises the first FN3 domain that binds EGFR comprising the sequence:

LPAPKNLVVSEVTEDSLRLSWX$_1$X$_2$X$_3$X$_4$X$_5$X$_6$X$_7$X$_8$DSFLI-QYQESEKVGEAINLTVP GSERSYDLTGLKPGTEYTVSIYGVHNVYKDTNX$_9$RGL PLSAEFTT (SEQ ID NO: 182), or the sequence LPAPKNLVVSEVTEDSLRLSWX$_1$X$_2$X$_3$X$_4$X$_5$X$_6$X$_7$X$_8$ DSFLIQYQESEKVGEAINLTVP GSERSY-DLTGLKPGTEYTVSIYGV LGSYVFEHDVM-LPLSAEFTT (SEQ ID NO: 183), wherein in the SEQ ID NOs: 182 and 183;
$X_1$ is A, T, G or D;
$X_2$ is A, D, Y or W;
$X_3$ is P, D or N;
$X_4$ is L or absent;
$X_5$ is D, H, R, G, Y or W;
$X_6$ is G, D or A;
$X_7$ is A, F, G, H or D;
$X_8$ is Y, F or L; and
$X_9$ is M or I.
In another embodiment, the bispecific molecule comprises the second FN3 domain that binds c-Met comprising the sequence LPAPKNLVVSRVTEDSARLSWTAPDAAF DSFX$_{10}$IRYX$_{11}$E X$_{12}$X$_{13}$X$_{14}$X$_{15}$GX$_{16}$AIVLTVPGSERSYDLTGLKPG TEYX$_{17}$VX$_{18}$IX$_{19}$X$_{20}$VKGGX$_{21}$X$_{22}$SX$_{23}$PLSAEFTT (SEQ ID NO: 186), wherein
$X_{10}$ is W, F or V; and
$X_{11}$ is D, F or L;
$X_{12}$ is V, F or L;
$X_{13}$ is V, L or T;
$X_{14}$ is V, R, G, L, T or S;
$X_{15}$ is G, S, A, T or K;
$X_{16}$ is E or D;
$X_{17}$ is Y, W, I, V, G or A;
$X_{18}$ is N, T, Q or G;
$X_{19}$ is L, M, N or I;
$X_{20}$ is G or S;
$X_{21}$ is S, L, G, Y, T, R, H or K;
$X_{22}$ is I, V or L; and
$X_{23}$ is V, T, H, I, P, Y or L.

Exemplary bispecific EGFR/c-Met FN3 domain containing molecules comprise the amino acid sequence shown in SEQ ID NOs: 50-72, 106, 118-121, or 138-167.

The bispecific EGFR/c-Met molecules of the invention comprise certain structural characteristics associated with their functional characteristics, such as inhibition of EGFR autophosphorylation, such as the FG loop of the first FN3 domain that binds EGFR comprising the sequence HNVYKDTNX$_9$RGL (SEQ ID NO: 179) or the sequence LGSYVFEHDVML (SEQ ID NO: 180), wherein $X_9$ is M or I.

In one embodiment, the bispecific EGFR/c-Met FN3 domain containing molecules of the invention inhibit EGF-induced EGFR phosphorylation at EGFR residues Tyrosine 1173 with an IC$_{50}$ value of less than about $8 \times 10^{-7}$ M when measured in H292 cells using 50 ng/mL human EGF;

inhibit HGF-induced c-Met phosphorylation at c-Met residue Tyrosine 1349 with an IC$_{50}$ value of less than about $8.4 \times 10^{-7}$ M when measured in NCI-H441 cells using 100 ng/mL human HGF;

inhibit HGF-induced NCI-H292 cell proliferation with an IC$_{50}$ value of less than about $9.5 \times 10^{-6}$ M wherein the cell proliferation is induced with 10% FBS containing 7.5 ng HGF;

bind EGFR with a K$_D$ of less than about $2.0 \times 10^{-8}$ M; or
bind c-Met with a K$_D$ of less than about $2.0 \times 10^{-8}$ M.

In another embodiment, the bispecific EGFR/c-Met FN3 domain containing molecules of the invention inhibit EGF-induced EGFR phosphorylation at EGFR residues Tyrosine 1173 with and IC$_{50}$ of between about $4.2 \times 10^{-9}$ M and $8 \times 10^{-7}$ M when measured in H292 cells using 50 ng/mL human EGF;

inhibit HGF-induced c-Met phosphorylation at c-Met residues Tyrosine 1349 with an IC$_{50}$ value of between about $2.4 \times 10^{-8}$ M to about $8.4 \times 10^{-7}$ M when measured in NCI-H441 cells using 100 ng/mL human HGF;

inhibit HGF-induced NCI-H292 cell proliferation with an IC$_{50}$ value between about $2.3 \times 10^{-8}$ M to about $9.5 \times 10^{-6}$ M wherein the cell proliferation is induced with 10% FBS containing 7.5 ng HGF;

bind EGFR with a K$_D$ of between about $2 \times 10^{-10}$ M to about $2.0 \times 10^{-8}$ M; or
bind c-Met with a K$_D$ of between about $1 \times 10^{-9}$ M to about $2.0 \times 10^{-8}$ M.

In one embodiment, the bispecific EGFR/c-Met molecules comprise the EGFR-binding FN3 domain comprising the sequence LPAPKNLVVSEVTEDSLRLSWX$_1$X$_2$X$_3$X$_4$X$_5$X$_6$X$_7$X$_8$DSFLIQ-YQESEKVGEAINLTVP GSERSYDLTGLK-PGTEYTVSIYGV HNVYKDTNX$_9$RGL PLSAEFTT (SEQ ID NO: 182), wherein $X_1$ is D;
$X_2$ is D;
$X_3$ is P;
$X_4$ is absent;
$X_5$ is H or W;
$X_6$ is A;
$X_7$ is F
$X_8$ is Y; and $X_9$ is M or I; and
the c-Met-binding FN3 domain comprising the sequence LPAPKNLVVSRVTEDSARLSWTAPDAAF
DSFX$_{10}$IRYX$_{11}$E X$_{12}$X$_{13}$X$_{14}$X$_{15}$GX$_{16}$ AIVLT-
VPGSERSYDLTGLKPG
TEYX$_{17}$VX$_{18}$IX$_{19}$X$_{20}$VKGGX$_{21}$X$_{22}$SX$_{23}$
PLSAEFTT (SEQ ID NO: 186), wherein
$X_{10}$ is W;
$X_{11}$ is F;
$X_{12}$ is F;
$X_{13}$ is V or L;
$X_{14}$ is G or S;
$X_{15}$ is S or K;
$X_{16}$ is E or D;
$X_{17}$ is V;
$X_{18}$ is N;
$X_{19}$ is L or M;
$X_{20}$ is G or S;
$X_{21}$ is S or K;
$X_{22}$ is I; and
$X_{23}$ is P.

Exemplary bispecific EGFR/c-Met molecules are those having the sequence shown in SEQ ID NOs: 57, 61, 62, 63, 64, 65, 66, 67 and 68.

The bispecific molecules of the invention may further comprise substitutions at one or more residue positions in the first FN3 domain and/or the second FN3 domain corresponding to positions 11, 14, 17, 37, 46, 73 and 86 in Tencon (SEQ ID NO: 1) as described above, and a substitution at position 29. Exemplary substitutions are substitutions E11N, E14P, L17A, E37P, N46V, G73Y, E86I and D29E (numbering according to SEQ ID NO: 1). Skilled in the art will appreciate that other amino acids can be used for substitutions, such as amino acids within a family of amino acids that are related in their side chains as described infra. The generated variants can be tested for their stability and binding to EGFR and/or c-Met using methods herein.

In one embodiment, the bispecific EGFR/c-Met FN3 domain containing molecule comprises the first FN3 domain that binds specifically EGFR and the second FN3 domain that binds specifically c-Met, wherein the first FN3 domain comprises the sequence:

LPAPKNLVVSX$_{24}$VTX$_{25}$DSX$_{26}$RLSWDDPX$_{27}$AFYX$_{28}$SF-
LIQYQX$_{29}$SEKVGEAIX$_{30}$LT
VPGSERSYDLTGLKPGTEYTVSIYX$_{31}$VHNVYKD-
TNX$_{32}$RGLPLSAX$_{33}$FTT (SEQ ID NO: 187),
wherein $X_{24}$ is E, N or R;
$X_{25}$ is E or P;
$X_{26}$ is L or A;
$X_{27}$ is H or W;
$X_{28}$ is E or D;
$X_{29}$ is E or P;
$X_{30}$ is N or V;
$X_{31}$ is G or Y;
$X_{32}$ is M or I; and
$X_{33}$ is E or I;

and the second FN3 domain comprises the sequence:

LPAPKNLVVSX$_{34}$VTX$_{35}$DSX$_{36}$RLSWTAPDAAFDSFWIR-
YFX$_{37}$FX$_{38}$X$_{39}$X$_{40}$GX$_{41}$AIX$_{42}$
LTVPGSERSYDLTGLKPGTEYVVNIX$_{43}$X$_{44}$VKGG-
X$_{45}$ISPPLSAX$_{46}$FTT (SEQ ID NO: 188);
wherein $X_{34}$ is E, N or R;
$X_{35}$ is E or P;
$X_{36}$ is L or A;
$X_{37}$ is E or P;
$X_{38}$ is V or L;
$X_{39}$ is G or S;
$X_{40}$ is S or K;
$X_{41}$ is E or D;
$X_{42}$ is N or V;
$X_{43}$ is L or M;
$X_{44}$ is G or S;
$X_{45}$ is S or K; and
$X_{46}$ is E or I.

In other embodiments, the bispecific EGFR/c-Met FN3 domain containing molecule comprises the first FN3 domain comprising an amino acid sequence at least 87%, 88%, 89%, 90%, 91%, 92%, 93%, 94%, 95%, 96%, 97%, 98% or 99% identical to the amino acid sequence of SEQ ID NO: 27, and the second FN3 domain comprising an amino acid sequence at least 83%, 84%, 85%, 86%, 87%, 88%, 89%, 90%, 91%, 92%, 93%, 94%, 95%, 96%, 97%, 98% or 99% identical to the amino acid sequence of SEQ ID NO: 41.

The bispecific EGFR/c-Met FN3 domain containing molecules of the invention may be tailored to a specific affinity towards EGFR and c-Met to maximize tumor accumulation.

Another embodiment of the invention is an isolated bispecific FN3 domain containing molecule comprising a first fibronectin type III (FN3) domain and a second FN3 domain, wherein the first FN3 domain specifically binds epidermal growth factor receptor (EGFR) and blocks binding of epidermal growth factor (EGF) to EGFR, and the second FN3 domain specifically binds hepatocyte growth factor receptor (c-Met), and blocks binding of hepatocyte growth factor (HGF) to c-Met, wherein the first FN3 domain and the second FN3 domain is isolated from a library designed based on Tencon sequence of SEQ ID NO: 1.

The bispecific EGFR/c-Met FN3 domain containing molecule of the invention can be generated by covalently coupling the EGFR-binding FN3 domain and the c-Met binding FN3 domain of the invention using well known methods. The FN3 domains may be linked via a linker, for example a linker containing poly-glycine, glycine and serine, or alanine and proline. Exemplary linker include (GS)$_2$, (SEQ ID NO: 78), (GGGGS)$_5$ (SEQ ID NO: 79), (AP)$_2$ (SEQ ID NO: 80), (AP)$_5$ (SEQ ID NO: 81), (AP)$_{10}$ (SEQ ID NO: 82), (AP)$_{20}$ (SEQ ID NO: 83), A(EAAAK)$_5$AAA (SEQ ID NO: 84), linkers. The use of naturally occurring as well as artificial peptide linkers to connect polypeptides into novel linked fusion polypeptides is well known in the literature (Hallewell et al., *J Biol Chem* 264, 5260-5268, 1989; Alftan et al., *Protein Eng.* 8, 725-731, 1995; Robinson & Sauer, *Biochemistry* 35, 109-116, 1996; U.S. Pat. No. 5,856,456). The bispecific EGFR/c-Met molecules of the invention may be linked together from a C-terminus of the first FN3 domain to the N-terminus of the second FN3 domain, or from the C-terminus of the second FN3 domain to the N-terminus of the first FN3 domain. Any EGFR-binding FN3 domain may be covalently linked to a c-Met-binding FN3 domain. Exemplary EGFR-binding FN3 domains are domains having the amino acid sequence shown in SEQ ID NOs: 18-29, 107-110, and 122-137, and exemplary c-Met binding FN3 domains are domains having the amino acid sequence shown in SEQ ID NOs: 32-49 and 111-114. The EGFR-binding FN3 domains to be coupled to a bispecific molecule may additionally comprise an initiator methionine (Met) at their N-terminus.

Variants of the bispecific EGFR/c-Met FN3 domain containing molecules are within the scope of the invention. For example, substitutions can be made in the bispecific EGFR/c-Met FN3 domain containing molecule as long as the resulting variant retains similar selectivity and potency towards EGFR and c-Met when compared to the parent molecule. Exemplary modifications are for example conservative substitutions that will result in variants with similar characteristics to those of the parent molecules. Conservative substitutions are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981). Non-conservative substitutions can be made to the bispecific EGFR/c-Met FN3 domain containing molecule that involves substitutions of amino acid residues between different classes of amino acids to improve properties of the bispecific molecules. Whether a change in the amino acid sequence of a polypeptide or fragment thereof results in a functional homolog can be readily determined by assessing the ability of the modified polypeptide or fragment to produce a response in a fashion similar to the unmodified polypeptide or fragment using the assays described herein. Peptides, polypeptides or proteins in which more than one replacement has taken place can readily be tested in the same manner.

The bispecific EGFR/c-Met FN3 domain containing molecules of the invention may be generated as dimers or multimers, for example, as a means to increase the valency and thus the avidity of target molecule binding. The multimers may be generated by linking one or more EGFR-binding FN3 domain and one or more c-Met-binding FN3 domain to form molecules comprising at least three individual FN3 domains that are at least bispecific for either EGFR or c-Met, for example by the inclusion of an amino acid linker using well known methods.

Another embodiment of the invention is a bispecific FN3 domain containing molecule comprising a first fibronectin type III (FN3) domain and a second FN3 domain, wherein the first FN3 domain specifically binds epidermal growth factor receptor (EGFR) and blocks binding of epidermal growth factor (EGF) to EGFR, and the second FN3 domain specifically binds hepatocyte growth factor receptor (c-Met), and blocks binding of hepatocyte growth factor (HGF) to c-Met comprising the amino acid sequence shown in SEQ ID NOs: 50-72, 106 or 138-165.

Half-life Extending Moieties

The bispecific EGFR/c-Met FN3 domain containing molecules or the monospecific EGFR or c-Met binding FN3 domains of the invention may incorporate other subunits for example via covalent interaction. In one aspect of the invention, the bispecific EGFR/c-Met FN3 domain containing molecules of the invention further comprise a half-life extending moiety. Exemplary half-life extending moieties are albumin, albumin variants, albumin-binding proteins and/or domains, transferrin and fragments and analogues thereof, and Fc regions. An exemplary albumin-binding domain is shown in SEQ ID NO: 117.

All or a portion of an antibody constant region may be attached to the molecules of the invention to impart antibody-like properties, especially those properties associated with the Fc region, such as Fc effector functions such as C1q binding, complement dependent cytotoxicity (CDC), Fc receptor binding, antibody-dependent cell-mediated cytotoxicity (ADCC), phagocytosis, down regulation of cell surface receptors (e.g., B cell receptor; BCR), and can be further modified by modifying residues in the Fc responsible for these activities (for review; see Strohl, Curr Opin Biotechnol. 20, 685-691, 2009).

Additional moieties may be incorporated into the bispecific molecules of the invention such as polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the protein scaffold coding sequences and may be generated by standard cloning and expression techniques. Alternatively, well known chemical coupling methods may be used to attach the moieties to recombinantly produced molecules of the invention.

A pegyl moiety may for example be added to the bispecific or monospecific molecules of the invention by incorporating a cysteine residue to the C-terminus of the molecule and attaching a pegyl group to the cysteine using well known methods. Exemplary bispecific molecules with the C-terminal cysteine are those having the amino acid sequence shown in SEQ IN NO: 170-178.

Monospecific and bispecific molecules of the invention incorporating additional moieties may be compared for functionality by several well known assays. For example, altered properties of monospecific and/or bispecific molecules due to incorporation of Fc domains and/or Fc domain variants may be assayed in Fc receptor binding assays using soluble forms of the receptors, such as the FcγRI, FcγRII, FcγRIII or FcRn receptors, or using well known cell-based assays measuring for example ADCC or CDC, or evaluating pharmacokinetic properties of the molecules of the invention in in vivo models.

Polynucleotides, Vectors, Host Cells

The invention provides for nucleic acids encoding the EGFR-binding or c-Met binding FN3 domains or the bispecific EGFR/c-Met FN3 domain containing molecules of the invention as isolated polynucleotides or as portions of expression vectors or as portions of linear DNA sequences, including linear DNA sequences used for in vitro transcription/translation, vectors compatible with prokaryotic, eukaryotic or filamentous phage expression, secretion and/or display of the compositions or directed mutagens thereof. Certain exemplary polynucleotides are disclosed herein, however, other polynucleotides which, given the degeneracy of the genetic code or codon preferences in a given expression system, encode the EGFR-binding or c-Met binding FN3 domains or the bispecific EGFR/c-Met FN3 domain containing molecules of the invention are also within the scope of the invention.

One embodiment of the invention is an isolated polynucleotide encoding the FN3 domain specifically binding EGFR having the amino acid sequence of SEQ ID NOs: 18-29, 107-110, or 122-137.

One embodiment of the invention is an isolated polynucleotide comprising the polynucleotide sequence of SEQ ID NOs: 97-98 or 168-169.

One embodiment of the invention is an isolated polynucleotide encoding the FN3 domain specifically binding c-Met having the amino acid sequence of the sequence shown in SEQ ID NOs: 32-49 or 111-114.

One embodiment of the invention is an isolated polynucleotide encoding the bispecific EGFR/-c-Met FN3 domain containing molecule having the amino acid sequence of SEQ ID NOs: 50-72, 106, 118-121 or 138-165.

One embodiment of the invention is an isolated polynucleotide comprising the polynucleotide sequence of SEQ ID NOs: 115-116 or 166-167.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

Another embodiment of the invention is a vector comprising at least one polynucleotide of the invention. Such vectors may be plasmid vectors, viral vectors, vectors for baculovirus expression, transposon based vectors or any other vector suitable for introduction of the polynucleotides of the invention into a given organism or genetic background by any means. Such vectors may be expression vectors comprising nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art.

Another embodiment of the invention is a host cell comprising the vector of the invention. A monospecific EGFR-binding or c-Met binding FN3 domain or the bispecific EGFR/c-Met FN3 domain containing molecule of the invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

The host cell chosen for expression may be of mammalian origin or may be selected from COS-1, COS-7, HEK293, BHK21, CHO, BSC-1, He G2, SP2/0, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as BL21, BL21(DE3), BL21-GOLD (DE3), XL1-Blue, JM109, HMS174, HMS174(DE3), and any of the natural or engineered *E. coli* spp, *Klebsiella* spp., or *Pseudomonas* spp strains.

Another embodiment of the invention is a method of producing the isolated FN3 domain specifically binding EGFR or c-Met of the invention or the isolated bispecific EGFR/c-Met FN3 domain containing molecule of the invention, comprising culturing the isolated host cell of the invention under conditions such that the isolated FN3 domain specifically binding EGFR or c-Met or the isolated bispecific EGFR/c-Met FN3 domain containing molecule is expressed, and purifying the domain or molecule.

The FN3 domain specifically binding EGFR or c-Met or the isolated bispecific EGFR/c-Met FN3 domain containing molecule of the invention can be purified from recombinant cell cultures by well-known methods, for example by protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography, or high performance liquid chromatography (HPLC).

Bispecific EGFR/c-Met Antibodies

The bispecific EGFR/c-Met antibodies may be generated de novo or may be engineered from existing monospecific anti-EGFR and anti-c-Met antibodies.

Exemplary anti-EGFR antibodies that may be used to engineer bispecific molecules are for example panitumumab (ABX-EGF), nimotuzumab, necitumumab, matuzumab, and those described for example in: U.S. Pat. Nos. 7,595,378, 7,247,301, U.S. Pat. Publ. No. US2011/0256142, U.S. Pat. Nos. 5,891,996, 5,212,290, 5,558,864, or 7,589,180. For example, antibody VH domain having the amino acid sequence shown in SEQ ID NO: 189 or 191 and antibody VL domain having the amino acid sequences shown in SEQ ID NO: 190 or 192 may be used.

Exemplary anti-c-Met antibodies that may be used to engineer bispecific molecules are for example Rilotumumab, Onartuzumab, Ficlatuzumab, and those described for example in PCT Intl. Publ. No. WO2011/110642, US Pat. Publ. No. US2004/0166544, PCT Intl. Publ. No. WO2005/016382, or PCT Intl. Publ. No. WO2006/015371. For example, antibody VH domain having the amino acid sequence shown in SEQ ID NO: 193 or 195 and antibody VL domain having the amino acid sequences shown in SEQ ID NO: 194 or 196 may be used. The heavy and light chain amino acid sequences of the antibodies identified by their United States Adopted Names (USAN) is available via the American Medical Association at http://_www_ama-ass-n_org or via the CAS registry.

Monospecific EGFR and c-Met biding variable domains may be selected de novo from for example a phage display library, where the phage is engineered to express human immunoglobulins or portions thereof such as Fabs, single chain antibodies (scFv), or unpaired or paired antibody variable regions (Knappik et al., J Mol Biol 296:57-86, 2000; Krebs et al., J Immunol Meth 254:67-84, 2001; Vaughan et al., Nature Biotechnology 14:309-314, 1996; Sheets et al., PITAS (USA) 95:6157-6162, 1998; Hoogenboom and Winter, J Mol Biol 227:381, 1991; Marks et al., J Mol Biol 222:581, 1991), and subsequently engineered into a bispecific format. The monospecific EGFR and c-Met binding variable domains may be isolated for example from phage display libraries expressing antibody heavy and light chain variable regions as fusion proteins with bacteriophage pIX coat protein as described in Shi et al (2010) *J. Mol. Biol.* 397:385-96 and PCT Intl. Publ. No. WO09/085462). The antibody libraries are screened for binding to human EGFR or c-Met extracellular domains and the obtained positive clones are further characterized and the Fabs isolated from the clone lysates. Such phage display methods for isolating human antibodies are established in the art. See for example: U.S. Pat. Nos. 5,223,409; 5,403,484; and 5,571,698, 5,427, 908, 5,580,717, 5,969,108, 6,172,197, 5,885,793; 6,521, 404; 6,544,731; 6,555,313; 6,582,915 and 6,593,081. The obtained de novo variable regions binding EGFR or c-Met are engineered to bispecific formats using the methods described herein.

Bispecific Antibody Formats

Antibodies of the present invention have two or more antigen binding sites and are bispecific. Bispecific antibodies of the invention include antibodies having a full length antibody structure.

"Full length antibody" as used herein refers to an antibody having two full length antibody heavy chains and two full length antibody light chains. A full length antibody heavy chain (HC) consists of well known heavy chain variable and constant domains VH, CH1, CH2, and CH3. A full length antibody light chain (LC) consists of well known light chain variable and constant domains VL and CL. The full length antibody may be lacking the C-terminal lysine (K) in either one or both heavy chains.

The term "Fab-arm" or "half molecule" refers to one heavy chain-light chain pair that specifically binds an antigen.

Full length bispecific antibodies of the invention may be generated for example using Fab arm exchange (or half molecule exchange) between two monospecific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent monospecific antibodies are reduced. The resulting free cysteines of one of the parent monospecific antibodies form an inter heavy-chain disulfide bond with cysteine residues of a second parent monospecific antibody molecule and simultaneously CH3 domains of the parent antibodies release and reform by dissociation-association. The CH3 domains of the Fab arms may be engineered to favor heterodimerization over homodimerization. The resulting product is a bispecific antibody having two Fab arms or half molecules which each bind a distinct epitope, i.e. an epitope on EGFR and an epitope on c-Met.

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Intl. Publ. No. WO 2006/028936) may be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

Other strategies such as promoting heavy chain heterodimerization using electrostatic interactions by substituting positively charged residues at one CH3 surface and negatively charged residues at a second CH3 surface may be used, as described in US Pat. Publ. No. US2010/0015133; US Pat. Publ. No. US2009/0182127; US Pat. Publ. No. US2010/028637 or US Pat. Publ. No. US2011/0123532. In other strategies, heterodimerization may be promoted by following substitutions (expressed as modified position in the first CH3 domain of the first heavy chain/modified position in the second CH3 domain of the second heavy chain): L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in U.S. Pat. Publ. No. US2012/0149876 or U.S. Pat. Publ. No. US2013/0195849

In addition to methods described above, bispecific antibodies of the invention may be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Intl. Pat. Publ. No. WO2011/131746. In the methods, the first monospecific bivalent antibody (e.g., anti-c-Met antibody) and the second monospecific bivalent antibody (e.g., anti-EGFR antibody) are engineered to have certain substitutions at the CH3 domain that promoter heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

Bispecific EGFR/c-Met Antibodies

The bispecific EGFR/c-Met antibodies of the invention may provide a benefit in terms of specificity and reduced off-target toxicity when compared to small molecule EGFR and/or c-Met inhibitors. The present invention is based at least in part on the surprising finding that the bispecific EGFR/c-Met antibodies of the invention provide a significantly improved synergistic inhibitory effect when compared to a mixture of EGFR-binding and c-Met-binding monospecific antibodies or published bispecific EGFR/c-Met antibodies. Depending on the assay, the synergistic effect observed varied between about 14- to over about 800-fold. The bispecific EGFR/c-Met antibodies of the invention provide more efficient inhibition of EGFR and c-Met signaling pathways and inhibit tumor growth more efficiently than cetuximab (Erbitux®). The bispecific EGFR/c-Met antibodies of the invention inhibit EGFR signaling in tumors and/or tumor cell ines having EGFR activating mutations and/or mutations in EGFR that are known to result in resistance to treatments with tyrosine kinase inhibitors such as gefitinib, and inhibit c-Met signaling pathway, a pathway identified to be upregulated and to provide a compensatory signaling upon treatment with EGFR tyrosine kinase inhibitors in cancers such as NSCLC. The bispecific EGFR/c-Met antibodies of the invention, in addition to directly inhibiting EGFR and c-Met signaling, display anti-tumor activity through enhanced antibody dependent cell cytotoxicity (ADCC) and degradation of the EGFR and c-Met receptors. Contrary to the current EGFR therapies (cetuximab and panitumumab), the bispecific EGFR/c-Met antibodies of the invention induce, via enhanced ADCC, killing of tumor cells having KRAS mutations.

Int. Pat. Publ. No. WO2010/115551 describes a bispecific EGFR/c-Met antibody (BSAB01) engineered in an IgG-scFv format using the EGFR bindingVH/VL pair of cetuximab, and the c-Met binding VH/VL pair of an antibody 5D5 (MetMab, onartuzumab) currently in Phase III trials. BSAB01 demonstrates approximately two-fold (additive) increased inhibition of A431 cell proliferation when compared to the parental antibodies (Example 7, FIG. 8b in WO2010/115551), and a modest additive inhibition of Ovarc-8 cell proliferation (FIG. 10a, Example 16 in WO2010/115551) when compared to the combination of the two parental antibodies (15% vs. 10% inhibition). Therefore, surprisingly and unexpectedly, the present invention provides bispecific EGFR/c-Met antibodies that demonstrate a significant synergistic effect in inhibition of EGFR and c-Met signaling, cancer cell survival and tumor growth. By not wishing to be bound by any theory, it is believed that the significant synergistic effect of the bispecific antibodies of the invention at least partially results from the epitope specificity of both the EGFR and the c-Met binding arms, possibly resulting in the inhibition of signaling through not only the EGFR and c-Met homodimers but also the EGFR/HERx heterodimers.

One embodiment of the invention is an isolated bispecific epidermal growth factor receptor (EGFR)/hepatocyte growth factor receptor (c-Met) antibody, comprising:
a) a first heavy chain (HC1) comprising a HC1 constant domain 3 (HC1 CH3) and a HC1 variable region 1 (VH1);
b) a second heavy chain (HC2) comprising a HC2 constant domain 3 (HC2 CH3) and a HC2 variable region 2 (VH2);
c) a first light chain (LC1) comprising a light chain variable region 1 (VL1); and
a second light chain (LC2) comprising a light chain variable region 2 (VL2), wherein the VH1 and the VL1 pair to form a first antigen-binding site that specifically binds EGFR and the VH2 and the VL2 pair to form a second antigen-binding site that specifically binds c-Met, wherein the HC1 comprises at least one substitution in the HC1 CH3 and the HC2 comprises at least one substitution in the HC2 CH3, wherein the substitution in the HC1 CH3 and the substitution in the HC2 CH3 occur at different amino acid residue positions, when residue numbering is according to the EU index.

In some embodiments described herein, the bispecific EGFR/c-Met antibody inhibits phosphorylation of extracellular signal-related kinases 1 and 2 (ERK1/2) in NCI-H292, NCI-H1975 or SKMES-1 cell line with an $IC_{50}$ value that is at least about 10-fold less, at least about 20-fold less, at least about 30-fold less, at least about 40-fold less, at least about 50-fold less or at least about 60-fold less when compared to the $IC_{50}$ value of inhibition of phosphorylation of ERK1/2 in NCI-H292, NCI-H1975 or SKMES-1 cell line with a mixture of a control monovalent EGFR antibody comprising a heavy chain 3 (HC3) and a light chain 3 (LC3) and a control monovalent c-Met antibody comprising a heavy chain 4 (HC4) and a light chain 4 (LC4), wherein the HC3 and the HC1, the LC3 and the LC1, the HC4 and the HC2, and the LC4 and the LC2 have identical amino acid sequences, respectively, and the phosphorylation of ERK1/2 is measured in whole cell lysates using a sandwich immunoassay using an anti-phosphoERK1/2 antibody as a capture antibody and an antibody binding to unphosphorylated and phosphorylated ERK1/2 conjugated with an electrochemiluminescent compound as a detection antibody. The bispecific EGFR/c-Met antibodies of the invention provide a synergistic more pronounced inhibition of EGFR and c-Met signaling when compared to the combination of monospecific EGFR antibodies and monospecific c-Met antibodies, when inhibition is assessed by inhibition of ERK1/2 phosphorylation. Such exemplary bispecific EGFR/c-Met antibody is the antibody EM1-mAb of the invention.

"Control monospecific EGFR antibody" as used herein refers to an antibody that has a first Fab arm that binds EGFR that is identical in amino acid sequence to the EGFR-binding Fab arm of the bispecific EGFR/c-Met antibody to be tested, and has a second Fab arm that is "inert" and binds an unrelated/irrelevant antigen, human immunodeficiency virus (HIV) gp120. The second Fab arm has a light chain having the sequence of SEQ ID NO: 209 and a heavy chain having the sequence of SEQ ID NO: 198 in instances when the EGFR binding Fab arm in the bispecific EGFR/c-Met antibody to be tested comprises the F405L substitution. The second Fab arm has a light chain having the sequence of SEQ ID NO: 209 and a heavy chain having the sequence of SEQ ID NO: 197 in instances when the EGFR binding Fab arm in the bispecific EGFR/c-Met antibody to be tested comprises the K409R substitution.

"Control monospecific c-Met antibody" as used herein refers to an antibody that has a first Fab arm that binds c-Met that is identical in amino acid sequence to the c-Met-binding Fab arm of the bispecific EGFR/c-Met antibody to be tested, and has a second Fab arm that is "inert" and binds the unrelated/irrelevant antigen HIV gp120. The second Fab Fab arm has a light chain having the sequence of SEQ ID NO: 209 and a heavy chain having the sequence of SEQ ID NO: 198 in instances when the c-Met binding Fab arm in the bispecific EGFR/c-Met antibody to be tested comprises the F405L substitution. The second inert Fab arm has a light chain having the sequence of SEQ ID NO: 209 and a heavy chain having the sequence of SEQ ID NO: 197 in instances when the c-Met binding Fab arm in the bispecific EGFR/c-Met antibody to be tested comprises the K409R substitution.

In some embodiments described herein, the bispecific EGFR/c-Met antibody inhibits phosphorylation of ERK1/2 with an $IC_{50}$ value of about $2\times10^{-9}$ M or less, about $1\times10^{-9}$ M or less, or about $1\times10^{-10}$ M or less.

In some embodiments described herein, ERK1 is phosphorylated at residues Thr202 and Tyr204, and ERK2 is phosphorylated at residues Thr185 and Tyr197.

In some embodiments described herein, the bispecific EGFR/c-Met antibody inhibits phosphorylation of protein kinase B (AKT) at Ser473 in NCI-H1975 cell line with an $IC_{50}$ value that is at least about 70-fold less when compared to the $IC_{50}$ value of inhibition of phosphorylation of AKT at Ser473 in NCI-H1975 cell line with the mixture of the control monovalent EGFR antibody comprising the HC3 and the LC3 and the control monovalent c-Met antibody comprising the HC4 and the LC4, wherein the HC3 and the HC1, the LC3 and the LC1, the HC4 and the HC2, and the LC4 and the LC2 have identical amino acid sequences, respectively, wherein the phosphorylation of AKT at Ser473 is measured in whole cell lysates using a sandwich immunoassay using an antibody binding to unphosphorylated and phosphorylated AKT as a capture antibody and an anti-phosphoAKT Ser473 antibody conjugated to an electrochemiluminescent compound as a detection antibody.

In some embodiments described herein, the bispecific EGFR/c-Met antibody inhibits phosphorylation of protein kinase B (AKT) at Thr308 in NCI-H1975 cell line with an $IC_{50}$ value that is at least about 100-fold less when compared to the $IC_{50}$ value of inhibition of phosphorylation of AKT at Thr308 in NCI-H1975 cell line with the mixture of the control monovalent EGFR antibody comprising the HC3 and the LC3 and the control monovalent c-Met antibody comprising the HC4 and the LC4, wherein the HC3 and the HC1, the LC3 and the LC1, the HC4 and the HC2, and the LC4 and the LC2 have identical amino acid sequences, respectively, wherein the phosphorylation of AKT at Thr308 is measured in whole cell lysates using a sandwich immunoassay using an antibody binding to unphosphorylated and phosphorylated AKT as a capture antibody and an anti-phosphoAKT Thr308 antibody conjugated to an electrochemiluminescent compound as a detection antibody.

The bispecific EGFR/c-Met antibodies of the invention provide a synergistic more pronounced inhibition of EGFR and c-Met signaling when compared to the combination of monospecific EGFR antibodies and monospecific c-Met antibodies, when inhibition is assessed by inhibition of AKT phosphorylation. Such exemplary bispecific EGFR/c-Met antibody is the antibody EM1-mAb of the invention.

In some embodiments described herein, the bispecific EGFR/c-Met antibody inhibits phosphorylation of AKT at Ser473 or at Thr308 with and $IC_{50}$ value of about $1 \times 10^{-9}$ M or less.

In some embodiments described herein, the bispecific EGFR/c-Met antibody binds EGFR of SEQ ID NO: 73 at EGFR residues K489, 1491, K467 and 5492 and c-Met at residues PEFRDSYPIKYVHAF (SEQ ID NO: 238) and FAQSKPDSAEPMDRSA (SEQ ID NO: 239). Such an exemplary bispecific antibody is the EM1-mAb. The bispecific EM-1 antibody binds EGFR and c-Met at distinct epitopes when compared to the antibody BSAB01 as described above and in Int. Pat. Publ. No. WO2010/115551. The parental EGFR binding arm (cetuximab) of BSAB01 binds EGFR amino acid residues R353, Q384, Q408, H409, F412, 5418, 5440, K443, K465, 1467, 5468, and N473 in mature EGFR, corresponding to residues R367, Q408, Q432, H433, F436, 5442, 5464, K467, K489, 1491, S492 and N497 of full length EGFR of SEQ ID NO: 73 (Li et al., Cancer Cell 7:301-311, 2005). The parental c-Met binding arm of BSAB01 (mAb 5D5) binds c-Met residues 325-340 PGAQLARQIGASLNDD (SEQ ID NO: 240). Epitope mapping of the EGFR binding parental antibody (2F8) of the EM1-mAb is described in US. Pat. Publ. No. US2011/0256142A1. Cetuximab and the parental 2F8 antibody bind partially overlapping but distinct epitopes.

Epitope mapping can be done using standard methods. For example, when the structures of both individual components are known, in silico protein-protein docking can be carried out to identify compatible sites of interaction. Hydrogen-deuterium (H/D) exchange can be carried out with the antigen and antibody complex to map regions on the antigen that may be bound by the antibody. Segment and point mutagenesis of the antigen can be used to locate amino acids important for antibody binding.

In some embodiments described herein, the bispecific EGFR/c-Met antibody neutralizes EGFR and c-Met signaling.

The bispecific EGFR/c-Met antibody of the invention may neutralize EGFR and c-Met signaling by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to the level of signaling in the absence of the bispecific EGFR/c-Met molecule of the invention using the same assay conditions.

Binding of a ligand such as EGF to EGFR stimulates receptor dimerization, autophosphorylation, activation of the receptor's internal, cytoplasmic tyrosine kinase domain, and initiation of multiple signal transduction and transactivation pathways involved in regulation of DNA synthesis (gene activation) and cell cycle progression or division. Neutralization of EGFR signaling may result in inhibition in one or more EGFR downstream signaling pathways and therefore neutralizing EGFR may have various effects, including inhibition of cell proliferation and differentiation, angiogenesis, cell motility and metastasis, and inhibition of downstream signaling pathways.

EGFR signaling and neutralization of EGFR signaling may be measured using various well know methods, for example measuring the autophosphorylation of the receptor at any of the tyrosines Y1068, Y1148, and Y1173 (Downward et al., Nature 311:483-5, 1984) and/or phosphorylation of natural or synthetic substrates, and inhibition of autophosphorylation and/or phosphorylation of natural or synthetic substrates by the bispecific antibodies of the invention. Phosphorylation can be detected using well known methods such as an ELISA assay or a western plot using a phosphotyrosine specific antibody. Exemplary assays can be found in Panek et al., J Pharmacol Exp Thera 283:1433-44, 1997 and Batley et al., Life Sci 62:143-50, 1998, and as described herein.

Binding of HGF to c-Met stimulates receptor dimerization, autophosphorylation, activation of the receptor's cytoplasmic tyrosine kinase domain, and initiation of multiple signal transduction and transactivation pathways involved in regulation of DNA synthesis (gene activation) and cell cycle progression or division. Inhibition of c-Met signaling may result in inhibition in one or more c-Met downstream signaling pathways and therefore neutralizing c-Met may have various effects, including inhibition of cell proliferation and differentiation, angiogenesis, cell motility and metastasis.

c-Met signaling and neutralization of c-Met signaling may be measured using various well know methods, for example measuring the autophosphorylation of the receptor on at least one tyrosine residues Y1230, Y1234, Y1235 or Y1349, and/or phosphorylation of natural or synthetic substrates. Phosphorylation can be detected, for example, using an antibody specific for phosphotyrosine in an ELISA assay or on a western blot. Exemplary assays can be found in Panek et al., J Pharmacol Exp Thera 283:1433-44, 1997 and Batley et al., Life Sci 62:143-50, 1998, and as described herein.

EGFR and c-Met signaling may be measured using various well know methods as described herein, such as measuring inhibition of ERK1/2 and AKT phosphorylation. Inhibition of ERK1 phosphorylation at Thr202 and Tyr204 and ERK2 phosphorylation at Thr185 and Tyr187 and inhibition of AKT at Ser473 or Thr308 can be measured for example in NCI-H1975 cell lysates utilizing a sandwich assay with capture antibody coated on solid support, and the detection antibody conjugated with an electrohemiluminescent compound such as Meso Scale Discover (MSD) SULFO-TAG label, followed by detection of the signal with a plate reader.

In some embodiments described herein, the bispecific EGFR/c-Met antibody inhibits growth of NCI-H292 or NCI-H1975 cells with an $IC_{50}$ value that is at least about 300-fold less, at least about 400-fold less, at least about 500-fold less, at least about 600-fold less, at least about 700-fold less or at least about 800-fold less when compared to the $IC_{50}$ value of inhibition of growth of NCI-H292 or NCI-H1975 cells with cetuximab, when NCI-H292 or NCI-H1975 cells are grown in low attachment conditions.

Inhibition of cell growth may be assessed by known methods. For example, the cells may be plated in plates coated with hydrogels or biomimetic polymers (for example Ultra Low Attachment plates by Corning) to prevent or reduce cell attachment, and the effect of antibodies on 7.5 ng/mL HGF-induced cell growth can be assessed by measuring percent cell viability after incubation for 72 hours using standard methods.

The bispecific EGFR/c-Met antibodies of the invention provide a synergistic more pronounced inhibition of EGFR and/or c-Met expressing cancer cells when compared to the combination of monospecific EGFR antibodies and monospecific c-Met antibodies and to the standard of care cetuximab. Such an exemplary bispecific EGFR/c-Met antibody is the antibody EM1-mAb of the invention. The bispecific EGFR/c-Met antibodies of the invention inhibit cancer cells that express the wild type EGFR and the wild type c-Met, and also cancer cells that express the EGFR L858R/T790M mutant, which mutation is identified to contribute to resistance to treatments with small molecule tyrosine kinase inhibitors (TKIs) such as gefitinib. Therefore the bispecific EGFR/c-Met antibodies of the invention may provide a benefit in a broader patient population when compared to cetuximab and TKIs.

In some embodiments described herein, the bispecific EGFR/c-Met antibody inhibits growth of HGF-expressing SKMES-1 cell tumor in SCID Beige mice with a percentage (%) T/C value of at least 500-fold less on day 36 when compared to cetuximab, when the bispecific antibody and cetuximab are administered at 20 mg/kg dose.

Tumor xenograft models using SCID Beige mice are well known. SKMES-1 cells may be engineered to express human HGF using standard methods. Typically, SCID Beige mice may be subcutaneously inoculated with SKMES-1 cells expressing human HGF embedded in extracellular matrix such as Culturex in the dorsal flank of each animal. One week after implantation, mice may be stratified into groups with equivalent tumor volumes, and thereafter dosed for example three times per week with the bispecific EGFR/c-Met antibodies of the invention, control or benchmark antibodies or small molecules. Tumor volumes may be recorded twice weekly, and tumor growth inhibition (TGI) may be observed by calculating the percentage (%) T/C value. The % T/C value is indicative of anti-tumor efficacy. T and C are the mean volumes of the treated and control groups, respectively, on a given day.

The bispecific EGFR/c-Met antibodies of the invention provide a significantly improved efficacy in in vivo tumor killing when compared to the standard of care cetuximab, and therefore may provide a benefit in a patient population when compared to cetuximab.

In some embodiments described herein, the bispecific EGFR/c-Met antibody comprises the HC1 and the HC2 of IgG1, IgG2, IgG3 or IgG4 isotype.

In some embodiments described herein, the bispecific EGFR/c-Met antibody comprises the HC1 and the HC2 of IgG1 isotype.

In some embodiments described herein, the bispecific EGFR/c-Met antibody HC1 CH3 comprises at least one, two, three, four, five, six, seven or eight substitutions and the HC2 CH3 comprises at least one, two, three, four, five, six, seven or eight substitutions at residue positions 350, 366, 368, 370, 399, 405, 407 or 409, when residue numbering is according to the EU index.

In some embodiments described herein, the bispecific EGFR/c-Met antibody HC1 CH3 comprises at least one, two, three or four substitutions and the HC2 CH3 comprises at least one, two, three or four substitutions at residue positions 350, 370, 405 or 409, when residue numbering is according to the EU index.

Antibody domains and numbering are well known. Two CH3 domains (or CH3 regions) are non-identical when they differ with at least one amino acid substitution from each other. An IgG1 CH3 region typically consists of residues 341-446 on IgG1 (residue numbering according to the EU index). An exemplary IgG1 constant region is shown in SEQ ID NO: 203. The CH3 domain spans residues 224-329 of SEQ ID NO: 203, and correspond to residues 341-446 according to EU index.

In some embodiments described herein, the bispecific EGFR/c-Met antibody HC1 CH3 comprises at least one substitution and the HC2 CH3 comprises at least one substitution at residue positions 405 or 409, when residue numbering is according to the EU index.

In some embodiments described herein, the bispecific EGFR/c-Met antibody HC1 CH3 comprises a K409R or a F405L substitution and the HC2 CH3 comprises a K409R or a F405L substitution, wherein residue numbering is according to the EU index.

In some embodiments described herein, the bispecific EGFR/c-Met antibody HC1 CH3 comprises the F405L substitution and the HC2 CH3 comprises the K409R substitution.

In some embodiments described herein, the HC1 CH3 and the HC2 CH3 substitutions are substitutions at position 366, 368, 370, 399, 405, 407 or 409 (numbering according to the EU index). These positions correspond to linear residue positions 248, 250, 252, 281, 287, 289 and 291, respectively, in a heavy chain constant region of SEQ ID NO: 203 and 204.

In some embodiments described herein, the HC1 CH3 position 409 has an amino acid substitution other than Lys, Leu or Met and the HC2 CH3 position 405 has an amino acid substitution other than Phe.

In some embodiments described herein, the HC1 CH3 position 405 has an amino acid substitution other than Phe and the HC2 CH3 position 409 has an amino acid substitution other than Lys, Leu or Met.

In some embodiments described herein, the HC1 CH3 position 409 has an amino acid substitution other than Lys, Leu or Met and the HC2 CH3 position 405 has an amino acid substitution other than Phe, Arg or Gly.

In some embodiments described herein, the HC1 CH3 position 405 has an amino acid substitution other than Phe, Arg or Gly and the HC2 CH3 position 409 has an amino acid substitution other than Lys, Leu or Met In some embodiments described herein, the HC1 CH3 has Phe at position 405 and an amino acid other than Lys, Leu or Met at position 409 and the HC2 CH3 has an amino acid other than Phe at position 405 and a Lys at position 409.

In some embodiments described herein, the HC1 CH3 has an amino acid other than Phe at position 405 and Lys at position 409 and the HC2 CH3 has Phe at position 405 and an amino acid other than Lys, Leu or Met at position 409.

In some embodiments described herein, the HC1 CH3 has Phe at position 405 and an amino acid other than Lys, Leu or Met at position 409 and the HC2 CH3 has a substitution other than Phe, Arg or Gly at position 405 and Lys at position 409.

In some embodiments described herein, the HC1 CH3 has a substitution other than Phe, Arg or Gly at position 405 and Lys at position 409 and the HC2 CH3 has Phe at position 405 and an amino acid other than Lys, Leu or Met at position 409.

In some embodiments described herein, the HC1 CH3 has Phe at position 405 and an amino acid other than Lys, Leu or Met at position 409 and the HC2 CH3 has Leu at position 405 and Lys at position 409.

In some embodiments described herein, the HC1 CH3 has Leu at position 405 and Lys at position 409 and the HC2 CH3 has Phe at position 405 and an amino acid other than Lys, Leu or Met at position 409.

In some embodiments described herein, the HC1 CH3 has Phe at position 405 and aArg at position 409 and the HC2 CH3 has an amino acid other than Phe, Arg or Gly at position 405 and Lys at position 409.

In some embodiments described herein, the HC1 CH3 has an amino acid other than Phe, Arg or Gly at position 405 and Lys at position 409 and the HC2 CH3 has Phe at position 405 and Arg at position 409.

In some embodiments described herein, the HC1 CH3 has Phe at position 405 and Arg at position 409 and the HC2 CH3 has Leu at position 405 and Lys at position 409.

In some embodiments described herein, the HC1 CH3 has Leu at position 405 and Lys at position 409 and the HC2 CH3 has Phe at position 405 and Arg at position 409.

In some embodiments described herein, the HC1 CH3 has Phe at position 405 and Lys at position 409 and the HC2 CH3 has Leu at position 405 and aArg at position 409.

In some embodiments described herein, the HC1 CH3 has Leu at position 405 and aArg at position 409 and the HC2 CH3 has Phe at position 405 and Lys at position 409.

In some embodiments described herein, the HC1 CH3 has an amino acid other than Lys, Leu or Met at position 409 and the HC2 CH3 has Lys at position 409, Thr at position 370 and Leu at position 405.

In some embodiments described herein, the HC1 CH3 has Lys at position 409, Thr at position 370 and Leu at position 405 and the HC2 CH3 has an amino acid other than Lys, Leu or Met at position 409.

In some embodiments described herein, the HC1 CH3 has Arg at position 409 and the HC2 CH3 has Lys at position 409, Thr at position 370 and Leu at position 405.

In some embodiments described herein, the HC1 CH3 has Lys at position 409, Thr at position 370 and Leu at position 405 and the HC2 CH3 has Arg at position 409.

In some embodiments described herein, the HC1 CH3 has Lys at position 370, Phe at position 405 and aArg at position 409 and the HC2 CH3 has Lys at position 409, Thr at position 370 and Leu at position 405.

In some embodiments described herein, the HC1 CH3 has Lys at position 409, Thr at position 370 and Leu at position 405 and the HC2 CH3 has Lys at position 370, Phe at position 405 and Arg at position 409.

In some embodiments described herein, the HC1 CH3 has an amino acid other than Lys, Leu or Met at position 409 and the HC2 CH3 has an amino acid other than Tyr, Asp, Glu, Phe, Lys, Gln, Arg, Ser or Thr at position 407.

In some embodiments described herein, the HC1 CH3 has an amino acid other than Tyr, Asp, Glu, Phe, Lys, Gln, Arg, Ser or Thr at position 407 and the HC2 CH3 has an amino acid other than Lys, Leu or Met at position 409.

In some embodiments described herein, the HC1 CH3 has an amino acid other than Lys, Leu or Met at position 409 and the HC2 CH3 has Ala, Gly, His, Ile, Leu, Met, Asn, Val or Trp at position 407.

In some embodiments described herein, the HC1 CH3 has Ala, Gly, His, Ile, Leu, Met, Asn, Val or Trp at position 407 and the HC2 CH3 has an amino acid other than Lys, Leu or Met at position 409.

In some embodiments described herein, the HC1 CH3 has an amino acid other than Lys, Leu or Met at position 409 and the HC2 CH3 has Gly, Leu, Met, Asn or Trp at position 407.

In some embodiments described herein, the HC1 CH3 has Gly, Leu, Met, Asn or Trp at position 407 and the HC2 CH3 has an amino acid other than Lys, Leu or Met at position 409.

In some embodiments described herein, the HC1 CH3 has Tyr at position 407 and an amino acid other than Lys, Leu or Met at position 409 and the HC2 CH3 has an amino acid other than Tyr, Asp, Glu, Phe, Lys, Gln, Arg, Ser or Thr at position 407 and Lys at position 409.

In some embodiments described herein, the HC1 CH3 has an amino acid other than Tyr, Asp, Glu, Phe, Lys, Gln, Arg, Ser or Thr at position 407 and Lys at position 409 and the HC2 CH3 has Tyr at position 407 and an amino acid other than Lys, Leu or Met at position 409.

In some embodiments described herein, the HC1 CH3 has Tyr at position 407 and an amino acid other than Lys, Leu or Met at position 409 and the HC2 CH3 has Ala, Gly, His, Ile, Leu, Met, Asn, Val or Trp at position 407 and Lys at position 409.

In some embodiments described herein, the HC1 CH3 has Ala, Gly, His, Ile, Leu, Met, Asn, Val or Trp at position 407 and Lys at position 409 and the HC2 CH3 has Tyr at position 407 and an amino acid other than Lys, Leu or Met at position 409.

In some embodiments described herein, the HC1 CH3 has Tyr at position 407 and an amino acid other than Lys, Leu or Met at position 409 and the HC2 CH3 has Gly, Leu, Met, Asn or Trp at position 407 and Lys at position 409.

In some embodiments described herein, the HC1 CH3 has Gly, Leu, Met, Asn or Trp at position 407 and Lys at position 409 and the HC2 CH3 has Tyr at position 407 and an amino acid other than Lys, Leu or Met at position 409.

In some embodiments described herein, the HC1 CH3 has Tyr at position 407 and Arg at position 409 and the HC2 CH3 has an amino acid other than Tyr, Asp, Glu, Phe, Lys, Gln, Arg, Ser or Thr at position 407 and Lys at position 409.

In some embodiments described herein, the HC1 CH3 has an amino acid other than Tyr, Asp, Glu, Phe, Lys, Gln, Arg, Ser or Thr at position 407 and Lys at position 409 and the HC2 CH3 has Tyr at position 407 and Arg at position 409.

In some embodiments described herein, the HC1 CH3 has Tyr at position 407 and Arg at position 409 and the HC2 CH3 has Ala, Gly, His, Ile, Leu, Met, Asn, Val or Trp at position 407 and Lys at position 409.

In some embodiments described herein, the HC1 CH3 has Ala, Gly, His, Ile, Leu, Met, Asn, Val or Trp at position 407 and Lys at position 409 and the HC2 CH3 has Tyr at position 407 and Arg at position 409.

In some embodiments described herein, the HC1 CH3 has Tyr at position 407 and Arg at position 409 and the HC2 CH3 has Gly, Leu, Met, Asn or Trp at position 407 and Lys at position 409.

In some embodiments described herein, the HC1 CH3 has Gly, Leu, Met, Asn or Trp at position 407 and Lys at position 409 and the HC2 CH3 has Tyr at position 407 and Arg at position 409.

In some embodiments described herein, the HC1 CH3 has an amino acid other than Lys, Leu or Met at position 409, and the HC2 CH3 has (i) an amino acid other than Phe, Leu and Met at position 368, or (ii) a Trp at position 370, or (iii) an amino acid other than Asp, Cys, Pro, Glu or Gln at position 399.

In some embodiments described herein, the HC1 CH3 has (i) an amino acid other than Phe, Leu and Met at position 368, or (ii) a Trp at position 370, or (iii) an amino acid other than Asp, Cys, Pro, Glu or Gln at position 399 and the HC2 CH3 has an amino acid other than Lys, Leu or Met at position 409.

In some embodiments described herein, the HC1 CH3 has Arg, Ala, His or Gly at position 409, and the HC2 CH3 has (i) Lys, Gln, Ala, Asp, Glu, Gly, His, Ile, Asn, Arg, Ser, Thr, Val, or Trp at position 368, or (ii) Trp at position 370, or (iii) Ala, Gly, Ile, Leu, Met, Asn, Ser, Thr, Trp, Phe, His, Lys, Arg or Tyr at position 399.

In some embodiments described herein, the HC1 CH3 has (i) Lys, Gln, Ala, Asp, Glu, Gly, His, Ile, Asn, Arg, Ser, Thr, Val, or Trp at position 368, or (ii) Trp at position 370, or (iii) Ala, Gly, Ile, Leu, Met, Asn, Ser, Thr, Trp, Phe, His, Lys, Arg or Tyr at position 399 and the HC2 CH3 has Arg, Ala, His or Gly at position 409.

In some embodiments described herein, the HC1 CH3 has Arg at position 409, and the HC2 CH3 has (i) Asp, Glu, Gly, Asn, Arg, Ser, Thr, Val, or Trp at position 368, or (ii) Trp at position 370, or (iii) Phe, His, Lys, Arg or Tyr at position 399.

In some embodiments described herein, the HC1 CH3 has (i) Asp, Glu, Gly, Asn, Arg, Ser, Thr, Val, or Trp at position 368, or (ii) Trp at position 370, or (iii) Phe, His, Lys, Arg or Tyr at position 399 and the HC2 CH3 has Arg at position 409.

In some embodiments described herein, the HC1 CH3 comprises a K409R substitution or a F405L substitution and the HC2 CH3 comprises a K409R substitution or a F405L substitution, wherein the residue numbering is according to the EU index.

In some embodiments described herein, the HC1 CH3 comprises the F405L substitution and the HC2 CH3 comprises the K409R substitution.

Substitutions are typically made at the DNA level to a molecule such as the constant domain of the antibody using standard methods.

In some embodiments described herein, the bispecific EGFR/c-Met antibody comprises the VH1 and the VL1, wherein the VH1 comprises the heavy chain complementarity determining region (HCDR) 1 (HCDR1), HCDR 2 (HCDR2) and HCDR 3 (HCDR3) amino acid sequences of SEQ ID NOs: 210, 211 and 212, respectively; and the VL1 comprises the light chain complementarity determining region (LCDR) 1 (LCDR1), LCDR 2 (LCDR2) and LCDR 3 (LCDR3) amino acid sequences of SEQ ID NOs: 213, 214 and 215, respectively.

In some embodiments described herein, the bispecific EGFR/c-Met antibody comprises the VH2 and the VL2, wherein the VH2 comprises the HCDR1, the HCDR2, and the HCDR3 amino acid sequences of SEQ ID NOs: 216, 217 and 218, respectively; and the VL2 comprises the LCDR1, the LCDR2 and the LCDR3 amino acid sequences of SEQ ID NOs: 219, 220 and 221, respectively.

In some embodiments described herein, the bispecific EGFR/c-Met antibody comprises the VH1, the VL1, the VH2 and the VL2 amino acid sequences of SEQ ID NOs: 189, 190, 193 and 194, respectively.

In some embodiments described herein, the bispecific EGFR/c-Met antibody comprises the HC1, the LC1, the HC2 and the LC2 amino acid sequences of SEQ ID NOs: 199, 200, 201 and 202, respectively, optionally having a C-terminal lysine removed from the HC1, the HC2, or both the HC1 and the HC2.

In some embodiments described herein, the bispecific EGFR/c-Met antibody comprises the VH1 and the VL1, wherein the VH1 comprises the HCDR1, the HCDR2, and the HCDR3 amino acid sequences of SEQ ID NOs: 222, 223 and 224, respectively; and the VL1 comprises the LCDR1, the LCDR2 and the LCDR3 amino acid sequences of SEQ ID NOs: 225, 226 and 227, respectively.

In some embodiments described herein, the bispecific EGFR/c-Met antibody comprises the VH2 and the VL2, wherein the VH2 comprises the HCDR1, the HCDR2, and the HCDR3 amino acid sequences of SEQ ID NOs: 228, 229 and 230, respectively; and the VL2 comprises the LCDR1, the LCDR2 and the LCDR3 amino acid sequences of SEQ ID NOs: 231, 232 and 233, respectively.

In some embodiments described herein, the bispecific EGFR/c-Met antibody comprises the VH1, the VL1, the VH2 and the VL2 amino acid sequences of SEQ ID NOs: 191, 192, 195 and 196, respectively.

In some embodiments described herein, the bispecific EGFR/c-Met antibody comprises the HC1, the LC1, the HC2 and the LC2 amino acid sequences of SEQ ID NOs: 234, 235, 236 and 237, respectively, optionally having the C-terminal lysine removed from the HC1, the HC2, or both the HC1 and the HC2.

In some embodiments described herein, the bispecific EGFR/c-Met antibodies may block EGF binding to the EGFR and HGF binding to c-Met with an $IC_{50}$ value of less than about $1\times10^{-8}$ M, less than about $1\times10^{-9}$ M, less than about $1\times10^{-10}$ M, less than about $1\times10^{-11}$ M, or less than about $1\times10^{-12}$ M in a competition assay employing recombinant human EGFR or recombinant human c-Met extracellular domains coated on plates and incubated with or without the bispecific EGFR/c-Met antibodies of the invention. The bispecific EGFR/c-Met antibodies described herein may block EGF binding to EGFR and HGF binding to c-Met by at least 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% when compared to binding of EGF to the EGFR and HGF binding to c-Met in the absence of the bispecific EGFR/c-Met antibodies of the invention described herein using the same assay conditions.

In some embodiments described herein, the bispecific EGFR/c-Met antibody comprises the HC1, LC1, HC2 and LC2, wherein the HC1, the LC1, the HC2 and the LC2 are encoded by synthetic polynucleotides comprising the sequence of SEQ ID NOs: 205, 206, 207 and 208, respectively.

The bispecific EGFR/c-Met antibodies of the invention may be generated using techniques described herein, such as utilizing CH3 engineering and generating the antibodies using in vitro Fab arm exchange. An exemplary bispecific antibody may be generated from two monospecific antibodies by combining about 1-20 mg/mL of each antibody at a 1:1 molar ratio in PBS at pH 7.0-7.4 in a buffer having a final concentration of 75 mM 2-mercaptoethanolamine (2-MEA), incubating for 2-6 hours at 25-37° C., followed by removal of 2-MEA via dialysis, diafiltration, tangential flow filtration, and spinned cell filtration. The yield of the bispecific antibody may be more than about 80%, more than about 90%, more than about 91%, 92%, 93%, 94%, 95%, 96%, 97%, 98% or 99%.

Some embodiments described herein provide for methods of producing the isolated bispecific EGFR/c-Met antibody, comprising:

combining an isolated monospecific bivalent anti-EGFR antibody comprising two heavy chains of SEQ ID NO: 199 and two light chains of SEQ ID NO: 200 and an isolated monospecific bivalent anti-c-Met antibody comprising two heavy chains of SEQ ID NO: 201 and two light chains of SEQ ID NO: 202 in a mixture of about 1:1 molar ratio;

introducing a reducing agent into the mixture;

incubating the mixture about ninety minutes to about six hours;

removing the reducing agent; and purifying the bispecific EGFR/c-Met antibody that comprises a first heavy chain of SEQ ID NO: 199 and a second heavy chain of SEQ ID NO: 201, a first light chain of SEQ ID NO: 200 and a second light chain of SEQ ID NO: 202, wherein the first heavy chain of SEQ ID NO: 199 pairs with the first light chain of SEQ ID NO: 200 to form the first binding domain that specifically binds EGFR, and the second heavy chain of SEQ ID NO: 201 pairs with the second light chain of SEQ ID NO: 202 to form the second binding domain that specifically binds c-Met.

In some embodiments described herein, the reducing agent is 2-mercaptoethanolamine (2-MEA).

In some embodiments described herein, 2-MEA is present at a concentration of about 25 mM to about 75 mM.

In some embodiments described herein, the incubating step is performed at a temperature of about 25° C. to about 37° C.

Some embodiments described herein provide for an isolated bispecific EGFR/-c-Met antibody comprising a HC1, a LC1, a HC2 and a LC2, wherein the HC1 comprises the sequence of SEQ ID NO: 199, the LC1 comprises the sequence of SEQ ID NO: 200, the HC2 comprises the sequence of SEQ ID NO: 201, and the LC2 comprises the sequence of SEQ ID NO: 202, wherein the HC1, the LC1, the HC2 and/or the LC2 further comprises 1, 2, 3, 4, 5, 6, 7, 8, 9, 10, 11, 12, 13, 14 or 15 conservative amino acid substitutions.

Some embodiments described herein provide for an isolated bispecific EGFR/-c-Met antibody comprising the HC1, the LC1, the HC2 and the LC2, wherein the HC1 comprises the sequence of SEQ ID NO: 234, the LC1 comprises the sequence of SEQ ID NO: 235, the HC2 comprises the sequence of SEQ ID NO: 236, and the LC2 comprises the sequence of SEQ ID NO: 237, wherein the HC1, the LC1, the HC2 and/or the LC2 further comprises 1, 2, 3, 4, 5, 6, 7, 8, 9, 10, 11, 12, 13, 14 or 15 conservative amino acid substitutions.

Bispecific EGFR/c-Met antibodies whose HC1, LC1, HC2 and LC2 amino acid sequences differ insubstantially from those antibodies disclosed herein are encompassed within the scope of the invention. Typically, this involves one or more conservative amino acid substitutions with an amino acid having similar charge, hydrophobic, or stereochemical characteristics in the antigen-binding sites or in the frameworks without adversely altering the properties of the antibody. Conservative substitutions may also be made to improve antibody properties, for example stability or affinity. 1, 2, 3, 4, 5, 6, 7, 8, 9, 10, 11, 12, 13, 14, or 15 amino acid substitutions may be made for example to the VH1, the VL1, the VH2 and/or the VL2. For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for alanine scanning mutagenesis (MacLennan et al., Acta Physiol Scand Suppl 643:55-67, 1998; Sasaki et al., Adv Biophys 35:1-24, 1998). Desired amino acid substitutions may be determined by those skilled in the art at the time such substitutions are desired. For example, amino acid substitutions can be used to identify important residues of the molecule sequence, or to increase or decrease the affinity of the molecules described herein. Exemplary conservative amino acid substitutions are described supra.

Amino acid substitutions may be done for example by PCR mutagenesis (U.S. Pat. No. 4,683,195). Libraries of variants may be generated using well known methods, for example using random (NNK) or non-random codons, for example DVK codons, which encode 11 amino acids (Ala, Cys, Asp, Glu, Gly, Lys, Asn, Arg, Ser, Tyr, Trp) and screening the libraries for variants with desired properties.

In some embodiments described herein, amino acid substitutions can be made to the constant region of the antibody. For example different IgG1 allotypes can be used in the bispecific EGFR/c-Met antibodies of the invention, such as well known Glm17 allotype, Glm3 allotype or Glm1 allotype, or a combination thereof In some embodiments described herein, pharmacokinetic properties of the bispecific EGFR/c-Met antibodies may be enhanced by substitutions in the Fc domain that modulate antibody halflife. In some embodiments described herein, the bispecific EGFR/c-Met antibody comprises a substitution M252Y/S254T/T256E in the HC1 and/or the HC2, wherein residue numbering is according to the EU index. M252Y/S254T/T256E substitutions have been show to increase antibody half life (Dall'Acqua et al., J Biol Chem 281:23514-24, 2006).

The bispecific EGFR/c-Met antibodies having conservative substitutions and/or additional substitutions in their Fc region are tested for their characteristics using the methods described herein.

In some embodiment described herein, immune effector properties of the bispecific EGFR/c-Met antibodies may be enhanced or silenced through Fc modifications by techniques known to those skilled in the art. For example, Fc effector functions such as Clq binding, complement dependent cytotoxicity (CDC), antibody-dependent cell-mediated cytotoxicity (ADCC), antibody-dependent cell-mediated phagocytosis (ADCP), down regulation of cell surface receptors (e.g., B cell receptor; BCR), etc. may be provided and/or controlled by modifying residues in the Fc responsible for these activities.

"Antibody-dependent cell-mediated cytotoxicity" or "ADCC" refers to a cell-mediated reaction in which non-specific cytotoxic cells that express Fc receptors (FcRs) (e.g. Natural Killer (NK) cells, neutrophils, and macrophages) recognize bound antibody on a target cell and subsequently cause lysis of the target cell.

The ability of monoclonal antibodies to induce ADCC can be enhanced by engineering their oligosaccharide component. Human IgG1 or IgG3 are N-glycosylated at Asn297 with the majority of the glycans in the well known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such mAbs can be achieved using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the α 1,6-fucosyltrasferase (FUT8) gene (Mori et al., Biotechnol Bioeng 88:901-908, 2004), or coexpression of β-1,4-N-acetylglucosaminyltransferase III and Golgi α-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008).

In some embodiments described herein, ADCC elicited by the bispecific EGFR/c-Met antibodies may also be enhanced by certain substitutions in the antibody Fc. Exemplary substitutions are for example substitutions at amino acid positions 256, 290, 298, 312, 356, 330, 333, 334, 360, 378 or 430 (residue numbering according to the EU index) as described in U.S. Pat. No. 6,737,056.

In some embodiments described herein, the bispecific EGFR/c-Met antibody of the invention has a biantennary glycan structure with fucose content of about between 1% to about 15%, for example 15%, 14%, 13%, 12%, 11% 10%, 9%, 8%, 7%, 6%, 5%, 4%, 3%, 2% or 1% In some embodiments, the bispecific EGFR/c-Met antibody has a glycan structure with fucose content of about 50%, 40%, 45%, 40%, 35%, 30%, 25%, or 20%.

"Fucose content" means the amount of the fucose monosaccharide within the sugar chain at Asn297. The relative amount of fucose is the percentage of fucose-containing structures related to all glycostructures. These may be characterized and quantified by multiple methods, for example: 1) using MALDI-TOF of N-glycosidase F treated sample (e.g. complex, hybrid and oligo- and high-mannose structures) as described in Int Pat. Publ. No. WO2008/077546 2); 2) by enxymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (e.g., trypsin or endopeptidase Lys-C), and subsequent separation, detection and quantitation by HPLC-MS (UPLC-MS); 5) Separation of the mAb oligosaccharides from the mAb protein by specific enzymatic deglycosylation with PNGase F at Asn 297. The oligosaccharides thus released can be labeled with a fluorophore, separated and identified by various complementary techniques which allow: fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosacharride forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" as used in the application refers to antibodies with fucose content of about between 1%-15%.

"Normal fucose" or "normal fucose content" as used herein refers to antibodies with fucose content of about over 50%, typically about over 80% or over 85%.

Some embodiments of the invention provide a synthetic nucleic acid encoding the heavy chains and the light chains of the bispecific EGFR/c-Met binding antibodies of the invention as described herein as isolated polynucleotides or as portions of expression vectors or as portions of linear DNA sequences, including linear DNA sequences used for in vitro transcription/translation, vectors compatible with prokaryotic, eukaryotic or filamentous phage expression, secretion and/or display of the compositions or directed mutagens thereof.

Some embodiments of the invention provide an isolated polynucleotide comprising the polynucleotide sequence of SEQ ID NOs: 205, 206, 207 or 208.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such as PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

Some embodiments described herein provide for a vector comprising the polynucleotide of the invention. Such vectors may be plasmid vectors, viral vectors, vectors for baculovirus expression, transposon based vectors or any other vector suitable for introduction of the polynucleotide of the invention into a given organism or genetic background by any means. For example, polynucleotides encoding heavy and light chains of the bispecific antibodies of the invention may be inserted into expression vectors. The light and heavy chains may be be cloned in the same or different expression vectors. The DNA segments encoding immunoglobulin chains may be operably linked to control sequences in the expression vector(s) that ensure the expression of immunoglobulin polypeptides. Such control sequences include signal sequences, promoters (e.g. naturally associated or heterologous promoters), enhancer elements, and transcription termination sequences, and may be chosen to be compatible with the host cell chosen to express the antibody. Once the vector has been incorporated into the appropriate host, the host may be maintained under conditions suitable for high level expression of the proteins encoded by the incorporated synthetic polynucleotides.

Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed with the desired DNA sequences.

Some embodiments described herein provide for a host cell comprising the vector of the invention. The term "host cell" refers to a cell into which a vector has been introduced. It is understood that the term host cell is intended to refer not only to the particular subject cell but to the progeny of such a cell. Because certain modifications may occur in succeeding generations due to either mutation or environmental influences, such progeny may not be identical to the parent cell, but are still included within the scope of the term "host cell" as used herein. Such host cells may be eukaryotic cells, prokaryotic cells, plant cells or archeal cells.

Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics, Walkersville, Md.), CHO-K1 (ATCC CRL-61) or DG44.

Uses of Bispecific EGFR/c-Met FN3 Domain Containing Molecules, Bispecific EGFR/-c-Met Antibodies and EGFR-binding or c-Met Binding FN3 Domains of the Invention The bispecific EGFR/c-Met FN3 domain containing molecules, the EGFR binding FN3 domains, the c-Met binding FN3 domains or the bispecific EGFR-c-Met antibodies of the invention may be used to diagnose, monitor, modulate, treat, alleviate, help prevent the incidence of, or reduce the symptoms of human disease or specific pathologies in cells, tissues, organs, fluid, or, generally, a host. The methods of the invention may be used to treat an animal patient belonging to any classification. Examples of such animals include mammals such as humans, rodents, dogs, cats and farm/domestic animals.

One aspect of the invention is a method for inhibiting growth or proliferation of cells that express EGFR and/or c-Met, comprising contacting the cells with the isolated bispecific EGFR/c-Met FN3 domain containing molecule, the EGFR binding FN3 domain, the c-Met binding FN3 domain or the bispecific EGFR/c-Met antibody of the invention.

Another aspect of the invention is a method for inhibiting growth or metastasis of EGFR and/or c-Met-expressing tumor or cancer cells in a subject comprising administering to the subject an effective amount of the isolated bispecific EGFR/c-Met FN3 domain containing molecule, the EGFR binding FN3 domain, the c-Met binding FN3 domain or the bispecific EGFR/c-Met antibody of the invention so that the growth or metastasis of EGFR- and/or c-Met-expressing tumor or cancer cell is inhibited.

Another aspect of the invention is a method of treating a subject having cancer, comprising administering a therapeutically effective amount of the isolated bispecific EGFR/c-Met FN3 domain containing molecule, the EGFR binding FN3 domain, the c-Met binding FN3 domain or the bispecific EGFR/c-Met antibody of the invention to a patient in need thereof for a time sufficient to treat the cancer.

The bispecific EGFR/c-Met FN3 domain containing molecule, the EGFR binding FN3 domain, the c-Met binding FN3 domain or the bispecific EGFR/c-Met antibodies of the invention may be used for treatment of any disease or disorder characterized by abnormal activation or production of EGFR, c-Met, EGF, soluble EGFR, soluble c-Met or other EGFR ligand or HGF, or disorder related to EGFR or c-Met expression, which may or may not involve malignancy or cancer, where abnormal activation and/or production of EGFR, c-Met, EGF or other EGFR ligand, or HGF is occurring in cells or tissues of a subject having, or predisposed to, the disease or disorder.

The FN3 domains that specifically bind c-Met and block binding of HGF to c-Met of the invention may be for treatment of tumors, including cancers and benign tumors. Cancers that are amenable to treatment by the c-Met binding FN3 domains of the invention include those that overexpress c-Met. Exemplary cancers that are amenable to treatment by the FN3 domains of the invention include epithelial cell cancers, breast cancer, ovarian cancer, lung cancer, colorectal cancer, anal cancer, prostate cancer, kidney cancer, bladder cancer, head and neck cancer, gastric cancer, ovarian cancer, pancreatic cancer, skin cancer, oral cancer, esophageal cancer, vaginal cancer, cervical cancer, cancer of the spleen, testicular cancer, and cancer of the thymus.

The FN3 domains that specifically bind EGFR and blocks binding of EGF to the EGFR of the invention may be used for treatment of tumors, including cancers and benign tumors. Cancers that are amenable to treatment by the FN3 domains of the invention include those that overexpress EGFR or variants. Exemplary cancers that are amenable to treatment by the FN3 domains of the invention include epithelial cell cancers, breast cancer, ovarian cancer, lung cancer, colorectal cancer, anal cancer, prostate cancer, kidney cancer, bladder cancer, head and neck cancer, ovarian cancer, pancreatic cancer, skin cancer, oral cancer, esophageal cancer, vaginal cancer, cervical cancer, cancer of the spleen, testicular cancer, and cancer of the thymus. The bispecific EGFR/c-Met FN3 domain containing molecules or the bispecific EGFR/c-Met antibodies of the invention may be used for treatment of tumors, including cancers and benign tumors. Exemplary cancers that are amenable to treatment by the bispecific EGFR/c-Met FN3 domain containing molecule or the bispecific EGFR/c-Met antibody of the invention include those that over-express EGFR and/or c-Met, cancers associated with elevated EGFR activity and/or expression levels (such as, for example, an EGFR activating mutation, an EGFR gene amplification, or ligand mediated EGFR activation) and elevated c-Met activity and/or expression levels (such as, for example, a c-Met activating mutation, a c-Met gene amplification, or HGF mediated c-Met activation).

Exemplary EGFR activating mutations that may be associated with cancer include point mutations, deletion mutations, insertion mutations, inversions or gene amplifications that lead to an increase in at least one biological activity of EGFR, such as elevated tyrosine kinase activity, formation of receptor homodimers and heterodimers, enhanced ligand binding etc. Mutations can be located in any portion of an EGFR gene or regulatory region associated with an EGFR gene and include mutations in exon 18, 19, 20 or 21 or mutations in the kinase domain. Exemplary activating EGFR mutations are G719A, L861X (X being any amino acid), L858R, E746K, L747S, E749Q, A750P, A755V, V765M, L858P or T790M substitutions, deletion of E746-A750, deletion of R748-P753, insertion of Ala between M766 and A767, insertion of SVA (Ser, Val, Ala) between 5768 and V769, and insertion of NS (Asn, Ser) between P772 and H773. Other examples of EGFR activating mutations are known in the art (see e.g., U.S. Pat. Publ. No. US2005/0272083). Information about EGFR and other ErbB receptors including receptor homo- and hetero-dimers, receptor ligands, autophosphorylation sites, and signaling molecules involved in ErbB mediated signaling is known in the art (see e.g., Hynes and Lane, Nature Reviews Cancer 5: 341-354, 2005).

Exemplary c-Met activating mutations include point mutations, deletion mutations, insertion mutations, inversions or gene amplifications that lead to an increase in at least one biological activity of a c-Met protein, such as elevated tyrosine kinase activity, formation of receptor homodimers and heterodimers, enhanced ligand binding etc. Mutations can be located in any portion of the c-Met gene or regulatory regions associated with the gene, such as mutations in the kinase domain of c-Met. Exemplary c-Met activating mutations are mutations at residue positions N375, V13, V923, R175, V136, L229, S323, R988, S1058/T1010 and E168. Methods for detecting EGFR and c-Met mutations or gene amplifications are well known.

Exemplary cancers that are amenable to treatment by the bispecific molecules of the invention such as the bispecific EGFR/c-Met antibodies of the invention include epithelial cell cancers, breast cancer, ovarian cancer, lung cancer, non-small cell lung cancer (NSCLC), lung adenocarcinoma, small cell lung cancer, colorectal cancer, anal cancer, prostate cancer, kidney cancer, bladder cancer, head and neck cancer, pharynx cancer, cancer of the nose, pancreatic cancer, skin cancer, oral cancer, cancer of the tongue, esophageal cancer, vaginal cancer, cervical cancer, cancer of the spleen, testicular cancer, gastric cancer, cancer of the thymus, colon cancer, thyroid cancer, liver cancer (hepatocellular carcinoma (HCC)) or sporadic or hereditary papillary renal cell carcinoma (PRCC).

Another aspect of the invention is a method of treating a subject having cancer, comprising administering a therapeutically effective amount of the isolated bispecific EGFR/c-Met antibody of the invention to a patient in need thereof for a time sufficient to treat the cancer, wherein the subject is homozygous for phenylalanine at position 158 of CD16 (FcγRIIIa-158F/F genotype) or heterozygous for valine and pheynylalanine at position 158 of CD16 (FcγRIIIa-158F/V genotype). CD16 is also known as the Fc gamma receptor IIIa (FcγRIIIa) or the low affinity immunoglobulin gamma Fc region receptor III-A isoform. Valine/phenylalanine (V/F) polymorphism at FcγRIIIa protein residue position 158 has been shown to affect FcγRIIIa affinity to human IgG. Receptor with FcγRIIIa-158F/F or FcγRIIIa-158FN polymorphisms demonstrates reduced Fc engagement and therefore reduced ADCC when compared to the FcγRIIIa-158V/V. The lack of or low amount of fucose on human N-linked oligosaccharides improves the ability of the antibodies to induce ADCC due to improved binding of the antibodies to human FcγRIIIa (CD16) (Shields et al., J Biol Chem 277: 26733-40, 2002). The antibodies of the invention have reduced fucose content of about between 1% to about 10%. In some embodiments, the bispecific EGFR/c-Met antibody has a glycan structure with fucose content of about 50%, 40%, 45%, 40%, 35%, 30%, 25%, 20%, 15%, 10%, 9%, 8%, 7%, 6%, 5%, 4%, 3%, 2% or 1%. Therefore, the antibodies of the invention may be more efficacious in the treatment of patients with FcγRIIIa-158F/F or FcγRIIIa-158FN genotypes. Patients can be analyzed for their FcγRIIIa polymorphism using routine methods.

In some methods described herein, the antibodies of the invention may be used to treat a subject having cancer that is resistant or has acquired resistance to treatment with one or more EGFR inhibitors. Exemplary EGFR inhibitors for which cancer may acquire resistance are anti-EGFR antibodies cetuximab (Erbitux®), pantinumumab (Vectibix®), matuzumab, nimotuzumab, small molecule EGFR inhibitors Tarceva® (erlotinib), IRESSA (gefitinib), EKB-569 (pelitinib, irreversible EGFR TKI), pan-ErbB and other receptor tyrosine kinase inhibitors, lapatinib (EGFR and HER2 inhibitor), pelitinib (EGFR and HER2 inhibitor), vandetanib (ZD6474, ZACTIMA™, EGFR, VEGFR2 and RET TKI), PF00299804 (dacomitinib, irreversible pan-ErbB TKI), CI-1033 (irreversible pan-erbB TKI), afatinib (BIBW2992, irreversible pan-ErbB TKI), AV-412 (dual EGFR and ErbB2 inhibitor), EXEL-7647 (EGFR, ErbB2, GEVGR and EphB4 inhibitor), CO-1686 (irreversible mutant-selective EGFR TKI), AZD9291 (irreversible mutant-selective EGFR TKI), and HKI-272 (neratinib, irreversible EGFR/ErbB2 inhibitor). The methods described herein may be used to treat cancer that is resistant to treatment with gefitinib, erlotinib, afatinib, CO-1686, AZD9291 and/or cetuximab. An exemplary antibody that can be used is EM1-mAb.

Another aspect of the invention is a method of treating a subject having cancer, comprising administering a therapeutically effective amount of the isolated bispecific EGFR/c-Met antibody of the invention to a patient in need thereof for a time sufficient to treat the cancer, wherein the subject is resistant or has acquired resistance to treatment with erlotinib, gefitinib, afatinib, CO-1686, AZD9291 or cetuximab.

Various qualitative and/or quantitative methods may be used to determine if a subject is resistant, has developed or is susceptible to developing a resistance to treatment with an EGFR inhibitor. Symptoms that may be associated with resistance to an EGFR inhibitor include, for example, a decline or plateau of the well-being of the patient, an increase in the size of a tumor, arrested or slowed decline in growth of a tumor, and/or the spread of cancerous cells in the body from one location to other organs, tissues or cells. Re-establishment or worsening of various symptoms associated with cancer may also be an indication that a subject has developed or is susceptible to developing resistance to EGFR inhibitors, such as anorexia, cognitive dysfunction, depression, dyspnea, fatigue, hormonal disturbances, neutropenia, pain, peripheral neuropathy, and sexual dysfunction. The symptoms associated with cancer may vary according to the type of cancer. For example, symptoms associated with cervical cancer may include abnormal bleeding, unusual heavy vaginal discharge, pelvic pain that is not related to the normal menstrual cycle, bladder pain or pain during urination, and bleeding between regular menstrual periods, after sexual intercourse, douching, or pelvic exam. Symptoms associated with lung cancer may include persistent cough, coughing up blood, shortness of breath, wheezing chest pain, loss of appetite, losing weight without trying and fatigue. Symptoms for liver cancer may include loss of appetite and weight, abdominal pain, especially in the upper right part of abdomen that may extend into the back and shoulder, nausea and vomiting, general weakness and fatigue, an enlarged liver, abdominal swelling (ascites), and a yellow discoloration of the skin and the whites of eyes (jaundice). One skilled in oncology may readily identify symptoms associated with a particular cancer type.

Others means to determine if a subject has developed a resistance to an EGFR inhibitor include examining EGFR phosphorylation, ERK1/2 phosphorylation and/or AKT phosphorylation in cancer cells, where increased phosphorylation may be indicative that the subject has developed or is susceptible to developing resistance to an EGFR inhibitor. Methods of determining EGFR, ERK1/2 and/or AKT phosphorylation are well known and described herein. Identification of a subject who has developed a resistance to an EGFR inhibitor may involve detection of elevated c-Met expression levels or elevated c-Met activity, for example, arising from increased levels of circulating HGF, an activating mutation of the c-Met gene or a c-Met gene amplification.

Another embodiment of the invention is a method of treating NSCLC in a patient having an NSCLC tumor or tumor metastasis having an activating EGFR mutation or EGFR gene amplification, comprising administering to the patient a therapeutically effective amount of the bispecific EGFR/c-Met antibody of the invention.

The bispecific EGFR/c-Met antibodies of the invention can be used to treat non-small cell lung cancer (NSCLC), which includes squamous cell carcinoma, adenocarcinoma, and large cell carcinoma. In some embodiments, cells of the NSCLC have an epithelial phenotype. In some embodiments, the NSCLC has acquired resistance to treatment with one or more EGFR inhibitors.

In NSCLC, specific mutations in the EGFR gene are associated with high response rates (70-80%) to EGFR tyrosine kinase inhibitors (EGFR-TKIs). A 5 amino acid deletion in exon 19 or the point mutation L858R in EGFR are associated with EGFR-TKI sensitivity (Nakata and Gotoh, Expert Opin Ther Targets 16:771-781, 2012). These mutations result in a ligand-independent activation of the EGFR kinase activity. Activating EGFR mutations occur in 10-30% of NSCLC patients and are significantly more common in East Asians, women, never smokers, and patients with adenocarcinoma histology (Janne and Johnson Clin Cancer Res 12(14 Suppl): 4416s-4420s, 2006). EGFR gene amplification is also strongly correlated with response after EGFR-TKI treatment (Cappuzzo et al., J Natl Cancer Inst 97:643-55, 2005).

Although the majority of NSCLC patients with EGFR mutations initially respond to EGFR TKI therapy, virtually all acquire resistance that prevents a durable response. 50-60% of patients acquire resistance due to a second-site point mutation in the kinase domain of EGFR (T790M). Nearly 60% of all tumors that become resistant to EGFR tyrosine kinase inhibitors increase c-Met expression, amplify the c-Met gene, or increase its only known ligand, HGF (Turke et al., Cancer Cell, 17:77-88, 2010).

Another embodiments of the invention is a method of treating patient having cancer, comprising administering a therapeutically effective amount of the bispecific EGFR/c-Met antibody of the invention to a patient in need thereof for a time sufficient to treat the cancer, wherein the cancer is associated with an EGFR activating mutation, an EGFR gene amplification, increased levels of circulating HGF, a c-Met activating mutation, a c-Met gene amplification or a mutant KRAS.

In some embodiments the EGFR activating mutation is G719A, G719X (X being any amino acid), L861X (X being any amino acid), L858R, E746K, L747S, E749Q, A750P, A755V, V765M, L858P or T790M substitution, deletion of E746-A750, deletion of R748-P753, insertion of Ala (A) between M766 and A767, insertion of Ser, Val and Ala (SVA) between 5768 and V769, and insertion of Asn and Ser (NS) between P772 and H773.

Another embodiments of the invention is a method of treating patient having cancer, comprising administering a therapeutically effective amount of the bispecific EGFR/c-Met antibody of the invention to a patient in need thereof for a time sufficient to treat the cancer, wherein the cancer is associated with an EGFR mutation L858R, T790M or deletion of residues E746-A750 (del(E746, A750)), EGFR amplification or c-Met amplification.

In some embodiments, the cancer is associated with wild type EGFR and wild type c-Met.

In some embodiments, the cancer is associated with wild type EGFR and c-Met amplification.

In some embodiments, the cancer is associated with EGFR L858R and T790M mutations and wild type c-Met.

In some embodiments, the cancer is associated with EGFR deletion del (E764, A750) and wild type c-Met.

In some embodiments, the cancer is associated with EGFR deletion del(E764, A750) and c-Met amplification.

In some embodiments, the cancer is associated with EGFR deletion del(E764, A750), EGFR amplification and c-Met amplification.

In some embodiments, the patient has a NSCLC associated with EGFR L858R and T790M mutations and wild type c-Met.

In some embodiments, the patient has a NSCLC associated with EGFR amplification and wild type c-Met.

In some embodiments, the patient has a NSCLC associated with EGFR amplification and c-Met amplification.

In some embodiments, the patient has a NSCLC associated with EGFR deletion del(E764, A750) and wild type c-Met.

In some embodiments, the patient has a NSCLC associated with EGFR deletion del(E764, A750) and c-Met amplification.

In some embodiments, the patients are treated with the EM1-mAb of the invention. The EM1-mAb of the invention shows efficacy in in vivo tumor animal models, when the tumors are associated with L858R, T790M, del(E746, A750) EGFR, EGFR amplification, wild type c-Met and/or c-Met amplification. Amplification of EGFR or c-Met may be evaluated by standard methods, for example by determining the copy number of the EGFR or c-Met gene by southern blotting, FISH, or comparative genomic hybridization (CGH).

Another embodiments of the invention is a method of treating patient having cancer, comprising administering a therapeutically effective amount of the bispecific EGFR/c-Met antibody of the invention to a patient in need thereof for a time sufficient to treat the cancer, wherein the cancer is associated with EGFR mutations L858R, T790M or deletion of residues E746-A750 (del(E746, A750)), EGFR amplification or c-Met amplification, and mutant KRAS.

In some embodiments, the mutant KRAS has a G12V substitution. KRAS belongs to the family of RAS proto-oncogenes encoding guanosine triphosphatases (GTPases), and mediates EGFR signal transduction downstream of the receptor. Tumors with proto-oncogenic KRAS mutations such as the activating G12V or G12C mutation would therefore not be expected to be treatable by EGFR antibodies. Clinical studies with anti-EGFR antibodies cetuximab or panitumumab demonstrated that patients with KRAS-mutated colorectal tumors do not respond to these agents (Van Cutsem et al., N Eng J Med 360:1408-1417, 2009; Lievre et al., J Clin Oncol 26:374-379, 2008; Amado et al., J Clin Oncol 26:1626-1634m 2008). The bispecific EGFR/c-Met antibodies of the invention mediate KRAS mutant cell line killing via effective ADCC, and therefore, contrary to the current anti-EGFR therapies, may be efficacious in treatment of patients whose cancer is associated with KRAS activating mutations. Such exemplary antibody is the EM1-mAb.

The terms "treat" or "treatment" refers to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "therapeutically effective amount" refers to an amount effective, at dosages and for periods of time necessary, to achieve a desired therapeutic result. A therapeutically effective amount of the bispecific EGFR/c-Met antibody of the invention may vary according to factors such as the disease state, age, sex, and weight of the individual, and the ability of the bispecific EGFR/c-Met antibody of the invention to elicit a desired response in the individual. Exemplary indicators of an effective EGFR/c-Met therapeutic that may decline or abate in association with resistance include, for example, improved well-being of the patient, decrease or shrinkage of the size of a tumor, arrested or slowed growth of a tumor, and/or absence of metastasis of cancer cells to other locations in the body.

Administration/Pharmaceutical Compositions

The invention provides for pharmaceutical compositions comprising the bispecific EGFR/c-Met antibody of the invention and a pharmaceutically acceptable carrier. For therapeutic use, the bispecific EGFR/c-Met FN3 domain containing molecules, the EGFR-binding FN3 domains, the c-Met-binding FN3 domains or the bispecific EGFR/c-Met antibodies of the invention may be prepared as pharmaceutical compositions containing an effective amount of the domain, molecule or antibody as an active ingredient in a pharmaceutically acceptable carrier. The term "carrier" refers to a diluent, adjuvant, excipient, or vehicle with which the active compound is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules or antibodies of the invention in such pharmaceutical formulation may vary widely, i.e., from less than about 0.5%, usually to at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration for therapeutic use of the bispecific EGFR/c-Met FN3 domain containing molecules, the EGFR-binding FN3 domains, the c-Met-binding FN3 domains or the bispecific EGFR/c-Met antibodies of the invention may be any suitable route that delivers the agent to the host, such as parenteral administration, e.g., intradermal, intramuscular, intraperitoneal, intravenous or subcutaneous, pulmonary, transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Thus, a pharmaceutical composition of the invention for intramuscular injection may be prepared to contain 1 ml sterile buffered water, and between about 1 ng to about 100 mg/kg, e.g. about 50 ng to about 30 mg/kg or more preferably, about 5 mg to about 25 mg/kg, of the bispecific EGFR/c-Met FN3 domain containing molecules, the EGFR-binding FN3 domains or the c-Met-binding FN3 domains of the invention.

The bispecific EGFR/c-Met antibodies of the invention may be administered to a patient by any suitable route, for example parentally by intravenous (IV) infusion or bolus injection, intramuscularly or subcutaneously or intraperitoneally. IV infusion can be given over as little as 15 minutes, but more often for 30 minutes, 60 minutes, 90 minutes or even 2 or 3 hours. The bispecific EGFR/c-Met antibodies of the invention may also be injected directly into the site of disease (e.g., the tumor itself). The dose given to a patient having a cancer is sufficient to alleviate or at least partially arrest the disease being treated ("therapeutically effective amount") and may be sometimes 0.1 to 10 mg/kg body weight, for example 1, 2, 3, 4, 5, 6, 7, 8, 9 or 10 mg/kg, but may even higher, for example 15, 20, 30, 40, 50, 60, 70, 80, 90 or 100 mg/kg. A fixed unit dose may also be given, for example, 50, 100, 200, 500 or 1000 mg, or the dose may be based on the patient's surface area, e.g., 400, 300, 250, 200, or 100 mg/m$^2$. Usually between 1 and 8 doses, (e.g., 1, 2, 3, 4, 5, 6, 7 or 8) may be administered to treat cancer, but 10, 12, 20 or more doses may be given. Administration of the bispecific EGFR/c-Met antibody of the invention may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose.

For example, a pharmaceutical composition comprising the bispecific EGFR/c-Met antibody of the invention for intravenous infusion may be made up to contain about 200 ml of sterile Ringer's solution, and about 8 mg to about 2400 mg, about 400 mg to about 1600 mg, or about 400 mg to about 800 mg of the bispecific EGFR/c-Met antibody for administration to a 80 kg patient. Methods for preparing parenterally administrable compositions are well known and are described in more detail in, for example, "Remington's Pharmaceutical Science", 15th ed., Mack Publishing Company, Easton, Pa.

The bispecific EGFR/c-Met FN3 domain containing molecules, the EGFR-binding FN3 domains, the c-Met-binding FN3 domains or the bispecific EGFR/c-Met antibodies of the invention may be lyophilized for storage and reconstituted in a suitable carrier prior to use. This technique has been shown to be effective with conventional protein preparations and well known lyophilization and reconstitution techniques can be employed.

The bispecific EGFR/c-Met FN3 domain containing molecules, the EGFR-binding FN3 domains, the c-Met-binding FN3 domains or the bispecific EGFR/c-Met antibodies of the invention may be administered in combination with a second therapeutic agent simultaneously, sequentially or separately. The second therapeutic agent may be a chemotherapeutic agent or a targeted anti-cancer therapy.

The bispecific EGFR/c-Met antibody may be administered together with any one or more of the chemotherapeutic drugs or other anti-cancer therapeutics known to those of skill in the art. Chemotherapeutic agents are chemical compounds useful in the treatment of cancer and include growth inhibitory agents or other cytotoxic agents and include alkylating agents, anti-metabolites, anti-microtubule inhibitors, topoisomerase inhibitors, receptor tyrosine kinase inhibitors, angiogenesis inhibitors and the like. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophsphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-FU; folic acid analogues such as denopterin, methotrexate, pteropterin, trimetrexate; purine analogues such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; members of taxoid or taxane family, such as paclitaxel (TAXOL®docetaxel (TAXOTERE®) and analogues thereof; chlorambucil; gemcitabine; 6-thioguanine; mercaptopurine; methotrexate; platinum analogues such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; inhibitors of receptor tyrosine kinases and/or angiogenesis, including sorafenib (NEXAVAR®), sunitinib (SUTENT®), pazopanib (VOTRIENT™), toceranib (PALLADIA™), vandetanib (ZACTIMA™), cediranib (RECENTIN®), regorafenib (BAY 73-4506), axitinib (AG013736), lestaurtinib (CEP-701), erlotinib (TARCEVA®), gefitinib (IRESSA™), BIBW 2992 (TOVOK™), lapatinib (TYKERB®), neratinib (HKI-272), and the like, and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (FARESTON®); and anti-androgens such as flutamide, nilutamide, bicalutamide, leuprolide, and goserelin; and pharmaceutically acceptable salts, acids or derivatives of any of the above. Other conventional cytotoxic chemical compounds as those disclosed in Wiemann et al., 1985, in *Medical Oncology* (Calabresi et aL, eds.), Chapter 10, McMillan Publishing, are also applicable to the methods of the present invention.

Exemplary agents that may be used in combination with the bispecific EGFR/c-Met FN3 domain containing molecules, the EGFR-binding FN3 domains, the c-Met-binding FN3 domains or the bispecific EGFR/c-Met antibodies of the invention include tyrosine kinase inhibitors and targeted anti-cancer therapies such as Iressa® (gefitinib) and Tarceva (erlotinib) and other antagonists of HER2, HER3, HER4 or VEGF. Exemplary HER2 antagonists include CP-724-714, HERCEPTIN™ (trastuzumab), OMNITARG™ (pertuzumab), TAK-165, lapatinib (EGFR and HER2 inhibitor), and GW-282974. Exemplary HER3 antagonists include anti-Her3 antibodies (see e.g., U.S. Pat. Publ. No. US2004/0197332). Exemplary HER4 antagonists include anti-HER4 siRNAs (see e.g., Maatta et al., Mol Biol Cell 17: 67-79, 2006. An exemplary VEGF antagonist is Bevacizumab (Avastin™)

When a small molecule is used in combination with the bispecific EGFR/c-Met antibody of the invention, it is typically administered more often, preferably once a day, but 2, 3, 4 or more times per day is also possible, as is every two days, weekly or at some other interval. Small molecule drugs are often taken orally but parenteral administration is also possible, e.g., by IV infusion or bolus injection or subcutaneously or intramuscularly. Doses of small molecule drugs may typically be from 10 to 1000 mg, or about 100, 150, 200 or 250 mg.

When the bispecific EGFR/c-Met antibody of the invention is administered in combination with a second therapeutic agent, the combination may take place over any convenient timeframe. For example, the bispecific EGFR/c-Met antibody and the second therapeutic agent may be administered to a patient on the same day, and even in the same intravenous infusion. However, the bispecific EGFR/c-Met antibody and the second therapeutic agent may also be administered on alternating days or alternating weeks, fortnights or months, and so on. In some methods, the bispecific EGFR/c-Met antibody and the second therapeutic agent are administered with sufficient proximity in time that they are simultaneously present (e.g., in the serum) at detectable levels in the patient being treated. In some methods, an entire course of treatment of the bispecific EGFR/c-Met antibody consisting of a number of doses over a time period is followed or preceded by a course of treatment of the second therapeutic agent also consisting of a number of doses. In some methods, treatment with the bispecific EGFR/c-Met antibody administered second is begun if the patient has resistance or develops resistance to the second therapeutic agent administered initially. The patient may receive only a single course or multiple courses of treatment with one or both the bispecific EGFR/c-Met antibody and the second therapeutic agent. A recovery period of 1, 2 or several days or weeks may be used between administration of the bispecific EGFR/c-Met antibody and the second therapeutic agent. When a suitable treatment regiment has already been established for the second therapeutic agent, that regimen may be used in combination with the bispecific EGFR/c-Met antibody of the invention. For example, Tarceva® (erlotinib) is taken as a 100 mg or 150 mg pill once a day, and Iressa® (gefitinib) is taken as 250 mg tablet daily.

The bispecific EGFR/c-Met antibody, optionally in combination with the second therapeutic agent may be administered together with any form of radiation therapy including external beam radiation, intensity modulated radiation therapy (IMRT) and any form of radiosurgery including Gamma Knife, Cyberknife, Linac, and interstitial radiation (e.g. implanted radioactive seeds, GliaSite balloon), and/or with surgery. Combination with radiation therapy can be especially appropriate for head and neck cancer and brain tumors.

While having described the invention in general terms, the embodiments of the invention will be further disclosed in the following examples that should not be construed as limiting the scope of the claims.

EXAMPLE 1

Construction of Tencon libraries

Tencon (SEQ ID NO: 1) is an immunoglobulin-like scaffold, fibronectin type III (FN3) domain, designed from a consensus sequence of fifteen FN3 domains from human tenascin-C (Jacobs et al., Protein Engineering, Design, and Selection, 25:107-117, 2012; U.S. Pat. Publ. No. 2010/0216708). The crystal structure of Tencon shows six surface-exposed loops that connect seven beta-strands. These loops, or selected residues within each loop, can be randomized in order to construct libraries of fibronectin type III (FN3) domains that can be used to select novel molecules that bind to specific targets.

Tencon:
(SEQ ID NO 1)
LPAPKNLVVSEVTEDSLRLSWTAPDAAFDSFLIQYQESEKVGEAINLTV
PGSERSYDLTGLKPGTEYTVSIYGVKGGHRSNPLSAEFTT:

Construction of TCL1 Library

A library designed to randomize only the FG loop of Tencon (SEQ ID NO: 1), TCL1, was constructed for use with the cis-display system (Jacobs et al., Protein Engineering, Design, and Selection, 25:107-117, 2012). In this system, a single-strand DNA incorporating sequences for a Tac promoter, Tencon library coding sequence, RepA coding sequence, cis-element, and ori element is produced. Upon expression in an in vitro transcription/translation system, a complex is produced of the Tencon-RepA fusion protein bound in cis to the DNA from which it is encoded. Complexes that bind to a target molecule are then isolated and amplified by polymerase chain reaction (PCR), as described below.

Construction of the TCL1 library for use with cis-display was achieved by successive rounds of PCR to produce the final linear, double-stranded DNA molecules in two halves; the 5' fragment contains the promoter and Tencon sequences, while the 3' fragment contains the repA gene and the cis- and ori elements. These two halves are combined by restriction digest in order to produce the entire construct. The TCL1 library was designed to incorporate random amino acids only in the FG loop of Tencon, KGGHRSN (SEQ ID NO: 86). NNS codons were used in the construction of this library, resulting in the possible incorporation of all 20 amino acids and one stop codon into the FG loop. The TCL1 library contains six separate sub-libraries, each having a different randomized FG loop length, from 7 to 12 residues, in order to further increase diversity. Design of Tencon-based libraries are shown in Table 2.

TABLE 2

| Library | BC Loop Design | FG Loop Design |
|---------|----------------|----------------|
| WT Tencon | TAPDAAFD* | KGGHRSN** |
| TCL1 | TAPDAAFD* | XXXXXXX |
|  |  | XXXXXXXX |
|  |  | XXXXXXXXX |
|  |  | XXXXXXXXXX |
|  |  | XXXXXXXXXXX |
|  |  | XXXXXXXXXXXX |
| TCL2 | ######## | #####S## |

*TAPDAAFD: residues 22-28 of SEQ ID NO: 1;
**KGGHRSN: SEQ ID NO: 86
X refers to degenerate amino acids encoded by NNS codons.
# refers to the "designed distribution of amino acids" described in the text.

To construct the TCL1 library, successive rounds of PCR were performed to append the Tac promoter, build degeneracy into the FG loop, and add necessary restriction sites for final assembly. First, a DNA sequence containing the promoter sequence and Tencon sequence 5' of the FG loop was generated by PCR in two steps. DNA corresponding to the full Tencon gene sequence was used as a PCR template with primers POP2220 (SEQID NO: 2) and TC5'toFG (SEQID NO: 3). The resulting PCR product from this reaction was used as a template for the next round of PCR amplification with primers 130mer (SEQID NO: 4) and Tc5'toFG to complete the appending of the 5' and promoter sequences to Tencon. Next, diversity was introduced into the FG loop by amplifying the DNA product produced in the first step with forward primer POP2222 (SEQID NO: 5), and reverse primers TCF7 (SEQID NO: 6), TCF8 (SEQID NO: 7), TCF9 (SEQID NO: 8), TCF10 (SEQID NO: 9), TCF11 (SEQID N NO: 10), or TCF12 (SEQID NO: 11), which contain degenerate nucleotides. At least eight 100 µL PCR reactions were performed for each sub-library to minimize PCR cycles and maximize the diversity of the library. At least 5 µg of this PCR product were gel-purified and used in a subsequent PCR step, with primers POP2222 (SEQ ID NO: 5) and POP2234 (SEQID NO: 12), resulting in the attachment of a 6xHis tag and NotI restriction site to the 3' end of the Tencon sequence. This PCR reaction was carried out using only fifteen PCR cycles and at least 500 ng of template DNA. The resulting PCR product was gel-purified, digested with NotI restriction enzyme, and purified by Qiagen column.

The 3' fragment of the library is a constant DNA sequence containing elements for display, including a PspOMI restriction site, the coding region of the repA gene, and the cis- and ori elements. PCR reactions were performed using a plasmid (pCR4Blunt) (Invitrogen) containing this DNA fragment with M13 Forward and M13 Reverse primers. The resulting PCR products were digested by PspOMI overnight and gel-purified. To ligate the 5' portion of library DNA to the 3' DNA containing the repA gene, 2 pmol of 5' DNA were ligated to an equal molar amount of 3' repA DNA in the presence of NotI and PspOMI enzymes and T4 ligase. After overnight ligation at 37° C., a small portion of the ligated DNA was run on a gel to check ligation efficiency. The ligated library product was split into twelve PCR amplifications and a 12-cycle PCR reaction was run with primer pair POP2250 (SEQID NO: 13) and DidLigRev (SEQID NO: 14). The DNA yield for each sub-library of TCL1 library ranged from 32-34 µg.

To assess the quality of the library, a small portion of the working library was amplified with primers Tcon5new2 (SEQID NO: 15) and Tcon6 (SEQID NO: 16), and was cloned into a modified pET vector via ligase-independent cloning. The plasmid DNA was transformed into BL21-GOLD (DE3) competent cells (Stratagene) and 96 randomly picked colonies were sequenced using a T7 promoter primer. No duplicate sequences were found. Overall, approximately 70-85% of clones had a complete promoter and Tencon coding sequence without frame-shift mutation. The functional sequence rate, which excludes clones with STOP codons, was between 59% and 80%.

Construction of TCL2 Library

TCL2 library was constructed in which both the BC and the FG loops of Tencon were randomized and the distribution of amino acids at each position was strictly controlled. Table 3 shows the amino acid distribution at desired loop positions in the TCL2 library. The designed amino acid distribution had two aims. First, the library was biased toward residues that were predicted to be structurally important for Tencon folding and stability based on analysis of the Tencon crystal structure and/or from homology modeling. For example, position 29 was fixed to be only a subset of hydrophobic amino acids, as this residue was buried in the hydrophobic core of the Tencon fold. A second layer of design included biasing the amino acid distribution toward that of residues preferentially found in the heavy chain HCDR3 of antibodies, to efficiently produce high-affinity binders (Birtalan et al., J Mol Biol 377:1518-28, 2008; Olson et al., Protein Sci 16:476-84, 2007). Towards this goal, the "designed distribution" of Table 3 refers to the distribution as follows: 6% alanine, 6% arginine, 3.9% asparagine, 7.5% aspartic acid, 2.5% glutamic acid, 1.5% glutamine, 15% glycine, 2.3% histidine, 2.5% isoleucine, 5% leucine, 1.5% lysine, 2.5% phenylalanine, 4% proline, 10% serine, 4.5% threonine, 4% tryptophan, 17.3% tyrosine, and 4% valine. This distribution is devoid of methionine, cysteine, and STOP codons.

TABLE 3

| Residue Position* | WT residues | Distribution in the TCL2 library |
|---|---|---|
| 22 | T | designed distribution |
| 23 | A | designed distribution |
| 24 | P | 50% P + designed distribution |
| 25 | D | designed distribution |
| 26 | A | 20% A + 20% G + designed distribution |
| 27 | A | designed distribution |
| 28 | F | 20% F, 20% I, 20% L, 20% V, 20% Y |
| 29 | D | 33% D, 33% E, 33% T |
| 75 | K | designed distribution |
| 76 | G | designed distribution |
| 77 | G | designed distribution |
| 78 | H | designed distribution |
| 79 | R | designed distribution |
| 80 | S | 100% S |
| 81 | N | designed distribution |
| 82 | P | 50% P + designed distribution |

*residue numbering is based on Tencon sequence of SEQ ID NO: 1

The 5' fragment of the TCL2 library contained the promoter and the coding region of Tencon (SEQ ID NO: 1), which was chemically synthesized as a library pool (Sloning Biotechnology). This pool of DNA contained at least $1 \times 10^{11}$ different members. At the end of the fragment, a BsaI restriction site was included in the design for ligation to RepA.

The 3' fragment of the library was a constant DNA sequence containing elements for display including a 6xHis tag, the coding region of the repA gene, and the cis-element. The DNA was prepared by PCR reaction using an existing DNA template (above), and primers LS1008 (SEQID NO: 17) and DidLigRev (SEQID NO: 14). To assemble the complete TCL2 library, a total of 1 µg of BsaI-digested 5' Tencon library DNA was ligated to 3.5 µg of the 3' fragment that was prepared by restriction digestion with the same enzyme. After overnight ligation, the DNA was purified by Qiagen column and the DNA was quantified by measuring absorbance at 260 nm. The ligated library product was amplified by a 12-cycle PCR reaction with primer pair POP2250 (SEQID NO: 13) and DidLigRev (SEQID NO: 14). A total of 72 reactions were performed, each containing 50 ng of ligated DNA products as a template. The total yield of TCL2 working library DNA was about 100 µg. A small portion of the working library was sub-cloned and sequenced, as described above for library TCL1. No duplicate sequences were found. About 80% of the sequences contained complete promoter and Tencon coding sequences with no frame-shift mutations.

Construction of TCL14 Library

The top (BC, DE, and FG) and the bottom (AB, CD, and EF) loops, e.g., the reported binding surfaces in the FN3 domains are separated by the beta-strands that form the center of the FN3 structure. Alternative surfaces residing on the two "sides" of the FN3 domains having different shapes than the surfaces formed by loops only are formed at one side of the FN3 domain by two anti-parallel beta-strands, the C and the F beta-strands, and the CD and FG loops, and is herein called the C-CD-F-FG surface.

A library randomizing an alternative surface of Tencon was generated by randomizing select surface exposed residues of the C and F strands, as well as portions of the CD and FG loops as shown in FIG. 1. A Tencon variant, Tencon27 (SEQ ID NO: 99) having following substitutions when compared to Tencon (SEQ ID NO: 1) was used to generate the library; E11R L17A, N46V, E86I. A full description of the methods used to construct this library is described in US. Pat. Publ. No. US2013/0226834

EXAMPLE 2

Selection of Fibronectin Type III (FN3) Domains that Bind EGFR and Inhibit EGF Binding Library Screening Cis-display was used to select EGFR binding domains from the TCL1 and TCL2 libraries. A recombinant human extracellular domain of EGFR fused to an IgG1 Fc (R&D Systems) was biotinylated using standard methods and used for panning (residues 25-645 of full length EGFR of SEQ ID NO: 73). For in vitro transcription and translation (ITT), 2-6 µg of library DNA were incubated with 0.1 mM complete amino acids, 1×S30 premix components, and 30 µL, of S30 extract (Promega) in a total volume of 100 µL, and incubated at 30° C. After 1 hour, 450 µL, of blocking solution (PBS pH 7.4, supplemented with 2% bovine serum albumin, 100 µg/mL herring sperm DNA, and 1 mg/mL heparin) were added and the reaction was incubated on ice for 15 minutes. EGFR-Fc:EGF complexes were assembled at molar ratios of 1:1 and 10:1 EGFR to EGF by mixing recombinant human EGF (R&D Systems) with biotinylated recombinant EGFR-Fc in blocking solution for 1 hour at room temperature. For binding, 500 µL, of blocked ITT reactions were mixed with 100 µL, of EGFR-Fc:EGF complexes and incubated for 1 hour at room temperature, after which bound complexes were pulled down with magnetic neutravidin or streptavidin beads (Seradyne). Unbound library members were removed by successive washes with PBST and PBS. After washing, DNA was eluted from the bound complexes by heating to 65° C. for 10 minutes, amplified by PCR, and attached to a DNA fragment encoding RepA by restriction digestion and ligation for further rounds of panning. High affinity binders were isolated by successively lowering the concentration of target EGFR-Fc during each round from 200 nM to 50 nM and increasing the washing stringency. In rounds 4 and 5, unbound and weakly bound FN3 domains were removed by washing in the presence of a 10-fold molar excess of non-biotinylated EGFR-Fc overnight in PBS.

Following panning, selected FN3 domains were amplified by PCR using oligonucleotides Tcon5new2 (SEQID NO: 15) and Tcon6 (SEQID NO: 16), subcloned into a pET vector modified to include a ligase independent cloning site, and transformed into BL21-GOLD (DE3) (Stratagene) cells for soluble expression in E. coli using standard molecular biology techniques. A gene sequence encoding a C-terminal poly-histidine tag was added to each FN3 domain to enable purification and detection. Cultures were grown to an optical density of 0.6-0.8 in 2YT medium supplemented with 100 µg/mL carbenicillin in 1-mL 96-well blocks at 37° C. before the addition of IPTG to 1 mM, at which point the temperature was reduced to 30° C. Cells were harvested approximately 16 hours later by centrifugation and frozen at −20° C. Cell lysis was achieved by incubating each pellet in 0.6 mL of BugBuster® HT lysis buffer (Novagen EMD Biosciences) with shaking at room temperature for 45 minutes.

Selection of FN3 Domains that Bind EGFR on Cells

To assess the ability of different FN3 domains to bind EGFR in a more physiological context, their ability to bind A431 cells was measured. A431 cells (American Type Culture Collection, cat. #CRL-1555) over-express EGFR with ~2×10$^6$ receptors per cell. Cells were plated at 5,000/well in opaque black 96-well plates and allowed to attach overnight at 37° C., in a humidified 5% CO$_2$ atmosphere. FN3 domain-expressing bacterial lysates were diluted 1,000-fold into FACS stain buffer (Becton Dickinson) and incubated for 1 hour at room temperature in triplicate plates. Lysates were removed and cells were washed 3 times with 150 µL/well of FACS stain buffer. Cells were incubated with 50 µL/well of anti-penta His-Alexa488 antibody conjugate (Qiagen) diluted 1:100 in FACS stain buffer for 20 minutes at room temperature. Cells were washed 3 times with 150 µL/well of FACS stain buffer, after which wells were filled with 100 µL of FACS stain buffer and read for fluorescence at 488 nm using an Acumen eX3 reader. Bacterial lysates containing FN3 domains were screened for their ability to bind A431 cells (1320 crude bacterial lysates for TCL1 and TCL2 libraries) and 516 positive clones were identified, where binding was ≥10-fold over the background signal. 300 lysates from the TCL14 library were screened for binding, resulting in 58 unique FN3 domain sequences that bind to EGFR.

Selection of FN3 Domains that Inhibit EGF Binding to EGFR on Cells

To better characterize the mechanism of EGFR binding, the ability of various identified FN3 domain clones to bind EGFR in an EGF-competitive manner was measured using A431 cells and run in parallel with the A431 binding assay screen. A431 cells were plated at 5,000/well in opaque black 96-well plates and allowed to attach overnight at 37° C. in a humidified 5% CO$_2$ atmosphere. Cells were incubated with 50 µL/well of 1:1,000 diluted bacterial lysate for 1 hour at room temperature in triplicate plates. Biotinylated EGF (Invitrogen, cat. #E-3477) was added to each well for a final concentration of 30 ng/mL and incubated for 10 minutes at room temperature. Cells were washed 3 times with 150 µL/well of FACS stain buffer. Cells were incubated with 50 µL/well of streptavidin-phycoerythrin conjugate (Invitrogen) diluted 1:100 in FACS stain buffer for 20 minutes at room temperature. Cells were washed 3 times with 150 µL/well of FACS stain buffer, after which wells were filled with 100 µL of FACS stain buffer and read for fluorescence at 600 nm using an Acumen eX3 reader.

Bacterial lysates containing the FN3 domains were screened in the EGF competition assay described above. 1320 crude bacterial lysates from TCL1 and TCL2 libraries were screened resulting in 451 positive clones that inhibited EGF binding by >50%.

Expression and Purification of Identified FN3 Domains Binding EGFR

His-tagged FN3 domains were purified from clarified E. coli lysates with His MultiTrap™ HP plates (GE Healthcare) and eluted in buffer containing 20 mM sodium phosphate, 500 mM sodium chloride, and 250 mM imidazole at pH 7.4. Purified samples were exchanged into PBS pH 7.4 for analysis using PD MultiTrap™ G-25 plates (GE Healthcare).

Size Exclusion Chromatography Analysis

Size exclusion chromatography was used to determine the aggregation state of the FN3 domains binding EGFR. Aliquots (10 μL) of each purified FN3 domain were injected onto a Superdex 75 5/150 column (GE Healthcare) at a flow rate of 0.3 mL/min in a mobile phase of PBS pH 7.4. Elution from the column was monitored by absorbance at 280 nm. FN3 domains that exhibited high levels of aggregation by SEC were excluded from further analysis.

Off-Rate of Selected EGFR-binding FN3 Domains from EGFR-Fc

Select EGFR-binding FN3 domains were screened to identify those with slow off-rates ($k_{off}$) in binding to EGFR-Fc on a ProteOn XPR-36 instrument (Bio-Rad) to facilitate selection of high affinity binders. Goat anti-human Fc IgG (R&D systems), at a concentration of 5 μg/mL, was directly immobilized via amine coupling (at pH 5.0) on all 6 ligand channels in horizontal orientation on the chip with a flow rate of 30 μL/min in PBS containing 0.005% Tween-20. The immobilization densities averaged about 1500 Response Units (RU) with less than 5% variation among different channels. EGFR-Fc was captured on the anti-human Fc IgG surface to a density around 600 RU in vertical ligand orientation. All tested FN3 domains were normalized to a concentration of 1 μM and tested for their binding in horizontal orientation. All 6 analyte channels were used for the FN3 domains to maximize screening throughput. The dissociation phase was monitored for 10 minutes at a flow rate of 100 μL/min. The inter-spot binding signals were used as references to monitor non-specific binding between analytes and the immobilized IgG surface, and were subtracted from all binding responses. The processed binding data were locally fit to a 1:1 simple Langmuir binding model to extract the $k_{off}$ for each FN3 domain binding to captured EGFR-Fc.

Inhibition of EGF-Stimulated EGFR Phosphorylation

Purified EGFR-binding FN3 domains were tested for their ability to inhibit EGF-stimulated phosphorylation of EGFR in A431 cells at a single concentration. EGFR phosphorylation was monitored using the EGFR phospho(Tyr1173) kit (Meso Scale Discovery). Cells were plated at 20,000/well in clear 96-well tissue culture-treated plates (Nunc) in 100 μL/well of RPMI medium (Gibco) containing GlutaMAX™ with 10% fetal bovine serum (FBS) (Gibco) and allowed to attach overnight at 37° C. in a humidified 5% CO₂ atmosphere. Culture medium was removed completely and cells were starved overnight in 100 μL/well of medium containing no FBS at 37° C. in a humidified 5% CO₂ atmosphere. Cells were then treated with 100 μL/well of pre-warmed (37° C.) starvation medium containing EGFR-binding FN3 domains at a concentration of 2 μM for 1 hour at 37° C. in a humidified 5% CO₂ atmosphere. Controls were treated with starvation medium only. Cells were stimulated by the addition and gentle mixing of 100 μL/well of pre-warmed (37° C.) starvation medium containing 100 ng/mL recombinant human EGF (R&D Systems, cat. #236-EG), for final concentrations of 50 ng/mL EGF and 1 μM EGFR-binding FN3 domain, and incubation at 37° C., 5% CO₂ for 15 minutes. One set of control wells was left un-stimulated as negative controls. Medium was completely removed and cells were lysed with 100 μL/well of Complete Lysis Buffer (Meso Scale Discovery) for 10 minutes at room temperature with shaking, as per the manufacturer's instructions. Assay plates configured for measuring EGFR phosphorylated on tyrosine 1173 (Meso Scale Discovery) were blocked with the provided blocking solution as per the manufacturer's instructions at room temperature for 1.5-2 hours. Plates were then washed 4 times with 200 μL/well of 1× Tris Wash Buffer (Meso Scale Discovery). Aliquots of cell lysate (30 μL/well) were transferred to assay plates, which were covered with plate sealing film (VWR) and incubated at room temperature with shaking for 1 hour. Assay plates were washed 4 times with 200 μL/well of Tris Wash Buffer, after which 25 μL of ice-cold Detection Antibody Solution (Meso Scale Discovery) were added to each well, being careful not to introduce bubbles. Plates were incubated at room temperature with shaking for 1 hour, followed by 4 washes with 200 μL/well of Tris Wash Buffer. Signals were detected by addition of 150 μL/well of Read Buffer (Meso Scale Discovery) and reading on a SECTOR® Imager 6000 instrument (Meso Scale Discovery) using manufacturer-installed assay-specific default settings. Percent inhibition of the EGF-stimulated positive control signal was calculated for each EGFR-binding FN3 domain.

Inhibition of EGF-stimulated EGFR phosphorylation was measured for 232 identified clones from the TCL1 and TCL2 libraries. 22 of these clones inhibited EGFR phosphorylation by ≥50% at 1 μM concentration. After removal of clones that either expressed poorly or were judged to be multimeric by size exclusion chromatography, nine clones were carried forward for further biological characterization. The BC and FG loop sequences of these clones are shown in Table 4. Eight of the nine selected clones had a common FG loop sequence (HNVYKDTNMRGL; SEQ ID NO: 95) and areas of significant similarity were seen between several clones in their BC loop sequences.

TABLE 4

| FN3 Domain | | BC Loop | | FG Loop | |
|---|---|---|---|---|---|
| Clone ID | SEQ ID NO: | Sequence | SEQ ID NO: | Sequence | SEQ ID NO: |
| P53A1R5-17 | 18 | ADPHGFYD | 87 | HNVYKDTNMRGL | 95 |
| P54AR4-17 | 19 | TYDRDGYD | 88 | HNVYKDTNMRGL | 95 |
| P54AR4-47 | 20 | WDPFSFYD | 89 | HNVYKDTNMRGL | 95 |
| P54AR4-48 | 21 | DDPRGFYE | 90 | HNVYKDTNMRGL | 95 |
| P54AR4-73 | 22 | TWPYADLD | 91 | HNVYKDTNMRGL | 95 |
| P54AR4-74 | 23 | GYNGDHFD | 92 | HNVYKDTNMRGL | 95 |
| P54AR4-81 | 24 | DYDLGVYD | 93 | HNVYKDTNMRGL | 95 |
| P54AR4-83 | 25 | DDPWDFYE | 94 | HNVYKDTNMRGL | 95 |
| P54CR4-31 | 26 | TAPDAAFD | 85 | LGSYVFEHDVM | 96 |

EXAMPLE 3

Characterization of EGFR-binding FN3 Domains that Inhibit EGF Binding

Large-scale Expression, Purification, and Endotoxin Removal

The FN3 domains shown in Table 4 were scaled up to provide more material for detailed characterization. An overnight culture containing each EGFR-binding FN3 domain variant was used to inoculate 0.8 L of Terrific broth medium supplemented with 100 μg/mL ampicillin at a 1/80 dilution of overnight culture into fresh medium, and incubated with shaking at 37° C. The culture was induced when the optical density at 600 nm reached ~1.2-1.5 by addition of IPTG to a final concentration of 1 mM and the temperature was reduced to 30° C. After 4 hours, cells were collected by centrifugation and the cell pellet was stored at −80° C. until needed.

For cell lysis, the thawed pellet was resuspended in 1× BugBuster® supplemented with 25 U/mL Benzonase® (Sigma-Aldrich) and 1 kU/mL rLysozyme™ (Novagen EMD Biosciences) at a ratio of 5 mL of BugBuster® per gram of pellet. Lysis proceeded for 1 hour at room temperature with gentle agitation, followed by centrifugation at 56,000×g for 50 minutes at 4° C. The supernatant was collected and filtered through a 0.2 μm filter, then loaded on to a 5-mL HisTrap FF column pre-equilibrated with Buffer A (50 mM Tris-HCl pH 7.5, 500 mM NaCl, 10 mM imidazole) using a GE Healthcare ÄKTAexplorer 100s chromatography system. The column was washed with 20 column volumes of Buffer A and further washed with 16% Buffer B (50 mM Tris-HCl pH7.5, 500 mM NaCl, 250 mM imidazole) for 6 column volumes. The FN3 domains were eluted with 50% B for 10 column volumes, followed by a gradient from 50-100% B over 6 column volumes. Fractions containing the FN3 domain protein were pooled, concentrated using a Millipore 10K MWCO concentrator, and filtered before loading onto a HiLoad™ 16/60 Superdex™ 75 column (GE Healthcare) pre-equilibrated with PBS. The protein monomer peak eluting from the size exclusion column was retained.

Endotoxins were removed using a batch approach with ActiClean Etox resin (Sterogene Bioseparations). Prior to endotoxin removal, the resin was pre-treated with 1 N NaOH for 2 hours at 37° C. (or overnight at 4° C.) and washed extensively with PBS until the pH had stabilized to ~7 as measured with pH indicator paper. The purified protein was filtered through a 0.2 μm filter before adding to 1 mL of Etox resin at a ratio of 10 mL of protein to 1 mL of resin. The binding of endotoxin to resin was allowed to proceed at room temperature for at least 2 hours with gentle rotation. The resin was removed by centrifugation at 500×g for 2 minutes and the protein supernatant was retained. Endotoxin levels were measured using EndoSafe®-PTS™ cartridges and analyzed on an EndoSafe®-MCS reader (Charles River). If endotoxin levels were above 5 EU/mg after the first Etox treatment, the above procedure was repeated until endotoxin levels were decreased to ≥5 EU/mg. In cases where the endotoxin level was above 5 EU/mg and stabilized after two consecutive treatments with Etox, anion exchange or hydrophobic interaction chromatography conditions were established for the protein to remove the remaining endotoxins.

Affinity Determination of Selected EGFR-binding FN3 Domains to EGFR-Fc (EGFR-Fc Affinity)

Binding affinity of selected EGFR-binding FN3 domains to recombinant EGFR extracellular domain was further characterized by surface Plasmon resonance methods using a Proteon Instrument (BioRad). The assay set-up (chip preparation, EGFR-Fc capture) was similar to that described above for off-rate analysis. Selected EGFR binding FN3 domains were tested at 1 μM concentration in 3-fold dilution series in the horizontal orientation. A buffer sample was also injected to monitor the baseline stability. The dissociation phase for all concentrations of each EGFR-binding FN3 domain was monitored at a flow rate of 100 μL/min for 30 minutes (for those with $k_{off}$~$10^{-2}$ s$^{-1}$ from off-rate screening), or 1 hour (for those with $k_{off}$~$10^{-3}$ s$^{-1}$ or slower). Two sets of reference data were subtracted from the response data: 1) the inter-spot signals to correct for the non-specific interactions between the EGFR-binding FN3 domain and the immobilized IgG surface; 2) the buffer channel signals to correct for baseline drifting due to the dissociation of captured EGFR-Fc surface over time. The processed binding data at all concentrations for each FN3 domain were globally fit to a 1:1 simple Langmuir binding model to extract estimates of the kinetic ($k_{on}$, $k_{off}$) and affinity ($K_D$) constants. Table 5 shows the kinetic constants for each of the constructs, with the affinity varying from 200 pM to 9.6 nM.

Binding of Selected EGFR-binding FN3 Domains to EGFR on Cells ("A431 Cell Binding Assay")

A431 cells were plated at 5,000/well in opaque black 96-well plates and allowed to attach overnight at 37° C., in a humidified 5% $CO_2$ atmosphere. Purified EGFR-binding FN3 domains (1.5 nM to 30 μM) were added to the cells (in 50 uL) for 1 hour at room temperature in triplicate plates. Supernatant was removed and cells were washed 3 times with 150 μL/well of FACS stain buffer. Cells were incubated with 50 μL/well of anti-penta His-Alexa488 antibody conjugate (Qiagen) diluted 1:100 in FACS stain buffer for 20 minutes at room temperature. Cells were washed 3 times with 150 μL/well of FACS stain buffer, after which wells were filled with 100 μL of FACS stain buffer and read for fluorescence at 488 nm using an Acumen eX3 reader. Data were plotted as raw fluorescence signal against the logarithm of the FN3 domain molar concentration and fitted to a sigmoidal dose-response curve with variable slope using GraphPad Prism 4 (GraphPad Software) to calculate $EC_{50}$ values. Table 5 reports the $EC_{50}$ for each of the constructs ranging from 2.2 nM to >20 μM.

Inhibition of EGF Binding to EGFR on Cells using Selected EGFR-binding FN3 Domains (A431 cell EGF Competition Assay)

A431 cells were plated at 5,000/well in opaque black 96-well plates and allowed to attach overnight at 37° C., in a humidified 5% $CO_2$ atmosphere. Purified EGFR-binding FN3 domains (1.5 nM to 30 μM) were added to the cells (50 μL/well) for 1 hour at room temperature in triplicate plates. Biotinylated EGF (Invitrogen, Cat #: E-3477) was added to each well to give a final concentration of 30 ng/mL and incubated for 10 minutes at room temperature. Cells were washed 3 times with 150 μL/well of FACS stain buffer. Cells were incubated with 50 μL/well of streptavidin-phycoerythrin conjugate (Invitrogen) diluted 1:100 in FACS stain buffer for 20 minutes at room temperature. Cells were washed 3 times with 150 μL/well of FACS stain buffer, after which wells were filled with 100 μL of FACS stain buffer and read for fluorescence at 600 nm using an Acumen eX3 reader. Data were plotted as the raw fluorescence signal against the logarithm of FN3 domain molar concentration and fitted to a sigmoidal dose-response curve with variable slope using GraphPad Prism 4 (GraphPad Software) to calculate $IC_{50}$ values. Table 5 reports the $IC_{50}$ values ranging from 1.8 nM to 121 nM.

Inhibition of EGF-Stimulated EGFR Phosphorylation (Phoshpo EGFR Assay)

Select FN3 domains that significantly inhibited EGF-stimulated EGFR phosphorylation were assessed more completely by measuring $IC_{50}$ values for inhibition. Inhibition of EGF-stimulated EGFR phosphorylation was assessed at varying FN3 domain concentrations (0.5 nM to 10 μM) as described above in "inhibition of EGF stimulated EGFR phosphorylation". Data were plotted as electrochemiluminescence signal against the logarithm of the FN3 domain molar concentration and $IC_{50}$ values were determined by fitting data to a sigmoidal dose response with variable slope using GraphPad Prism 4 (GraphPad Software). Table 5 shows the $IC_{50}$ values which ranged from 18 nM to >2.5 μm.

Inhibition of Human Tumor Cell Growth (NCI-H292 growth and NCI-H322 Growth Assay)

Inhibition of EGFR-dependent cell growth was assessed by measuring viability of the EGFR over-expressing human tumor cell lines, NCI-H292 and NCI-H322 (American Type Culture Collection, cat. #CRL-1848 & #CRL-5806, respectively), following exposure to EGFR-binding FN3 domains. Cells were plated at 500 cells/well (NCI-H292) or 1,000 cells/well (NCI-H322) in opaque white 96-well tissue culture-treated plates (Nunc) in 100 µL/well of RPMI medium (Gibco) containing GlutaMAX™ and 10 mM HEPES, supplemented with 10% heat inactivated fetal bovine serum (Gibco) and 1% penicillin/streptomycin (Gibco), and allowed to attach overnight at 37° C. in a humidified 5% $CO_2$ atmosphere. Cells were treated by addition of 5 µL/well of phosphate-buffered saline (PBS) containing a concentration range of EGFR-binding FN3 domains. Controls were treated with 5 µL/well of PBS only or 25 mM ethylenediaminetetraacetic acid in PBS. Cells were incubated at 37° C., 5% $CO_2$ for 120 hours. Viable cells were detected by addition of 75 µL/well of CellTiter-Glo® reagent (Promega), followed by mixing on a plate shaker for 2 minutes, and incubation in the dark at room temperature for a further 10 minutes. Plates were read on a SpectraMax M5 plate reader (Molecular Devices) set to luminescence mode, with a read time of 0.5 seconds/well against a blank of medium only. Data were plotted as a percentage of PBS-treated cell growth against the logarithm of FN3 domain molar concentration. $IC_{50}$ values were determined by fitting data to the equation for a sigmoidal dose response with variable slope using GraphPad Prism 4 (GraphPad Software). Table 5 shows $IC_{50}$ values ranging from 5.9 nM to 1.15 µM and 9.2 nM to >3.1 µM, using the NCI-H292 and NCI-H322 cells respectively. Table 5 shows the summary of biological properties of EGFR-binding FN3 domains for each assay.

that each variant molecule was stabilized significantly, with an average increase in the $T_m$ of 18.5° C.

TABLE 6

| FN3 domain Clone | SEQ ID NO: | $T_m$ (° C.) |
|---|---|---|
| P54AR4-83 | 25 | 50.6 |
| P54AR4-83v2 | 27 | 69.8 |
| P54CR4-31 | 26 | 60.9 |
| P54CR4-31v2 | 28 | 78.9 |
| P54AR4-37 | 22 | 45.9 |
| P54AR4-37v2 | 29 | 64.2 |

EXAMPLE 5

Selection of Fibronectin Type III (FN3) Domains that Bind c-Met and Inhibit HGF Binding Panning on Human c-Met The TCL14 library was screened against biotinylated-human c-Met extracellular domain (bt-c-Met) to identify FN3 domains capable of specifically binding c-Met. For selections, 3 µg of TCL14 library was in vitro transcribed and translated (IVTT) in *E. coli* S30 Linear Extract (Promega, Madison, Wis.) and the expressed library blocked with Cis Block (2% BSA (Sigma-Aldrich, St. Louis, Mo.), 100 µg/ml Herring Sperm DNA (Promega), 1 mg/mL heparin (Sigma-Aldrich)). For selections, bt-c-Met was added at concentrations of 400 nM (Round 1), 200 nM (Rounds 2 and 3) and 100 nM (Rounds 4 and 5). Bound library members were recovered using neutravidin magnetic beads (Thermo Fisher, Rockford, Ill.) (Rounds 1, 3, and 5) or streptavidin magnetic beads (Promega) (Rounds 2 and 4) and unbound

TABLE 5

| FN3 Domain Clone ID | SEQ ID NO: | EGFR-Fc Affinity (nM) | A431 Cell Binding $EC_{50}$ (nM) | A431 Cell EGF Competition $IC_{50}$ (nM) | Phospho-EGFR $IC_{50}$ (nM) | NCI-H292 Growth $IC_{50}$ (nM) | NCI-H322 Growth $IC_{50}$ (nM) |
|---|---|---|---|---|---|---|---|
| P53A1R5-17 | 18 | 1.89 | 4.0 | 9.8 | >2500 | 86 | 65 |
| P54AR4-17 | 19 | 9.62 | 16 | 21 | 184 | ND | ND |
| P54AR4-47 | 20 | 2.51 | 8.6 | 7.1 | 295 | 44 | 39 |
| P54AR4-48 | 21 | 7.78 | 12 | 9.8 | 170 | ND | ND |
| P54AR4-73 | 22 | 0.197 | 9.4 | 4.6 | 141 | 83 | 73 |
| P54AR4-74 | 23 | ND | 77 | ND | ND | ND | ND |
| P54AR4-81 | 24 | ND | 84 | 121 | ND | ND | ND |
| P54AR4-83 | 25 | 0.255 | 2.2 | 1.8 | 18 | 5.9 | 9.2 |
| P54CR4-31 | 26 | 0.383 | >20000 | 55 | 179 | 1150 | >3073 |

EXAMPLE 4

Engineering of EGFR-Binding FN3 Domains

A subset of the EGFR binding FN3 domains was engineered to increase the conformational stability of each molecule. The mutations L17A, N46V, and E86I which have been shown to improve FN3 domain stability (described in US Pat. Publ. No. US2011/0274623) were incorporated into clones P54AR4-83, P54CR4-31, and P54AR4-37 by DNA synthesis. The new mutants, P54AR5-83v2, P54CR431-v2, and P54AR4-37v2 were expressed and purified as described above. Differential scanning calorimetry in PBS was used to assess the stability of each mutant in order to compare it to that of the corresponding parent molecule. Table 6 shows library members were removed by washing the beads 5-14 times with 500 uL PBS-T followed by 2 washes with 500 µL PBS.

Additional selection rounds were performed to identify FN3 domains molecules with improved affinities. Briefly, outputs from round 5 were prepared as described above and subjected to additional iterative rounds of selection with the following changes: incubation with bt-c-Met was decreased from 1 hour to 15 minutes and bead capture was decreased from 20 minutes to 15 minutes, bt-c-Met decreased to 25 nM (Rounds 6 and 7) or 2.5 nM (Rounds 8 and 9), and an additional 1 hour wash was performed in the presence of an excess of non-biotinylated c-Met. The goal of these changes was to simultaneously select for binders with a potentially faster on-rate and a slower off-rate yielding a substantially lower $K_D$.

Rounds 5, 7 and 9 outputs were PCR cloned into a modified pET 15 vector (EMD Biosciences, Gibbstown, N.J.) containing a ligase independent cloning site (pET15-LIC) using TCON6 (SEQID No. 30) and TCON5 E86I short (SEQID No. 31) primers, and the proteins were expressed as C-terminal His6-tagged proteins after transformations and IPTG induction (1 mM final, 30° C. for 16 hours) using standard protocols. The cells were harvested by centrifugation and subsequently lysed with Bugbuster HT (EMD Biosciences) supplemented with 0.2 mg/mL Chicken Egg White Lysozyme (Sigma-Aldrich). The bacterial lysates were clarified by centrifugation and the supernatants were transferred to new 96 deep-well plates.

Screening for FN3 Domains that Inhibit HGF Binding to c-Met

FN3 domains present in $E.\ coli$ lysates were screened for their ability to inhibit HGF binding to purified c-Met extracellular domain in a biochemical format. Recombinant human c-Met Fc chimera (0.5 µg/mL in PBS, 100 µL/well) was coated on 96-well White Maxisorp Plates (Nunc) and incubated overnight at 4° C. The plates were washed two times with 300 µl/well of Tris-buffered saline with 0.05% Tween 20 (TBS-T, Sigma-Aldrich) on a Biotek plate washer. Assay plates were blocked with StartingBlock T20 (200 µL/well, Thermo Fisher Scientific, Rockland, Ill.) for 1 hour at room temperature (RT) with shaking and again washed twice with 300 µl of TBS-T. FN3 domain lysates were diluted in StartingBlock T20 (from 1:10 to 1:100,000) using the Hamilton STARplus robotics system. Lysates (50 µL/well) were incubated on assay plates for 1 hour at RT with shaking. Without washing the plates, bt-HGF (1 µg/mL in StartingBlock T20, 50 µL/well, biotinylated) was added to the plate for 30 min at RT while shaking. Control wells containing Tencon27 lysates received either Starting Block T20 or diluted bt-HGF. Plates were then washed four times with 300 µl/well of TBS-T and incubated with 100 µl/well of Streptavidin-HRP (1:2000 in TBS-T, Jackson Immunoresearch, West Grove, Pa.) for 30-40 minutes at RT with shaking. Again the plates were washed four times with TBS-T. To develop signal, POD Chemiluminescence Substrate (50 µL/well, Roche Diagnostics, Indianapolis, Ind.), prepared according to manufacturer's instructions, was added to the plate and within approximately 3 minutes luminescence was read on the Molecular Devices M5 using SoftMax Pro. Percent inhibition was determined using the following calculation: $100-((RLU_{sample}-Mean\ RLU_{No\ bt-HGF\ control})/(Mean\ RLU_{bt-HGF\ control}-Mean\ RLU_{No\ bt-HGF\ control})*100)$. Percent inhibition values of 50% or greater were considered hits.

High-throughput Expression and Purification of FN3 Domains

His-tagged FN3 domains were purified from clarified $E.\ coli$ lysates with His MultiTrap™ HP plates (GE Healthcare) and eluted in buffer containing 20 mM sodium phosphate, 500 mM sodium chloride, and 250 mM imidazole at pH 7.4. Purified samples were exchanged into PBS pH 7.4 for analysis using PD MultiTrap™ G-25 plates (GE Healthcare).

$IC_{50}$ Determination of Inhibition of HGF Binding to c-Met

Select FN3 domains were further characterized in the HGF competition assay. Dose response curves for purified FN3 domains were generated utilizing the assay described above (starting concentrations of 5 µM). Percent inhibition values were calculated. The data were plotted as % inhibition against the logarithm of FN3 domain molar concentrations and $IC_{50}$ values were determined by fitting data to a sigmoidal dose response with variable slope using GraphPad Prism 4.

35 unique sequences were identified from Round 5 to exhibit activity at dilutions of 1:10, with $IC_{50}$ values ranging from 0.5 to 1500 nM. Round 7 yielded 39 unique sequences with activity at dilutions of 1:100 and $IC_{50}$ values ranging from 0.16 to 2.9 nM. 66 unique sequences were identified from Round 9, where hits were defined as being active at dilutions of 1:1000. $IC_{50}$ values as low as 0.2 nM were observed in Round 9 (Table 8).

Affinity Determination of Selected c-Met-Binding FN3 Domains to c-Met-Fc (EGFR-Fc Affinity)

Affinities were determined for select c-Met binding FN3 domains as is described in Example 3 for affinity determination fo selected EGFR-binding FN3 domains, except that c-Met-Fc was used in the assays.

EXAMPLE 6

Characterization of FN3 Domains that Bind c-Met and Inhibit HGF Binding

FN3 domains were expressed and purified as described above in Example 2. Size exclusion chromatography and kinetic analysis was done as described above in Examples 1 and 2, respectively. Table 7 shows the sequences of the C-strand, CD loop, F-strand, and FG loop, and a SEQ ID NO: for the entire amino acid sequence for each domain.

TABLE 7

| Clone Name | SEQ ID NO: | C loop | CD strand | F loop | FG strand |
|---|---|---|---|---|---|
| P114AR5P74-A5 | 32 | FDSFWIRYDE | VVVGGE | TEYYVNILGV | KGGSISV |
| P114AR5P75-E9 | 33 | FDSFFIRYDE | FLRSGE | TEYWVTILGV | KGGLVST |
| P114AR7P92-F3 | 34 | FDSFWIRYFE | FLGSGE | TEYIVNIMGV | KGGSISH |
| P114AR7P92-F6 | 35 | FDSFWIRYFE | FLGSGE | TEYVVNILGV | KGGGLSV |
| P114AR7P92-G8 | 36 | FDSFVIRYFE | FLGSGE | TEYVVQILGV | KGGYISI |
| P114AR7P92-H5 | 37 | FDSFWIRYLE | FLLGGE | TEYVVQIMGV | KGGTVSP |
| P114AR7P93-D11 | 38 | FDSFWIRYFE | FLGSGE | TEYVVGINGV | KGGYISY |
| P114AR7P93-G8 | 39 | FDSFWIRYFE | FLGSGE | TEYGVTINGV | KGGRVST |

TABLE 7-continued

| Clone Name | SEQ ID NO: | C loop | CD strand F loop | FG strand |
|---|---|---|---|---|
| P114AR7P93-H9 | 40 | FDSFWIRYFE | FLGSGE TEYVVQIIGV | KGGHISL |
| P114AR7P94-A3 | 41 | FDSFWIRYFE | FLGSGE TEYVVNIMGV | KGGKISP |
| P114AR7P94-E5 | 42 | FDSFWIRYFE | FLGSGE TEYAVNIMGV | KGGRVSV |
| P114AR7P95-B9 | 43 | FDSFWIRYFE | FLGSGE TEYVVQILGV | KGGSISV |
| P114AR7P95-D3 | 44 | FDSFWIRYFE | FLGSGE TEYVVNIMGV | KGGSISY |
| P114AR7P95-D4 | 45 | FDSFWIRYFE | FLGSGE TEYVVQILGV | KGGYISI |
| P114AR7P95-E3 | 46 | FDSFWIRYFE | FLGSGE TEYVVQIMGV | KGGTVSP |
| P114AR7P95-F10 | 47 | FDSFWIRYFE | FTTAGE TEYVVNIMGV | KGGSISP |
| P114AR7P95-G7 | 48 | FDSFWIRYFE | LLSTGE TEYVVNIMGV | KGGSISP |
| P114AR7P95-H8 | 49 | FDSFWIRYFE | FVSKGE TEYVVNIMGV | KGGSISP |

C loop residues correspond to residues 28-37 of indicated SEQ ID NO
CD strand residues correspond to residues 38-43 of indicated SEQ ID NO
F loop residues correspond to residues 65-74 of indicated SEQ ID NO
FG strand residues correspond to residues 75-81 of indicated SEQ ID NO Binding of Selected c-Met-binding FN3 Domains to c-Met on Cells ("H441 Cell Binding Assay")

NCI-H441 cells (Cat # HTB-174, American Type Culture Collection, Manassas, Va.) were plated at 20,000 cells per well in Poly-D-lysine coated black clear bottom 96-well plates (BD Biosciences, San Jose, Calif.) and allowed to attach overnight at 37° C., 5% $CO_2$. Purified FN3 domains (50 µL/well; 0 to 1000 nM) were added to the cells for 1 hour at 4° C. in duplicate plates. Supernatant was removed and cells were washed three times with FACS stain buffer (150 µL/well, BD Biosciences, cat #554657). Cells were incubated with biotinylated-anti HIS antibody (diluted 1:160 in FACS stain buffer, 50 µL/well, R&D Systems, cat # BAM050) for 30 minutes at 4° C. Cells were washed three times with FACS stain buffer (150 µL/well), after which wells were incubated with anti mouse IgG1-Alexa 488 conjugated antibody (diluted 1:80 in FACS stain buffer, 50 µL/well, Life Technologies, cat # A21121) for 30 minutes at 4° C. Cells were washed three times with FACS stain buffer (150 µL/well) and left in FACS stain buffer (50 µL/well). Total fluorescence was determined using an Acumen eX3 reader. Data were plotted as raw fluorescence signal against the logarithm of the FN3 domain molar concentration and fitted to a sigmoidal dose-response curve with variable slope using GraphPad Prism 4 (GraphPad Software) to calculate $EC_{50}$ values. FN3 domains were found to exhibit a range of binding activities, with $EC_{50}$ values between 1.4 nM and 22.0 nM, as shown in Table 8.

Inhibition of HGF-Stimulated c-Met Phosphorylation

Purified FN3 domains were tested for their ability to inhibit HGF-stimulated phosphorylation of c-Met in NCI-H441, using the c-Met phospho(Tyr1349) kit from Meso Scale Discovery (Gaithersburg, Md.). Cells were plated at 20,000/well in clear 96-well tissue culture-treated plates in 100 µL/well of RPMI medium (containing Glutamax and HEPES, Life Technologies) with 10% fetal bovine serum (FBS; Life Technologies) and allowed to attach overnight at 37° C., 5% $CO_2$. Culture medium was removed completely and cells were starved overnight in serum-free RPMI medium (100 µL/well) at 37° C., 5% $CO_2$. Cells were then replenished with fresh serum-free RPMI medium (100 µL/well) containing FN3 domains at a concentration of 20 µM and below for 1 hour at 37° C., 5% $CO_2$. Controls were treated with medium only. Cells were stimulated with 100 ng/mL recombinant human HGF (100 µL/well, R&D Systems cat #294-HGN) and incubated at 37° C., 5% $CO_2$ for 15 minutes. One set of control wells was left un-stimulated as negative controls. Medium was then completely removed and cells were lysed with Complete Lysis Buffer (50 µL/well, Meso Scale Discovery) for 10 minutes at RT with shaking, as per manufacturer's instructions. Assay plates configured for measuring phosphorylated c-Met were blocked with the provided blocking solution as per the manufacturer's instructions at room temperature for 1 hour. Plates were then washed three times with Tris Wash Buffer (200 µL/well, Meso Scale Discovery). Cell lysates (30 µL/well) were transferred to assay plates, and incubated at RT with shaking for 1 hour. Assay plates were then washed four times with Tris Wash Buffer, after which ice-cold Detection Antibody Solution (25 µL/well, Meso Scale Discovery) was added to each well for 1 hr at RT with shaking. Plates were again rinsed four times with Tris Wash Buffer. Signals were detected by addition of 150 Read Buffer (150 µL/well, Meso Scale Discovery) and reading on a SECTOR® Imager 6000 instrument (Meso Scale Discovery) using manufacturer-installed assay-specific default settings. Data were plotted as electrochemiluminescence signal against the logarithm of FN3 domain molar concentration and $IC_{50}$ values were determined by fitting data to a sigmoidal dose response with variable slope using GraphPad Prism 4. FN3 domains were found to inhibit phosphorylated c-Met with $IC_{50}$ values ranging from 4.6 nM to 1415 nM as shown in Table 8.

Inhibition of Human Tumor Cell Growth or Viability

Inhibition of c-Met-dependent cell growth was assessed by measuring viability of U87-MG cells (American Type Culture Collection, cat # HTB-14), following exposure to c-Met-binding FN3 domains. Cells were plated at 8000 cells per well in opaque white 96-well tissue culture-treated plates (Nunc) in 100 µL/well of RPMI medium, supplemented with 10% FBS and allowed to attach overnight at 37° C., 5% CO$_2$. Twenty-four hours after plating, medium was aspirated and cells were replenished with serum-free RPMI medium. Twenty-four hours after serum starvation, cells were treated by addition of serum-free medium containing c-Met-binding FN3 domains (30 µL/well). Cells were incubated at 37° C., 5% CO$_2$ for 72 hours. Viable cells were detected by addition of 100 µL/well of CellTiter-Glo® reagent (Promega), followed by mixing on a plate shaker for 10 minutes. Plates were read on a SpectraMax M5 plate reader (Molecular Devices) set to luminescence mode, with a read time of 0.5 seconds/well. Data were plotted as raw luminescence units (RLU) against the logarithm of FN3 domain molar concentration. IC$_{50}$ values were determined by fitting data to an equation for a sigmoidal dose response with variable slope using GraphPad Prism 4. Table 8 reports IC$_{50}$ values ranging from 1 nM to >1000 nM. Characteristics of the c-Met binding FN3 domains are summarized in Table 8.

TABLE 8

| Clone Name | SEQ ID NO: | Affinity (Kd, nM) | HGF competition IC$_{50}$ (nM) | H441 Cell binding (EC$_{50}$, nM) | pMet inhibition in H441 cells (IC$_{50}$, nM) | Inhibition of Proliferation of U87-MG cells (IC$_{50}$, nM) |
|---|---|---|---|---|---|---|
| P114AR5P74-A5 | 32 | 10.1 | 5.2 | 18.7 | 1078 | 464.4 |
| P114AR5P75-E9 | 33 | 45.8 | 51.9 | ND | 1415 | 1193.9 |
| P114AR7P92-F3 | 34 | 0.4 | 0.2 | 1.5 | 8.3 | 2.7 |
| P114AR7P92-F6 | 35 | 3.1 | 2.2 | 4.9 | 165.3 | 350.5 |
| P114AR7P92-G8 | 36 | 1.0 | 1.6 | 5.9 | 155.3 | 123.9 |
| P114AR7P92-H5 | 37 | 11.6 | ND | 22.0 | 766.4 | 672.3 |
| P114AR7P93-D11 | 38 | ND | ND | 2.3 | 16 | 14.4 |
| P114AR7P93-G8 | 39 | 6.9 | 1 | 3.8 | 459.5 | 103.5 |
| P114AR7P93-H9 | 40 | 3.3 | 2.9 | 12.9 | 288.2 | 269.9 |
| P114AR7P94-A3 | 41 | 0.4 | 0.2 | 1.4 | 5 | 9.3 |
| P114AR7P94-E5 | 42 | 4.2 | 0.7 | 3.4 | 124.3 | 195.6 |
| P114AR7P95-B9 | 43 | 0.5 | 0.3 | ND | 9.8 | 17.4 |
| P114AR7P95-D3 | 44 | 0.3 | 0.2 | 1.5 | 4.6 | 1.7 |
| P114AR7P95-D4 | 45 | 0.4 | ND | 1.4 | 19.5 | 19.4 |
| P114AR7P95-E3 | 46 | 1.5 | ND | 3.2 | 204.6 | 209.2 |
| P114AR7P95-F10 | 47 | 4.2 | 1.4 | 4.4 | 187.6 | 129.7 |
| P114AR7P95-G7 | 48 | 20.0 | ND | 11.3 | 659.3 | 692 |
| P114AR7P95-H8 | 49 | 3.7 | ND | 4.1 | 209.8 | 280.7 |

Thermal Stability of c-Met-Binding FN3 Domains
Differential Scanning Calorimetry in PBS was used to Assess the Stability of each FN3 Domain. Results of the Experiment are shown in Table 9.

TABLE 9

| Clone Name | SEQ ID NO: | Thermal Stability (Tm, C.) |
|---|---|---|
| P114AR5P74-A5 | 32 | 74.1 |
| P114AR5P75-E9 | 33 | ND |
| P114AR7P92-F3 | 34 | 81.5 |
| P114AR7P92-F6 | 35 | 76.8 |
| P114AR7P92-G8 | 36 | 90.9 |
| P114AR7P92-H5 | 37 | 87 |
| P114AR7P93-D11 | 38 | ND |
| P114AR7P93-G8 | 39 | 76.8 |
| P114AR7P93-H9 | 40 | 88.2 |
| P114AR7P94-A3 | 41 | 86.2 |
| P114AR7P94-E5 | 42 | 80 |
| P114AR7P95-B9 | 43 | 86.3 |
| P114AR7P95-D3 | 44 | 82 |
| P114AR7P95-D4 | 45 | 85.3 |
| P114AR7P95-E3 | 46 | 94.2 |
| P114AR7P95-F10 | 47 | 85.2 |
| P114AR7P95-G7 | 48 | 87.2 |
| P114AR7P95-H8 | 49 | 83 |

EXAMPLE 7

Generation and Characterization of Bispecific Anti-EGFR/c-Met Molecules

Generation of Bispecific EGFR/c-Met Molecules
Numerous combinations of the EGFR and c-Met-binding FN3 domains described in Examples 1-6 were joined into bispecific molecules capable of binding to both EGFR and c-Met. Additionally, EGFR-binding FN3 domains having amino acid sequences shown in SEQ ID NOs: 107-110 and c-Met binding FN3 domains having amino acid sequences shown in SEQ ID NOs: 111-114 were made and joined into bispecific molecules. Synthetic genes were created to encode for the amino acid sequences described in SEQ ID NOs: 50-72 and 106 (Table 10) such that the following format was maintained: EGFR-binding FN3 domain followed by a peptide linker followed by a c-Met-binding FN3 domain. A poly-histidine tag was incorporated at the C-terminus to aid purification. In addition to those molecules described in Table 10, the linker between the two FN3 domains was varied according to length, sequence composition and structure according to those listed in Table 11. It is envisioned that a number of other linkers could be used to link such FN3 domains Bispecific EGFR/c-Met molecules were expressed and purified from E. coli as described for monospecific EGFR or c-Met FN3 domains using IMAC and gel filtration chromatography steps.

TABLE 10

| Bispecifcic EGFR/c-Met molecule Clone ID | SEQ ID NO: | EGFR-binding FN3 comain Clone ID | SEQ ID NO: | cMET-binding FN3 domain Clone ID | SEQ ID NO: | Linker Sequence | SEQ ID NO: |
|---|---|---|---|---|---|---|---|
| ECB1 | 50 | P54AR4-83v2 | 27 | P114AR5P74-A5 | 32 | (GGGGS)$_4$ | 79 |
| ECB2 | 51 | P54AR4-83v2 | 27 | P114AR7P94-A3 | 41 | (GGGGS)$_4$ | 79 |
| ECB3 | 52 | P54AR4-83v2 | 27 | P114AR7P93-H9 | 40 | (GGGGS)$_4$ | 79 |
| ECB4 | 53 | P54AR4-83v2 | 27 | P114AR5P75-E9 | 33 | (GGGGS)$_4$ | 79 |
| ECB5 | 54 | P53A1R5-17v2 | 107 | P114AR7P94-A3 | 41 | (GGGGS)$_4$ | 79 |
| ECB6 | 55 | P53A1R5-17v2 | 107 | P114AR7P93-H9 | 40 | (GGGGS)$_4$ | 79 |
| ECB7 | 56 | P53A1R5-17v2 | 107 | P114AR5P75-E9 | 33 | (GGGGS)$_4$ | 79 |
| ECB15 | 57 | P54AR4-83v2 | 27 | P114AR7P94-A3 | 41 | (AP)$_5$ | 81 |
| ECB27 | 58 | P54AR4-83v2 | 27 | P114AR5P74-A5 | 32 | (AP)$_5$ | 81 |
| ECB60 | 59 | P53A1R5-17v2 | 107 | P114AR7P94-A3 | 41 | (AP)$_5$ | 81 |
| ECB37 | 60 | P53A1R5-17v2 | 107 | P114AR5P74-A5 | 32 | (AP)$_5$ | 81 |
| ECB94 | 61 | P54AR4-83v22 | 108 | P114AR7P94-A3v22 | 111 | (AP)$_5$ | 81 |
| ECB95 | 62 | P54AR4-83v22 | 108 | P114AR9P121-A6v2 | 112 | (AP)$_5$ | 81 |
| ECB96 | 63 | P54AR4-83v22 | 108 | P114AR9P122-A7v2 | 113 | (AP)$_5$ | 81 |
| ECB97 | 64 | P54AR4-83v22 | 108 | P114AR7P95-C5v2 | 114 | (AP)$_5$ | 81 |
| ECB106 | 65 | P54AR4-83v23 | 109 | P114AR7P94-A3v22 | 111 | (AP)$_5$ | 81 |
| ECB107 | 66 | P54AR4-83v23 | 109 | P114AR9P121-A6v2 | 112 | (AP)$_5$ | 81 |
| ECB108 | 67 | P54AR4-83v23 | 109 | P114AR9P122-A7v2 | 113 | (AP)$_5$ | 81 |
| ECB109 | 68 | P54AR4-83v23 | 109 | P114AR7P95-C5v2 | 114 | (AP)$_5$ | 81 |
| ECB118 | 69 | P53A1R5-17v22 | 110 | P114AR7P94-A3v22 | 111 | (AP)$_5$ | 81 |
| ECB119 | 70 | P53A1R5-17v22 | 110 | P114AR9P121-A6v2 | 112 | (AP)$_5$ | 81 |
| ECB120 | 71 | P53A1R5-17v22 | 110 | P114AR9P122-A7v2 | 113 | (AP)$_5$ | 81 |
| ECB121 | 72 | P53A1R5-17v22 | 110 | P114AR7P95-C5v2 | 114 | (AP)$_5$ | 81 |
| ECB91 | 106 | P54AR4-83v22 | 108 | P114AR7P95-C5v2 | 114 | (AP)$_5$ | 81 |
| ECB18 | 118 | P54AR4-83v2 | 27 | P114AR5P74-A5 | 32 | (AP)$_5$ | 81 |
| ECB28 | 119 | P53A1R5-17v2 | 107 | P114AR5P74-A5 | 32 | (AP)$_5$ | 81 |
| ECB38 | 120 | P54AR4-83v2 | 27 | P114AR7P94-A3 | 41 | (AP)$_5$ | 81 |
| ECB39 | 121 | P53A1R5-17v2 | 107 | P114AR7P94-A3 | 41 | (AP)$_5$ | 81 |

TABLE 11

| Linker | SEQ ID NO: | Linker length in amino acids | Structure |
|---|---|---|---|
| GS | 78 | 2 | Disordered |
| GGGGS | 105 | 5 | Disordered |
| (GGGGS)$_4$ | 79 | 20 | Disordered |
| (AP)$_2$ | 80 | 4 | Rigid |
| (AP)$_5$ | 81 | 5 | Rigid |
| (AP)$_{10}$ | 82 | 20 | Rigid |
| (AP)$_{20}$ | 83 | 40 | Rigid |
| A(EAAAK)$_5$AAA | 84 | 29 | α-helical |

Bispecific EGFR/c-Met Molecules Enhance Potency Compared to Monospecific Molecules Alone, Suggesting Avidity NCI-H292 cells were plated in 96 well plates in RPMI medium containing 10% FBS. 24 hours later, medium was replaced with serum free RPMI. 24 hours after serum starvation, cells were treated with varying concentrations of FN3 domains: either a high affinity monospecific EGFR FN3 domain (P54AR4-83v2), a weak affinity monospecific c-Met FN3 domain (P114AR5P74-A5), the mixture of the two monospecific EGFR and c-Met FN3 domains, or a bispecific EGFR/c-Met molecules comprised of the low affinity c-Met FN3 domain linked to the high affinity EGFR FN3 domain (ECB1). Cells were treated for 1 h with the monospecific or bispecific molecules and then stimulated with EGF, HGF, or a combination of EGF and HGF for 15 minutes at 37° C., 5% CO$_2$. Cells were lysed with MSD Lysis Buffer and cell signaling was assessed using appropriate MSD Assay plates, according to manufacturer's instructions, as described above.

Figure 4:
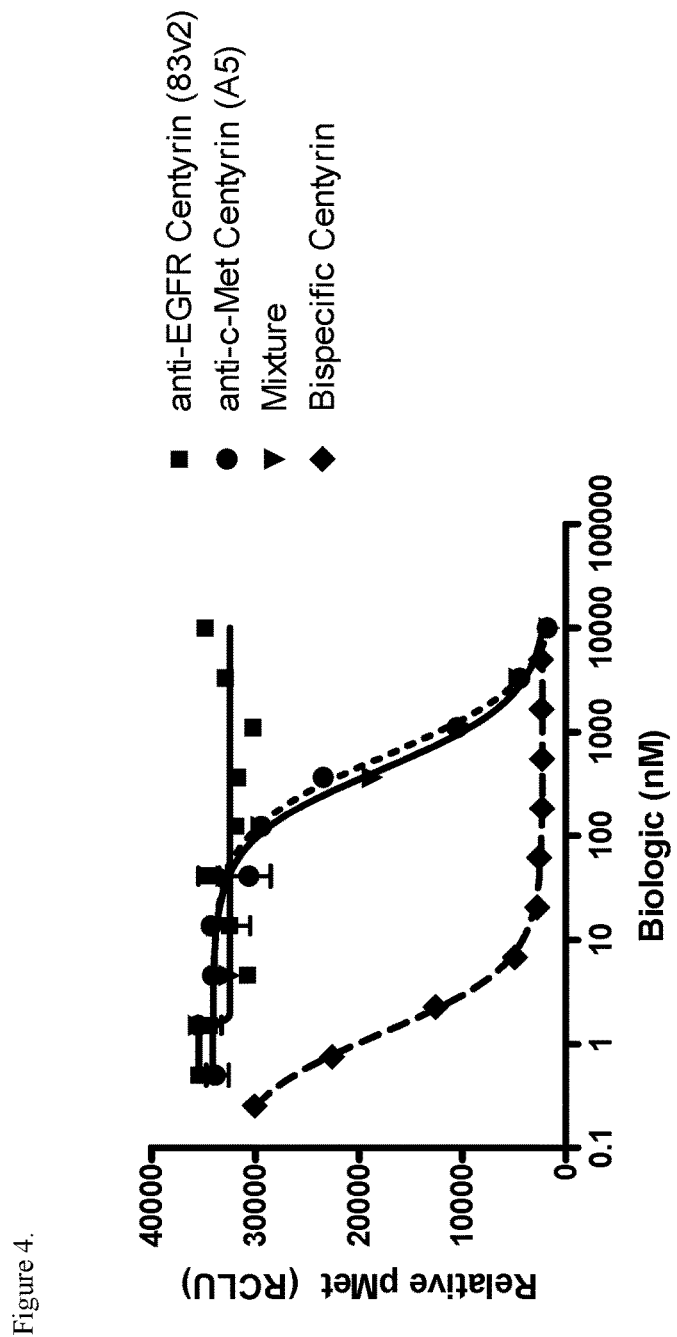
FIG. 4. Inhibition of c-Met phosphorylation in NCI-H292 cells pre-treated with monospecific or bispecific FN3 domain containing molecules and stimulated with HGF is shown. Substantial increase in the potency of the bispecific EGFR/c-Met molecule (ECB1) was observed when compared to a monospecific c-Met-binding FN3 domain (P114AR5P74-A5, shown as A5 in the Figure) on its own or in combination with an EGFR-binding FN3 domain (P54AR4-83v2, shown as 83v2 in the Figure).

The low affinity c-Met FN3 domain inhibited phosphorylation of c-Met with an IC$_{50}$ of 610 nM (FIG. 4). As expected the EGFR FN3 domain was not able to inhibit c-Met phosphorylation and the mixture of the mono-specific molecules looked identical to the c-Met FN3 domain alone. However, the bi-specific EGFR/c-Met molecule inhibited phosphorylation of c-Met with an IC$_{50}$ of 1 nM (FIG. 4), providing more than a 2-log shift in improving potency relative to the c-Met monospecific alone.

Figure 5:
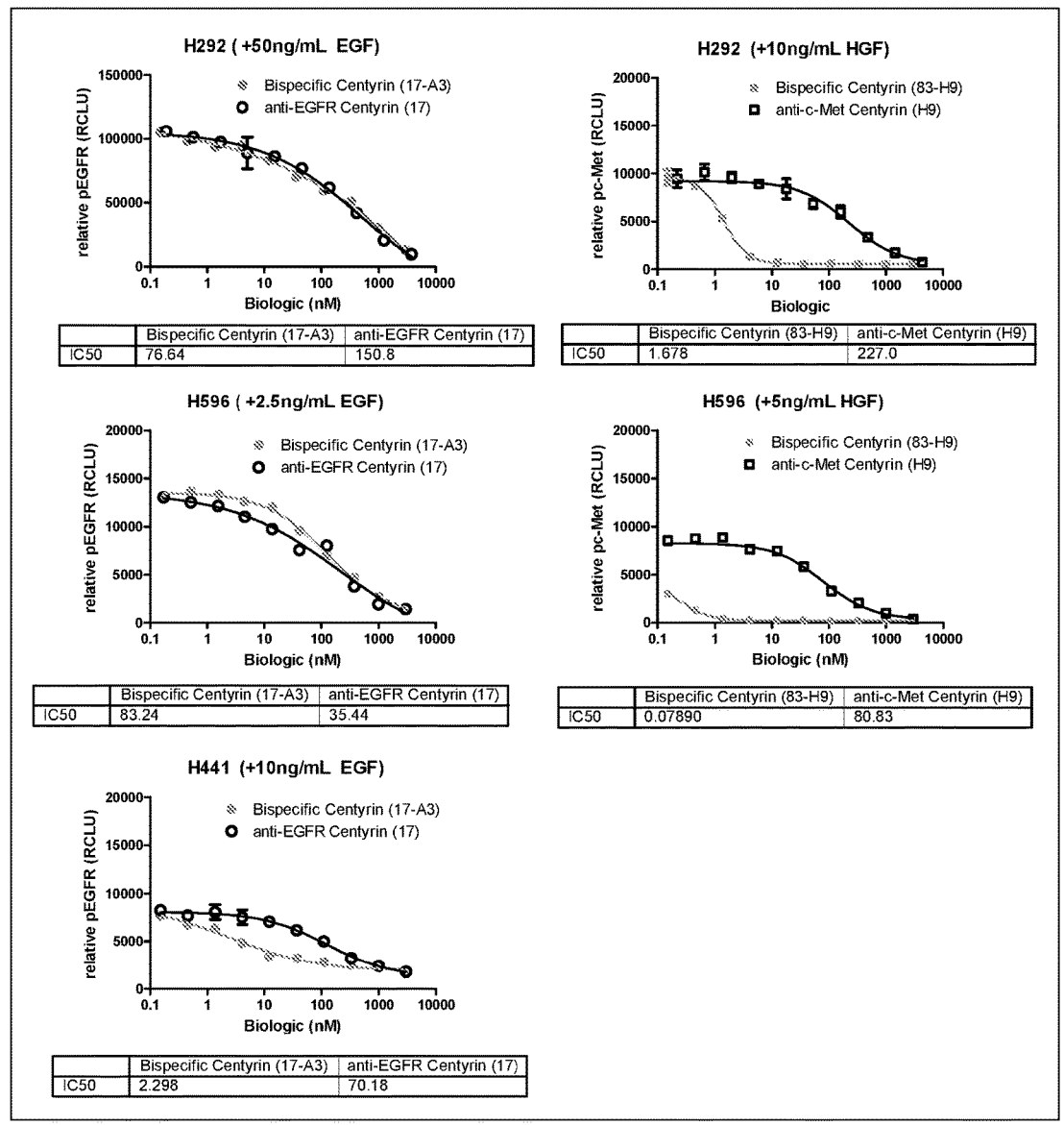
FIG. 5. Inhibition of EGFR and c-Met phosphorylation in cells pre-treated with monospecific or bispecific FN3 domain containing molecules. In cell lines expressing high levels of EGFR, NCI-H292 (FIG. 5A) and H596 (FIG. 5B), anti-EGFR monospecific and bispecific FN3 domain containing molecules are equally potent at decreasing EGFR phosphorylation. In cell lines expressing low levels of EGFR relative to c-Met, NCI-H441 (FIG. 5C), bispecific EGFR/c-Met molecules improve the potency for inhibition of EGFR phosphorylation compared to the monospecific EGFR-binding FN3 domain alone. In cell lines with low levels of c-Met, relative to EGFR, NCI-H292 (FIG. 5D) and H596 (FIG. 5E), inhibition of c-Met phosphorylation is significantly potentiated with bispecific EGFR/c-Met molecule, compared to monospecific c-Met-binding FN3 domain only. Molecules used in the study were: bispecific ECB5 (shown as 17-A3 in the Figure), monospecific EGFR-binding FN3 domain P53A1R5-17 (shown as "17" in the Figure), bispecific EGFR/c-Met molecule ECB3 (shown as 83-H9 in the Figure), and monospecific c-Met binding FN3 domain P114AR7P93-H9 (shown as H9 in the Figure).

The potential for the bispecific EGFR/c-Met molecule to enhance the inhibition of c-Met and/or EGFR phosphorylation through an avidity effect was evaluated in multiple cell types with variable c-Met and EGFR densities and ratios (FIG. 5). NCI-H292, NCI-H441, or NCI-H596 cells were plated in 96 well plates in RPMI medium containing 10% FBS. 24 hours later, medium was replaced with serum free RPMI. 24 hours after serum starvation, cells were treated with varying concentrations of either monospecific EGFR-binding FN3 domain, monospecific c-Met FN3 domain, or a bispecific EGFR/c-Met molecule (ECB5, comprised of P53A1R5-17v2 and P114AR7P94-A3). Cells were treated for 1 h with the monospecific or bispecific molecules and then stimulated with EGF, HGF, or a combination of EGF and HGF for 15 minutes at 37° C., 5% CO$_2$. Cells were lysed with MSD Lysis Buffer and cell signaling was assessed using appropriate MSD Assay plates, according to manufacturer's instructions, as described above.

FIG. 5 (A-C) shows the inhibition of EGFR using a monospecific EGFR-binding FN3 domain compared to a bispecific EGFR/cMet molecule in three different cell lines. To assess avidity in an EGFR phosphorylation assay, a medium affinity EGFR-binding FN3 domain (1.9 nM) (P53A1R5-17v2) was compared to a bispecific EGFR/c-Met molecule containing the same EGFR-binding FN3 domain linked to a high-affinity c-Met-binding FN3 domain (0.4 nM) (P114AR7P94-A3). In NCI-H292 and H596 cells, inhibition of phosphorylation of EGFR was comparable for the monospecific and bispecific molecules (FIGS. 5A and 5B), likely because these cell lines have a high ratio of EGFR to c-Met receptors. To test this theory, inhibition of EGFR phosphorylation was evaluated in NCI-H441 cells which exhibit more c-Met receptors than EGFR. Treatment of NCI-H441 cells with the bispecific EGFR/c-Met molecule decreased the $IC_{50}$ for inhibition of EGFR phosphorylation compared to the monospecific EGFR-binding FN3 domain by 30-fold (FIG. 5C).

The potential for enhanced potency with a bi-specific EGFR/c-Met molecule was evaluated in a c-Met phosphorylation assay using a molecule with a high affinity to EGFR (0.26 nM) and medium affinity to c-Met (10.1 nM). In both NCI-H292 and NCI-H596 cells, the inhibition of phosphorylation of c-Met was enhanced with the bispecific molecule compared to the monospecific c-Met-binding FN3 domain, by 134 and 1012 fold, respectively (FIG. 3D and 3E).

It was verified that the enhanced potency for inhibition of EGFR and c-Met phosphorylation with the bispecific EGFR/c-Met molecules translated into an enhanced inhibition of signaling and proliferation. For these experiments, the mixture of FN3 EGFR-binding and c-Met-binding FN3 domains was compared to a bispecific EGFR/c-Met molecule. As described in Tables 12 and 13, the $IC_{50}$ values for ERK phosphorylation (Table 12) and proliferation of NCI-H292 cells (Table 13) were decreased when cells were treated with the bispecific EGFR/c-Met molecule compared to the mixture of the monospecific binders. The $IC_{50}$ for inhibition of ERK phosphorylation for the bi-specific EGFR/c-Met molecule was 143-fold lower relative to the mixture of the two monospecific EGFR and c-Met FN3 domains, showing the effect of avidity to the potency of the molecules in this assay. In Table 12, the monospecific EGFR- and c-Met binding FN3 domains do not fully inhibit activity and therefore the $IC_{50}$ values shown should be considered lower limits. The proliferation assay was completed using different combinations EGFR and c-Met binding FN3 domains either as a mixture or linked in a bispecific format. The $IC_{50}$ for inhibition of proliferation for the bispecific EGFR/c-Met molecule was 34-236-fold lower relative to the mixture of the monospecific parent EGFR or c-Met binding FN3 domains. This confirmed that the avidity effect observed at the level of the receptors (FIG. 4 and FIG. 5) translates into an improvement in inhibiting cell signaling (Table 12) and cell proliferation (Table 13).

TABLE 12

| Specificity of the FN3-domain molecule | Clone name | Type | $IC_{50}$ (nM) (ERK phosphorylation) |
|---|---|---|---|
| EGFR | P54AR4-83v2 | monospecific | >10,000 |
| c-Met | P114AR5P74-A5 | monospecific | 2366 |
| EGFR or c-Met | P54AR4-83v2 + P114AR5P74-A5 | mixture of monospecific molecules | 798.4 |
| EGFR and c-Met | ECB1 | bispecific | 5.6 |

TABLE 13

| EGFR-binding FN3 domain (affinity) | c-Met binding FN3 domain (affinity) | $IC_{50}$ for mixture of monospecific molecules (nM) | $IC_{50}$ for bispecific molecule (nM) | Fold increase in $IC_{50}$ for mixture of monospecific/bispecific |
|---|---|---|---|---|
| P54AR4-83v2 (0.26 nM) | P114ARP94-A3 (0.4 nM) | 36.5 | 1.04 | 35 |
| P54AR4-83v2 (0.26 nM) | P114AR7P93-H9 (3.3 nM) | 274.5 | 8.05 | 34 |
| P54AR4-83v2 (0.26 nM) | P114AR5P74-A5 (10.1 nM) | 1719 | 7.29 | 236 |

In vivo Tumor Xenografts: PK/PD

In order to determine efficacy of the monospecific and bispecific FN3 domain molecules in vivo, tumor cells were engineered to secrete human HGF (murine HGF does not bind to human c-Met). Human HGF was stably expressed in NCI-H292 cells using lentiviral infection (Lentiviral DNA vector expressing human HGF (Accession #X16322) and lentiviral packaging kit from Genecopoeia). After infection, HGF-expressing cells were selected with 4 µg/mL puromycin (Invitrogen). Human HGF protein was detected in the conditioned medium of pooled cells using assay plates from MesoScale Discovery.

SCID Beige mice were subcutaneously inoculated with NCI-H292 cells expressing human HGF ($2.0\times10^6$ cells in Cultrex (Trevigen) in a volume of 200 µL) on the dorsal flank of each animal. Tumor measurements were taken twice weekly until tumor volumes ranged between 150-250 mm³. Mice were then given a single i.p. dose of bispecific EGFR/c-Met molecules (linked to an albumin binding domain to increase half-life) or PBS vehicle. At 6 h or 72 h after dosing, tumors were extracted and immediately frozen in liquid nitrogen. Blood samples were collected via cardiac puncture into 3.8% citrate containing protease inhibitors Immediately after collection, the blood samples were centrifuged and the resulting plasma was transferred to sample tubes and stored at −80° C. Tumors were weighed, cut into small pieces, and lysed in Lysing Matrix A tubes (LMA) containing RIPA buffer with HALT protease/phosphatase inhibitors (Pierce), 50 mM sodium fluoride (Sigma), 2 mM activated sodium orthovanadate (Sigma), and 1 mM PMSF (MesoScale Discovery). Lysates were removed from LMA matrix and centrifuged to remove insoluble protein. The soluble tumor protein was quantified with a BCA protein assay and diluted to equivalent protein levels in tumor lysis buffer. Phosphorylated c-Met, EGFR and ERK were measured using assay plates from MesoScale Discovery (according to Manufacturer's protocol and as described above).

Figure 6:
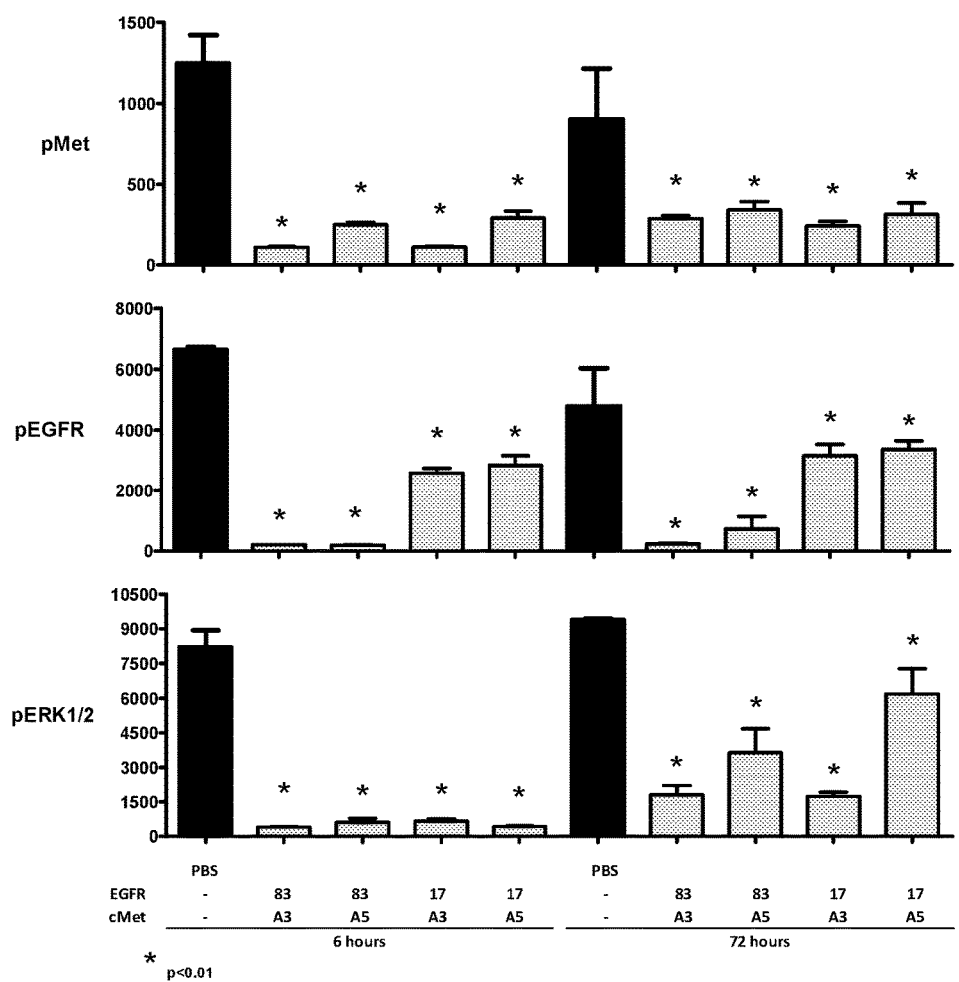
FIG. 6. Pharmacodynamic signaling in tumors isolated from mice dosed with bispecific EGFR/c-Met molecules for 6 h or 72 h. All molecules significantly reduced c-Met, EGFR and ERK phosphorylation at 6 h and 72 h, the degree if inhibition was dependent on the affinity of the FN3 domains to EGFR and/or c-Met. Bispecific molecules were generated by joining EGFR-binding FN3 domain with a high ("83" in the Figure is p54AR4-83v2) or medium ("17v2" in the Figure is P53A1R5-17v2) affinity to a c-Met-binding FN3 domain with high ("A3" in the Figure is P114AR7P94-A3) or medium ("A5" in the Figure is P114AR5P74-A5) affinity.

FIG. 6 shows the results of the experiments. Each bispecific EGFR/c-Met molecule significantly reduced the levels of phosphorylated c-Met, EGFR, and ERK at both 6 h and 72 h. The data presented in FIG. 6 show the importance of inhibiting both c-Met and EGFR simultaneously and how the affinity of the bispecific EGFR/c-Met molecule for each receptor plays a role in inhibition of downstream ERK. The molecules containing the high affinity EGFR-binding FN3 domains (P54AR4-83v2; shown as "8" in the Figure, $K_D$=0.26 nM) inhibited phosphorylation of EGFR to a larger extent compared to those containing the medium affinity EGFR-binding FN3 domains (P53A1R5-17v2; shown as "17" in the figure $K_D$=1.9 nM) at both 6 h and 72 h. All four bispecific molecules tested completely inhibited phosphorylation of ERK at the 6 hour time point, regardless of affinity. At the 72 hour time point, the molecules containing the tight affinity c-Met-binding domain (P114AR7P94-A3;

shown as "A3" in the figure $K_D$=0.4 nM) significantly inhibited phosphorylation of ERK compared to the medium affinity c-Met-binding FN3 domain (P114AR5P74-A5; shown as "A5" in the Figure; $K_D$=10.1 nM; FIG. 6).

Figure 7:
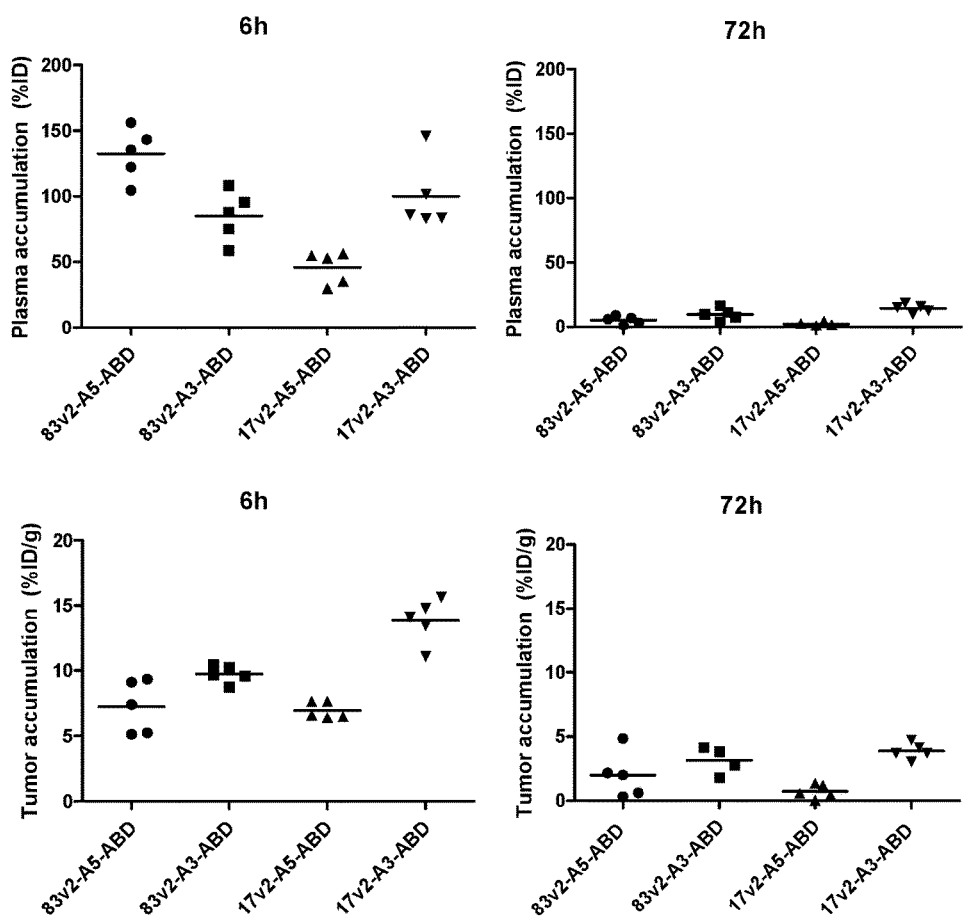
FIG. 7. Plasma (top) and tumor (bottom) accumulation of bispecific EGFR/cMet molecules of variable affinities linked to an albumin binding domain (ABD) are shown 6 h (left) and 72 h (right) after IP dosing. Six hours after dosing, tumor accumulation is maximal in mice dosed with a bispecific molecule harboring a medium affinity EGFR-binding FN3 domain (17v2) or high affinity EGFR binding domain (83v2). The bispecific molecules incorporated high or medium affinity EGFR or c-Met binding FN3 domains as follows: 83v2-A5-ABD (ECB18; high/medium for EGFR/cMet) 83v2-A3-ABD (ECB38; high/high) 17v2-A5 (ECB28; medium/medium) 17v2-A3-ABD (ECB39; medium/high). In the figure, 83v2 refers to p54AR4-83v2; 17v2 refers to p53A1R5-17v2; A3 refers to p114AR7P94-A3 and A5 refers to p114AR5P74-A5.

The concentration of each bispecific EGFR/c-Met molecule was measured at 6 and 72 hours after dosing in the blood and in the tumor (FIG. 7). Interestingly, the bispecific molecule with the medium affinity EGFR-binding domain (P53A1R5-17v2; $K_D$=1.9 nM) but high affinity c-Met-binding FN3 domain (P114AR7P94-A3; $K_D$=0.4 nM) had significantly more tumor accumulation at 6 hours relative to the other molecules, while the difference is diminished by 72 hours. It can be hypothesized that cells outside the tumor have lower levels of both EGFR and c-Met surface expression and therefore the medium affinity EGFR molecule doesn't bind to normal tissue as tightly compared to the higher affinity EGFR-binding FN3 domain. Therefore there is more free medium affinity EGFR-binding FN3 domain available to bind in the tumor. Therefore, identifying the appropriate affinities to each receptor may allow for identification of a therapeutic with decreased systemic toxicities and increased tumor accumulation.

Tumor Efficacy Studies with Bispecific EGFR/c-Met Molecules

Figure 8:
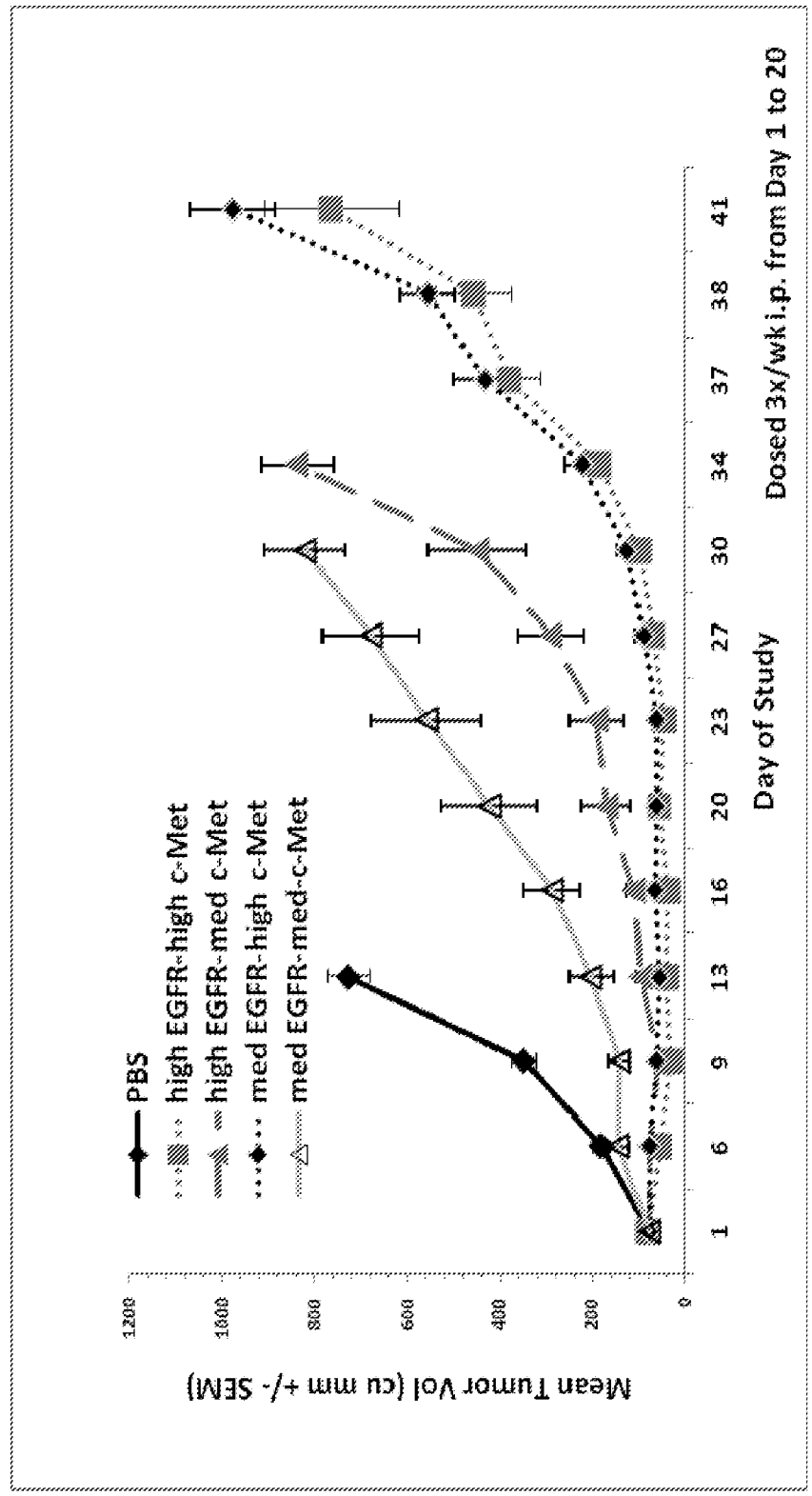
FIG. 8. H292-HGF tumor xenografts were implanted into SCID Beige mice. When tumors reached an average volume of approximately 80 mm$^3$, mice were dosed three times per week with bispecific EGFR/c-Met molecules (25 mg/kg) or PBS vehicle. All bispecific molecules reduced tumor growth, the tumor growth inhibition (TGI) being dependent on the affinities of the molecules for c-Met and EGFR (high EGFR-high cMet refers to p54AR4-83v2-p114AR7P94-A3 (ECB38); high EGFR-med cMet refers to p54AR4-83v2-p114AR5P74-A5 (ECB18); med EGFR-high cMet refers to p53A1R5-17v2-p114AR7P94-A3 (ECB39); med EGFR-med-cMet refers to p53A1R5-17-p114AR5P74-A5 (ECB28)).

SCID Beige mice were subcutaneously inoculated with NCI-H292 cells expressing human HGF (2.0×10⁶ cells in Cultrex (Trevigen) in 200 μL) in the dorsal flank of each animal. One week after implantation, mice were stratified into groups with equivalent tumor volumes (mean tumor volume=77.9+/−1.7 mm³) Mice were dosed three times per week with the bispecific molecules and tumor volumes were recorded twice weekly. Tumor growth inhibition (TGI) was observed with four different bispecific molecules, with variable affinities for c-Met and EGFR. FIG. 8 shows the benefit of inhibiting both c-Met and EGFR as a delay in tumor growth was observed in the mice treated with molecules containing the high affinity EGFR-binding FN3 domain compared to the medium affinity EGFR-binding FN3 domain when the c-Met-binding FN3 domain was medium affinity (open vs. closed triangles, P54AR4-83v2-P114AR5P74-A5 compared to P53A1R5-17-P114AR5P74-A5). In addition, the data shows the importance of having a high affinity c-Met-binding FN3 domain as bispecific molecules containing either the high or medium affinity EGFR-binding FN3 domain but high affinity c-Met-binding FN3 domain showed the most efficacy (dotted gray and black lines, P54AR4-83v2-P114AR7P94-A3 and P53A1R5-17v2-P114AR7P94-A3).

Efficacy of Bispecific Molecule and Other Inhibitors of EGFR and c-Met

The in vivo therapeutic efficacies of a bispecific EGFR/c-Met molecule (ECB38) and the small molecule inhibitors crizotinib (c-Met inhibitor) and erlotinib (EGFR inhibitor), cetuximab (anti-EGFR antibody), each as a single agent, and the combination of crizotinib and erlotinib were evaluated in the treatment of subcutaneous H292-HGF human lung cancer xenograft model in SCID/Beige mice.

The H292-HGF cells were maintained in vitro in RPMI1640 medium supplemented with fetal bovine serum (10% v/v), and L-glutamine (2 mM) at 37° C. in an atmosphere of 5% $CO_2$ in air. The cells were routinely subcultured twice weekly by trypsin-EDTA treatment. The cells growing in an exponential growth phase were harvested and counted for tumor inoculation.

Each mouse was inoculated subcutaneously at the right flank region with H292-HGF tumor cells (2×10⁶) in 0.1 ml of PBS with Cultrex (1:1) for tumor development. The treatments were started when the mean tumor size reached 139 mm³ The test article administration and the animal numbers in each study group were shown in the following experimental design table. The date of tumor cell inoculation was denoted as day 0. Table 14 shows the treatment groups.

TABLE 14

| Group | N | Treatment | Dose (mg/kg) | Dosing Route | Planned Schedule | Actual Schedule |
|---|---|---|---|---|---|---|
| 1 | 10 | Vehicle Control | 0 | i.p. | QD × 3 weeks | QD × 3 weeks |
| 2 | 10 | bispecific EGFR/c-Met molecule | 25 | i.p. | 3 times/week × 3 weeks | 3 times/week × 3 weeks |
| 3 | 10 | crizotinib | 50 | p.o. | QD × 3 weeks | QD × 17 days |
| 4 | 10 | erlotinib | 50 | p.o. | QD × 2 weeks | QD × 3 weeks |
| 5 | 10 | crizotinib | 50 | p.o. | QD × 3 weeks | QD × 3 weeks |
| 6 | 10 | cetuximab | 1 mg/mouse | i.p. | Q4d*6 | Q4d*6 |

N: animal number; p.o.: oral administration; i.p.: intraperitoneal injection 3 times/week; doses were given on days 1, 3 and 5 of the week.
QD: once daily Q4d: once every four days; the interval of the combination of crizotinib and erlotinib was 0.5 hrs; dosing volume was adjusted based on body weight (10 l/g); a: dosing was not given on day 14 post grouping.

Before commencement of treatment, all animals were weighed and the tumor volumes were measured. Since the tumor volume can affect the effectiveness of any given treatment, mice were assigned into groups using randomized block design based upon their tumor volumes. This ensures that all the groups are comparable at the baseline. The randomized block design was used to assign experimental animals to groups. First, the experimental animals were divided into homogeneous blocks according to their initial tumor volume. Secondly, within each block, randomization of experimental animals to treatments was conducted. Using randomized block design to assign experimental animals ensured that each animal had the same probability of being assigned to a given treatment and therefore systematic error was reduced.

At the time of routine monitoring, the animals were checked for any effects of tumor growth and treatments on normal behavior, such as mobility, visual estimation of food and water consumption, body weight gain/loss (body weights were measured twice weekly), eye/hair matting and any other abnormal effect.

The endpoint was whether tumor growth can be delayed or tumor bearing mice can be cured. Tumor size was measured twice weekly in two dimensions using a caliper, and the volume was expressed in mm³ using the formula: V=0.5 a×b² where a and b are the long and short diameters of the tumor, respectively. The tumor size was then used for calculations of both T−C and T/C values. T−C was calculated with T as the time (in days) required for the mean tumor size of the treatment group to reach 1000 mm³, and C was the time (in days) for the mean tumor size of the control group to reach the same size. The T/C value (in percent) was an indication of antitumor efficacy; T and C were the mean tumor volume of the treated and control groups, respectively, on a given day. Complete tumor regression (CR) is defined as tumors that are reduced to below the limit of palpation (62.5 mm³) Partial tumor regression (PR) is defined as tumors that are reduced from initial tumor volume. A minimum duration of CR or PR in 3 or more successive tumor measurements is required for a CP or PR to be considered durable.

Animals for which the body weight loss exceeded 20%, or for which the mean tumor size of the group exceeds 2000 mm³ were euthanized. The study was terminated after two weeks of observation after the final dose.

Summary statistics, including mean and the standard error of the mean (SEM), are provided for the tumor volume of each group at each time point are shown in Table 15. Statistical analyses of difference in tumor volume among the groups were evaluated using a one-way ANOVA followed by individual comparisons using Games-Howell (equal variance not assumed). All data were analyzed using SPSS 18.0. $p<0.05$ was considered to be statistically significant.

TABLE 15

| | | Tumor volume (mm³)a | | | | |
|---|---|---|---|---|---|---|
| Days | Vehicle | bispecific EGFR/c-Met molecule at 25 mg/kg | crizotinib at 50 mg/kg | erlotinib at 50 mg/kg | crizotinib; erlotinib at 50 mg/kg; 50 mg/kg | cetuximab at 1 mg/mouse |
| 7  | 139 ± 7    | 137 ± 7 | 140 ± 9    | 141 ± 8    | 139 ± 8  | 139 ± 10 |
| 9  | 230 ± 20   | 142 ± 7 | 217 ± 20   | 201 ± 19   | 134 ± 9  | 168 ± 13 |
| 13 | 516 ± 45   | 83 ± 6  | 547 ± 43   | 392 ± 46   | 109 ± 10 | 212 ± 20 |
| 16 | 808 ± 104  | 44 ± 7  | 914 ± 92   | 560 ± 70   | 127 ± 15 | 252 ± 28 |
| 20 | 1280 ± 209 | 30 ± 6  | 1438 ± 239 | 872 ± 136  | 214 ± 30 | 371 ± 48 |
| 23 | 1758 ± 259 | 23 ± 7  | 2102 ± 298 | 1122 ± 202 | 265 ± 40 | 485 ± 61 |
| 27 | 2264 ± 318 | 21 ± 5  | —          | 1419 ± 577 | 266 ± 42 | 640 ± 82 |
| 30 | —          | 23 ± 6  | —          | 1516 ± 623 | 482 ± 61 | 869 ± 100 |

The mean tumor size of the vehicle treated group (Group 1) reached 1,758 mm³ at day 23 after tumor inoculation. Treatment with the bispecific EGFR/c-Met molecule at 25 mg/kg dose level (Group 2) led to complete tumor regression (CR) in all mice which were durable in >3 successive tumor measurements (average TV=23 mm³, T/C value=1%, p=0.004 compared with the vehicle group at day 23).

Treatment with crizotinib as a single agent at 50 mg/kg dose level (Group 3) showed no antitumor activity; the mean tumor size was 2,102 mm³ at day 23 (T/C value=120%, p=0.944 compared with the vehicle group).

Treatment with erlotinib as a single agent at 50 mg/kg dosing level (Group 4) showed minor antitumor activity, but no significant difference was found compared with the vehicle group; the mean tumor size was 1,122 mm³ at day 23 (T/C value=64%, p=0.429 compared with the vehicle group), with 4 days of tumor growth delay at tumor size of 1,000 mm³ compared with the vehicle group.

The combination of crizotinib (50 mg/kg, Group 5) and erlotinib (50 mg/kg, Group 5) showed significant antitumor activity; the mean tumor size was 265 mm³ at day 23 (T/C=15%; p=0.008), with 17 days of tumor growth delay at tumor size of 1,000 mm³ compared with the vehicle group.

Cetuximab at 1 mg/mouse dosing level as a single agent (Group 6) showed significant antitumor activities; the mean tumor size was 485 mm³ at day 23 (T/C=28%; p=0.018), with 17 days of tumor growth delay at tumor size of 1,000 mm³ compared with the vehicle group. FIG. 15 and Table 16 show the anti-tumor activities of the various therapies.

TABLE 16

| Treatment | Tumor Size (mm³) at day 23 | T/C (%) | T − C (days) at 1000 mm³ | P value |
|---|---|---|---|---|
| Vehicle | 1758 ± 259 | — | — | — |
| bispecific EGFR/c-Met molecule (25 mg/kg) | 23 ± 7 | 1 | — | 0.004 |
| crizotinib (50 mg/kg) | 2102 ± 298 | 120 | −1 | 0.944 |
| erlotinib (50 mg/kg) | 1122 ± 202 | 64 | 4 | 0.429 |
| crizotinib + erlotinib (50 mg/kg + 50 mg/kg) | 265 ± 40 | 15 | 17 | 0.008 |
| cetuximab (1 mg/mouse) | 485 ± 61 | 28 | 17 | 0.018 |

Medium to severe body weight loss was observed in the vehicle group which might be due to the increasing tumor burden; 3 mice died and 1 mouse were euthanized when BWL>20% by day 23. Slight toxicity of the bispecific EGFR/c-Met molecule was observed in Group 2; 3 mice were euthanized when BWL>20% during the treatment period; the body weight was gradually recovered when the treatment was withdrawn during the 2 weeks of observation period. More severe body weight loss was observed in the crizotinib or erlotinib monotherapy group compared to the vehicle group, suggesting the treatment related toxicity. The combination of crizotinib and erlotinib was generally tolerated during the dosing phase, but severe body weight loss was observed at the end of the study, which might be due to the resumption of the fast tumor growth during the non-treatment period. The monotherapy of cetuximab was well tolerated in the study; body weight loss was only observed at the end of the study due to the resume of the tumor growth.

Figure 9:
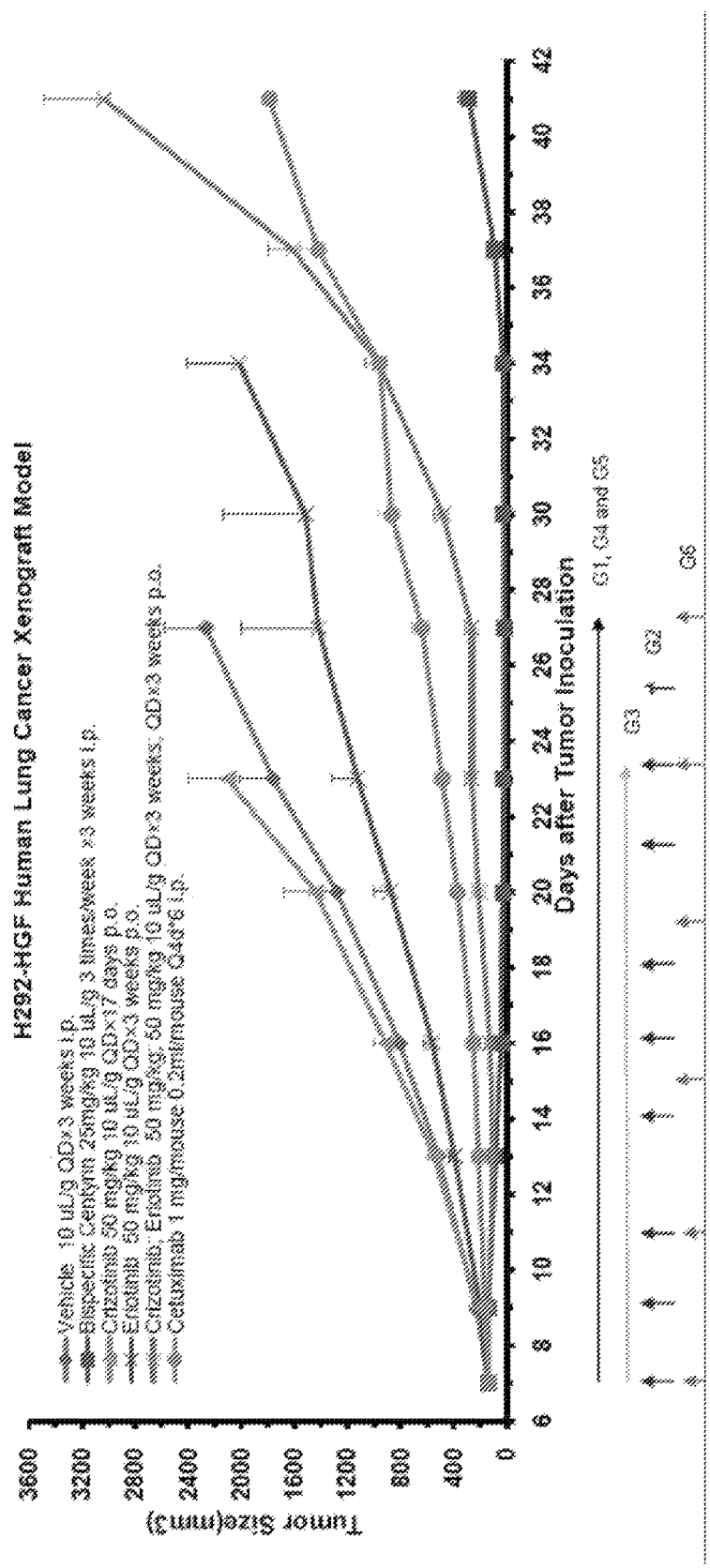
FIG. 9. H292-HGF tumor xenografts were implanted into SCID Beige mice and they were treated with different therapies. The anti-tumor activity of the therapies is shown (bispecific EGFR/c-Met molecule refers to p54AR4-83v2- p114AR7P94-A3-ABD (ECB38); the other therapies are crizotinib, erlotinib, cetuximab, and the combination of crizotinib and erlotinib).

In summary, the bispecific EGFR/c-Met molecule at 25 mg/kg (3 times/week×3 weeks) produced a complete response in H292-HGF human lung cancer xenograft model in SCID/Beige mice. The treatment was tolerated in 7 out of 10 mice, and resulted in severe body weight loss in 3 out of 10 mice. FIG. 9 shows the impact of the various therapies on tumor size during the time points after treatment.

EXAMPLE 8

Half-life Extension of the Bispecific EGFR/c-Met Molecules

Numerous methods have been described to reduce kidney filtration and thus extend the serum half-life of proteins including modification with polyethylene glycol (PEG) or other polymers, binding to albumin, fusion to protein domains which bind to albumin or other serum proteins, genetic fusion to albumin, fusion to IgG Fc domains, and fusion to long, unstructured amino acid sequences.

Bispecific EGFR/c-Met molecules were modified with PEG in order to increase the hydrodynamic radius by incorporating a free cysteine at the C-terminus of the molecule. Most commonly, the free thiol group of the cysteine residue is used to attach PEG molecules that are functionalized with maleimide or iodoacetemide groups using standard methods. Various forms of PEG can be used to modify the protein including linear PEG of 1000, 2000, 5000, 10,000, 20,000, or 40,000 kDa. Branched PEG molecules of these molecular weights can also be used for modification. PEG groups may also be attached through primary amines in the bispecific EGFR/c-Met molecules in some instances.

In addition to PEGylation, the half-life of bispecific EGFR/c-Met molecules was extended by producing these proteins as fusion molecules with a naturally occurring 3-helix bundle serum albumin binding domain (ABD) or a consensus albumin binding domain (ABDCon). These protein domains were linked to the C-terminus of the c-Met-binding FN3 domain via any of the linkers described in Table 12. The ABD or ABDCon domain may also be placed between the EGFR-binding FN3 domain and the c-Met binding FN3 domain in the primary sequence.

EXAMPLE 9

Characterization of Select Bispecific EGFR/c-Met Molecules

Select bispecific EGFR/c-Met molecules were characterized for their affinity to both EGFR and c-Met, their ability to inhibit EGFR and c-Met autophosphorylation, and their effect on proliferation of HGF cells. Binding affinity of the bispecific EGFR/c-Met molecules to recombinant EGFR and/or c-Met extracellular domain was further evaluated by surface Plasmon resonance methods using a Proteon Instrument (BioRad) according to protocol described in Example 3. Results of the characterization are shown in Table 17.

TABLE 17

| | $K_D$ (EGFR, nM) | $K_D$ (c-Met, nM) | pMet inhibition in H441 cells ($IC_{50}$, nM) | pEGFR inhibition in H292 cells ($IC_{50}$, nM) | H292-HGF Proliferation inhibition in HGF-induced H292 cells ($IC_{50}$, nM) |
|---|---|---|---|---|---|
| ECB15 | 0.2 | 2.6 | n/a | 4.2 | 23 |
| ECB94 | 1 | 4.3 | 53.8 | 5.1 | 29.6 |
| ECB95 | 1.1 | 6.2 | 178.8 | 13.6 | 383.4 |
| ECB96 | 1.6 | 22.1 | 835.4 | 24.7 | 9480 |
| ECB97 | 1.3 | 1.7 | 24.2 | 16.6 | 31.0 |
| ECB106 | 16.7 | 5.1 | 53.3 | 367.4 | 484.5 |
| ECB107 | 16.9 | 9 | 29.9 | 812.3 | 2637 |
| ECB108 | 15.3 | 25.5 | 126.2 | 814.4 | 11372 |
| ECB109 | 17.3 | 2.1 | 26 | 432 | 573.6 |

EXAMPLE 10

Generation of Bispecific EGFR/cMet Antibodies

Several monospecific EGFR and c-Met antibodies were expressed as IgG1, kappa, having Fc substitutions K409R or F405L (numbering according to the EU index) in their Fc regions. The monospecific antibodies were expressed in two CHO cell lines, one cell line having reduced fucosylation ability resulting in antibodies with 1-15% fucose content in the antibody polysaccharide chain.

The monospecific antibodies were purified using standard methods using a Protein A column (HiTrap MabSelect SuRe column). After elution, the pools were dialyzed into D-PBS, pH 7.2

Bispecific EGFR/c-Met antibodies were generated by combining a monospecific EGFR mAb and a monospecific c-Met mAb in in vitro Fab arm exchange (as described in WO2011/131746). Briefly, at about 1-20 mg/ml at a molar ratio of 1:1 of each antibody in PBS, pH 7-7.4 and 75 mM 2-mercaptoethanolamine (2-MEA) was mixed together and incubated at 25-37° C. for 2-6 h, followed by removal of the 2-MEA via dialysis, diafiltration, tangential flow filtration and/or spinned cell filtration using standard methods.

Several monospecific anti-EGFR antibodies and anti-c-Met antibodies were combined in matrix in in vitro Fab arm exchange to generate bispecific antibodies that were subsequently characterized further. The generated bispecific antibodies were ranked using a four step strategy using assays as follows: Step 1: binding to NCI-H441, NCI-H1975 and A549 cells in a FACS assay. Step 2: inhibition of pMet phosphorylation in A549 cells. Step 3: inhibition of proliferation in NCI-H1975, KP4 and NCI-H441 cells. Step 4: inhibition of EGFR phosphorylation in A549 and SNU-5 cells. Noteworthy, the characteristics of the parental antibodies were not preserved in the bispecific antibody. For example, the presence of certain EGFR binding arms in the bispecific antibody resulted in a loss or reduced inhibition, or enhanced c-Met phosphorylation. Based on the characterization studies select pairs were chosen.

A monospecific bivalent anti-EGFR antibody E1-K409R was generated comprising the VH and VL regions of an anti-EGFR antibody 2F8 having the VH of SEQ ID NO: 189 and the VL of SEQ ID NO: 190 (antibody 2F8 is described in Int. Pat. Publ. No. WO2002/100348) and an IgG1 constant region with a K409R substitution.

A monospecific bivalent anti-EGFR antibody E1-F405L was generated comprising the VH and VL regions of an anti-EGFR antibody 2F8 having the VH of SEQ ID NO: 189 and the VL of SEQ ID NO: 190 (antibody 2F8 is described in Int. Pat. Publ. No. WO2002/100348) and an IgG1 constant region with a F405L substitution.

A monospecific bivalent anti-EGFR antibody E2-K409R was generated comprising the VH and VL regions of an anti-EGFR antibody 018 having the VH of SEQ ID NO: 191 and the VL of SEQ ID NO: 192 (antibody 018 is described in Int. Pat. Publ. No. WO2009/030239) and an IgG1 constant region with a K409R substitution.

A monospecific bivalent anti-EGFR antibody E2-F405L was generated comprising the VH and VL regions of an anti-EGFR antibody 018 having the VH of SEQ ID NO: 191 and the VL of SEQ ID NO: 192 (antibody 018 is described in Int. Pat. Publ. No. WO2009/030239) and an IgG1 constant region with a F405L substitution.

A monospecific bivalent anti-c-Met antibody M1-K409R was generated comprising the VH and VL regions of an anti-c-Met antibody 069 having the VH of SEQ ID NO: 193 and the VL of SEQ ID NO: 194 (antibody 069 is described in WO2011/110642) and an IgG1 constant region with a K409R substitution.

A monospecific bivalent anti-c-Met antibody M1-F405L was generated comprising the VH and VL regions of an anti-c-Met antibody 069 having the VH of SEQ ID NO: 193 and the VL of SEQ ID NO: 194 (antibody 069 is described in WO2011/110642) and an IgG1 constant region with a F405L substitution.

A monospecific anti-c-Met antibody M2-K409R was generated comprising the VH and VL regions of an anti-c-Met antibody 058 having the VH of SEQ ID NO: 195 and the VL of SEQ ID NO: 196 (antibody 058 is described in WO2011/110642) and an IgG1 constant region with a K409R substitution.

A monospecific anti-c-Met antibody M2-F405L was generated comprising the VH and VL regions of an anti-c-Met antibody 058 having the VH of SEQ ID NO: 195 and the VL of SEQ ID NO: 196 (antibody 058 is described in WO2011/110642) and an IgG1 constant region with a F405L substitution.

The VH, VL, HC and LC sequences of the antibodies are shown below:

```
EGFR mAb E1 VH
                                      >SEQ ID NO: 189
QVQLVESGGGVVQPGRSLRLSCAASGFTFSTYGMHWVRQAPGKGLEWVAV
IWDDGSYKYYGDSVKGRFTISRDNSKNTLYLQMNSLRAEDTAVYYCARDG
ITMVRGVMKDYFDYWGQGTLVTVSS

EGFR mAb E1 VL
                                      >SEQ ID NO: 190
AIQLTQSPSSLSASVGDRVTITCRASQDISSALVWYQQKPGKAPKLLIYD
ASSLESGVPSRFSGSESGTDFTLTISSLQPEDFATYYCQQFNSYPLTFGG
GTKVEIK

EGFR mAb E2 VH
                                      >SEQ ID NO: 191
EVQLVESGGG LVQPGGSLRL SCAASGFTFS SYWMNWVRQA
PGKGLEWVAN IKKDGSEKYY VDSVKGRFTI SRDNAKNSLY
LQMNSLRAED TAVYYCARDL GWGWGWYFDL WGRGTLVTVSS

EGFR mAb E2 VL
                                      >SEQ ID NO: 192
EIVLTQSPAT LSLSPGERAT LSCRASQSVS SYLAWYQQKP
GQAPRLLIYD ASNRATGIPARFSGSGSGTD FTLTISSLEP
EDFAVYYCQQ RSNWPPTFGQ GTKVEIK cMet mAb M1 VH
                                      >SEQ ID NO: 193
QVQLVQSGAEVKKPGASVKVSCETSGYTFTSYGISWVRQAPGHGLEWMGW
ISAYNGYTNYAQKLQGRVTMTTDTSTSTAYMELRSLRSDDTAVYYCARDL
RGTNYFDYWGQGTLVTVSS cMet mAb M1VL
                                      >SEQ ID NO: 194
DIQMTQSPSSVSASVGDRVTITCRASQGISNWLAWFQHKPGKAPKLLIYA
ASSLLSGVPSRFSGSGSGTDFTLTISSLQPEDFATYYCQQANSFP-ITFG
QGTRLEIK cMet mAb M2 VH
                                      >SEQ ID NO: 195
EVQLVESGGGLVKPGGSLKLSCAASGFTFSDYYMYWVRQTPEKRLEWVAT
ISDDGSYTYYPDSVKGRFTISRDNAKNNLYLQMSSLKSEDTAMYYCAREG
LYYYGSGSYYNQDYWGQGTLVTVSS cMet mAb M2 VL
                                      >SEQ ID NO: 196
QLTQSPSSLSASVGDRVTITCRASQGLSSALAWYRQKPGKAPKLLIYDAS
SLESGVPSRFSGSGSGTDFTLTISSLQPEDFATYYCQQFTSYPQITFGQG
TRLEIK

EM1-mAb H1 (anti-EGFR, 405L)
                                      >SEQ ID NO: 199
QVQLVESGGGVVQPGRSLRLSCAASGFTFSTYGMHWVRQAPGKGLEWVAV
IWDDGSYKYYGDSVKGRFTISRDNSKNTLYLQMNSLRAEDTAVYYCARDG
ITMVRGVMKDYFDYWGQGTLVTVSSASTKGPSVFPLAPSSKSTSGGTAAL
GCLVKDYFPEPVTVSWNSGALTSGVHTFPAVLQSSGLYSLSSVVTVPSSS
LGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSLS
LSPGK EM-1 mAb L1
                                      >SEQ ID NO: 200
AIQLTQSPSSLSASVGDRVTITCRASQDISSALVWYQQKPGKAPKLLIYD
ASSLESGVPSRFSGSESGTDFTLTISSLQPEDFATYYCQQFNSYPLTFGG
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC EM-1 mAb H2 (K409R, anti-cMet)
                                      >SEQ ID NO: 201
QVQLVQSGAEVKKPGASVKVSCETSGYTFTSYGISWVRQAPGHGLEWMGW
ISAYNGYTNYAQKLQGRVTMTTDTSTSTAYMELRSLRSDDTAVYYCARDL
RGTNYFDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKRVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSRLTVDKSRWQQGNVFSCSVMHEALHNHYTQKSLSLSPGK EM-1 mAb L2
                                      >SEQ ID NO: 202
DIQMTQSPSSVSASVGDRVTITCRASQGISNWLAWFQHKPGKAPKLLIYA
ASSLLSGVPSRFSGSGSGTDFTLTISSLQPEDFATYYCQQANSFPITFGQ
GTRLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC E2 mAb HC1 (EGFR-F405L)
                                      >SEQ ID NO: 234
EVQLVESGGG LVQPGGSLRL SCAASGFTFS SYWMNWVRQA
PGKGLEWVAN IKKDGSEKYY VDSVKGRFTI SRDNAKNSLY
LQMNSLRAED TAVYYCARDL GWGWGWYFDLWGRGTLVTVSSASTKGPS
VFPLAPSSKSTSGGTAALGCLVKDYFPEPVTVSWNSGALTSGVHTFPAVL
QSSGLYSLSSVVTVPSSSLGTQTYICNVNHKPSNTKVDKRVEPKSCDKTH
TCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYP
SDIAVEWESNGQPENNYKTTPPVLDSDGSFLLYSKLTVDKSRWQQGNVFS
CSVMHEALHNHYTQKSLSLSPGK E2 mAb LC1 (EGFR)
                                      >SEQ ID NO: 235
EIVLTQSPAT LSLSPGERAT LSCRASQSVS SYLAWYQQKP
GQAPRLLIYD ASNRATGIPARFSGSGSGTD FTLTISSLEP
EDFAVYYCQQ RSNWPPTFGQ GTKVEIKRTVAAPSVFIFPPSDEQLKSG
TASVVCLLNNFYPREAKVQWKVDNALQSGNSQESVTEQDSKDSTYSLSST
LTLSKADYEKHKVYACEVTHQGLSSPVTKSFNRGEC E2 mAb HC2 (c-Met-K409R)
                                      >SEQ ID NO: 236
EVQLVESGGGLVKPGGSLKLSCAASGFTFSDYYMYWVRQTPEKRLEWVAT
ISDDGSYTYYPDSVKGRFTISRDNAKNNLYLQMSSLKSEDTAMYYCAREG
LYYYGSGSYYNQDYWGQGTLVTVSSASTKGPSVFPLAPSSKSTSGGTAAL
GCLVKDYFPEPVTVSWNSGALTSGVHTFPAVLQSSGLYSLSSVVTVPSSS
LGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYK
TTPPVLDSDGSFFLYSRLTVDKSRWQQGNVFSCSVMHEALHNHYTQKSLS
LSPGK E2 mAb LC2 (cMet)
                                      >SEQ ID NO: 237
QLTQSPSSLSASVGDRVTITCRASQGLSSALAWYRQKPGKAPKLLIYDAS
SLESGVPSRFSGSGSGTDFTLTISSLQPEDFATYYCQQFTSYPQITFGQG
TRLEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC
```

The generated monospecific anti-EGFR and c-Met antibodies were mixed for in vitro Fab arm exchange in matrix and characterized in various assays. The bispecific antibody EM1-mAb comprises the EGFR binding arm of mAb E1-F405L and the c-Met binding arm of mAb M1-K409R. The bispecific antibody EM2-mAb comprises the EGFR binding arm of mAb E2-F405L and the c-Met binding arm of mAb M2-K409R. The bispecific antibody EM3-mAb comprises the EGFR binding arm of mAb E1-K409R and the c-Met binding arm of mAb M1-F405L. The bispecific antibody EM4-mAb comprises the EGFR binding arm of mAb E2-K409R and the c-Met binding arm of mAb M2-F405L. EM1-mAb and EM3-mAb had comparable characteristics.

The bispecific EM1-mAb was cultured in a CHO cell line having reduced fucosylation ability of glycoproteins, and hence have a fucosyl content of about 1-15%. The removal of the core fucose from the biantennary complex-type oligosaccharides attached to the Fc regions significantly enhances the ADCC of antibodies via improved FcγRIIIa binding without altering antigen binding or CDC activity. Such mAbs can be achieved using different methods reported to lead to the successful expression of relatively high defucosylated therapeutic antibodies bearing the biantennary complex-type of Fc oligosaccharides and are described supra.

EXAMPLE 11

Purification of Bispecific EGFR/c-Met Antibodies

The bispecific EM1-mAb was further purified after the in vitro Fab-arm exchange using hydrophobic interaction chromatography to minimize residual parental c-Met and EGFR antibodies using standard methods.

EXAMPLE 12

Characterization of Bispecific EGFR/c-Met Antibodies

The EGFR/c-Met bispecific antibody EM1-mAb was tested in various assays for its characteristics including inhibition of EGF-stimulated EGFR phosphorylation, HGF-stimulated c-Met phosphorylation, ERK1/2 phosphorylation, AKT phosphorylation, inhibition of ligand binding and cell viability. The characteristics of the EM1-mAb was compared to control monovalent EGFR- or c-Met binding antibodies, and to known EGFR inhibitors such as erlotinib (CAS 183321-74-6; tyrosine kinase inhibitor) and cetuximab (CAS 205923-56-4).

As the parent antibodies of the EM-1 mAb antibodies are bivalent, control monovalent EGFR and c-Met antibodies were generated in a bispecific format combined with a Fab arm that binds to an unrelated/irrelevant antigen to accurately compare the synergy and avidity of a bispecific EM-1 mAb in comparison to a mixture of corresponding control monovalent molecules.

To generate the control monovalent EGFR and c-Met antibodies, a monospecific anti-HIV gp120 antibody gp120-K409R was generated comprising heavy chain of SEQ ID NO: 198 and a light chain of SEQ ID NO: 209. A monospecific anti-HIV gp120 antibody gp120-F405L was generated comprising the heavy chain of SEQ ID NO: 197 and the light chain of SEQ ID NO: 209.

The control monovalent anti-EGFR mAb E1-F405L-gp120-K409R was generated by in vitro Fab arm exchange between E1-F405L and gp120-K409R, and the control monovalent anti-cMet mAb M1-K409R-gp120-F405L was generated by in vitro Fab-arm exchange between M1-K409R and gp120-F405L and purified as described earlier.

The following cell lines were used in characterization of the bispecific antibodies: NCI-H292 (American Type Culture Collection (ATCC), Cat. No. CRL-1848), NCI-H1975 (ATCC Cat. No. CRL-5908), SKMES-1 (ATCC Cat. No. HTB-58), A431 (ATCC Cat. No. CRL-1555), NCI-H441 (ATCC Cat. No. HTB-174), NCI-H3255 (DCTD tumor/cell line repository, NCI, Frederick, NCI-Navy Medical oncology Cell Line supplement. J Cell Biochem suppl 24, 1996; Tracy S. cancer Res 64:7241-4, 2004; Shimamura T. cancer Res 65:6401-8, 2005) and HCC-827 (ATCC Cat. No. CRL-2868). NCI-H292 and SKMES-1 cells express both wild type EGFR and wild type c-Met. NCI-3255 expresses mutant L858R EGFR and displays EGFR and c-Met amplification. H1975 expresses mutant L858R/T790M EGFR and wild type c-Met. HCC-827 expresses A (E746, A750) EGFR and displays EGFR amplification. Cell line NCI-H292, NCI-H975, NCI-H441 and NCI-H3255 are interchangeably referred to as H292, H975, H441 and H3255, respectively, in the specification.

Binding of Bispecific EGFR/cMet Antibodies to EGFR and c-Met on Cells (A431 Cell Binding Assay)

The bispecific EGFR/c-Met antibody EM1-mAb was tested for binding to EGFR and c-Met on cells using protocol described in Example 3 ("A431 Cell Binding Assay") and Example 6 ("H441 Cell Binding Assay"). Cetuximab and a control antibody monovalent towards EGFR E1-F405L-gp120-K409R were used as controls for the A431 cells. Cetuximab had an $EC_{50}$ value of 5.0 nM. Table 18 shows the $EC_{50}$ values for binding. EM1-mAb demonstrated a 1.9-fold (A431 cells) and 2.3-fold (H441 cells) decrease in binding when compared to the bivalent monospecific parental control antibodies. Cetuximab was comparable to the bivalent parental control antibodies. EM1-mAb displays higher $EC_{50}$ binding values than the values for the parental mAbs due to the monovalent binding of EGFR and c-Met. EM1-mAb has similar binding $EC_{50}$ values as the single arm E1/inert arm and E2/inert arm bispecific monovalent mAbs.

TABLE 18

| | $EC_{50}$ (nM) binding to cells | | |
|---|---|---|---|
| | EM1-mAb | Parental mAbs | E1-F405L-gp120-K409R (A431 cells) or M1-K409R-gp120-F405L (H441 cells) |
| A431 (assay for EGFR binding) | 9.6 ± 3 | 5.1 ± 0.3 | 10.1 ± 0.6 |
| H441 (assay for c-Met binding) | 1.5 ± 0.7 | 0.65 ± 0.1 | 1.0 ± 0.3 |

Inhibition of Ligand Binding to the Receptor

The bispecific antibodies were tested for their ability to block binding of EGF to EGFR extracellular domain and HGF to c-Met extracellular domain in an ELISA assay. Recombinant human EGF R-Fc (R&D Systems, Cat #: 344-ER-050) or human HGF (R&D Systems, Cat #: 294-HGN-025/CF) was coated onto MSD HighBind plates (Meso Scale Discovery, Gaithersburg, Md.) for 2 hr at room temperature. MSD Blocker A buffer (Meso Scale Discovery, Gaithersburg, Md.) was added to each well and incubated for 2 hr at room temperature. Plates were washed three times with 0.1 M HEPES buffer, pH 7.4, followed by the addition of a mixture of either flurescent dy labeled (MSD) EGF or biotinylated HGF proteins with different concentrations of antibodies. Ruthenium-labeled EGF protein was incubated for 30 min at RT with increasing concentrations of different antibodies, from 1 nM to 4 µM. After 2-hour incubation with gentle shaking at room temperature, the plates were washed 3 times with 0.1M HEPES buffer (pH 7.4). MSD Read Buffer T was diluted and dispensed and the signals were analyzed with a SECTOR Imager 6000. The HGF inhibition assays were performed as the EGF/EGFR inhibition assays except that 10 nM of biotinylated HGF was incubated for 30 min at RT with increasing concentrations of different antibodies, from 1 nM to 2 μM.

EM1-mAb inhibited EGF binding to EGFR with an $IC_{50}$ value of 10.7 nM±1.2 in the presence of 50 nM EGF and with an $IC_{50}$ value of 10.6±1.5 nM in the presence of 80 nM EGF. The parental bivalent antibody inhibited EGF binding to EGFR with an $IC_{50}$ value of 0.14±1.5 nM in the presence of 50 nM EGF and with an $IC_{50}$ value of 1.7±1.4 nM in the presence of 80 nM EGF. EM1 mAb had a weaker inhibition of EGF binding to the EGFR extracellular domain because of the monovalent binding of EM1 mAb as compared to the parental bivalent mAb.

EM1-mAb inhibited HGF binding to c-Met with an $IC_{50}$ value of 29.9±1.5 nM. The parental bivalent antibody inhibited HGF binding to c-Met with and $IC_{50}$ of 14.8±1.6 nM. EM1 mAb had a weaker inhibition of HGF binding to the cMet extracellular domain because of the monovalent binding of EM1-mAb as compared to the parental bivalent mAb.
Inhibition of EGF-Stimulated EGFR Phosphorylation and HGF-Stimulated c-Met Phosphorylation Antibodies were tested to determine $IC_{50}$ values for inhibition of EGFR and c-Met phosphorylation Inhibition of EGF-stimulated EGFR phosphorylation and HGF-stimulated c-Met phosphorylation were assessed at varying antibody concentrations (0.035-700 nM final) as described in Example 2 ("Inhibition of EGF-Stimulated EGFR Phosphorylation") and Example 6 ("Inhibition of HGF-Stimulated c-Met Phosphorylation"). In some experiments, both EGF and HGF were added to the cells so the same cell lysate could be used to detect both EGFR and c-Met phosphorylation.

The control anti-EGFR mAb E1-F405L-gp120-K409R monovalent for EGFR and the parental bivalent anti-EGFR antibody with low fucose content were used as control antibodies. Table 19 shows the $IC_{50}$ values of the assays.

TABLE 19

| | pEGFR ($IC_{50}$, nM) | | pMet ($IC_{50}$, nM) | |
|---|---|---|---|---|
| | Cell line | | | |
| Antibody | H292 | H1975 | H292 | H1975 |
| EM1-mAb | 8.6-29 | 1.5 | 0.55-0.83 | 0.64 |
| E1-F405L-gp120-K409R | 10.9-13.1 | ND | 0.7-4 | ND |
| Parental EGFR (F405L)mAb* | 1.5 | ND | No effect | ND |

*Antibody had low fucose content

Enhanced Inhibition of pERK and pAKT with EM1-mAb Compared to Mixture of Monovalent Antibodies (mAb pERK Assay) (mAb pAKT Assay)

The potential for enhanced potency with a bispecific EGFR/c-Met antibody was evaluated by assessing mAb effects on pERK and pAKT downstream signaling. For these experiments, the mixture of monovalent control EGFR and monovalent control c-Met antibodies was compared to the bispecific EM1-mAb. Cells were plated in clear 96-well tissue culture-treated plates (Nunc) in 100 μL/well of RPMI medium containing GlutaMAX and 25 mM Hepes (Invitrogen), supplemented with 1 mM sodium pyruvate (Gibco), 0.1 mM NEAA (Gibco), 10% heat inactivated fetal bovine serum (Gibco), and 7.5 ng/mL HGF (R&D Systems cat #294-HGN) and allowed to attach overnight at 37° C. in a humidified 5% $CO_2$ atmosphere. Cells were not serum-starved. Cells were treated for 30 min (pERK assay) or 1 hour (pAkt assay) with varying concentrations (0.11-700 nM final) of monovalent control antibodies or EM1-mAb.

Cells were assessed for pERK or pAKT levels using the following kits and according to manufacturer's instructions from Meso Scale Discovery: Phospho-ERK1/2 (Thr202/Tyr204; Thr185/Tyr187) Assay Whole Cell Lysate Kit (cat# K151DWD, Phospho-Akt (Ser473) Assay Whole Cell Lysate Kit (cat#K151CAD), Phospho-Akt (Thr308) Assay Whole Cell Lysate Kit (cat#K151DYD). For the pERK assay, cells were lysed, and whole cell lysates were added to plates coated with anti-phospho-ERK1/2 antibody (recognizing ERK1 phosphoryated at residues Thr202 and Tyr204 and ERK2 phosphorylated at residues Thr185 and Tyr187), and phosphorylated ERK1/2 was detected with anti-total ERK1/2 antibody conjugated with MSD SULFO-TAG™ reagent. For the pAKT Ser473 assay, the capture antibody was anti-totalAKT antibody and the detection antibody anti-pAKT Ser473 antibody conjugated with MSD SULFO-TAG™ reagent. For the pAKT Thr308 assay, the capture antibody was anti-totalAKT antibody and the detection antibody anti-pAKT Thr308 antibody conjugated with MSD SULFO-TAG™ reagent.

Plates were read on a SECTOR® Imager 6000 instrument (Meso Scale Discovery) using manufacturer-installed assay-specific default settings. Data were plotted as electrochemiluminescence signal against the logarithm of antibody concentration and $IC_{50}$ values were determined by fitting the data to a sigmoidal dose response with variable slope using GraphPad Prism 5 software. NCI-H292, H1975 and SKMES-1 cell lines were used in these assays.

The $IC_{50}$ for inhibition of ERK phosphorylation by the bispecific EM1-mAb was about 14-63 fold lower relative to the mixture of the two monovalent control antibodies, depending on a cell line tested (Table 20). The improved potency of the EM1-mAb compared to the mixture of two monovalent control antibodies suggests a cooperative or avidity effect due to enhanced binding of EM1-mAb to these cell lines. The $IC_{50}$ for inhibition of Ser475 (pAKTS475) and Thr308 (pAKTT308) AKT phosphorylation in NCI-H1975 cell line was about 75-fold and 122-fold lower, respectively, when compared to the mixture of the two monovalent control antibodies (Table 21). The improved potency of the EM1-mAb compared to the mixture of two monovalent control antibodies suggests a cooperative or avidity effect due to enhanced binding of EM1-mAb to these cell lines. Thus, the bispecific nature of the EM1-mAb resulted in an enhanced effect on downstream signaling effectors.

TABLE 20

| | $IC_{50}$ (nM) pERK Antibody | | |
|---|---|---|---|
| Cell line | Bispecific EM1-mAb | Mixture of E1-F405L-gp120-K409R and M1-K409R-gp120-F405L | Fold change bispecific vs. mixture of two monovalent control antibodies |
| H292 | 0.64 | 34.94 | 55 |
| H1975 | 1.67 | 106 | 63 |
| SKMES-1 | 0.54 | 7.63 | 14 |

TABLE 21

| Antibody | $IC_{50}$ (nM) pAKTS473 | $IC_{50}$ (nM) pAKTT308 |
|---|---|---|
| Bispecific EM1-mAb | 0.87 | 0.96 |
| Mixture of E1-F405L-gp120-K409R and M1-K409R-gp120-F405L | 65 | 117 |
| Fold change mixture of two monovalent vs. bispecific | 75 | 122 |

Inhibition of Human Tumor Cell Growth or Viability by Antibodies

Inhibition of c-Met-dependent cell growth was assessed by measuring viability of various tumor cells following exposure to the bispecific EM1-mAb. NCI-H292, SKMES-1, NCI-H1975 and NCI-H3255 cells were used in the studies.

Cells were cultured in standard 2D and low attachment formats. Erlotinib and cetuximab were used as controls. Table 22 summarizes the $IC_{50}$ values for the assay.

Inhibition of Human Tumor Cell Growth or Viability by Antibodies—Standard 2D Format The inhibition of cell growth was assessed by measuring the viability of NCI-H292 and NCI-H1975 following exposure to antibodies in two formats. For the standard 2D format cells were plated in opaque white 96-well tissue culture-treated plates (PerkinElmer) in RPMI medium containing GlutaMAX and 25 mM Hepes (Invitrogen), supplemented with 1 mM sodium pyruvate (Gibco), 0.1 mM NEAA (Gibco), and 10% heat inactivated fetal bovine serum (Gibco), and allowed to attach overnight at 37° C., 5% $CO_2$. Cells were treated with varying concentrations of antibodies (0.035-700 nM final), along with HGF (7.5 ng/mL, R&D Systems cat #294-HGF), then incubated at 37° C., 5% $CO_2$ for 72 hours. Some wells were left untreated with either HGF or antibodies as controls. Viable cells were detected using CellTiter-Glo® reagent (Promega), and data were analyzed as described in Example 3 in "Inhibition of Human Tumor Cell Growth (NCI-H292 growth and NCI-H322 growth assay)".

Inhibition of Human Tumor Cell Growth or Viability by Antibodies—Low Attachment Format To assess survival in low attachment conditions, cells were plated in Ultra Low Attachment 96-well plates (Corning Costar) in 50 μt/well of RPMI medium (Invitrogen) containing GlutaMAX and 25 mM Hepes, supplemented with 1 mM sodium pyruvate (Gibco), 0.1 mM NEAA (Gibco), and 10% heat inactivated fetal bovine serum (Gibco), and allowed to attach overnight at 37° C., 5% $CO_2$. Cells were treated with varying concentrations of antibodies (0.035-700 nM final), along with HGF (7.5 ng/mL, R&D Systems cat#294-HGN), then incubated at 37° C., 5% $CO_2$ for 72 hours. Some wells were left untreated with either HGF or antibodies as controls. Viable cells were detected using CellTiter-Glo® reagent (Promega), and data were analyzed as described above in "Inhibition of Human Tumor Cell Growth (NCI-H292 growth and NCI-H322 growth assay)" in Example 3, except that lysates were transferred to opaque white 96-well tissue culture-treated plates (PerkinElmer) prior to reading luminescence.

In the standard 2D culture, EM1-mAb inhibited NCI-H292 growth with an $IC_{50}$ of 31 nM, and in low attachment conditions with an $IC_{50}$ of 0.64 nM. EM-1 mAb inhibited NCI-H1975 cell growth with an $IC_{50}$ of >700 nM and 0.8-1.35 nM in standard 2D and low attachment culture, respectively. In NCI-H292 cells expressing both wild type EGFR and cMet, EM1-mAb had over 22 fold improved potency in the standard 2D and about 330-fold improved potency in the low attachment culture conditions when compared to cetuximab. In NCI-H1975 cell, which express L858R, T790M EGFR mutant and wild type cMet, EM-1 mAb had at least a 518-fold improved potency when compared to cetuximab in low attachment culture conditions. Table 22 shows the summary of the assays.

TABLE 22

| Cell line | EGFR state | cMet state | EM1-mAb Standard 2D culture $IC_{50}$ (nM) | EM1-mAb Low attachment $IC_{50}$ (nM) | Cetuximab Standard 2D culture $IC_{50}$ (nM) | Cetuximab Low attachment $IC_{50}$ (nM) |
|---|---|---|---|---|---|---|
| NCI-H292 | WT | WT | 31 | 0.64 | >700 | 212 |
| NCI-H1975 | L858R, T790M | WT | >700 | 0.8-1.35 | >700 | >700 |

Combination of Erlotinib and EM1-mAb is Efficient in Inhibition of Growth of EGFR Mutant Cell Lines The inhibition of cell growth by the combination of erlotinib plus EM1-mAb was evaluated in both standard 2D culture conditions and in the low attachment format. NCI-H3255 and HCC-827 cells were plated as described above in "Inhibition of Human Tumor Cell Growth or Viability by Antibodies". HGF (7.5 ng/mL, R&D Systems cat #294-HGN) was added to cells along with treatment with antibodies. Cells were treated with varying concentrations of antibodies (0.11-700 nM final), or erlotinib (0.46-3000 nM final), or the combination of erlotinib plus antibody, using increasing amounts of each in a fixed ratio (e.g. lowest concentration of combination=lowest concentration of antibody (0.11 nM)+lowest concentration of erlotinib (0.46 nM)). Some wells were left untreated with either HGF or antibodies as controls. Cells were incubated at 37° C., 5% $CO_2$ for 72 hours, then viable cells were detected using CellTiter-Glo® reagent (Promega), and data were analyzed as described above in "Inhibition of Human Tumor Cell Growth (NCI-H292 growth and NCI-H322 growth assay)". Table 23 summarizes the results of the experiment. In the table, the $IC_{50}$ values for the combinations are relative to either the antibody, or erlotinib, depending on what is indicated in parentheses.

In both NCI-H3255 and HCC-827 cells (EGFR mutant cell lines) the addition of EM1-mAb to erlotinib both increased the potency of inhibition of cell viability and was more effective resulting in fewer viable cells overall. In the NCI-H3255 cells using standard 2D conditions, the $IC_{50}$ for erlotinib alone was 122 nM, whereas the combination was 49 nM. Similarly, in HCC-827 cells, the $IC_{50}$ for erlotinib alone was 27 nM, whereas the combination was 15 nM. Also, the combination of erlotinib plus EM1-mAb was more effective than the combination of erlotinib plus cetuximab. Thus, in the presence of HGF, addition of EM1-mAb increased the effectiveness of erlotinib in this assay.

NCI-H3255 cells express L858R mutant EGFR and amplified cMet. HCC-827 cells express EGFR mutants with deletions at amino acid positions 746 and 750 and wild type c-Met. EM1-mAb has stronger effects in the viability of HCC-827 and NCI-3255 in the presence of erlotinib than erlotinib alone in either standard or low attachment cultures.

TABLE 23

| Samples | EM1 mAb + erlotinib IC$_{50}$ (nM) | erlotinib IC$_{50}$ (nM) |
|---|---|---|
| NCI-H3255, standard 2D culture | 49.0 | 122 |
| NCI-H3255, low attachment culture | 10.6 | 47.1 |
| HCC-827, standard 2D culture | 14.6 | 27.4 |
| HCC-827, low attachment culture | 3.5 | 9.5 |

EXAMPLE 13

Antibody Mediated Cellular Cytotoxicity (ADCC) of EM1-mAb in in vitro Cell Lines ADCC assays were performed as previously described (Scallon et al., Mol Immunol 44:1524-1534 2007). Briefly, PBMCs were purified from human blood by Ficoll gradients and used as effector cells for ADCC assays. NCI-H292, NCI-H1975 or NCI-H441 cells were used as target cells with a ratio of 1 target cell to 50 effector cells. Target cells were pre-labeled with BATDA (PerkinElmer) for 20 minutes at 37° C., washed twice and resuspended in DMEM, 10% heat-inactivated FBS, 2 mM L-glutamine (all from Invitrogen). Target (1×10$^4$ cells) and effector cells (0.5×10$^6$ cells) were combined and 100 µl of cells were added to the wells of 96-well U-bottom plates. An additional 100 µl was added with or without wild type and protease-resistant mAb constructs. All samples were performed in duplicate. The plates were centrifuged at 200 g for 3 minutes, incubated at 37° C. for 2 hours, and then centrifuged again at 200 g for 3 minutes. A total of 20 µl of supernatant was removed per well and cell lysis was measured by the addition of 200 µl of the DELPHIA Europium-based reagent (PerkinElmer). Fluorescence was measured using an Envision 2101 Multi-label Reader (PerkinElmer). Data were normalized to maximal cytotoxicity with 0.67% Triton X-100 (Sigma Aldrich) and minimal control determined by spontaneous release of BATDA from target cells in the absence of any antibody using the following equation: (experimental release−spontaneous release)/(maximal release−spontaneous release)× 100%. Data were fit to a sigmoidal dose-response model using GraphPad Prism v5.

The ADCC results for the EM1 mAbs and comparators are summarized in the Table 24 (NCI-H292 cells), Table 25 (NCI-H1975 cells) and Table 26 (NCI-H441 cells) and Table 27 (NCI-H1993 cells) list the EC$_{50}$ values and maximum lysis achieved. NCI-H292 cells express wild type (WT) EGFR, WT c-Met, and WT KRAS; NCI-H1975 cells express mutant EGFR (L858R T790M), WT cMet and WT KRAS; NCI-H441 express WT EGFR, WT cMet, and mutant KRAS (G12V), and NCI-H1993 cells express WT EGFR, amplified cMet, WT KRAS. KRAS is also known as GTPase KRas and as V-Ki-ras2 Kirsten rat sarcoma viral oncogene homolog.

The EM1-mAb has higher potency of ADCC responses than cetuximab and the normal fucose version of EM1-mAb as indicated by having lower EC$_{50}$ values. The EM1 mAb has higher efficacy in terms of maximum lysis achieved than cetuximab and the normal fucose bispecific mAb. From profiles of on Tables 24-27, the EM-1 mAb has ADCC activity on cells that have mutant and WT EGFR, WT with normal and amplified levels of cMet, and WT and mutant KRAS.

TABLE 24

| mAb | Potency (EC$_{50}$ µg/ml) | R$^2$ | Efficacy (maximum lysis achieved) |
|---|---|---|---|
| EM1 mAb | 0.0058 | 0.93 | 19% |
| Anti-EGFR x cMet normal fucose bispecific mAb | 0.22 | 0.85 | 13% |
| Cetuximab | 0.0064 | 0.94 | 12% |

TABLE 25

| mAb | Potency (EC$_{50}$ µg/ml) | R$^2$ | Efficacy (maximum lysis achieved) |
|---|---|---|---|
| EM1 mAb | 0.022 | 0.91 | 19% |
| Anti-EGFR x cMet normal fucose bispecific mAb | 1.8 | 0.79 | 13% |
| Cetuximab | 0.029 | 0.70 | 11% |

TABLE 26

| mAb | Potency (EC$_{50}$ µg/ml) | R$^2$ | Efficacy (maximum lysis achieved) |
|---|---|---|---|
| EM1 mAb | 0.022 | 0.97 | 24% |
| Anti-EGFR x cMet normal fucose bispecific mAb | 0.52 | 0.87 | 7.9% |
| Cetuximab | 0.013 | 0.85 | 15% |

TABLE 27

| mAb | Potency (EC$_{50}$ µg/ml) | R$^2$ | Efficacy (maximum lysis achieved) |
|---|---|---|---|
| EM1 mAb | 0.0013 | 0.95 | 27% |
| Anti-EGFR x cMet normal fucose bispecific mAb | 0.054 | 0.87 | 17% |
| Cetuximab | 0.0042 | 0.76 | 21% |

EXAMPLE 14

Tumor Efficacy Studies with the EM1-mAb

The efficacy of the EM1 mAb against tumor growth was conducted as described in Example 7 "Tumor efficacy studies with bispecific EGFR/c-Met molecules". In brief, NCI-H292-HGF cells were implanted subcutaneously (s.c.) with Cultrex at 2×10$^6$ into female SCID Beige mice' The mice were stratified by tumor volume 7 days after implant into 5 Groups with 10 mice per group. The dosing began after the starting mean tumor volume per group ranged from 62-66 mm$^3$ (small tumors). PBS or therapeutic were dosed intraperitoneally (i.p.) 2 times per week.

The evaluation of the efficacy also employed SKMES-HGF, a human squamous cell carcinoma that was transfected with human HGF (hepatic growth factor). These cells were implanted s.c. at 10×10$^6$ into female SCID Beige mice' These mice were stratified by tumor volume 12 days after implant into 5 groups with 8 mice per group. The first study began with starting mean tumor volume per group ranged from 98-101 mm$^3$ (large tumors). PBS or therapeutic mAbs were dosed i.p. 2x/week for 4 weeks. In the larger sized tumor study, the mice that were stratified after the tumor volumes were about 200-300 mm³ by splitting into 2 groups. These mice were then treated with either cetuximab (20 mg/kg) or EM1-mAb (20 mg/kg), i.p., 2×/week (3 weeks).

The summary of the data is shown in Table 28. FIG. 10 shows the efficacy of the molecules over time. EM1-mAb has an improved tumor suppression profile when compared to cetuximab in H292-HGF small tumor model and in SKMES-HGF small and large tumor models.

TABLE 28

| Sample and time | Cell line | Dosing at mg per kg | Partial regression | Complete regression |
|---|---|---|---|---|
| EM1 at day 35 | H292-HGF small tumor | 20 | 10/10 | 10/10 |
| | | 5 | 10/10 | 10/10 |
| | | 1 | 0/10 | 0/10 |
| Cetuximab at day 35 | H292-HGF small tumor | 20 | 0/10 | 0/10 |
| EM1 at day 67 | SKMES - HGF small tumor | 20 | 0/8 | 8/8 |
| | | 5 | 1/8 | 6/8 |
| | | 1 | 2/8 | 4/8 |
| Cetuximab at day 67 | | 20 | 0/8 | 6/8 |
| EM1 at day 70 | SKMES - HGF large tumor | 20 | 4/7 | 3/7 |
| Cetuximab at day 35 | | 20 | 0/7 | 0/7 |

Table 29 shows the tumor sizes in treatment groups from the SKMES-HGF tumors, and table 30 shows the anti-tumor activity.

EM1-mAb inhibited tumor growth in the SKMES-HGF model 97% or more at multiple doses down to 1 mg/kg. While initially cetuximab was very effective (88% TGI at 20 mg/kg), after dosing ended the cetuximab-treated tumors grew back. In contrast, the tumors treated with EM1-mAb at either 5 or 20 mg/kg did not grow back over the course of the study (>2 months).

TABLE 29

| | | Tumor volume (mm³) | | | |
|---|---|---|---|---|---|
| Days | Vehicle | bispecific EM1 at 20 mg/kg | bispecific EM1 at 5 mg/kg | bispecific EM1 at 1 mg/kg | Cetuximab at 20 mg/kg |
| 1 | 99 ± 6 | 99 ± 7 | 101 ± 6 | 101 ± 6 | 98 ± 5 |
| 8 | 146 ± 14 | 48 ± 10 | 49 ± 9 | 49 ± 10 | 60 ± 8 |
| 15 | 192 ± 21 | 9 ± 1 | 22 ± 10 | 41 ± 13 | 44 ± 23 |
| 22 | 326 ± 43 | 3 ± 2 | 17 ± 12 | 33 ± 15 | 42 ± 23 |
| 29 | 577 ± 55 | 2 ± 1 | 15 ± 9 | 38 ± 17 | 85 ± 60 |
| 36 | 994 ± 114 | 0.2 ± 0.1 | 13 ± 9 | 26 ± 14 | 125 ± 62 |
| 50 | — | 0.04 ± 0.04 | 10 ± 7 | 18 ± 9 | 423 ± 115 |
| 57 | — | 0.1 ± 0.2 | 3 ± 2 | 21 ± 10 | 650 ± 116 |
| 67 | — | 0 ± 0 | 8 ± 7 | 34 ± 22 | 1257 ± 151 |

TABLE 30

| Treatment | Tumor Size (mm³)a at day 36 | T/C (%) | T − C (days) at 1000 mm³ | P value |
|---|---|---|---|---|
| Vehicle | 994 ± 114 | — | — | — |
| bispecific EM1 at 20 mg/kg | 0.19 ± 0.12 | 0.02 | — | |
| bispecific EM1 at 5 mg/kg | 13 ± 9 | 1.3 | — | |
| bispecific EM1 at 1 mg/kg | 26 ± 14 | 2.6 | — | |
| Cetuximab (20 mg/kg) | 125 ± 62 | 13 | 31 | |

EXAMPLE 15

Inhibition of Cell Migration with EM1-mAb in vitro

Method

Effect of the EM-mAb and the control monovalent antibodies on inhibition of tumor cell migration was assessed in NIH-1650 cells. EGFR mutant cell line H1650 (Lung Bronchioloalveolar carcinoma cells harboring an exon 19 mutation [deletion E746, A750]) was cultured in tissue culture flasks under normal culture conditions (37° C., 5% $CO_2$, 95% humidity). All media and supplementation were as suggested by the supplier of the cells (American Type Culture Collection, Manassas, Va., USA).

Spheroids were generated by plating H1650 lung tumor cells at 10,000 cells/well into "U" bottom Ultra Low Adherence (ULA) 96-well plates (Corning, Tewksbury, USA) at 200 μl/well. These plates stimulate spontaneous formation of a single spheroid of cells within 24 hours (upon incubation at 37° C., 5% $CO_2$) and the spheroids were grown for four days under normal culture conditions.

Round bottom 96-well plates (BD Bioscience) were coated with 0.1% gelatin (EMD Millipore, Billerica, USA) in sterile water for 1 h at 37° C. For compound evaluation studies, day 4 10,000 cell tumor spheroids (H1650 and NCI-H1975) were transferred to the coated round bottom plates and treated with the EM1-mAb, the control monovalent anti-EGFR mAb E1-F405L-gp120-K409R having low fucose content, the control monovalent anti-cMet mAb M1-K409R-gp120-F405L having low fucose content, and a combination of the two monovalent antibodies E1-F405L-gp120-K409R and M1-K409R-gp120-F405L (produced in low fucose) in a dilution series with 20 ng/ml of HGF (R&D systems). Controls were treated with vehicle which was $IgG_1$ kappa isotype control (concentration equal to highest drug-treated cells). Effects of compounds were analyzed at 48 hrs by measuring the area covered by migrating cells using bright field images in a fully automated Operetta high content imaging system (Perkin Elmer) with a 2× objective Inhibition of cell migration (total area) due to treatment effect was assessed by normalizing data by dividing by media only control to create a percentage cell migration to control. Thus, a value less than 1 would be inhibitory to cell migration.

Results

The EM1-mAb demonstrated potent synergistic inhibition of cell migration in H1650 (L858R EGFR mutant) and H1975 (L858R/T790M EGFR mutant) cells when compared to a combination of the control monovalent anti-EGRF and anti-c-Met antibodies E1-F405L-gp120-K409R and M1-K409R-gp120-F405L. In H1650 cells, the six highest concentrations of the EM1-mAb significantly inhibited cell migration (p<0.001) compared to the isotype control. The $EC_{50}$ value for the EM1-mAb was 0.23 nM, whereas the $EC_{50}$ value for the combination of the monospecific control antibodies was 4.39 nM. The EM1-mAb therefore was about 19 fold more efficient in inhibiting H1650 cell migration when compared to the combination of the monovalent control antibodies. The level of cell migration inhibition of EM1-mAb was superior to the combination of monospecific control mAbs for H1650 and H1975 cells. Table 31 shows the $EC_{50}$ values for the assay.

TABLE 31

| Samples | H1650 | | H1975 |
|---|---|---|---|
| | EC$_{50}$ (nM) | Inhibition at 30 nM | Inhibition at 30 nM |
| EM1-mAb | 0.23 | 64% | 38% |
| Mixture of E1-F405L-gp120-K409R* and M1-K409R-gp120-F405L* | 4.39 | 59% | 20% |
| E1-F405L-gp120-K409R* | 5.44 | 15% | 7% |
| M1-K409R-gp120-F405L* | 7.36 | 43 | 10% |

*antibodies have low fucose content

EXAMPLE 16

Epitope Mapping of Anti-c-Met Antibody 069 and 5D5

The anti-c-Met mAb 069 binding epitope was mapped using the linear and constrained CLIPS peptide technology. The peptides scanned the SEMA, PSI, and Ig domains of human cMet. The linear and CLIPS peptides were synthesized using the amino acid sequence of the aforementioned cMet using standard Fmoc chemistry and deprotected using trifluoric acid with scavengers. The constrained peptides were synthesized on chemical scaffolds in order to reconstruct conformational epitopes using Chemically linked Peptides on Scaffolds (CLIPS) Technology (Timmerman et al., J Mol Recognition 20:283, 2007). The linear and constrained peptides were coupled to PEPSCAN cards and screened using a PEPSCAN based ELISA (Slootstra et al., Molecular Diversity 1, 87-96, 1996). The anti-c-Met mab 069 binding epitope is a discontinuous epitope consisting of c-Met amino acids 239-253 PEFRDSYPIKYVHAF (SEQ ID NO: 238) and 346-361 FAQSKPDSAEPMDRSA (SEQ ID NO: 239). c-Met amino acid sequence is shown in SEQ ID NO: 201.

Similar methods were used to map mAb 5D5 (MetMab, Onartuzumab) epitope. mAb 5D5 binds c-Met residues 325-340 PGAQLARQIGASLNDD (SEQ ID NO: 240).

EXAMPLE 17

In vivo Tumor Efficacy Studies with EM1-mAb

The efficacy of EM1 mAb against tumor growth was conducted as described in Example 7 "Tumor efficacy studies with bispecific EGFR/c-Met molecules" and Example 14 employing additional tumor cell lines with EGFR mutation or EGFR and/or c-Met amplifications. In brief, SNU-5, H1975, HCC827 cells, H1975 cells expressing human HGF, or a clone of HCC827 cells selected for its increased resistance to erlotinib (HCC827-ER1 cells) were implanted subcutaneously (s.c.) into female nude mice, except that SNU-5 cells were implanted in CR17/SCID mice. Mice were dosed intraperitoneally with PBS or EM1-mAb, cetuximab (CAS 205923-56-4), erlotinib (CAS 183321-74-6), afatinib (CAS 439081-18-2), or a combination of EM-1 mAb and afatinib and EM-1 mAb and erlotinib at indicated dosage and schedule shown in Table 32. Antitumor efficacy was measured as % TGI (tumor growth inhibition) calculated as 100−%T/C (T=mean tumor size of the treatment group; C=mean tumor size of the control group on a given day as described in Example 7).

In tumors with primary EGFR activating mutations (no resistance to EGFR TKIs): (HCC827 tumor, EGFR del (E746, A750)), EM1-mAb dosed 10 mg/kg inhibited tumor growth by 82%. Erlotinib was similarly effective in this model, as was the combination of erlotinib and EM1-mAb. FIG. 11 shows efficacy of the therapeutics over time in the HCC827 tumor model.

In tumors with wild type EGFR and c-Met gene amplification (gastric cancer model SNU-5), EM1-mAb showed antitumor activity with full tumor regression (98% TGI, at day 34 p<0.01, compared to vehicle using one-way ANOVA followed by individual comparisons using Games-Howell). Antitumor activity of anti-EGFR mAb cetuximab was less, 49% at day 34, in this model. FIG. 12 shows the efficacy of the therapeutics over time in the SNU-5 model.

EM1-mAb was tested in a NSCLC model containing primary EGFR activating mutation and the T790M EGFR mutation which renders tumors resistant to $1^{st}$ generation EGFR TKIs (H1975 model). EM1-mAb inhibited tumor growth with a 57% TGI in the H1975 cell line model implanted in nude mice (p<0.0001, compared to PBS vehicle using Logrank analysis with Prism 3.03). As expected, erlotinib was not effective in this model with the T790M mutation. Afatinib was equally effective as the EM1-mAb (57% TGI). Cetuximab and the combination of EM1-mAb with afatinib were the most effective, regressing tumors with 91% and 96% tumor growth inhibition, respectively, (p<0.0001 for both cetuximab compared to PBS and EM1-mAb+afatinib compared to the PBS+afatinib vehicles group using Logrank analysis with Prism 3.03). c-Met signaling pathways are not activated in this model as the mouse HGF does not bind to human c-Met.

EM1-mAb was tested in several models that were engineered to express human HGF using a lentiviral transduction system. This allows modeling of ligand activation of the c-Met pathway in vivo because mouse HGF does not activate the human c-Met on the implanted human tumor cells. Results with SKMES-HGF model are shown in Example 14 and FIG. 10, and the % TGI summarized in Table 32. EM1-mAb inhibited tumor growth in the H1975-HGF model 71% (p<0.0001, compared to PBS vehicle using Logrank analysis with Prism 3.03). Afatinib, erlotinib and cetuximab were less efficacious in this model. The combination of EM1-mAb and afatinib was very effective (96% TGI, p<0.0001, compared to the PBS+afatinib vehicles group using Logrank analysis with Prism 3.03). FIG. 13 shows the efficacy of the molecules over time in the H1975-HGF model. Erlotinib, afatinib and cetuximab thus lose their antitumor efficacy in tumor models in which c-Met pathway is activated.

EM1-mAb was tested in a tumor model characterized by primary EGFR activating mutation and increased resistance to $1^{st}$ generation EGFR TKI (erlotinib) due to c-Met gene amplification (HCC827-ER1 model). EM1-mAb dosed at 10 mg/kg partially regressed HCC827-ER1 tumors implanted with 86% TGI at day 25, and was more efficacious than erlotinib alone (65% TGI at day 25). Combination of EM1-mAb and erlotinib did not further improve efficacy. FIG. 14 shows the efficacy of the molecules over time.

EM1-mAb thus demonstrates efficacy in tumor models with wild type EGFR, with primary activating EGFR mutations, with the EGFR mutation T790M associated with resistance to EGFR therapeutics, as well as in models where c-Met is activated in either a ligand-dependent (autocrine HGF expression) or ligand-independent (c-Met gene amplification) manner. Combination of EM1-mAb with erlotinib or afatinib may improve efficacy in some tumor models.

TABLE 32

| Tumor Type | EGFR | cMet | Treatment (dose in mg/kg), schedule | % TGI (day of study); compared to PBS vehicle |
|---|---|---|---|---|
| SKMES-HGF lung squamous | WT | WT | EM1-mAb(20), BIWx4wk | 100 (36) |
| | | | cetuximab (20), BIWx4wk | 88 (36) |
| SNU-5 gastric | WT | AMP | EM1-mAb(10), BIWx4wk | 98 (34) |
| | | | cetuximab (10), BIWx4wk | 49 (34) |
| H1975 NSCLC | L858R; T790M | WT | EM1-mAb(10), BIWx3wk | 57 (18) |
| | | | cetuximab (10), BIWx3wk | 91 (18) |
| | | | erlotinib (50), QDx21d | 9 (18) |
| | | | afatinib (15), QDx21d | 57 (18) |
| | | | EM1-mAb(10), BIWx3wk + afatinib (15), QDx21d | 96 (18) |
| H1975-HGF NSCLC | L858R; T790M | WT | EM1-mAb(10), BIWx3wk | 71 (16) |
| | | | cetuximab (10), BIWx3wk | 42 (16) |
| | | | erlotinib (50), QDx21d | 20 (16) |
| | | | afatinib (15), QDx21d | 29 (16) |
| | | | EM1-mAb(10), BIWx3wk + afatinib (15), QDx21d | 96 (16) |
| HCC827 NSCLC | del (E746, A750); AMP | WT | EM1-mAb(10), BIWx4wk | 82 (35) |
| | | | erlotinib (25), QDx28d | 79 (35) |
| | | | EM1-mAb(10), BIWx3wk + erlotinib (25), QDx28d | 78 (35) |
| HCC827-ER1 NSCLC | del (E746, A750); AMP | AMP | EM1-mAb(10), BIWx4wk | 86 (25) |
| | | | erlotinib (25), QDx28d | 65 (25) |
| | | | EM1-mAb(10), BIWx3wk + erlotinib (25), QDx28d | 87 (25) |

BIW = biweekly
QD = once per day
WT = wild tpe
AMP = amplified

EXAMPLE 18

EM1 mAb Induced Degradation of EGFR and c-Met in vivo

To demonstrate engagement of both EGFR and c-Met by EM1-mAb in the tumor, samples were taken from H1975-HGF tumors at various times after a single dose of 20 mg/kg EM1-mAb Tumor lysates were prepared, normalized to total protein, and samples run on SDS-PAGE gels. Gels were transferred to nitrocellulose and Western blotted for either EGFR (Mouse (mAb) Anti-human EGFR (EGF-R2); Santa Cruz Biotechnology, Cat# sc-73511) or c-Met (Mouse (mAb) Anti-human Met (L41G3); Cell Signaling Technology, Cat#3148). EGFR levels were normalized to GAPDH; c-Met levels were normalized to actin. The levels of receptors from EM1-mAb treated tumors were compared to those of PBS-treated tumors to get % total receptor. EM1-mAb treatment decreased the total EGFR and cMet receptor levels in H1975-HGF tumors to between 20% to 60% of control, depending on the time point analyzed. FIG. 15 shows the average receptor levels compared to PBS over time. pEGFR, pc-Met and pAKT were also decreased at 72 hours after the single dose of EM1.

EXAMPLE 19

Anti-Tumor Activity Comparing $IgG_1$ and $IgG_{2\sigma}$ Variant Isoforms of EGFR/c-Met Bispecific mAbs To better understand the contribution of effector function to the efficacy observed in the H1975-HGF model, a comparison was performed between EM1-mAb and a variant of EM1-mAb having an IgG2 Fc with effector silencing substitutions V234A/G237A/P238S/H268A/V309L/A330S/P331S on IgG2 (substitutions described in Intl. Pat. Appl. No. WO2011/066501) (numbering according to the EU index). An IgG2 antibody with V234A/G237A/P238S/H268A/V309L/A330S/P331S substitutions does not interact with Fc receptors or effector cells (such as NK cells and macrophages). Any loss of activity observed with the IgG2 V234A/G237A/P238S/H268A/V309L/A330S/P331S variant of the EM1-mAb may thus represent antitumor activity contributed by effector-mediated mechanisms such as ADCC and/or ADCP. After 32 day post tumor cell implant in the H1975-HGF model described above, there is an indication of loss of antitumor activity with the IgG2 V234A/G237A/P238S/H268A/V309L/A330S/P331S variant of the EM1-mAb when compared to the parental EM1-mAb, suggesting that effector-mediated mechanisms contribute to the function of EM-1 mAb. FIG. 16 shows the antitumor activity of the molecules.

SEQUENCE LISTING

| SEQ ID NO: | Type | Species | Description | Sequence |
|---|---|---|---|---|
| 1 | PRT | Artificial | Tencon | LPAPKNLVVSEVTEDSLRLSWTAPDAAFDSFLIQYQESEKVGEAINLT VPGSERSYDLTGLKPGTEYTVSIYGVKGGHRSNPLSAEFTT |
| 2 | DNA | Artificial | POP2220 | GGAAACAGGATCTACCATGCTGCCGGCGCCGAAAAACCTGGTTGT TTCTGAAGTTACC |
| 3 | DNA | Artificial | TC5'toFG | AACACCGTAGATAGAAACGGT |
| 4 | DNA | Artificial | 130mer | CGGCGGTTAGAACGCGGCTACAATTAATACATAACCCCATCCCCC TGTTGACAATTAATCATCGGCTCGTATAATGTGTGGAATTGTGAGC GGATAACAATTTCACACAGGAAACAGGATCTACCATGCTG |
| 5 | DNA | Artificial | POP2222 | CGGCGGTTAGAACGCGGCTAC |

| | | | | SEQUENCE LISTING |
|---|---|---|---|---|
| 6 | DNA | Artificial | TCF7 | GGTGGTGAATTCCGCAGACAGCGGSNNSNNSNNSNNSNNSNN AACACCGTAGATAGAAACGGT |
| 7 | DNA | Artificial | TCF8 | GGTGGTGAATTCCGCAGACAGCGGSNNSNNSNNSNNSNNSNN SNNAACACCGTAGATAGAAACGGT |
| 8 | DNA | Artificial | TCF9 | GGTGGTGAATTCCGCAGACAGCGGSNNSNNSNNSNNSNNSNN SNNSNNAACACCGTAGATAGAAACGGT |
| 9 | DNA | Artificial | TCF10 | GGTGGTGAATTCCGCAGACAGCGGSNNSNNSNNSNNSNNSNN SNNSNNSNNAACACCGTAGATAGAAACGGT |
| 10 | DNA | Artificial | TCF11 | GGTGGTGAATTCCGCAGACAGCGGSNNSNNSNNSNNSNNSNN SNNSNNSNNSNNAACACCGTAGATAGAAACGGT |
| 11 | DNA | Artificial | TCF12 | GGTGGTGAATTCCGCAGACAGCGGSNNSNNSNNSNNSNNSNN SNNSNNSNNSNNSNNAACACCGTAGATAGAAACGGT |
| 12 | DNA | Artificial | POP2234 | AAGATCAGTTGCGGCCGCTAGACTAGAACCGCTGCCATGGTGATG GTGATGGTGACCGCCGGTGGTGAATTCCGCAGACAG |
| 13 | DNA | Artificial | POP2250 | CGGCGGTTAGAACGCGGCTACAATTAATAC |
| 14 | DNA | Artificial | DidLigRev | CATGATTACGCCAAGCTCAGAA |
| 15 | DNA | Artificial | Tcon5new2 | GAGCCGCCGCCACCGGTTTAATGGTGATGGTGATGGT GACCACCGGTGGTGAATTCCGCAGACAG |
| 16 | DNA | Artificial | Tcon6 | AAGAAGGAGAACCGGTATGCTGCCGGCGCCGAAAAAC |
| 17 | DNA | Artificial | LS1008 | TTTGGGAAGCTTCTAGGTCTCGGCGGTCACCATCACC ATCACCATGGCAGCCGGTTCTAGTCTAGCGGCCCCAAC TGATCTTCACCAAAC |
| 18 | PRT | Artificial | P53A1R5-17 without met | LPAPKNLVVSEVTEDSLRLSWADPHGFYDSFLIQYQES EKVGEAINLTVPGSERSYDLTGLKPGTEYTVSIYGVHNV YKDTNMRGLPLSAEFTT |
| 19 | PRT | Artificial | P54AR4-17 without met | LPAPKNLVVSEVTEDSLRLSWTYDRDGYDSFLIQYQES EKVGEAINLTVPGSERSYDLTGLKPGTEYTVSIYGVHNV YKDTNMRGLPLSAEFTT |
| 20 | PRT | Artificial | P54AR4-47 without met | LPAPKNLVVSEVTEDSLRLSWGYNGDHFDSFLIQYQES EKVGEAINLTVPGSERSYDLTGLKPGTEYTVSIYGVHNV YKDTNMRGLPLSAEFTT |
| 21 | PRT | Artificial | P54AR4-48 without met | LPAPKNLVVSEVTEDSLRLSWDDPRGFYESFLIQYQES EKVGEAINLTVPGSERSYDLTGLKPGTEYTVSIYGVHNV YKDTNMRGLPLSAEFTT |
| 22 | PRT | Artificial | P54AR4-37 without met | LPAPKNLVVSEVTEDSLRLSWTWPYADLDSFLIQYQES EKVGEAINLTVPGSERSYDLTGLKPGTEYTVSIYGVHNV YKDTNMRGLPLSAEFTT |
| 23 | PRT | Artificial | 54AR4-74 without met | LPAPKNLVVSEVTEDSLRLSWGYNGDHFDSFLIQYQES EKVGEAINLTVPGSERSYDLTGLKPGTEYTVSIYGVHNV YKDTNMRGLPLSAEFTT |
| 24 | PRT | Artificial | P54AR4-81 without met | LPAPKNLVVSEVTEDSLRLSWDYDLGVYFDSFLIQYQE SEKVGEAINLTVPGSERSYDLTGLKPGTEYTVSIYGVHN VYKDTNMRGLPLSAEFTT |
| 25 | PRT | Artificial | P54AR4-83 without met | LPAPKNLVVSEVTEDSLRLSWDDPWAFYESFLIQYQES EKVGEAINLTVPGSERSYDLTGLKPGTEYTVSIYGVHNV YKDTNMRGLPLSAEFTT |
| 26 | PRT | Artificial | P54CR4-31 without Met | LPAPKNLVVSEVTEDSLRLSWTAPDAAFDSFLIQYQESE KVGEAINLTVPGSERSYDLTGLKPGTEYTVSIYGVLGSY VFEHDVMLPLSAEFTT |
| 27 | PRT | Artificial | P54AR4-83v2 without Met | LPAPKNLVVSEVTEDSARLSWDDPWAFYESFLIQYQES EKVGEAIVLTVPGSERSYDLTGLKPGTEYTVSIYGVHNV YKDTNMRGLPLSAIFTT |
| 28 | PRT | Artificial | P54CR4-31v2 without Met | LPAPKNLVVSEVTEDSARLSWTAPDAAFDSFLIQYQESE KVGEAIVLTVPGSERSYDLTGLKPGTEYTVSIYGVLGSY VFEHDVMLPLSAIFTT |

| | | | | SEQUENCE LISTING |
|---|---|---|---|---|
| 29 | PRT | Artificial | P54AR4-73v2 wihtout Met | LPAPKNLVVSEVTEDSLRLSWTWPYADLDSFLIQYQES EKVGEAINLTVPGSERSYDLTGLKPGTEYTVSIYGVHNV YKDTNMRGLPLSAEFTT |
| 30 | DNA | Artificial | TCON6 | AAG AAG GAG AAC CGG TAT GCT GCC GGC GCC GAA AAA C |
| 31 | DNA | Artificial | TCON5 E86Ishort | GAG CCG CCG CCA CCG GTT AAT GGA TGA TGG TGG TGA CCA CCG GTG GTG AAG ATC GCA GAC AG |
| 32 | PRT | Artificial | P114AR5P74-A5 | LPAPKNLVVSRVTEDSARLSWTAPDAAFDSFWIRYDEV VVGGEAIVLTVPGSERSYDLTGLKPGTEYYVNILGVKGG SISVPLSAIFTT |
| 33 | PRT | Artificial | P114AR5P75-E9 | LPAPKNLVVSRVTEDSARLSWTAPDAAFDSFFIRYDEFL RSGEAIVLTVPGSERSYDLTGLKPGTEYWVTILGVKGGL VSTPLSAIFTT |
| 34 | PRT | Artificial | P114AR7P92-F3 | LPAPKNLVVSRVTEDSARLSWTAPDAAFDSFWIRYFEFL GSGEAIVLTVPGSERSYDLTGLKPGTEYIVNIMGVKGGSI SHPLSAIFTT |
| 35 | PRT | Artificial | P114AR7P92-F6 | LPAPKNLVVSRVTEDSARLSWTAPDAAFDSFWIRYFEFL GSGEAIVLTVPGSERSYDLTGLKPGTEYVVNILGVKGGGL SVPLSAIFTT |
| 36 | PRT | Artificial | P114AR7P92-G8 | LPAPKNLVVSRVTEDSARLSWTAPDAAFDSFVIRYFEFLG SGEAIVLTVPGSERSYDLTGLKPGTEYVVQILGVKGGYISI PLSAIFTT |
| 37 | PRT | Artificial | P114AR7P92-H5 | LPAPKNLVVSRVTEDSARLSWTAPDAAFDSFWIRYLEFLL GGEAIVLTVPGSERSYDLTGLKPGTEYVVQIMGVKGGTVS PPLSAIFTT |
| 38 | PRT | Artificial | P114AR7P93-D11 | LPAPKNLVVSRVTEDSARLSWTAPDAAFDSFWIRYFEFL GSGEAIVLTVPGSERSYDLTGLKPGTEYVVGINGVKGGYI SYPLSAIFTT |
| 39 | PRT | Artificial | P114AR7P93-G8 | LPAPKNLVVSRVTEDSARLSWTAPDAAFDSFWIRYFEFL GSGEAIVLTVPGSERSYDLTDLKPGTEYGVTINGVKGGRV STPLSAIFTT |
| 40 | PRT | Artificial | P114AR7P93-H9 | LPAPKNLVVSRVTEDSARLSWTAPDAAFDSFWIRYFEFL GSGEAIVLTVPGSERSYDLTGLKPGTEYVVQIIGVKGGHIS LPLSAIFTT |
| 41 | PRT | Artificial | P114AR7P94-A3 | LPAPKNLVVSRVTEDSARLSWTAPDAAFDSFWIRYFEFL GSGEAIVLTVPGSERSYDLTGLKPGTEYVVNIMGVKGGKI SPPLSAIFTT |
| 42 | PRT | Artificial | P114AR7P94-E5 | LPAPKNLVVSRVTEDSARLSWTAPDAAFDSFWIRYFEFL GSGEAIVLTVPGSERSYDLTGLKPGTEYAVNIMGVKGGRV SVPLSAIFTT |
| 43 | PRT | Artificial | P114AR7P95-B9 | LPAPKNLVVSRVTEDSARLSWTAPDAAFDSFWIRYFEFL GSGEAIVLTVPGSERSYDLTGLKPGTEYVVQILGVKGGSI SVPLSAIFTT |
| 44 | PRT | Artificial | P114AR7P95-D3 | LPAPKNLVVSRVTEDSARLSWTAPDAAFDSFWIRYFEFL GSGEAIVLTVPGSERSYDLTGLKPGTEYVVNIMGVKGGSI SYPLSAIFTT |
| 45 | PRT | Artificial | P114AR7P95-D4 | LPAPKNLVVSRVTEDSARLSWTAPDAAFDSFWIRYFEFL GSGEAIVLTVPGSERSYDLTGLKPGTEYVVQILGVKGGYI SIPLSAIFTT |
| 46 | PRT | Artificial | P114AR7P95-E3 | LPAPKNLVVSRVTEDSARLSWTAPDAAFDSFWIRYFEFL GSGEAIVLTVPGSERSYDLTGLKPGTEYVVQIMGVKGGTV SPPLSAIFTT |
| 47 | PRT | Artificial | P114AR7P95-F10 | LPAPKNLVVSRVTEDSARLSWTAPDAAFDSFWIRYFEFTT AGEAIVLTVPGSERSYDLTGLKPGTEYVVNIMGVKGGSIS PPLSAIFTT |

| | | | | SEQUENCE LISTING |
|---|---|---|---|---|
| 48 | PRT | Artificial | P114AR7P95-G7 | LPAPKNLVVSRVTEDSARLSWTAPDAAFDSFWIRYFELLS TGEAIVLTVPGSERSYDLTGLKPGTEYVVNIMGVKGGSIS PPLSAIFTT |
| 49 | PRT | Artificial | P114AR7P95-H8 | LPAPKNLVVSRVTEDSARLSWTAPDAAFDSFWIRYFEFV SKGEAIVLTVPGSERSYDLTGLKPGTEYVVNIMGVKGGSI SPPLSAIFTT |
| 50 | PRT | Artificial | ECB1 | MLPAPKNLVVSEVTEDSARLSWDDPWAFYESFLIQYQES EKVGEAIVLTVPGSERSYDLTGLKPGTEYTVSIYGVHNVY KDTNMRGLPLSAIFTTGGGGSGGGGSGGGGSGGGGSM LPAPKNLVVSRVTEDSARLSWTAPDAAFDSFWIRYDEVV VGGEAIVLTVPGSERSYDLTGLKPGTEYYVNILGVKGGSIS VPLSAIFTT |
| 51 | PRT | Artificial | ECB2 | MLPAPKNLVVSEVTEDSARLSWDDPWAFYESFLIQYQES EKVGEAIVLTVPGSERSYDLTGLKPGTEYTVSIYGVHNVY KDTNMRGLPLSAIFTTGGGGSGGGGSGGGGSGGGGSL PAPKNLVVSRVTEDSARLSWTAPDAAFDSFWIRYFEFLG SGEAIVLTVPGSERSYDLTGLKPGTEYVVNIMGVKGGKIS PPLSAIFTT |
| 52 | PRT | Artificial | ECB3 | MLPAPKNLVVSEVTEDSARLSWDDPWAFYESFLIQYQES EKVGEAIVLTVPGSERSYDLTGLKPGTEYTVSIYGVHNVY KDTNMRGLPLSAIFTTGGGGSGGGGSGGGGSGGGGSM LPAPKNLVVSRVTEDSARLSWTAPDAAFDSFWIRYFEFL GSGEAIVLTVPGSERSYDLTGLKPGTEYVVQIIGVKGGHIS LPLSAIFTT |
| 53 | PRT | Artificial | ECB4 | MLPAPKNLVVSEVTEDSARLSWDDPWAFYESFLIQYQES EKVGEAIVLTVPGSERSYDLTGLKPGTEYTVSIYGVHNVY KDTNMRGLPLSAIFTTGGGGSGGGGSGGGGSGGGGSM LPAPKNLVVSRVTEDSARLSWTAPDAAFDSFFIRYDEFLR SGEAIVLTVPGSERSYDLTGLKPGTEYWVTILGVKGGLVS TPLSAIFTT |
| 54 | PRT | Artificial | ECB5 | MLPAPKNLVVSEVTEDSARLSWADPHGFYDSFLIQYQES EKVGEAIVLTVPGSERSYDLTGLKPGTEYTVSIYGVHNVY KDTNMRGLPLSAIFTTGGGGSGGGGSGGGGSGGGGSM LPAPKNLVVSRVTEDSARLSWTAPDAAFDSFWIRYFEFL GSGEAIVLTVPGSERSYDLTGLKPGTEYVVNIMGVKGGKI SPPLSAIFTT |
| 55 | PRT | Artificial | ECB6 | MLPAPKNLVVSEVTEDSARLSWADPHGFYDSFLIQYQES EKVGEAIVLTVPGSERSYDLTGLKPGTEYTVSIYGVHNVY KDTNMRGLPLSAIFTTGGGGSGGGGSGGGGSGGGGSM LPAPKNLVVSRVTEDSARLSWTAPDAAFDSFWIRYFEFL GSGEAIVLTVPGSERSYDLTGLKPGTEYVVQIIGVKGGHIS LPLSAIFTT |
| 56 | PRT | Artificial | ECB7 | MLPAPKNLVVSEVTEDSARLSWADPHGFYDSFLIQYQES EKVGEAIVLTVPGSERSYDLTGLKPGTEYTVSIYGVHNVY KDTNMRGLPLSAIFTTGGGGSGGGGSGGGGSGGGGSM LPAPKNLVVSRVTEDSARLSWTAPDAAFDSFWIRYFEFL GSGEAIVLTVPGSERSYDLTGLKPGTEYVVQIIGVKGGHIS LPLSAIFTT |
| 57 | PRT | Artificial | ECB15 | MLPAPKNLVVSEVTEDSARLSWDDPWAFYESFLIQYQES EKVGEAIVLTVPGSERSYDLTGLKPGTEYTVSIYGVHNVY KDTNMRGLPLSAIFTTAPAPAPAPAPLPAPKNLVVSRVTED SARLSWTAPDAAFDSFWIRYFEFLGSGEAIVLTVPGSERS YDLTGLKPGTEYVVNIMGVKGGKISPPLSAIFTT |
| 58 | PRT | Artificial | ECB27 | MLPAPKNLVVSEVTEDSARLSWDDPWAFYESFLIQYQES EKVGEAIVLTVPGSERSYDLTGLKPGTEYTVSIYGVHNVY KDTNMRGLPLSAIFTTAPAPAPAPAPLPAPKNLVVSRVTED SARLSWTAPDAAFDSFWIRYDEVVVGGEAIVLTVPGSER SYDLTGLKPGTEYYVNILGVKGGSISVPLSAIFTT |
| 59 | PRT | Artificial | ECB60 | MLPAPKNLVVSEVTEDSARLSWADPHGFYDSFLIQYQES EKVGEAIVLTVPGSERSYDLTGLKPGTEYTVSIYGVHNVY KDTNMRGLPLSAIFTTAPAPAPAPAPMLPAPKNLVVSRVT EDSARLSWTAPDAAFDSFWIRYFEFLGSGEAIVLTVPGSE RSYDLTGLKPGTEYVVNIMGVKGGKISPPLSAIFTT |

| | | | | |
|---|---|---|---|---|
| SEQUENCE LISTING | | | | |
| 60 | PRT | Artificial | ECB37 | MLPAPKNLVVSEVTEDSARLSWADPHGFYDSFLIQYQES EKVGEAIVLTVPGSERSYDLTGLKPGTEYTVSIYGVHNVY KDTNMRGLPLSAIFTTAPAPAPAPAPLPAPKNLVVSRVTED SARLSWTAPDAAFDSFWIRYDEVVVGGEAIVLTVPGSER SYDLTGLKPGTEYYVNILGVKGGSISVPLSAIFTT |
| 61 | PRT | Artificial | ECB94 | MLPAPKNLVVSEVTEDSARLSWDDPWAFYESFLIQYQES EKVGEAIVLTVPGSERSYDLTGLKPGTEYTVSIYGVHNVY KDTNIRGLPLSAIFTTAPAPAPAPAPLPAPKNLVVSRVTED SARLSWTAPDAAFDSFWIRYFEFLGSGEAIVLTVPGSERS YDLTGLKPGTEYVVNILGVKGGKISPPLSAIFTT |
| 62 | PRT | Artificial | ECB95 | MLPAPKNLVVSEVTEDSARLSWDDPWAFYESFLIQYQES EKVGEAIVLTVPGSERSYDLTGLKPGTEYTVSIYGVHNVY KDTNIRGLPLSAIFTTAPAPAPAPAPLPAPKNLVVSRVTED SARLSWTAPDAAFDSFWIRYFEFVGSGEAIVLIVPGSER SYDLTGLKPGTEYVVNILGVKGGSISPPLSAIFTT |
| 63 | PRT | Artificial | ECB96 | MLPAPKNLVVSEVTEDSARLSWDDPWAFYESFLIQYQES EKVGEAIVLTVPGSERSYDLTGLKPGTEYTVSIYGVHNVY KDTNIRGLPLSAIFTTAPAPAPAPAPLPAPKNLVVSRVTED SARLSWTAPDAAFDSFWIRYFEFVSKGDAIVLTVPGSERS YDLTGLKPGTEYVVNILGVKGGSISPPLSAIFTT |
| 64 | PRT | Artificial | ECB97 | MLPAPKNLVVSEVTEDSARLSWDDPWAFYESFLIQYQES EKVGEAIVLTVPGSERSYDLTGLKPGTEYTVSIYGVHNVY KDTNIRGLPLSAIFTTAPAPAPAPAPLPAPKNLVVSRVTED SARLSWTAPDAAFDSFWIRYFEFLGSGEAIVLTVPGSERS YDLTGLKPGTEYVVNILSVKGGSISPPLSAIFTT |
| 65 | PRT | Artificial | ECB106 | MLPAPKNLVVSEVTEDSARLSWDDPHAFYESFLIQYQES EKVGEAIVLTVPGSERSYDLTGLKPGTEYTVSIYGVHNVY KDTNIRGLPLSAIFTTAPAPAPAPAPLPAPKNLVVSRVTED SARLSWTAPDAAFDSFWIRYFEFLGSGEAIVLTVPGSERS YDLTGLKPGTEYVVNILGVKGGKISPPLSAIFTT |
| 66 | PRT | Artificial | ECB107 | MLPAPKNLVVSEVTEDSARLSWDDPHAFYESFLIQYQES EKVGEAIVLTVPGSERSYDLTGLKPGTEYTVSIYGVHNVY KDTNIRGLPLSAIFTTAPAPAPAPAPLPAPKNLVVSRVTED SARLSWTAPDAAFDSFWIRYFEFVGSGEAIVLTVPGSER SYDLTGLKPGTEYVVNILGVKGGSISPPLSAIFTT |
| 67 | PRT | Artificial | ECB108 | MLPAPKNLVVSEVTEDSARLSWDDPHAFYESFLIQYQES EKVGEAIVLTVPGSERSYDLTGLKPGTEYTVSIYGVHNVY KDTNIRGLPLSAIFTTAPAPAPAPAPLPAPKNLVVSRVTED SARLSWTAPDAAFDSFWIRYFEFVSKGDAIVLTVPGSERS YDLTGLKPGTEYVVNILGVKGGSISPPLSAIFTT |
| 68 | PRT | Artificial | ECB109 | MLPAPKNLVVSEVTEDSARLSWDDPHAFYESFLIQYQES EKVGEAIVLTVPGSERSYDLTGLKPGTEYTVSIYGVHNVY KDTNIRGLPLSAIFTTAPAPAPAPAPLPAPKNLVVSRVTED SARLSWTAPDAAFDSFWIRYFEFLGSGEAIVLTVPGSERS YDLTGLKPGTEYVVNILSVKGGSISPPLSAIFTT |
| 69 | PRT | Artificial | ECB118 | MLPAPKNLVVSEVTEDSARLSWADPHGFYDSFLIQYQES EKVGEAIVLTVPGSERSYDLTGLKPGTEYTVSIYGVHNVY KDTNIRGLPLSAIFTTAPAPAPAPAPLPAPKNLVVSRVTED SARLSWTAPDAAFDSFWIRYFEFLGSGEAIVLTVPGSERS YDLTGLKPGTEYVVNILGVKGGKISPPLSAIFTT |
| 70 | PRT | Artificial | ECB119 | MLPAPKNLVVSEVTEDSARLSWADPHGFYDSFLIQYQES EKVGEAIVLTVPGSERSYDLTGLKPGTEYTVSIYGVHNVY KDTNIRGLPLSAIFTTAPAPAPAPAPLPAPKNLVVSRVTED SARLSWTAPDAAFDSFWIRYFEFVGSGEAIVLTVPGSER SYDLTGLKPGTEYVVNILGVKGGSISPPLSAIFTT |
| 71 | PRT | Artificial | ECB120 | MLPAPKNLVVSEVTEDSARLSWADPHGFYDSFLIQYQES EKVGEAIVLTVPGSERSYDLTGLKPGTEYTVSIYGVHNVY KDTNIRGLPLSAIFTTAPAPAPAPAPLPAPKNLVVSRVTED SARLSWTAPDAAFDSFWIRYFEFVSKGDAIVLTVPGSERS YDLTGLKPGTEYVVNILGVKGGSISPPLSAIFTT |

| | | | | | |
|---|---|---|---|---|---|
| 72 | PRT | Artificial | | ECB121 | MLPAPKNLVVSEVTEDSARLSWADPHGFYDSFLIQYQES EKVGEAIVLTVPGSERSYDLTGLKPGTEYTVSIYGVHNVY KDTNIRGLPLSAIFTTAPAPAPAPAPLPAPKNLVVSRVTED SARLSWTAPDAAFDSFWIRYFEFLGSGEAIVLTVPGSERS YDLTGLKPGTEYVVNILSVKGGSISPPLSAIFTT |

SEQ ID NO: 73, PRT, *Homo Sapiens*, EGFR (includes signal sequence of 24 aa. Mature protein starts at residue 25)

```
   1 MRPSGTAGAA LLALLAALCP ASRALEEKKV CQGTSNKLTQ LGTFEDHFLS LQRMFNNCEV
  61 VLGNLEITYV QRNYDLSFLK TIQEVAGYVL IALNTVERIP LENLQIIRGN MYYENSYALA
 121 VLSNYDANKT GLKELPMRNL QEILHGAVRF SNNPALCNVE SIQWRDIVSS DFLSNMSMDF
 181 QNHLGSCQKC DPSCPNGSCW GAGEENCQKL TKIICAQQCS GRCRGKSPSD CCHNQCAAGC
 241 TGPRESDCLV CRKFRDEATC KDTCPPLMLY NPTTYQMDVN PEGKYSFGAT CVKKCPRNYV
 301 VTDHGSCVRA CGADSYEMEE DGVRKCKKCE GPCRKVCNGI GIGEFKDSLS INATNIKHFK
 361 NCTSISGDLH ILPVAFRGDS FTHTPPLDPQ ELDILKTVKE ITGFLLIQAW PENRTDLHAF
 421 ENLEIIRGRT KQHGQFSLAV VSLNITSLGL RSLKEISDGD VIISGNKNLC YANTINWKKL
 481 FGTSGQKTKI ISNRGENSCK ATGQVCHALC SPEGCWGPEP RDCVSCRNVS RGRECVDKCN
 541 LLEGEPREFV ENSECIQCHP ECLPQAMNIT CTGRGPDNCI QCAHYIDGPH CVKTCPAGVM
 601 GENNTLVWKY ADAGHVCHLC HPNCTYGCTG PGLEGCPTNG PKIPSIATGM VGALLLLLVV
 661 ALGIGLFMRR RHIVRKRTLR RLLQERELVE PLTPSGEAPN QALLRILKET EFKKIKVLGS
 721 GAFGTVYKGL WIPEGEKVKI PVAIKELREA TSPKANKEIL DEAYVMASVD NPHVCRLLGI
 781 CLTSTVQLIT QLMPFGCLLD YVREHKDNIG SQYLLNWCVQ IAKGMNYLED RRLVHRDLAA
 841 RNVLVKTPQH VKITDFGLAK LLGAEEKEYH AEGGKVPIKW MALESILHRI YTHQSDVWSY
 901 GVTVWELMTF GSKPYDGIPA SEISSILEKG ERLPQPPICT IDVYMIMVKC WMIDADSRPK
 961 FRELIIEFSK MARDPQRYLV IQGDERMHLP SPTDSNFYRA LMDEEDMDDV VDADEYLIPQ
1021 QGFFSSPSTS RTPLLSSLSA TSNNSTVACI DRNGLQSCPI KEDSFLQRYS SDPTGALTED
1081 SIDDTFLPVP EYINQSVPKR PAGSVQNPVY HNQPLNPAPS RDPHYQDPHS TAVGNPEYLN
1141 TVQPTCVNST FDSPAHWAQK GSHQISLDNP DYQQDFFPKE AKPNGIFKGS TAENAEYLRV
1201 APQSSEFIGA
```

| | | | | | |
|---|---|---|---|---|---|
| 74 | PRT | *Homo sapiens* | | EGF | NSDSECPLSHDGYCLHDGVCMYIEALDKYACNCVVGYIG ERCQYRDLKWWELR |

SEQ ID NO: 75, PRT, *Homo Sapiens*, Tenascin-C

```
   1 mgamtqllag vflaflalat eggvlkkvir hkrqsgvnat lpeenqpvvf nhvyniklpv
  61 gsqcsvdles asgekdlapp sepsesfqeh tvdgenqivf thriniprra cgcaaapdvk
 121 ellsrleele nlvsslreqc tagagcclqp atgrldtrpf csgrgnfste gcgcvcepgw
 181 kgpncsepec pgnchlrgrc idqqcicddg ftgedcsqla cpsdcndqgk cvngvcicfe
 241 gyagadcsre icpvpcseeh gtcvdglcvc hdgfagddcn kplclnncyn rgrcvenecv
 301 cdegftgedc selicpndcf drgrcingtc yceegftged cgkptcphac htqgrceegq
 361 cvcdegfagv dcsekrcpad chnrgrcvdg rceeddgftg adcgelkcpn gcgshgrcvn
 421 gqcvcdegyt gedcsqlrcp ndchsrgrcv egkcvceqgf kgydcsdmsc pndchqhgrc
 481 vngmcvcddg ytgedcrdrq cprdcsnrgl cvdgqcvced gftgpdcael scpndchgqg
 541 rcvngqcvch egfmgkdcke qrcpsdchgq grcvdgqcic hegftgldcg qhscpsdcnn
 601 lgqcvsgrci cnegysgedc sevsppkdlv vtevteetvn lawdnemrvt eylvvytpth
 661 egglemqfrv pgdqtstiiq elepgveyfi rvfailenkk sipvsarvat ylpapeglkf
 721 ksiketsvev ewdpldiafe tweiifrnmn kedegeitks lrrpetsyrq tglapgqeye
 781 islhivknnt rgplkrvtt trldapsqie vkdvtdttal itwfkplaei dgieltygik
 841 dvpgdrttid ltedenqysi gnlkpdteye vslisrrgdm ssnpaketft tgldaprnlr
 901 rvsqtdnsit lewrngkaai dsyrikyapi sggdhaevdv pksqqattkt tltglrpgte
 961 ygigvsavke dkesnpatin aateldtpkd lqvsetaets ltllwktpla kfdryrlnys
1021 lptgqwvgvq lprnttsyvl rglepgqeyn vlltaekgrh kskparvkas teqapelenl
1081 tvtevgwdgl rlnwtaadqa yehfiiqvqe ankveaarnl tvpgslravd ipglkaatpy
1141 tvsiygviqg yrtpvlsaea stgetpnlge vvvaevgwda lklnwtapeg ayeyffiqvq
1201 eadtveaaqn ltvpgglrst dlpglkaath ytitirgvtq dfsttplsve vlteevpdmg
1261 nltvtevswd alrlnwttpd gtydqftiqv qeadqveeah nltvpgslrs meipglragt
1321 pytvtlhgev rghstrplav evvtedlpql gdlavsevgw dglrlnwtaa dnayehfviq
1381 vqevnkveaa qnltlpgslr avdipgleaa tpyrvsiygv irgyrtpvls aeastakepe
1441 ignlnvsdit pesfnlswma tdgifetfti eiidsnrlle tveynisgae rtahisglpp
1501 stdfivylsg lapsirtkti satattealp llenitisdi npygftvswm asenafdsfl
1561 vtvvdsgkll dpqeftlsgt qrklelrgli tgigyevmvs gftqghqtkp lraeivteae
1621 pevdnllvsd atpdgfrlsw tadegvfdnf vlkirdtkkq sepleitlla pertrditgl
1681 reateyeiel ygiskgrrsq tvsaiattam gspkevifsd itensatvsw raptaqvesf
1741 rityvpitgg tpsmvtvdgt ktqtrlvkli pgveylvsii amkgfeesep vsgsfttald
1801 gpsglvtani tdsealarwq paiatvdsyv isytgekvpe itrtvsgntv eyaltdlepa
1861 teytlrifae kgpqksstit akftttdldsp rdltatevqs etalltwrpp rasvtgyllv
1921 yesvdgtvke vivpgdttys sladlspsth ytakiqalng plrsnmiqti fttigllypf
1981 pkdcsqamln gdttsglyti ylngdkaeal evfcdmtsdg ggwivflrrk ngrenfyqnw
2041 kayaagfgdr reefwlgldn lnkitaqggy elrvdlrdhg etafavydkf svgdaktryk
2101 lkvegysgta gdsmayhngr sfstfdktd saitncalsy kgafwyrnch rvnlmgrygd
2161 nnhsqgvnwf hwkghehsiq faemklrpsn frnlegrrkr a
```

| | | | SEQUENCE LISTING | |
|---|---|---|---|---|
| 76 | PRT | Artificial | Fibcon | Ldaptdlqvtnvtdtsitvswtppsatitgyritytpsngpgepkeltvppsstsv titgltpgveyvvslyalkdnqespplvgtqtt |
| 77 | PRT | Artificial | 10th FN3 domain of fibronectin (FN10) | VSDVPRDLEVVAATPTSLLISWDAPAVTVRYYRITYGETGGNSPV QEFTVPGSKSTATISGLKPGVDYTITVYAVTGRGDSPASSKPISINY RT |
| 78 | PRT | Artificial | Linker | GSGS |
| 79 | PRT | Artificial | Linker | GGGGSGGGGSGGGGSGGGGSGGGGS |
| 80 | PRT | Artificial | Linker | APAP |
| 81 | PRT | Artificial | Linker | APAPAPAPAP |
| 82 | PRT | Artificial | Linker | APAPAPAPAPAPAPAPAP |
| 83 | PRT | Artificial | Linker | APAPAPAPAPAPAPAPAPAPAPAPAPAPAPA PAP |
| 84 | PRT | Artificial | Linker | AEAAAKEAAAKEAAAKEAAAKEAAAKAAA |
| 85 | PRT | Artificial | Tencon BC loop | TAPDAAFD |
| 86 | PRT | Artificial | Tencon GF loop | KGGHRSN |
| 87 | PRT | Artificial | P53A1R5-17 BC loop | ADPHGFYD |
| 88 | PRT | Artificial | P54AR4-17 BC loop | TYDRDGYD |
| 89 | PRT | Artificial | P54AR4-47 BC loop | WDPFSFYD |
| 90 | PRT | Artificial | P54AR4-48 BC loop | DDPRGFYE |
| 91 | PRT | Artificial | P54AR4-73 BC loop | TWPYADLD |
| 92 | PRT | Artificial | P54AR4-74 BC loop | GYNGDHFD |
| 93 | PRT | Artificial | P54AR4-81 BC loop | DYDLGVYD |
| 94 | PRT | Artificial | P54AR4-83 BC loop | DDPWDFYE |
| 95 | PRT | Artificial | FG loops of EGFR | HNVYKDTNMRGL |
| 96 | PRT | Artificial | FG loops of EGFR | LGSYVFEHDVM |
| 97 | DNA | Artificial | >EGFR part ECB97; P54AR4-83v22 | Atgttgccagcgccgaagaacctggtagttagcgaggttactgaggac agcgcgcgtctgagctgggacgatccgtgggcgttctacgagagctttct gatccagtatcaagagagcgagaaagtcggtgaagcgattgtgctgac cgtcccgggctccgagcgttcctacgacctgaccggtttgaagccggt accgagtatacggtgagcatctacggtgttcacaatgtctataaggaca ctaatatccgcggtctgcctctgagcgccattttcaccacc |
| 98 | DNA | Artificial | >EGFR part ECB15; P54AR4-83v2 | Atgctgccagcccctaagaatctggtcgtgagcgaagtaaccgagga cagcgcccgcctgagctgggacgacccgtgggcgttctatgagtctttcc tgattcagtatcaagaaagcgaaaaagttggcgaagcgatcgtcctga ccgtcccgggtagcgagcgcctccgatctgaccggcctgaaaccgg gtacggagtacacggtgtccatttacggtgttcacaatgtgtataaagac accaacatgcgtggcctgccgctgtcggcgattttcaccacc |
| 99 | PRT | Artificial | tencon 27 | LPAPKNLVVSRVTEDSARLSWTAPDAAFDSFLIQYQ ESEKVGEAIVLTVPGSERSYDLTGLKPGTEYTVSIYG VKGGHRSNPLSAIFTT |
| 100 | PRT | Artificial | TCL14 library | LPAPKNLVVSRVTEDSARLSWTAPDAAFDSFXIXYX EXXXXGEAIVLTVPGSERSYDLTGLKPGTEYXVXIXG VKGGXXSXPLSAIFTT |

>SEQ ID NO: 101 PRT Homo sapiens cMet

```
  1 mkapavlapg ilvllftlvq rsngeckeal aksemnynmk yqlpnftaet piqnvilheh
 61 hiflgatnyi yvineedlqk vaeyktgpvl ehpdcfpcqd cssskanlsgg vwkdninmal
121 vvdtyyddql iscgsvnrgt cqrhvfphnh tadiqsevhc ifspqieeps qcpdcvvsal
181 gakvlssvkd rfinffvgnt inssyfpdhp lhsisvrrlk etkdgfmflt dqsyidvlpe
241 frdsypikyv hafesnnfiy fltvqretld aqtfhtriir fcsinsglhs ymemplecil
301 tekrkkrstk kevfnilqaa yyskpgaqla rqigaslndd ilfgvfaqsk pdsaepmdrs
361 amcafpikyv ndffnkivnk nnvrclqhfy gpnehcfnr tllrnssgce arrdeyrtef
```

SEQUENCE LISTING

```
 421 ttalqrvdlf mgqfsevllt sistfikgdl tianlgtseg rfmqvvvsrs gpstphvnfl
 481 ldshpvspev ivehtlnqng ytlvitgkki tkiplnglgc rhfqscsqcl sappfvqcgw
 541 chdkcvrsee clsgtwtqqi clpaiykvfp nsapleggtr lticgwdfgf rrnnkfdlkk
 601 trvllgnesc tltlsestmn tlkctvgpam nkhfnmsiii snghgttqys tfsyvdpvit
 661 sispkygpma ggtlltltgn ylnsgnsrhi siggktctlk svsnsilecy tpaqtistef
 721 avklkidlan retsifsyre dpivyeihpt ksfistwwke plnivsflfc fasggstitg
 781 vgknlnsvsv prmvinvhea grnftvacqh rsnseiicct tpslqqlnlq lplktkaffm
 841 ldgilskyfd liyvhnpvfk pfekpvmism gnenvleikg ndidpeavkg evlkvgnksc
 901 enihlhseav lctvpndllk lnseleniewk qaisstvlgk vivqpdqnft gliagvvsis
 961 tallllllgff lwlkkrkqik dlgselvryd arvhtphldr lvsarsyspt temvsnesvd
1021 yratfpedqf pnssqngscr qvqypltdms piltssgdsdi sspllqntvh idlsalnpel
1081 vqavqhvvig psslivhfne vigrghfgcv yhgtlldndg kkihcavksl nritdigevs
1141 qflteqiimk dfshpnvlsl lgiclrsegs plvvlpymkh gdlrnfirne thnptvkdli
1201 gfglqvakgm kylaskkfvh rdlaamcml dekftvkvad fglardmydk eyysvhnktg
1261 aklpvkwmal eslqtqkftt ksdvwsfgvl lwelmtrgap pypdvntfdi tvyllqgrrl
1321 lqpeycpdpl yevmlkcwhp kaemrpsfse lvsrisaifs tfigehyvhv natyvnvkcv
1381 apypsllsse dnaddevdtr pasfwets
```

| 102 | PRT | Homo sapiens | HGF | QRKRRNTIHEFKKSAKTTLIKIDPALKIK TKKVNTADQCANRCTRNKGLPFTCKAFVFDKARKQCLWFPFNSMS SGVKKEFGHEFDLYE NKDYIRNCIIGKGRSYKGTVSITKSGIKCQPWSSMIPHEHSFLPSSYRG KDLQENYCRNP RGEEGGPWCFTSNPEVRYEVCDIPQCSEVECMTCNGESYRGLMDH TESGKICQRWDHQTP HRHKFLPERYPDKGFDDNYCRNPDGQPRPWCYTLDPHTRWEYCAIK TCADNTMNDTDVPL ETTECIQGQEGYRGTVNTIWNGIPCQRWDSQYPHEHDMTPENFKC KDLRENYCRNPDGS ESPWCFTTDPNIRVGYCSQIPNCDMSHGQDCYRGNGKNYMGNLSQT RSGLTCSMWDKNME DLHRHIFWEPDASKLNENYCRNPDDDAHGPWCYTGNPLIPWDYCPIS RCEGDTTPTIVNL DHPVISCAKTKQLRVVNGIPTRTNIGWMVSLRYRNKHICGGSLIKESW VLTARQCFPSRD LKDYEAWLGIHDVHGRGDEKCKQVLNVSQLVYGPEGSDLVLMKLAR PAVLDDFVSTIDLP NYGCTIPEKTSCSVYGWGYTGLINYDGLLRVAHLYIMGNEKCSQHHRG KVTLNESEICAG AEKIGSGPCEGDYGGPLVCEQHKMRMVLGVIVPGRGCAIPNRPGIFV RVAYYAKWIHKII LTYKVPQS |
|---|---|---|---|---|
| 103 | DNA | Artificial | >cMET part ECB97 P114AR7P95-C5v2 | Ctgccggctccgaagaacttggtggtgagccgtgttaccgaagatagc gcacgcctgagctggacggcaccggatgcggcgttcgatagcttctgg attcgctattttgagtttctgggtagcggtgaggcaattgttctgacggtgcc gggctctgaacgctcctacgatttgaccggtctgaaaccgggcaccga gtatgtggtgaacattctgagcgttaagggcggtagcatcagcccaccg ctgagcgcgatcttcacgactggtggttgc |
| 104 | DNA | Artificial | >cMET part ECB15 P114AR7P94-A3 | Ctgccggcaccgaagaacctggttgtcagccgtgtgaccgaggatag cgcacgtttgagctggaccgctccggatgcagccttttgacagcttctgga ttcgttactttgaatttctgggtagcggtgaggcgatcgttctgacggtgccg ggctctgaacgcagctatgatttgacgggcctgaagccgggtactgagt acgtggttaacatcatgggcgttaagggtggtaaaatcagcccgccatt gtccgcgatctttaccacg |
| 105 | PRT | Artificial | linker | GGGGS |
| 106 | PRT | Artificial | ECB91 | mlpapknlvvsevtedsarlswddpwafyesfliqyqesekvgeaivltvpgse rsydltglkpgteytvsiygvhnvykdtnirglplsaifttapapapapapLPAP KNLVVSRVTEDSARLSWTAPDAAFDSFWIRYFEFLGSGEAIVLTV PGSERSYDLTGLKPGTEYVVNILSVKGGSISPPLSAIFTT |
| 107 | PRT | Artificial | P53A1R5-17v2 | lpapknlvvsevtedsarlswadphgfydsfliqyqesekvgeaivltvpgsersy dltglkpgteytvsiygvhnvykdtnmrglplsaiftt |
| 108 | PRT | Artificial | P54AR4-83v22 | lpapknlvvsevtedsarlswddpwafyesfliqyqesekvgeaivltvpgsers ydltglkpgteytvsiygvhnvykdtnirglplsaiftt |
| 109 | PRT | Artificial | P54AR4-83v23 | lpapknlvvsevtedsarlswddpwafyesfliqyqesekvgeaivltvpgsersy dltglkpgteytvsiygvhnvykdtnirglplsaiftt |
| 110 | PRT | Artificial | P53A1R5-17v22 | lpapknlvvsevtedsarlswadphgfydsfliqyqesekvgeaivltvpgsersy dltglkpgteytvsiygvhnvykdtnirglplsaiftt |

| | | | | |
|---|---|---|---|---|
| 111 | PRT | Artificial | P114AR7P94-A3v22 | lpapknlvvsrvtedsarlswtapdaafdsfwiryfeflgsgeaivltvpgsersyd<br>ltglkpgteyvvnilgvkggkispplsaiftt |
| 112 | PRT | Artificial | P114AR9P121-A6v2 | LPAPKNLVVSRVTEDSARLSWTAPDAAFDSFWIRYFEFVGSGEAI<br>VLTVPGSERSYDLTGLKPGTEYVVNILGVKGGSISPPLSAIFTT |
| 113 | PRT | Artificial | P114AR9P122-A7v2 | LPAPKNLVVSRVTEDSARLSWTAPDAAFDSFWIRYFEFVSKGDA<br>IVLTVPGSERSYDLTGLKPGTEYVVNILGVKGGSISPPLSAIFTT |
| 114 | PRT | Artificial | P114AR7P95-C5v2 | LPAPKNLVVSRVTEDSARLSWTAPDAAFDSFWIRYFEFLGSGEAI<br>VLTVPGSERSYDLTGLKPGTEYVVNILSVKGGSISPPLSAIFTT |
| 115 | DNA | Artificial | ECB97 | atgttgccagcgccgaagaacctggtagttagcgaggttactgaggac<br>agcgcgcgtctgagctgggacgatccgtgggcgttctacgagagctttct<br>gatccagtatcaagagagcgagaaagtcggtgaagcgattgtgctgac<br>cgtcccgggctccgagcgttcctacgacctgaccggtttgaagccgggt<br>accgagtatacggtgagcatctacggtgttcacaatgtctataaggaca<br>ctaatatccgcggtctgcctctgagcgccattttcaccaccgcaccggc<br>accggctccggcctctgccccgctgccggctccgaagaacttggtggtg<br>agccgtgttaccgaagatagcgcacgcctgagctggacggcaccgga<br>tgcggcgttcgatagcttctggattcgctattttgagtttctgggtagcggtga<br>ggcaattgttctgacggtgccgggctctgaacgctcctacgatttgaccg<br>gtctgaaaccgggcaccgagtatgtggtgaacattctgagcgttaaggg<br>cggtagcatcagcccaccgctgagcgcgatcttcacgactggtggttgc |
| 116 | DNA | Artificial | ECB15 | atgctgccagcccctaagaatctggtcgtgagcgaagtaaccgaggac<br>agcgcccgctgagctgggacgacccgtgggcgttctatgagtctttcct<br>gattcagtatcaagaaagcgaaaaagttggcgaagcgatcgtcctgac<br>cgtcccgggtagcgagcgctcctacgatctgaccggcctgaaaccggg<br>tacggagtacacggtgtccatttacggtgttcacaatgtgtataaagaca<br>ccaacatgcgtggcctgccgctgtcggcgattttcaccaccgcgcctgc<br>gccagcgcctgcaccggctccgctgccggcaccgaagaacctggttgt<br>cagccgtgtgaccgaggatagcgcacgtttgagctggaccgctccgga<br>tgcagcctttgacagcttctggattcgttactttgaatttctgggtagcggtg<br>aggcgatcgttctgacggtgccgggctctgaacgcagctatgatttgacg<br>ggcctgaagccgggtactgagtacgtggttaacatcatgggcgttaagg<br>gtggtaaaatcagcccgccattgtccgcgatctttaccacg |
| 117 | PRT | Artificial | albumin binding<br>domain | tidewllkeakekaieeelkkagitsdyyfdlinkaktvegvnalkdeilka |
| 118 | PRT | Artificial | ECB18 | mlpapknlvvsevtedsarlswddpwafyesfliqyqesekvgeaivltv<br>pgsersydltglkpgteytvsiygvhnvykdtnmrglplsaifttapapapa<br>paplpapknlvvsrvtedsarlswtapdaafdsfwirydevvvggeaivlt<br>vpgsersydltglkpgteyvvnilgvkggsisppllsaifttapapapapapl<br>aeakvlanreldkygvsdyyknlinnaktvegykalldeilaalp |
| 119 | PRT | Artificial | ECB28 | mlpapknlvvsevtedsarlswadphgfydsfliqyqesekvgeaivltv<br>pgsersydltglkpgteytvsiygvhnvykdtnmrglplsaifttapapapa<br>paplpapknlvvsrvtedsarlswtapdaafdsfwirydevvvggeaivlt<br>vpgsersydltglkpgteyvvnilgvkggsisvplsaifttapapapapapl<br>aeakvlanreldkygvsdyyknlinnaktvegvkalldeilaalp |
| 120 | PRT | Artificial | ECB38 | mlpapknlvvsevtedsarlswddpwafyesfliqyqesekvgeaivltv<br>pgsersydltglkpgteytvsiygvhnvykdtnmrglplsaifttapapapa<br>paplpapknlvvsrvtedsarlswtapdaafdsfwiryfeflgsgeaivltv<br>pgsersydltglkpgteyvvnimgvkggkispplsaifttapapapapapl<br>aeakvlanreldkygvsdyyknlinnaktvegvkalldeilaalp |
| 121 | PRT | Artificial | ECB39 | mlpapknlvvsevtedsarlswadphgfydsfliqyqesekvgeaivltv<br>pgsersydltglkpgteytvsiygvhnvykdtnmrglplsaifttapapapa<br>paplpapknlvvsrvtedsarlswtapdaafdsfwiryfeflgsgeaivltv<br>pgsersydltglkpgteyvvnimgvkggkispplsaifttapapapapapl<br>aeakvlanreldkygvsdyyknlinnaktvegvkalldeilaalp |
| 122 | PRT | Artificial | P53A1R5-17 wthMet | MLPAPKNLVVSEVTEDSLRLSWADPHGFYDSFLIQY<br>QESEKVGEAINLTVPGSERSYDLTGLKPGTEYTVSIY<br>GVHNVYKDTNMRGLPLSAEFTT |
| 123 | PRT | Artificial | P54AR4-17 with Met | MLPAPKNLVVSEVTEDSLRLSWTYDRDGYDSFLIQY<br>QESEKVGEAINLTVPGSERSYDLTGLKPGTEYTVSIY<br>GVHNVYKDTNMRGLPLSAEFTT |
| 124 | PRT | Artificial | P54AR4-47 with Met | MLPAPKNLVVSEVTEDSLRLSWGYNGDHFDSFLIQY<br>QESEKVGEAINLTVPGSERSYDLTGLKPGTEYTVSIY<br>GVHNVYKDTNMRGLPLSAEFTT |

| | | | | SEQUENCE LISTING |
|---|---|---|---|---|
| 125 | PRT | Artificial | P54AR4-48 with Met | MLPAPKNLVVSEVTEDSLRLSWDDPRGFYESFLIQY QESEKVGEAINLTVPGSERSYDLTGLKPGTEYTVSIY GVHNVYKDTNMRGLPLSAEFTT |
| 126 | PRT | Artificial | P54AR4-73 with Met | MLPAPKNLVVSEVTEDSLRLSWTWPYADLDSFLIQY QESEKVGEAINLTVPGSERSYDLTGLKPGTEYTVSIY GVHNVYKDTNMRGLPLSAEFTT |
| 127 | PRT | Artificial | 54AR4-74 with Met | MLPAPKNLVVSEVTEDSLRLSWGYNGDHFDSFLIQY QESEKVGEAINLTVPGSERSYDLTGLKPGTEYTVSIY GVHNVYKDTNMRGLPLSAEFTT |
| 128 | PRT | Artificial | P54AR4-81 with Met | MLPAPKNLVVSEVTEDSLRLSWDYDLGVYFDSFLIQ YQESEKVGEAINLTVPGSERSYDLTGLKPGTEYTVSI YGVHNVYKDTNMRGLPLSAEFTT |
| 129 | PRT | Artificial | P54AR4-83 with Met | MLPAPKNLVVSEVTEDSLRLSWDDPWAFYESFLIQY QESEKVGEAINLTVPGSERSYDLTGLKPGTEYTVSIY GVHNVYKDTNMRGLPLSAEFTT |
| 130 | PRT | Artificial | P54CR4-31 with Met | MLPAPKNLVVSEVTEDSLRLSWTAPDAAFDSFLIQY QESEKVGEAINLTVPGSERSYDLTGLKPGTEYTVSIY GVLGSYVFEHDVMLPLSAEFTT |
| 131 | PRT | Artificial | P54AR4-83v2 with Met | MLPAPKNLVVSEVTEDSARLSWDDPWAFYESFLIQY QESEKVGEAIVLTVPGSERSYDLTGLKPGTEYTVSIY GVHNVYKDTNMRGLPLSAIFTT |
| 132 | PRT | Artificial | P54CR4-31v2 with Met | MLPAPKNLVVSEVTEDSARLSWTAPDAAFDSFLIQY QESEKVGEAIVLTVPGSERSYDLTGLKPGTEYTVSIY GVLGSYVFEHDVMLPLSAIFTT |
| 133 | PRT | Artificial | P54AR4-73v2 withMet | MLPAPKNLVVSEVTEDSLRLSWTWPYADLDSFLIQY QESEKVGEAINLTVPGSERSYDLTGLKPGTEYTVSIY GVHNVYKDTNMRGLPLSAEFTT |
| 134 | PRT | Artificial | P53A1R5-17v2 with Met | mlpapknlvvsevtedsarlswadphgfydsfliqyqesekvgeaivltvpgser sydltglkpgteytvsiygvhnvykdtnmrglplsaiftt |
| 135 | PRT | Artificial | P54AR4-83v22 with Met | mlpapknlvvsevtedsarlswddpwafyesfliqyqesekvgeaivltvpgse rsydltglkpgteytvsiygvhnvykdtnirglplsaiftt |
| 136 | PRT | Artificial | P54AR4-83v23 with Met | mlpapknlvvsevtedsarlswddphafyesfliqyqesekvgeaivltvpgser sydltglkpgteytvsiygvhnvykdtnirglplsaiftt |
| 137 | PRT | Artificial | P53A1R5-17v22 with Met | mlpapknlvvsevtedsarlswadphgfydsfliqyqesekvgeaivltvpgser sydltglkpgteytvsiygvhnvykdtnirglplsaiftt |
| 138 | PRT | Artificial | ECB1 without Met | LPAPKNLVVSEVTEDSARLSWDDPWAFYESFLIQYQ ESEKVGEAIVLTVPGSERSYDLTGLKPGTEYTVSIYG VHNVYKDTNMRGLPLSAIFTTGGGGSGGGGSGGGG SGGGGSMLPAPKNLVVSRVTEDSARLSWTAPDAAF DSFWIRYDEVVVGGEAIVLTVPGSERSYDLTGLKPG TEYYVNILGVKGGSISVPLSAIFTT |
| 139 | PRT | Artificial | ECB2 without Met | LPAPKNLVVSEVTEDSARLSWDDPWAFYESFLIQYQ ESEKVGEAIVLTVPGSERSYDLTGLKPGTEYTVSIYG VHNVYKDTNMRGLPLSAIFTTGGGGSGGGGSGGGG SGGGGSLPAPKNLVVSRVTEDSARLSWTAPDAAFD SFWIRYFEFLGSGEAIVLTVPGSERSYDLTGLKPGT EYVVNIMGVKGGKISPPLSAIFTT |
| 140 | PRT | Artificial | ECB3 without Met | LPAPKNLVVSEVTEDSARLSWDDPWAFYESFLIQYQ ESEKVGEAIVLTVPGSERSYDLTGLKPGTEYTVSIYG VHNVYKDTNMRGLPLSAIFTTGGGGSGGGGSGGGG SGGGGSMLPAPKNLVVSRVTEDSARLSWTAPDAAF DSFWIRYFEFLGSGEAIVLTVPGSERSYDLTGLKPG TEYVVQIIGVKGGHISLPLSAIFTT |
| 141 | PRT | Artificial | ECB4 without Met | LPAPKNLVVSEVTEDSARLSWDDPWAFYESFLIQYQ ESEKVGEAIVLTVPGSERSYDLTGLKPGTEYTVSIYG VHNVYKDTNMRGLPLSAIFTTGGGGSGGGGSGGGG SGGGGSMLPAPKNLVVSRVTEDSARLSWTAPDAAF DSFFIRYDEFLRSGEAIVLTVPGSERSYDLTGLKPGT EYWVTILGVKGGLVSTPLSAIFTT |

| SEQUENCE LISTING | | | | |
|---|---|---|---|---|
| 142 | PRT | Artificial | ECB5 without Met | LPAPKNLVVSEVTEDSARLSWADPHGFYDSFLIQYQ ESEKVGEAIVLTVPGSERSYDLTGLKPGTEYTVSIYG VHNVYKDTNMRGLPLSAIFTTGGGGSGGGGSGGGG SGGGGSMLPAPKNLVVSRVTEDSARLSWTAPDAAF DSFWIRYFEFLGSGEAIVLTVPGSERSYDLTGLKPG TEYVVNIMGVKGGKISPPLSAIFTT |
| 143 | PRT | Artificial | ECB6 without Met | LPAPKNLVVSEVTEDSARLSWADPHGFYDSFLIQYQ ESEKVGEAIVLTVPGSERSYDLTGLKPGTEYTVSIYG VHNVYKDTNMRGLPLSAIFTTGGGGSGGGGSGGGG SGGGGSMLPAPKNLVVSRVTEDSARLSWTAPDAAF DSFWIRYFEFLGSGEAIVLTVPGSERSYDLTGLKPG TEYVVQIIGVKGGHISLPLSAIFTT |
| 144 | PRT | Artificial | ECB7 without Met | LPAPKNLVVSEVTEDSARLSWADPHGFYDSFLIQYQ ESEKVGEAIVLTVPGSERSYDLTGLKPGTEYTVSIYG VHNVYKDTNMRGLPLSAIFTTGGGGSGGGGSGGGG SGGGGSMLPAPKNLVVSRVTEDSARLSWTAPDAAF DSFWIRYFEFLGSGEAIVLTVPGSERSYDLTGLKPG TEYVVQIIGVKGGHISLPLSAIFTT |
| 145 | PRT | Artificial | ECB15 without Met | LPAPKNLVVSEVTEDSARLSWDDPWAFYESFLIQYQ ESEKVGEAIVLTVPGSERSYDLTGLKPGTEYTVSIYG VHNVYKDTNMRGLPLSAIFTTAPAPAPAPAPLPAPKN LVVSRVTEDSARLSWTAPDAAFDSFWIRYFEFLGSG EAIVLTVPGSERSYDLTGLKPGTEYVVNIMGVKGGKI SPPLSAIFTT |
| 146 | PRT | Artificial | ECB27 without Met | LPAPKNLVVSEVTEDSARLSWDDPWAFYESFLIQYQ ESEKVGEAIVLTVPGSERSYDLTGLKPGTEYTVSIYG VHNVYKDTNMRGLPLSAIFTTAPAPAPAPAPLPAPKN LVVSRVTEDSARLSWTAPDAAFDSFWIRYDEVVVGG EAIVLTVPGSERSYDLTGLKPGTEYVVNILGVKGGSI SVPLSAIFTT |
| 147 | PRT | Artificial | ECB60 without Met | LPAPKNLVVSEVTEDSARLSWADPHGFYDSFLIQYQ ESEKVGEAIVLTVPGSERSYDLTGLKPGTEYTVSIYG VHNVYKDTNMRGLPLSAIFTTAPAPAPAPAPMLPAPK NLVVSRVTEDSARLSWTAPDAAFDSFWIRYFEFLGS GEAIVLTVPGSERSYDLTGLKPGTEYVVNIMGVKGG KISPPLSAIFTT |
| 148 | PRT | Artificial | ECB37 without Met | LPAPKNLVVSEVTEDSARLSWADPHGFYDSFLIQYQ ESEKVGEAIVLTVPGSERSYDLTGLKPGTEYTVSIYG VHNVYKDTNMRGLPLSAIFTTAPAPAPAPAPLPAPKN LVVSRVTEDSARLSWTAPDAAFDSFWIRYDEVVVGG EAIVLTVPGSERSYDLTGLKPGTEYVVNILGVKGGSI SVPLSAIFTT |
| 149 | PRT | Artificial | ECB94 without Met | LPAPKNLVVSEVTEDSARLSWDDPWAFYESFLIQYQ ESEKVGEAIVLTVPGSERSYDLTGLKPGTEYTVSIYG VHNVYKDTNIRGLPLSAIFTTAPAPAPAPAPLPAPKNL VVSRVTEDSARLSWTAPDAAFDSFWIRYFEFLGSGE AIVLTVPGSERSYDLTGLKPGTEYVVNILGVKGGKIS PPLSAIFTT |
| 150 | PRT | Artificial | ECB95 without Met | LPAPKNLVVSEVTEDSARLSWDDPWAFYESFLIQYQ ESEKVGEAIVLTVPGSERSYDLTGLKPGTEYTVSIYG VHNVYKDTNIRGLPLSAIFTTAPAPAPAPAPLPAPKNL VVSRVTEDSARLSWTAPDAAFDSFWIRYFEFVGSG EAIVLTVPGSERSYDLTGLKPGTEYVVNILGVKGGSI SPPLSAIFTT |
| 151 | PRT | Artificial | ECB96 without Met | LPAPKNLVVSEVTEDSARLSWDDPWAFYESFLIQYQ ESEKVGEAIVLTVPGSERSYDLTGLKPGTEYTVSIYG VHNVYKDTNIRGLPLSAIFTTAPAPAPAPAPLPAPKNL VVSRVTEDSARLSWTAPDAAFDSFWIRYFEFVSKGD AIVLTVPGSERSYDLTGLKPGTEYVVNILGVKGGSIS PPLSAIFTT |
| 152 | PRT | Artificial | ECB97 without Met | LPAPKNLVVSEVTEDSARLSWDDPWAFYESFLIQYQ ESEKVGEAIVLTVPGSERSYDLTGLKPGTEYTVSIYG VHNVYKDTNIRGLPLSAIFTTAPAPAPAPAPLPAPKNL VVSRVTEDSARLSWTAPDAAFDSFWIRYFEFLGSGE AIVLTVPGSERSYDLTGLKPGTEYVVNILSVKGGSISP PLSAIFTT |

| SEQUENCE LISTING | | | | |
|---|---|---|---|---|
| 153 | PRT | Artificial | ECB106 without Met | LPAPKNLVVSEVTEDSARLSWDDPHAFYESFLIQYQ ESEKVGEAIVLTVPGSERSYDLTGLKPGTEYTVSIYG VHNVYKDTNIRGLPLSAIFTTAPAPAPAPAPLPAPKNL VVSRVTEDSARLSWTAPDAAFDSFWIRYFEFLGSGE AIVLTVPGSERSYDLTGLKPGTEYVVNILGVKGGKIS PPLSAIFTT |
| 154 | PRT | Artificial | ECB107 without Met | LPAPKNLVVSEVTEDSARLSWDDPHAFYESFLIQYQ ESEKVGEAIVLTVPGSERSYDLTGLKPGTEYTVSIYG VHNVYKDTNIRGLPLSAIFTTAPAPAPAPAPLPAPKNL VVSRVTEDSARLSWTAPDAAFDSFWIRYFEFVGSG EAIVLTVPGSERSYDLTGLKPGTEYVVNILGVKGGSI SPPLSAIFTT |
| 155 | PRT | Artificial | ECB108 without Met | LPAPKNLVVSEVTEDSARLSWDDPHAFYESFLIQYQ ESEKVGEAIVLTVPGSERSYDLTGLKPGTEYTVSIYG VHNVYKDTNIRGLPLSAIFTTAPAPAPAPAPLPAPKNL VVSRVTEDSARLSWTAPDAAFDSFWIRYFEFVSKGD AIVLTVPGSERSYDLTGLKPGTEYVVNILGVKGGSIS PPLSAIFTT |
| 156 | PRT | Artificial | ECB109 without Met | LPAPKNLVVSEVTEDSARLSWDDPHAFYESFLIQYQ ESEKVGEAIVLTVPGSERSYDLTGLKPGTEYTVSIYG VHNVYKDTNIRGLPLSAIFTTAPAPAPAPAPLPAPKNL VVSRVTEDSARLSWTAPDAAFDSFWIRYFEFLGSGE AIVLTVPGSERSYDLTGLKPGTEYVVNILSVKGGISP PLSAIFTT |
| 157 | PRT | Artificial | ECB118 without Met | LPAPKNLVVSEVTEDSARLSWADPHGFYDSFLIQYQ ESEKVGEAIVLTVPGSERSYDLTGLKPGTEYTVSIYG VHNVYKDTNIRGLPLSAIFTTAPAPAPAPAPLPAPKNL VVSRVTEDSARLSWTAPDAAFDSFWIRYFEFLGSGE AIVLTVPGSERSYDLTGLKPGTEYVVNILGVKGGKIS PPLSAIFTT |
| 158 | PRT | Artificial | ECB119 without Met | LPAPKNLVVSEVTEDSARLSWADPHGFYDSFLIQYQ ESEKVGEAIVLTVPGSERSYDLTGLKPGTEYTVSIYG VHNVYKDTNIRGLPLSAIFTTAPAPAPAPAPLPAPKNL VVSRVTEDSARLSWTAPDAAFDSFWIRYFEFVGSG EAIVLTVPGSERSYDLTGLKPGTEYVVNILGVKGGSI SPPLSAIFTT |
| 159 | PRT | Artificial | ECB120 without Met | LPAPKNLVVSEVTEDSARLSWADPHGFYDSFLIQYQ ESEKVGEAIVLTVPGSERSYDLTGLKPGTEYTVSIYG VHNVYKDTNIRGLPLSAIFTTAPAPAPAPAPLPAPKNL VVSRVTEDSARLSWTAPDAAFDSFWIRYFEFVSKGD AIVLTVPGSERSYDLTGLKPGTEYVVNILGVKGGSIS PPLSAIFTT |
| 160 | PRT | Artificial | ECB121 without Met | LPAPKNLVVSEVTEDSARLSWADPHGFYDSFLIQYQ ESEKVGEAIVLTVPGSERSYDLTGLKPGTEYTVSIYG VHNVYKDTNIRGLPLSAIFTTAPAPAPAPAPLPAPKNL VVSRVTEDSARLSWTAPDAAFDSFWIRYFEFLGSGE AIVLTVPGSERSYDLTGLKPGTEYVVNILSVKGGISP PLSAIFTT |
| 161 | PRT | Artificial | ECB91 without Met | lpapknlvvsevtedsarlswddpwafyesfliqyqesekvgeaivltvpgsers ydltglkpgteytvsiygvhnvykdtnirglplsaifttapapapapapLPAPK NLVVSRVTEDSARLSWTAPDAAFDSFWIRYFEFLGSGEAIVLTVP GSERSYDLTGLKPGTEYVVNILSVKGGSISPPLSAIFTT |
| 162 | PRT | Artificial | ECB18 without Met | lpapknlvvsevtedsarlswddpwafyesfliqyqesekvgeaivltvp gsersydltglkpgteytvsiygvhnvykdtnmrglplsaifttapapapap aplpapknlvvsrvtedsarlswtapdaafdsfwirydevvvggeaivlty pgsersydltglkpgteyyvnilgvkggsisvplsaifttapapapapapla eakvlanreldkygvsdyyknlinnaktvegvkallldeilaalp |
| 163 | PRT | Artificial | ECB28 without Met | lpapknlvvsevtedsarlswadphgfydsfliqyqesekvgeaivltvpg sersydltglkpgteytvsiygvhnvykdtnmrglplsaifttapapapapa plpapknlvvsrvtedsarlswtapdaafdsfwirydevvvggeaivltvp gsersydltglkpgteyyvnilgvkggsisvplsaifttapapapapaplae akvlanreldkygvsdyyknlinnaktvegvkallldeilaalp |

| | | | | SEQUENCE LISTING |
|---|---|---|---|---|
| 164 | PRT | Artificial | ECB38 without Met | lpapknlvvsevtedsarlswddpwafyesfliqyqesekvgeaivltvp gsersydltglkpgteytvsiygvhnvykdtnmrglplsaifttapapapap aplpapknlvvsrvtedsarlswtapdaafdsfwiryfeflgsgeaivltvp gsersydltglkpgteyvvnimgvkggkispplsaifttapapapapapla eakvlanreldkygvsdyyknlinnaktvegvkallldeilaalp |
| 165 | PRT | Artificial | ECB39 without Met | lpapknlvvsevtedsarlswadphgfydsfliqyqesekvgeaivltvpg sersydltglkpgteytysiygvhnvykdtnmrglplsaifttapapapapa plpapknlvvsrvtedsarlswtapdaafdsfwiryfeflgsgeaivltvpg sersydltglkpgteyvvnimgvkggkispplsaifttapapapapaplae akvlanreldkygvsdyyknlinnaktvegvkallldeilaalp |
| 166 | DNA | Artificial | ECB97 without Met | ttgccagcgccgaagaacctggtagttagcgaggttactgaggacagc gcgcgtctgagctgggacgatccgtgggcgttctacgagagctttctgat ccagtatcaagagagcgagaaagtcggtgaagcgattgtgctgaccgt cccgggctccgagcgttcctacgacctgaccggtttgaagccgggtacc gagtatacggtgagcatctacggtgttcacaatgtctataaggacactaa tatccgcggtctgcctctgagcgccattttcaccaccgcaccggcaccg gctccggctcctgccccgctgccggctccgaagaacttggtggtgagcc gtgttaccgaagatagcgcacgcctgagctggacggcaccggatgcg gcgttcgatagcttctggattcgctattttgagtttctgggtagcggtgaggc aattgttctgacggtgccgggctctgaacgctcctacgatttgaccggtct gaaaccgggcaccgagtatgtggtgaacattctgagcgttaagggcggt agcatcagcccaccgctgagcgcgatcttcacgactggtggttgc |
| 167 | DNA | Artificial | ECB15 without Met | ctgccagcccctaagaatctggtcgtgagcgaagtaaccgaggacag cgcccgcctgagctgggacgacccgtgggcgttctatgagtctttcctga ttcagtatcaagaaagcgaaaaagttggcgaagcgatcgtcctgaccg tcccgggtagcgagcgctcctacgatctgaccggcctgaaaccgggta cggagtacacggtgtccatttacggtgttcacaatgtgtataaagacacc aacatgcgtggcctgccgctgtcggcgattttcaccaccgcgcctgcgc cagcgcctgcaccggctccgctgccggcaccgaagaacctggttgtca gccgtgtgaccgaggatagcgcacgtttgagctggaccgctccggatg cagcctttgacagcttctggattcgttactttgaatttctgggtagcggtgag gcgatcgttctgacggtgccgggctctgaacgcagctatgatttgacggg cctgaagccgggtactgagtacgtggttaacatcatgggcgttaagggtg gtaaaatcagcccgccattgtccgcgatctttaccacg |
| 168 | DNA | Artificial | >EGFR part ECB97; P54AR4-83v22 without Met | ttgccagcgccgaagaacctggtagttagcgaggttactgaggacagc gcgcgtctgagctgggacgatccgtgggcgttctacgagagctttctgat ccagtatcaagagagcgagaaagtcggtgaagcgattgtgctgaccgt cccgggctccgagcgttcctacgacctgaccggtttgaagccgggtacc gagtatacggtgagcatctacggtgttcacaatgtctataaggacactaa tatccgcggtctgcctctgagcgccattttcaccacc |
| 169 | DNA | Artificial | >EGFR part ECB15; P54AR4-83v2 without Met | ctgccagcccctaagaatctggtcgtgagcgaagtaaccgaggacag cgcccgcctgagctgggacgacccgtgggcgttctatgagtctttcctga ttcagtatcaagaaagcgaaaaagttggcgaagcgatcgtcctgaccg tcccgggtagcgagcgctcctacgatctgaccggcctgaaaccgggta cggagtacacggtgtccatttacggtgttcacaatgtgtataaagacacc aacatgcgtggcctgccgctgtcggcgattttcaccacc |
| 170 | PRT | Artificial | ECB94 with C-ter cysteine | MLPAPKNLVVSEVTEDSARLSWDDPWAFYESFLIQY QESEKVGEAIVLTVPGSERSYDLTGLKPGTEYTVSIY GVHNVYKDTNIRGLPLSAIFTTAPAPAPAPAPLPAPKN LVVSRVTEDSARLSWTAPDAAFDSFWIRYFEFLGSG EAIVLTVPGSERSYDLTGLKPGTEYVVNILGVKGGKI SPPLSAIFTTC |
| 171 | PRT | Artificial | ECB95 with C-ter cysteine | MLPAPKNLVVSEVTEDSARLSWDDPWAFYESFLIQY QESEKVGEAIVLTVPGSERSYDLTGLKPGTEYTVSIY GVHNVYKDTNIRGLPLSAIFTTAPAPAPAPAPLPAPKN LVVSRVTEDSARLSWTAPDAAFDSFWIRYFEFVGSG EAIVLTVPGSERSYDLTGLKPGTEYVVNILGVKGGSI SPPLSAIFTTC |
| 172 | PRT | Artificial | ECB96 with C-ter cysteine | MLPAPKNLVVSEVTEDSARLSWDDPWAFYESFLIQY QESEKVGEAIVLTVPGSERSYDLTGLKPGTEYTVSIY GVHNVYKDTNIRGLPLSAIFTTAPAPAPAPAPLPAPKN LVVSRVTEDSARLSWTAPDAAFDSFWIRYFEFVSKG DAIVLTVPGSERSYDLTGLKPGTEYVVNILGVKGGSI SPPLSAIFTTC |

| | | | | |
|---|---|---|---|---|
| 173 | PRT | Artificial | ECB97 with C-ter cysteine | MLPAPKNLVVSEVTEDSARLSWDDPWAFYESFLIQY QESEKVGEAIVLTVPGSERSYDLTGLKPGTEYTVSIY GVHNVYKDTNIRGLPLSAIFTTAPAPAPAPAPLPAPKN LVVSRVTEDSARLSWTAPDAAFDSFWIRYFEFLGSG EAIVLTVPGSERSYDLTGLKPGTEYVVNILSVKGGSIS PPLSAIFTTC |
| 174 | PRT | Artificial | ECB106 with C-ter cysteine | MLPAPKNLVVSEVTEDSARLSWDDPHAFYESFLIQY QESEKVGEAIVLTVPGSERSYDLTGLKPGTEYTVSIY GVHNVYKDTNIRGLPLSAIFTTAPAPAPAPAPLPAPKN LVVSRVTEDSARLSWTAPDAAFDSFWIRYFEFLGSG EAIVLTVPGSERSYDLTGLKPGTEYVVNILGVKGGKI SPPLSAIFTTC |
| 175 | PRT | Artificial | ECB107 with C-ter cysteine | MLPAPKNLVVSEVTEDSARLSWDDPHAFYESFLIQY QESEKVGEAIVLTVPGSERSYDLTGLKPGTEYTVSIY GVHNVYKDTNIRGLPLSAIFTTAPAPAPAPAPLPAPKN LVVSRVTEDSARLSWTAPDAAFDSFWIRYFEFVGSG EAIVLTVPGSERSYDLTGLKPGTEYVVNILGVKGGSI SPPLSAIFTTC |
| 176 | PRT | Artificial | ECB108 with C-ter cysteine | MLPAPKNLVVSEVTEDSARLSWDDPHAFYESFLIQY QESEKVGEAIVLTVPGSERSYDLTGLKPGTEYTVSIY GVHNVYKDTNIRGLPLSAIFTTAPAPAPAPAPLPAPKN LVVSRVTEDSARLSWTAPDAAFDSFWIRYFEFVSKG DAIVLTVPGSERSYDLTGLKPGTEYVVNILGVKGGSI SPPLSAIFTTC |
| 177 | PRT | Artificial | ECB109 with C-ter cysteine | MLPAPKNLVVSEVTEDSARLSWDDPHAFYESFLIQY QESEKVGEAIVLTVPGSERSYDLTGLKPGTEYTVSIY GVHNVYKDTNIRGLPLSAIFTTAPAPAPAPAPLPAPKN LVVSRVTEDSARLSWTAPDAAFDSFWIRYFEFLGSG EAIVLTVPGSERSYDLTGLKPGTEYVVNILSVKGGSIS PPLSAIFTTC |
| 178 | PRT | Artificial | ECB91 with C-ter cysteine | mlpapknlwsevtedsarlswddpwafyesfliqyqesekvgeaivltvpgse rsydltglkpgteytvsiygvhnvykdtnirglplsaifttapapapapapLPAP KNLVVSRVTEDSARLSWTAPDAAFDSFWIRYFEFLGSGEAIVLTV PGSERSYDLTGLKPGTEYVVNILSVKGGSISPPLSAIFTTC |

>SEQ ID NO: 179
PRT
Artificial
An FG loop of EGFR binding FN3 domain
HNVYKDTNX$_9$RGL;
wherein X$_9$ is M or I >SEQ ID NO: 180
PRT
Artificial
A FG loop of EGFR binding FN3 domain
LGSYVFEHDVML (SEQ ID NO: 180), >SEQ ID NO: 181
PRT
Artificial
a BC loop of EGFR binding FN3 domain $X_1X_2X_3X_4X_5X_6X_7X_8$ (SEQ ID NO: 181); wherein $X_1$ is A, T, G or D;
$X_2$ is A, D, Y or W;
$X_3$ is P, D or N;
$X_4$ is L or absent;
$X_5$ is D, H, R, G, Y or W;
$X_6$ is G, D or A;
$X_7$ is A, F, G, H or D; and
$X_8$ is Y, F or L.

>SEQ ID NO: 182
PRT
Artificial
EGFR binding FN3 domain
LPAPKNLVVSEVTEDSLRLSWX$_1$X$_2$X$_3$X$_4$X$_5$X$_6$X$_7$X$_8$DSFLIQ-YQESEKVGEAINLTVP GSERSYDLTGLK-PGTEYTVSIYGVHN-VYKDTNX$_9$RGLPLSAEFTT (SEQ ID NO: 182), $X_1$ is A, T, G or D;
$X_2$ is A, D, Y or W;
$X_3$ is P, D or N;
$X_4$ is L or absent;
$X_5$ is D, H, R, G, Y or W;
$X_6$ is G, D or A;
$X_7$ is A, F, G, H or D;
$X_8$ is Y, F or L; and
$X_9$ is M or I >SEQ ID NO: 183
PRT
Artificial
EGFR binding FN3 domain
LPAPKNLVVSEVTEDSLRLSWX$_1$X$_2$X$_3$X$_4$X$_5$X$_6$X$_7$X$_8$D-SFLIQYQESEKVGEAINLTVP GSERSYDLT-GLKPGTEYTVSIYGVLGSYVFEHDVMLPL-SAEFTT (SEQ ID NO: 183), wherein
$X_1$ is A, T, G or D;
$X_2$ is A, D, Y or W;
$X_3$ is P, D or N;
$X_4$ is L or absent;

$X_5$ is D, H, R, G, Y or W;
$X_6$ is G, D or A;
$X_7$ is A, F, G, H or D; and
$X_8$ is Y, F or L.

>SEQ ID NO: 184
PRT
Artificial
A C-met binding FN3 domain C strand and a CD loop sequence DSFX$_{10}$IRYX$_{11}$E X$_{12}$X$_{13}$X$_{14}$X$_{15}$GX$_{16}$ (SEQ ID NO: 184), wherein $X_{10}$ is W, F or V;
$X_{11}$ is D, F or L;
$X_{12}$ is V, F or L;
$X_{13}$ is V, L or T;
$X_{14}$ is V, R, G, L, T or S;
$X_{15}$ is G, S, A, T or K; and
$X_{16}$ is E or D; and >SEQ ID NO: 185
PRT
Artificial
A c-Met binding FN3 domain F strand and a FG loop sequence TEYX$_{17}$VX$_{18}$IX$_{19}$X$_{20}$V KGGX$_{21}$X$_{22}$SX$_{23}$ (SEQ ID NO: 185), wherein $X_{17}$ is Y, W, I, V, G or A;
$X_{18}$ is N, T, Q or G;
$X_{19}$ is L, M, N or I;
$X_{20}$ is G or S;
$X_{21}$ is S, L, G, Y, T, R, H or K;
$X_{22}$ is I, V or L; and
$X_{23}$ is V, T, H, I, P, Y or L.

>SEQ ID NO: 186
PRT
Artificial
a c-Met binding FN3 domain

LPAPKNLVVSRVTEDSARLSWTAPDAAF
DSFX$_{10}$IRYX$_{11}$E X$_{12}$X$_{13}$X$_{14}$X$_{15}$GX$_{16}$
AIVLTVPGSERSYDLTGLKPGTEYX$_{17}$VX$_{18}$IX$_{19}$X$_{20}$-
VKGGX$_{21}$X$_{22}$SX$_{23}$PLSAEFTT (SEQ ID NO: 186), wherein
$X_{10}$ is W, F or V; and
$X_{11}$ is D, F or L;
$X_{12}$ is V, F or L;
$X_{13}$ is V, L or T;
$X_{14}$ is V, R, G, L, T or S;
$X_{15}$ is G, S, A, T or K;

$X_{16}$ is E or D;
$X_{17}$ is Y, W, I, V, G or A;
$X_{18}$ is N, T, Q or G;
$X_{19}$ is L, M, N or I;
$X_{20}$ is G or S;
$X_{21}$ is S, L, G, Y, T, R, H or K;
$X_{22}$ is I, V or L; and
$X_{23}$ is V, T, H, I, P, Y or L.

>SEQ ID NO: 187
PRT
Artificial
EGFR FN3 domain of a bispecific EGFR/c-Met FN3 domain containing molecule LPAPKNLVVSX$_{24}$VTX$_{25}$DSX$_{26}$RLSWDDPX$_{27}$AFYX$_{28}$SFLI-
QYQX$_{29}$SEKVGEAIX$_{30}$LT
VPGSERSYDLTGLKPGTEYTVSIYX$_{31}$VHNVYKDTN-
X$_{32}$RGLPLSAX$_{33}$FTT (SEQ ID NO: 187),
wherein $X_{24}$ is E, N or R;
$X_{25}$ is E or P;
$X_{26}$ is L or A;
$X_{27}$ is H or W;
$X_{28}$ is E or D;
$X_{29}$ is E or P;
$X_{30}$ is N or V;
$X_{31}$ is G or Y;
$X_{32}$ is M or I; and
$X_{33}$ is E or I;

>SEQ ID NO: 188
c-Met FN3 domain of a bispecific EGFR/c-Met FN3 domain containing molecule LPAPKNLVVSX$_{34}$VTX$_{35}$DSX$_{36}$RLSWTAPDAAFDSFWIRY-
FX$_{37}$FX$_{38}$X$_{39}$X$_{40}$GX$_{41}$AIX$_{42}$
LTVPGSERSYDLTGLKPGTEYVVNIX$_{43}$X$_{44}$VK-
GGX$_{45}$ISPPLSAX$_{46}$FTT (SEQ ID NO: 188);
wherein $X_{34}$ is E, N or R;
$X_{35}$ is E or P;
$X_{36}$ is L or A;
$X_{37}$ is E or P;
$X_{38}$ is V or L;
$X_{39}$ is G or S;
$X_{40}$ is S or K;
$X_{41}$ is E or D;
$X_{42}$ is N or V;
$X_{43}$ is L or M;
$X_{44}$ is G or S;
$X_{45}$ is S or K; and
$X_{46}$ is E or I.

```
EGFR mAb E1 VH
                                                                    >SEQ ID NO: 189
QVQLVESGGGVVQPGRSLRLSCAASGFTFSTYGMHWVRQAPGKGLEWVAVIWD
DGSYKYYGDSVKGRFTISRDNSKNTLY
LQMNSLRAEDTAVYYCARDGITMVRGVMKDYFDYWGQGTLVTVSS

EGFR mAb E1 VL
                                                                    >SEQ ID NO: 190
AIQLTQSPSSLSASVGDRVTITCRASQDISSALVWYQQKPGKAPKLLIYDASSLESG
VPSRFSGSESGTDFTLTISSLQP
EDFATYYCQQFNSYPLTFGGGTKVEIK

EGFR mAb E2 VH
                                                                    >SEQ ID NO: 191
  1 EVQLVESGGG LVQPGGSLRL SCAASGFTFS SYWMNWVRQA
    PGKGLEWVAN IKKDGSEKYY
 61 VDSVKGRFTI SRDNAKNSLY LQMNSLRAED TAVYYCARDL
    GWGWGWYFDL WGRGTLVTVS
121 S
```

EGFR mAb E2 VL

>SEQ ID NO: 192

```
  1 EIVLTQSPAT LSLSPGERAT LSCRASQSVS SYLAWYQQKP GQAPRLLIYD
ASNRATGIPA
 61 RFSGSGSGTD FTLTISSLEP EDFAVYYCQQ RSNWPPTFGQ GTKVEIK
``` cMet mAb M1 VH

>SEQ ID NO: 193

QVQLVQSGAEVKKPGASVKVSCETSGYTFTSYGISWVRQAPGHGLEWMGWISAY
NGYTNYAQKLQGRVTMTTDTSTSTAYMELRSLRSDDTAVYYCARDLRGTNYFD
YWGQGTLVTVSS cMet mAb M1VL

>SEQ ID NO: 194

DIQMTQSPSSVSASVGDRVTITCRASQGISNWLAWFQHKPGKAPKLLIYAASSLLS
GVPSRFSGSGSGTDFTLTISSLQPEDFATYYCQQANSFPITFGQGTRLEIK cMet mAb M2 VH

>SEQ ID NO: 195

EVQLVESGGGLVKPGGSLKLSCAASGFTFSDYYMYWVRQTPEKRLEWVATISDD
GSYTYYPDSVKGRFTISRDNAKNNLYLQMSSLKSEDTAMYYCAREGLYYYGSGS
YYNQDYWGQGTLVTVSS cMet mAb M2 VL

>SEQ ID NO: 196

QLTQSPSSLSASVGDRVTITCRASQGLSSALAWYRQKPGKAPKLLIYDASSLESGV
PSRFSGSGSGTDFTLTISSLQPEDFATYYCQQFTSYPQITFGQGTRLEIK

Gp120 heavy chain with F405L

>SEQ ID NO: 197 qvqlvqsgaevkkpgasvkvscqasgyrfsnfvihwvrqapgqrfewmgwinpyngnkefsakfqdrvtftadtsantay
melrslrsadtavyycarvgpyswddspqdnyymdvwgkgttvivssastkgpsvfplapssksstsggtaalgclvkdyfp
epvtvswnsgaltsgvhtfpavlqssglyslssvvtvpssslgtqtyicnvnhhkpsntkvdkrvepkscdkthtcppcpapell
ggpsvflfppkpkdtlmisrtpevtcvvvdvshedpevkfnwyvdgvevhnaktkpreeqynstyrvvsvltvlhqdwln
gkeykckvsnkalpapiektiskakgqprepqvytlppsreemtknqvsltclvkgfypsdiavewesngqpennykttpp
vldsdgsfllyskltvdksrwqqgnvfscsvmhealhnhytqkslslspgk Gp120 heavy chain with K409R

>SEQ ID NO: 198 qvqlvqsgaevkkpgasvkvscqasgyrfsnfvihwvrqapgqrfewmgwinpyngnkefsakfqdrvtftadtsantay
melrslrsadtavyycarvgpyswddspqdnyymdvwgkgttvivssastkgpsvfplapssksstsggtaalgclvkdyfp
epvtvswnsgaltsgvhtfpavlqssglyslssvvtvpssslgtqtyicnvnhhkpsntkvdkrvepkscdkthtcppcpapell
ggpsvflfppkpkdtlmisrtpevtcvvvdvshedpevkfnwyvdgvevhnaktkpreeqynstyrvvsvltvlhqdwln
gkeykckvsnkalpapiektiskakgqprepqvytlppsreemtknqvsltclvkgfypsdiavewesngqpennykttpp
vldsdgsfflysrltvdksrwqqgnvfscsvmhealhnhytqkslslspgk EM1-mAb H1 (anti-EGFR, 405L)

>SEQ ID NO: 199

QVQLVESGGGVVQPGRSLRLSCAASGFTFSTYGMHWVRQAPGKGLEWVAVIWD
DGSYKYYGDSVKGRFTISRDNSKNTLYLQMNSLRAEDTAVYYCARDGITMVRGV
MKDYFDYWGQGTLVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTK
VDKRVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMH
EALHNHYTQKSLSLSPGK

EM-1 mAb L1

>SEQ ID NO: 200

AIQLTQSPSSLSASVGDRVTITCRASQDISSALVWYQQKPGKAPKLLIYDASSLESG
VPSRFSGSESGTDFTLTISSLQPEDFATYYCQQFNSYPLTFGGGTKVEIKRTVAAPS
VFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC

EM-1 mAb H2 (K409R, anti-cMet)

>SEQ ID NO: 201

QVQLVQSGAEVKKPGASVKVSCETSGYTFTSYGISWVRQAPGHGLEWMGWISAY
NGYTNYAQKLQGRVTMTTDTSTSTAYMELRSLRSDDTAVYYCARDLRGTNYFD
YWGQGTLVTVSS
ASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKT
TPPVLDSDGSFFLYSRLTVDKSRWQQGNVFSCSVMHEALHNHYTQKSLSLSPGK

EM-1 mAb L2

>SEQ ID NO: 202

DIQMTQSPSSVSASVGDRVTITCRASQGISNWLAWFQHKPGKAPKLLIYAASSLLS
GVPSRFSGSGSGTDFTLTISSLQPEDFATYYCQQANSFPITFGQGTRLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC

H1 constant region

>SEQ ID NO: 203

ASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKT
TPPVLDSDGSFFLYSRLTVDKSRWQQGNVFSCSVMHEALHNHYTQKSLSLSPGK

H2 constant region

>SEQ ID NO: 204

ASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKT
TPPVLDSDGSFLLYSKLTVDKSRWQQGNVFSCSVMHEALHNHYTQKSLSLSPGK

EM1-mAb H1 cDNA pdr000015499

>SEQ ID NO: 205 caggtgcagctggtcgagagcggcggaggggtggtgcagcccggcagaagcctgaggctgtcctgcgccgccagcggcttc
accttcagcacctacgcgcatgcactgggtgcggcaggcccccaggcaagggcctggagtgggtggccgtgatctgggacgacg
gcagctacaagtactacggcgacagcgtgaagggcaggttcaccatcagcagggacaacagcaagaacaccctgtacctgca
gatgaacagcctgagggccgaggacaccgccgtgtactactgtgcgcagggacggcatcaccatcgctgcggggcgtgatgaag
gactacttcgactactggggccagggcaccctggtgaccgtgagcagcgccagcaccaagggcccaagcgtgttcccctggc
ccccagcagcaagagcaccagcggcggcacagccgccctgggctgcctggtgaaggactacttccccgagccagtgaccgtg
tcctggaactctggcgccctgacctccggcgtgcacaccttccccgccgtgctgcagagcagcggcctgtacagcctgagcagc
gtggtgaccgtgcccagcagcagcctgggcaacccagactacatctgcaacgtgaaccacaagcccagcaacaccaaggtgg
acaagagagtggagcccaagagctgcgacaagacccacacctgccccccctgcccagcccccagagctgctgggcggaccca
gcgtgttcctgttccccccaagcccaaggacacccctgatgatcagcaggacccccgaggtgacctgcgtggtggtggacgtga
gccacgaggaccagaggtgaagttcaactggtacgtggacggcgtggaggtgcacaacgccaagaccaagcccagagagg
agcagtacaacagcacctacagggtggtgtccgtgctgaccgtgctgcaccaggactggctgaacggcaaggaatacaagtgc
aaggtctccaacaaggccctgccagccccatcgaaaagaccatcagcaaggtccaagggccagccacgggagcccaggtg
tacaccctgcccccagccgggaggagatgaccaagaaccaggtgtccctgacctgtctggtgaagggcttctaccccagcgac
atcgccgtggagtgggagagcaacggccagcccgagaacaactacaagaccacccccccagtgctggacagcgacggcagc
ttcctcctgtacagcaagctgaccgtggacaagtccaggtggcagcagggcaacgtgttcagctgcagcgtgatgcacgaggcc
ctgcacaaccactacacccagaagtccctgagcctgagccccggcaaatga EM1-mAb L1 cDNA pDR000015499

>SEQ ID NO: 206 atccagctgacccagagccccagcagcctgagcgccagcgtgggcgaccgggtgaccatcacctgccgggccagccaggac
atcagcagcgccctggtctggtatcagcagaagcccggcaaggcccccaagctgctgatctacgacgccagctccctggaaag
cggcgtgcccagccggttcagcggcagcgagagcggcaccgacttcacccctgaccatcagcagcctgcagcccgaggacttc
gccacctactactgccagcagttcaacagctacccccctgacctttggcggcggaacaggtggagatcaagcgtacggtggcc
gctcccagcgtgttcatcttcccccccagcgacgagcagctgaagagcggcaccgccagcgtggtgtgcctgctgaacaacttct
accccagggaggccaaggtgcagtggaaggtggacaacgccctgcagagcggcaacagccaggagagcgtcaccgagcag
gacagcaaggactccacctacagcctgagcagcaccctgaccctgtccaaggccgactacgagaagcacaaggtgtacgcctg
cgaggtgacccaccagggcctgtccagccccgtgaccaagagcttcaacaggggcgagtgctga EM-1 mAb H2 cDNA pDR000016584

>SEQ ID NO: 207 caggttcagctggtgcagtctggagctgaggtgaagaagcctggggcctcagtgaaggtctcctgcgagacttctgttacacctt
taccagctatggtatcagctgggtgcgacaggcccctggacaggcttgagtggatggatcagcgcttacaatggttac
acaaaactatgcacagaagctccagggcagggtcaccatgaccacagacacatccacgagcacagcctacatggagctgagga
gcctgagatctgacgacacggccgtgtattactgtgcgagagatctgagaggaactaactactttgactactggggccagggaac
cctggtcaccgtctcctcagcctccaccaagggcccaagcgtgttccctctggccccagcagcaagagcacatctggcggaac
agccgcctgggctgcctggtgaaggactacttccccgagcctgtgaccgtgtcctggaactctggcgccctgaccagcggcgt
gcacaccttcagccgtgctgcagagcagcggcctgtacagcctgtccagcgtggtgaccgtgcccagcagctccctgggcac
ccagacctacatctgcaacgtgaaccacaagcccagcaacaccaaggtggacaagcgggtggaacccaagagctgcgacaag
acccacacctgtcccccctgccctgccctgaactgctgggcggaccctccgtgttcctgttcccccaaagcccaaggacacc
tgatgatcagccggacccccgaagtgacctgcgtggtggtggacgtgtcccacgaggaccctgaagtgaagttcaattggtacgt
ggacggcgtggaagtgcacaacgccaagaccaagccgagaggaacagtacaacagcacctaccgggtggtgtccgtgctg
acagtgctgcaccaggactggctgaacggcaaagagtacaagtgcaaggtctccaacaaggccctgcctgctcccatcgagaa
aaccatcagcaaggccaagggccagccccgcgagcctcaggtgtacacactgctcccagccgggaagagatgaccaagaa
ccaggtgtccctgacctgtctggtgaaaggcttctaccccagcgatatcgccgtggaatgggagagcaacggacagcccgagaa
caactacaagaccacccccccctgtgctggacagcgacggctccttcttcctgtactcccggctgaccgtggacaagagccggtgg
cagcagggaaacgtgttcagctgcagcgtgatgcacgaggccctgcacaaccactacacccagaagtccctgagcctgagccc
cgggaagtga EM-1 mAb L2 cDNA pDR000016584

>SEQ ID NO: 208 gacatccagatgacccagtcccctcctccgtgtccgcctctgtgggcgacagagtgaccatcacctgtcgggcctcccagggc
atctccaactggctggcctggttccagcacaagcccggcaaggcccccaagctgctgatctacgccgcctcctccctgctgtccg
gcgtgccctccagattctccggctctggctccggcaccgacttcaccctgaccatctccagcctgcagcccgaggacttcgccac -continued
```
ctactactgccagcaggccaactccttccccatcaccttcggccagggcaccggctggaaatcaagcgtacggtggccgctcc
cagcgtgttcatcttcccccccagcgacgagcagctgaagagcggcaccgccagcgtggtgtgcctgctgaacaacttctaccc
ccgggaggccaaggtgcagtggaaggtggacaacgccctgcagagcggcaacagccaggagagcgtcaccgagcaggaca
gcaaggactccacctacagcctgagcagcaccctgaccctgtccaaggccgactacgagaagcacaaggtgtacgcctgcgag
gtgacccaccagggcctgtccagccccgtgaccaagagcttcaacaggggcgagtgctga
```

Gp 120 light chain >SEQ ID NO: 209

Eivltqspgtlslspgeratfscrsshsirsrrvawyqhkpgqaprlvihgvsnrasgisdrfsgsgsgtdftltitrvepedfalyy
cqvygassytfgqgtklerkrtvaapsvfifppsdeqlksgtasvvcllnnfypreakvqwkvdnalqsgnsqesvteqdskd
styslsstltlskadyekhkvyacevthqglsspvtksfnrgec

E1 HC1 HCDR1 >SEQ ID NO: 210

TYGMH

E1 HC1 HCDR2 >SEQ ID NO: 211

VIWDDGSYKYYGDSVKG

E1 HC1 HCDR3 >SEQ ID NO: 212

DGITMVRGVMKDYFDY

E1 LC1 LCDR1 >SEQ ID NO: 213

RASQDISSALV

E1 LC1 LCDR2 >SEQ ID NO: 214

DASSLES

E1 LC1 LCDR3 >SEQ ID NO: 215

QQFNSYPLT

E1 HC2 HCDR1 >SEQ ID NO: 216

SYGIS

E1 HC2 HCDR2 >SEQ ID NO: 217

WISAYNGYTNYAQKLQG

E1 HC2 HCDR3 >SEQ ID NO: 218

DLRGTNYFDY

E1 LC2 LCDR1 >SEQ ID NO: 219

RASQGISNWLA

E1 LC2 LCDR2 >SEQ ID NO: 220

AASSLLS

E1 LC2 LCDR3 >SEQ ID NO: 221

QQANSFPIT

E2 mAB HC1 HCDR1 >SEQ ID NO: 222

SYWMN

E2 mAb HC1 HCDR2 >SEQ ID NO: 223

NIKKDGSEKYYVDSVKG

E2 mAb HC1 HCDR3 >SEQ ID NO: 224

DLGWGWGWYFDL

E2 mAB LC1 LCDR1 >SEQ ID NO: 225

RASQSVSSYLA

E2 mAb LC1 LCDR2 >SEQ ID NO: 226

DASNRAT

-continued

E2 mAb LC1 LCDR3 >SEQ ID NO: 227

QQRSNWPPT

E2 mAB HC2 HCDR1 >SEQ ID NO: 228

DYYMY

E2 mAb HC2 HCDR2 >SEQ ID NO: 229

TISDDGSYTYYPDSVKG

E2 mAb HC2 HCDR3 >SEQ ID NO: 230

EGLYYYGSGSYYNQDY

E2 mAB LC2 LCDR1 >SEQ ID NO: 231

RASQGLSSALA

E2 mAb LC2 LCDR2 >SEQ ID NO: 232

DASSLES

E2 mAb LC2 LCDR3 >SEQ ID NO: 233

QQFTSYPQIT

E2 mAb HC1 (EGFR-F405L) >SEQ ID NO: 234

EVQLVESGGG LVQPGGSLRL SCAASGFTFS SYWMNWVRQA PGKGLEWVAN
IKKDGSEKYY
VDSVKGRFTI SRDNAKNSLY LQMNSLRAED TAVYYCARDL GWGWGWYFDL
WGRGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKRVEP
KSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSN
KALPAPIEKTISKAKGQPREPQVYTLPPSREEMTKNQVSLTCLVKGFYPSDIAVEW
ESNGQPENNYKTTPPVLDSDGSFLLYSKLTVDKSRWQQGNVFSCSVMHEALHNH
YTQKSLSLSPGK

E2 mAb LC1 (EGFR) >SEQ ID NO: 235

EIVLTQSPAT LSLSPGERAT LSCRASQSVS SYLAWYQQKP GQAPRLLIYD
ASNRATGIPA
RFSGSGSGTD FTLTISSLEP EDFAVYYCQQ RSNWPPTFGQ GTKVEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC

E2 mAb HC2 (c-Met-K409R) >SEQ ID NO: 236

EVQLVESGGGLVKPGGSLKLSCAASGFTFSDYYMYWVRQTPEKRLEWVATISDD
GSYTYYPDSVKGRFTISRDNAKNNLYLQMSSLKSEDTAMYYCAREGLYYYGSGS
YYNQDYWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKV
DKRVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDI
AVEWESNGQPENNYKTTPPVLDSDGSFFLYSRLTVDKSRWQQGNVFSCSVMHEA
LHNHYTQKSLSLSPGK

E2 mAb LC2 (cMet) >SEQ ID NO: 237

QLTQSPSSLSASVGDRVTITCRASQGLSSALAWYRQKPGKAPKLLIYDASSLESGV
PSRFSGSGSGTDFTLTISSLQPEDFATYYCQQFTSYPQITFGQGTRLEIK
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC c-Met discontinuous epitope of mAb 069 >SEQ ID NO: 238

PEFRDSYPIKYVHAF c-Met discontinuous epitope of mAb 069 >SEQ ID NO: 239

FAQSKPDSAEPMDRSA

5D5 mAb epitope >SEQ ID nO: 240

PGAQLARQIGASLNDD

What is claimed:

1. An isolated bispecific epidermal growth factor receptor (EGFR)/hepatocyte growth factor receptor (c-Met) antibody, comprising:
   a) a first heavy chain (HC1);
   b) a second heavy chain (HC2);
   c) a first light chain (LC1); and
   d) a second light chain (LC2) wherein the HC1, the LC1, the HC2 and the LC2 comprise amino acid sequences of SEQ ID NOs: 199, 200, 201 and 202, respectively.

2. A pharmaceutical composition comprising the bispecific antibody of claim 1 and a pharmaceutically acceptable carrier.

* * * * *

SEQUENCE LISTING

<160> NUMBER OF SEQ ID NOS: 240

<210> SEQ ID NO 1
<211> LENGTH: 89
<212> TYPE: PRT
<213> ORGANISM: Artificial Sequence
<220> FEATURE:
<223> OTHER INFORMATION: Tencon FN3 scaffold

<400> SEQUENCE: 1

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85

<210> SEQ ID NO 2
<211> LENGTH: 58
<212> TYPE: DNA
<213> ORGANISM: Artificial Sequence
<220> FEATURE:
<223> OTHER INFORMATION: primer

<400> SEQUENCE: 2
ggaaacagga tctaccatgc tgccggcgcc gaaaaacctg gttgtttctg aagttacc        58

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
aacaccgtag atagaaacgg t                                                21

<210> SEQ ID NO 4
<211> LENGTH: 131
<212> TYPE: DNA
<213> ORGANISM: Artificial Sequence
<220> FEATURE:
<223> OTHER INFORMATION: primer

<400> SEQUENCE: 4
cggcggttag aacgcggcta caattaatac ataaccccat cccctgttg acaattaatc       60 atcggctcgt ataatgtgtg gaattgtgag cggataacaa tttcacacag gaaacaggat      120
ctaccatgct g                                                            131

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
cggcggttag aacgcggcta c         21

<210> SEQ ID NO 6
<211> LENGTH: 66
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t

<400> SEQUENCE: 6
ggtggtgaat tccgcagaca gcggsnnsnn snnsnnsnns nnsnnaacac cgtagataga      60
aacggt      66

<210> SEQ ID NO 7
<211> LENGTH: 69
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)

<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t

<400> SEQUENCE: 7
ggtggtgaat tccgcagaca gcggsnnsnn snnsnnsnns nnsnnsnnaa caccgtagat    60
agaaacggt                                                           69

<210> SEQ ID NO 8
<211> LENGTH: 72
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t

<400> SEQUENCE: 8
ggtggtgaat tccgcagaca gcggsnnsnn snnsnnsnns nnsnnsnnsn naacaccgta    60
gatagaaacg gt                                                       72

<210> SEQ ID NO 9
<211> LENGTH: 75
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature

```
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t

<400> SEQUENCE: 9
ggtggtgaat tccgcagaca gcggsnnsnn snnsnnsnns nnsnnsnnsn nsnnaacacc    60
gtagatagaa acggt                                                    75

<210> SEQ ID NO 10
<211> LENGTH: 80
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
```

<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t

<400> SEQUENCE: 10
rmggtggtga attccgcaga cagcggsnns nnsnnsnnsn nsnnsnnsnn snnsnnsnna    60
acaccgtaga tagaaacggt                                               80

<210> SEQ ID NO 11
<211> LENGTH: 81
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t

<400> SEQUENCE: 11
ggtggtgaat tccgcagaca gcggsnnsnn snnsnnsnns nnsnnsnnsn nsnnsnnsnn    60
aacaccgtag atagaaacgg t                                             81

```
<210> SEQ ID NO 12
<211> LENGTH: 81
<212> TYPE: DNA
<213> ORGANISM: Artificial Sequence
<220> FEATURE:
<223> OTHER INFORMATION: primer

<400> SEQUENCE: 12
aagatcagtt gcggccgcta gactagaacc gctgccatgg tgatggtgat ggtgaccgcc      60
ggtggtgaat ccgcagaca g                                                81

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
cggcggttag aacgcggcta caattaatac                                       30

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
catgattacg ccaagctcag aa                                               22

<210> SEQ ID NO 15
<211> LENGTH: 65
<212> TYPE: DNA
<213> ORGANISM: Artificial Sequence
<220> FEATURE:
<223> OTHER INFORMATION: primer

<400> SEQUENCE: 15
gagccgccgc caccggttta atggtgatgg tgatggtgac caccggtggt gaattccgca      60
gacag                                                                 65

<210> SEQ ID NO 16
<211> LENGTH: 37
<212> TYPE: DNA
<213> ORGANISM: Artificial Sequence
<220> FEATURE:
<223> OTHER INFORMATION: primer

<400> SEQUENCE: 16
aagaaggaga accggtatgc tgccggcgcc gaaaaac                               37

<210> SEQ ID NO 17
<211> LENGTH: 89
<212> TYPE: DNA
<213> ORGANISM: Artificial Sequence
<220> FEATURE:
<223> OTHER INFORMATION: primer

<400> SEQUENCE: 17
tttgggaagc ttctaggtct cggcggtcac catcaccatc accatggcag cggttctagt      60
ctagcggccc caactgatct tcaccaaac                                        89

<210> SEQ ID NO 18
```

-continued

```
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 18

Leu Pro Ala Pro Lys Asn Leu Val Val Ser Glu Val Thr Glu Asp Ser
1               5                   10                  15

Leu Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 19
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 19

Leu Pro Ala Pro Lys Asn Leu Val Val Ser Glu Val Thr Glu Asp Ser
1               5                   10                  15

Leu Arg Leu Ser Trp Thr Tyr Asp Arg Asp Gly Tyr Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 20
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 20

Leu Pro Ala Pro Lys Asn Leu Val Val Ser Glu Val Thr Glu Asp Ser
1               5                   10                  15

Leu Arg Leu Ser Trp Gly Tyr Asn Gly Asp His Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80
```

Thr Asn Met Arg Gly Leu Pro Leu Ser Ala Glu Phe Thr Thr
                85                  90

<210> SEQ ID NO 21
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 21

Leu Pro Ala Pro Lys Asn Leu Val Val Ser Glu Val Thr Glu Asp Ser
1               5                   10                  15

Leu Arg Leu Ser Trp Asp Asp Pro Arg Gly Phe Tyr Glu Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 22
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 22

Leu Pro Ala Pro Lys Asn Leu Val Val Ser Glu Val Thr Glu Asp Ser
1               5                   10                  15

Leu Arg Leu Ser Trp Thr Trp Pro Tyr Ala Asp Leu Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 23
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 23

Leu Pro Ala Pro Lys Asn Leu Val Val Ser Glu Val Thr Glu Asp Ser
1               5                   10                  15

Leu Arg Leu Ser Trp Gly Tyr Asn Gly Asp His Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly

```
                    50                  55                  60
Thr Glu Tyr Thr Val Ser Ile Tyr Gly Val His Asn Val Tyr Lys Asp
 65                  70                  75                  80

Thr Asn Met Arg Gly Leu Pro Leu Ser Ala Glu Phe Thr Thr
                     85                  90

<210> SEQ ID NO 24
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 24

Leu Pro Ala Pro Lys Asn Leu Val Val Ser Glu Val Thr Glu Asp Ser
  1               5                  10                  15

Leu Arg Leu Ser Trp Asp Tyr Asp Leu Gly Val Tyr Phe Asp Ser Phe
                 20                  25                  30

Leu Ile Gln Tyr Gln Glu Ser Glu Lys Val Gly Glu Ala Ile Asn Leu
             35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Glu Phe Thr Thr
                 85                  90                  95

<210> SEQ ID NO 25
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 25

Leu Pro Ala Pro Lys Asn Leu Val Val Ser Glu Val Thr Glu Asp Ser
  1               5                  10                  15

Leu Arg Leu Ser Trp Asp Asp Pro Trp Ala Phe Tyr Glu Ser Phe Leu
                 20                  25                  30

Ile Gln Tyr Gln Glu Ser Glu Lys Val Gly Glu Ala Ile Asn Leu Thr
             35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val His Asn Val Tyr Lys Asp
 65                  70                  75                  80

Thr Asn Met Arg Gly Leu Pro Leu Ser Ala Glu Phe Thr Thr
                 85                  90

<210> SEQ ID NO 26
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 26

Leu Pro Ala Pro Lys Asn Leu Val Val Ser Glu Val Thr Glu Asp Ser
  1               5                  10                  15

Leu Arg Leu Ser Trp Thr Ala Pro Asp Ala Ala Phe Asp Ser Phe Leu
                 20                  25                  30
```

```
Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Leu Gly Ser Tyr Val Phe
 65                  70                  75                  80

Glu His Asp Val Met Leu Pro Leu Ser Ala Glu Phe Thr Thr
                 85                  90

<210> SEQ ID NO 27
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 27

Leu Pro Ala Pro Lys Asn Leu Val Val Ser Glu Val Thr Glu Asp Ser
 1               5                  10                  15

Ala Arg Leu Ser Trp Asp Asp Pro Trp Ala Phe Tyr Glu Ser Phe Leu
             20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val His Asn Val Tyr Lys Asp
 65                  70                  75                  80

Thr Asn Met Arg Gly Leu Pro Leu Ser Ala Ile Phe Thr Thr
                 85                  90

<210> SEQ ID NO 28
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 28

Leu Pro Ala Pro Lys Asn Leu Val Val Ser Glu Val Thr Glu Asp Ser
 1               5                  10                  15

Ala Arg Leu Ser Trp Thr Ala Pro Ala Ala Phe Asp Ser Phe Leu
             20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Leu Gly Ser Tyr Val Phe
 65                  70                  75                  80

Glu His Asp Val Met Leu Pro Leu Ser Ala Ile Phe Thr Thr
                 85                  90

<210> SEQ ID NO 29
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 29
```

-continued

Leu Pro Ala Pro Lys Asn Leu Val Val Ser Glu Val Thr Glu Asp Ser
1               5                   10                  15

Leu Arg Leu Ser Trp Thr Trp Pro Tyr Ala Asp Leu Asp Ser Phe Leu
            20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Glu Phe Thr Thr
                85                  90

<210> SEQ ID NO 30
<211> LENGTH: 37
<212> TYPE: PRT
<213> ORGANISM: Artificial Sequence
<220> FEATURE:
<223> OTHER INFORMATION: primer

<400> SEQUENCE: 30

Ala Ala Gly Ala Ala Gly Gly Ala Gly Ala Ala Cys Cys Gly Gly Thr
1               5                   10                  15

Ala Thr Gly Cys Thr Gly Cys Cys Gly Gly Cys Gly Cys Cys Gly Ala
            20                  25                  30

Ala Ala Ala Ala Cys
            35

<210> SEQ ID NO 31
<211> LENGTH: 65
<212> TYPE: PRT
<213> ORGANISM: Artificial Sequence
<220> FEATURE:
<223> OTHER INFORMATION: primer

<400> SEQUENCE: 31

Gly Ala Gly Cys Cys Gly Cys Cys Gly Cys Cys Ala Cys Cys Gly Gly
1               5                   10                  15

Thr Thr Thr Ala Ala Thr Gly Thr Gly Ala Thr Gly Gly Thr Gly Gly
            20                  25                  30

Ala Thr Gly Gly Thr Gly Ala Cys Cys Ala Cys Cys Gly Gly Thr Gly
            35                  40                  45

Gly Thr Gly Ala Ala Gly Ala Thr Cys Gly Cys Ala Gly Ala Cys Ala
    50                  55                  60

Gly
65

<210> SEQ ID NO 32
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 32

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Asp Glu Val Val Val Gly Gly Glu Ala Ile Val Leu Thr 35                  40                  45

Val Pro Gly Ser Glu Arg Ser Tyr Asp Leu Thr Gly Leu Lys Pro Gly
             50                  55                  60

Thr Glu Tyr Tyr Val Asn Ile Leu Gly Val Lys Gly Gly Ser Ile Ser
 65                  70                  75                  80

Val Pro Leu Ser Ala Ile Phe Thr Thr
                 85

<210> SEQ ID NO 33
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 33

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Phe
                 20                  25                  30

Ile Arg Tyr Asp Glu Phe Leu Arg Ser Gly Glu Ala Ile Val Leu Thr
             35                  40                  45

Val Pro Gly Ser Glu Arg Ser Tyr Asp Leu Thr Gly Leu Lys Pro Gly
             50                  55                  60

Thr Glu Tyr Trp Val Thr Ile Leu Gly Val Lys Gly Gly Leu Val Ser
 65                  70                  75                  80

Thr Pro Leu Ser Ala Ile Phe Thr Thr
                 85

<210> SEQ ID NO 34
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 34

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
                 20                  25                  30

Ile Arg Tyr Phe Glu Phe Leu Gly Ser Gly Glu Ala Ile Val Leu Thr
             35                  40                  45

Val Pro Gly Ser Glu Arg Ser Tyr Asp Leu Thr Gly Leu Lys Pro Gly
             50                  55                  60

Thr Glu Tyr Ile Val Asn Ile Met Gly Val Lys Gly Gly Ser Ile Ser
 65                  70                  75                  80

His Pro Leu Ser Ala Ile Phe Thr Thr
                 85

<210> SEQ ID NO 35
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 35

Leu Pro Ala Pro Lys Asn Leu Val Val Ser Arg Val Thr Glu Asp Ser
 1               5                  10                  15

```
Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Leu Gly Val Lys Gly Gly Leu Ser
65                  70                  75                  80

Val Pro Leu Ser Ala Ile Phe Thr Thr
                    85
```

<210> SEQ ID NO 36
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 36

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Val
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Gln Ile Leu Gly Val Lys Gly Gly Tyr Ile Ser
65                  70                  75                  80

Ile Pro Leu Ser Ala Ile Phe Thr Thr
                    85
```

<210> SEQ ID NO 37
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 37

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Leu Glu Phe Leu Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Gln Ile Met Gly Val Lys Gly Gly Thr Val Ser
65                  70                  75                  80

Pro Pro Leu Ser Ala Ile Phe Thr Thr
                    85
```

<210> SEQ ID NO 38
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 38

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
                20                  25                  30

Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Gly Ile Asn Gly Val Lys Gly Gly Tyr Ile Ser
65              70                  75                  80

Tyr Pro Leu Ser Ala Ile Phe Thr Thr
                85

<210> SEQ ID NO 39
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 39

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
                20                  25                  30

Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Asp Leu Lys Pro Gly
        50                  55                  60

Thr Glu Tyr Gly Val Thr Ile Asn Gly Val Lys Gly Arg Val Ser
65              70                  75                  80

Thr Pro Leu Ser Ala Ile Phe Thr Thr
                85

<210> SEQ ID NO 40
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 40

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
                20                  25                  30

Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Gln Ile Ile Gly Val Lys Gly Gly His Ile Ser
65              70                  75                  80

Leu Pro Leu Ser Ala Ile Phe Thr Thr
                85

<210> SEQ ID NO 41

```
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 41

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Gly Lys Ile Ser
65                  70                  75                  80

Pro Pro Leu Ser Ala Ile Phe Thr Thr
                85

<210> SEQ ID NO 42
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 42

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ala Val Asn Ile Met Gly Val Lys Gly Gly Arg Val Ser
65                  70                  75                  80

Val Pro Leu Ser Ala Ile Phe Thr Thr
                85

<210> SEQ ID NO 43
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 43

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Gln Ile Leu Gly Val Lys Gly Gly Ser Ile Ser
65                  70                  75                  80
```

```
Val Pro Leu Ser Ala Ile Phe Thr Thr
            85

<210> SEQ ID NO 44
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 44

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Met Gly Val Lys Gly Ser Ile Ser
65                  70                  75                  80

Tyr Pro Leu Ser Ala Ile Phe Thr Thr
            85

<210> SEQ ID NO 45
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 45

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Gln Ile Leu Gly Val Lys Gly Tyr Ile Ser
65                  70                  75                  80

Ile Pro Leu Ser Ala Ile Phe Thr Thr
            85

<210> SEQ ID NO 46
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 46

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
```

```
              50                  55                  60
Thr Glu Tyr Val Val Gln Ile Met Gly Val Lys Gly Gly Thr Val Ser
 65                  70                  75                  80

Pro Pro Leu Ser Ala Ile Phe Thr Thr
                 85

<210> SEQ ID NO 47
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 47

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
                20                  25                  30

Ile Arg Tyr Phe Glu Phe Thr Thr Ala Gly Glu Ala Ile Val Leu Thr
                35                  40                  45

Val Pro Gly Ser Glu Arg Ser Tyr Asp Leu Thr Gly Leu Lys Pro Gly
         50                  55                  60

Thr Glu Tyr Val Val Asn Ile Met Gly Val Lys Gly Gly Ser Ile Ser
 65                  70                  75                  80

Pro Pro Leu Ser Ala Ile Phe Thr Thr
                 85

<210> SEQ ID NO 48
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 48

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
                20                  25                  30

Ile Arg Tyr Phe Glu Leu Leu Ser Thr Gly Glu Ala Ile Val Leu Thr
                35                  40                  45

Val Pro Gly Ser Glu Arg Ser Tyr Asp Leu Thr Gly Leu Lys Pro Gly
         50                  55                  60

Thr Glu Tyr Val Val Asn Ile Met Gly Val Lys Gly Gly Ser Ile Ser
 65                  70                  75                  80

Pro Pro Leu Ser Ala Ile Phe Thr Thr
                 85

<210> SEQ ID NO 49
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 49

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
                20                  25                  30
```

```
Ile Arg Tyr Phe Glu Phe Val Ser Lys Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Val Val Asn Ile Met Gly Val Lys Gly Gly Ser Ile Ser
 65                  70                  75                  80

Pro Pro Leu Ser Ala Ile Phe Thr Thr
                 85

<210> SEQ ID NO 50
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 50

Met Leu Pro Ala Pro Lys Asn Leu Val Val Ser Glu Val Thr Glu Asp
 1               5                  10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Ile Phe Thr Thr Gly
            85                  90                  95

Gly Gly Gly Ser Gly Gly Gly Gly Ser Gly Gly Gly Gly Ser Gly Gly
           100                 105                 110

Gly Gly Ser Met Leu Pro Ala Pro Lys Asn Leu Val Val Ser Arg Val
           115                 120                 125

Thr Glu Asp Ser Ala Arg Leu Ser Trp Thr Ala Pro Asp Ala Ala Phe
130                 135                 140

Asp Ser Phe Trp Ile Arg Tyr Asp Glu Val Val Val Gly Gly Glu Ala
145                 150                 155                 160

Ile Val Leu Thr Val Pro Gly Ser Glu Arg Ser Tyr Asp Leu Thr Gly
                165                 170                 175

Leu Lys Pro Gly Thr Glu Tyr Tyr Val Asn Ile Leu Gly Val Lys Gly
            180                 185                 190

Gly Ser Ile Ser Val Pro Leu Ser Ala Ile Phe Thr Thr
            195                 200                 205

<210> SEQ ID NO 51
<211> LENGTH: 204
<212> TYPE: PRT
<213> ORGANISM: Artificial Sequence
<220> FEATURE:
<223> OTHER INFORMATION: bispecific EGFR/cMet binding molecule

<400> SEQUENCE: 51

Met Leu Pro Ala Pro Lys Asn Leu Val Val Ser Glu Val Thr Glu Asp
 1               5                  10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
```

```
                35                  40                  45
Thr Val Pro Gly Ser Glu Arg Ser Tyr Asp Leu Thr Gly Leu Lys Pro
 50                  55                  60
Gly Thr Glu Tyr Thr Val Ser Ile Tyr Gly Val His Asn Val Tyr Lys
 65                  70                  75                  80
Asp Thr Asn Met Arg Gly Leu Pro Leu Ser Ala Ile Phe Thr Thr Gly
                 85                  90                  95
Gly Gly Gly Ser Gly Gly Gly Ser Gly Gly Gly Ser Gly Gly
                100                 105                 110
Gly Gly Ser Leu Pro Ala Pro Lys Asn Leu Val Val Ser Arg Val Thr
            115                 120                 125
Glu Asp Ser Ala Arg Leu Ser Trp Thr Ala Pro Asp Ala Ala Phe Asp
130                 135                 140
Ser Phe Trp Ile Arg Tyr Phe Glu Phe Leu Gly Ser Gly Glu Ala Ile
145                 150                 155                 160
Val Leu Thr Val Pro Gly Ser Glu Arg Ser Tyr Asp Leu Thr Gly Leu
                165                 170                 175
Lys Pro Gly Thr Glu Tyr Val Val Asn Ile Met Gly Val Lys Gly Gly
                180                 185                 190
Lys Ile Ser Pro Pro Leu Ser Ala Ile Phe Thr Thr
            195                 200
```

<210> SEQ ID NO 52
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 52

```
Met Leu Pro Ala Pro Lys Asn Leu Val Val Ser Glu Val Thr Glu Asp
 1               5                  10                  15
Ser Ala Arg Leu Ser Trp Asp Asp Pro Trp Ala Phe Tyr Glu Ser Phe
                20                  25                  30
Leu Ile Gln Tyr Gln Glu Ser Glu Lys Val Gly Glu Ala Ile Val Leu
                35                  40                  45
Thr Val Pro Gly Ser Glu Arg Ser Tyr Asp Leu Thr Gly Leu Lys Pro
 50                  55                  60
Gly Thr Glu Tyr Thr Val Ser Ile Tyr Gly Val His Asn Val Tyr Lys
 65                  70                  75                  80
Asp Thr Asn Met Arg Gly Leu Pro Leu Ser Ala Ile Phe Thr Thr Gly
                 85                  90                  95
Gly Gly Gly Ser Gly Gly Gly Ser Gly Gly Gly Ser Gly Gly
                100                 105                 110
Gly Gly Ser Met Leu Pro Ala Pro Lys Asn Leu Val Val Ser Arg Val
            115                 120                 125
Thr Glu Asp Ser Ala Arg Leu Ser Trp Thr Ala Pro Asp Ala Ala Phe
130                 135                 140
Asp Ser Phe Trp Ile Arg Tyr Phe Glu Phe Leu Gly Ser Gly Glu Ala
145                 150                 155                 160
Ile Val Leu Thr Val Pro Gly Ser Glu Arg Ser Tyr Asp Leu Thr Gly
                165                 170                 175
Leu Lys Pro Gly Thr Glu Tyr Val Val Gln Ile Ile Gly Val Lys Gly
                180                 185                 190
Gly His Ile Ser Leu Pro Leu Ser Ala Ile Phe Thr Thr
```

<210> SEQ ID NO 53
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 53

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Gly
                85                  90                  95

Gly Gly Gly Ser Gly Gly Gly Ser Gly Gly Gly Ser Gly Gly
            100                 105                 110

Gly Gly Ser Met Leu Pro Ala Pro Lys Asn Leu Val Val Ser Arg Val
            115                 120                 125

Thr Glu Asp Ser Ala Arg Leu Ser Trp Thr Ala Pro Asp Ala Ala Phe
        130                 135                 140

Asp Ser Phe Phe Ile Arg Tyr Asp Glu Phe Leu Arg Ser Gly Glu Ala
145                 150                 155                 160

Ile Val Leu Thr Val Pro Gly Ser Glu Arg Ser Tyr Asp Leu Thr Gly
                165                 170                 175

Leu Lys Pro Gly Thr Glu Tyr Trp Val Thr Ile Leu Gly Val Lys Gly
            180                 185                 190

Gly Leu Val Ser Thr Pro Leu Ser Ala Ile Phe Thr Thr
            195                 200                 205

<210> SEQ ID NO 54
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 54

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Gly
                85                  90                  95

```
Gly Gly Gly Ser Gly Gly Gly Ser Gly Gly Gly Ser Gly Gly
            100                 105                 110

Gly Gly Ser Met Leu Pro Ala Pro Lys Asn Leu Val Val Ser Arg Val
            115                 120                 125

Thr Glu Asp Ser Ala Arg Leu Ser Trp Thr Ala Pro Asp Ala Ala Phe
        130                 135                 140

Asp Ser Phe Trp Ile Arg Tyr Phe Glu Phe Leu Gly Ser Gly Glu Ala
145                 150                 155                 160

Ile Val Leu Thr Val Pro Gly Ser Glu Arg Ser Tyr Asp Leu Thr Gly
                165                 170                 175

Leu Lys Pro Gly Thr Glu Tyr Val Val Asn Ile Met Gly Val Lys Gly
            180                 185                 190

Gly Lys Ile Ser Pro Pro Leu Ser Ala Ile Phe Thr Thr
            195                 200                 205

<210> SEQ ID NO 55
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 55

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Gly
                85                  90                  95

Gly Gly Gly Ser Gly Gly Gly Ser Gly Gly Gly Ser Gly Gly
            100                 105                 110

Gly Gly Ser Met Leu Pro Ala Pro Lys Asn Leu Val Val Ser Arg Val
            115                 120                 125

Thr Glu Asp Ser Ala Arg Leu Ser Trp Thr Ala Pro Asp Ala Ala Phe
        130                 135                 140

Asp Ser Phe Trp Ile Arg Tyr Phe Glu Phe Leu Gly Ser Gly Glu Ala
145                 150                 155                 160

Ile Val Leu Thr Val Pro Gly Ser Glu Arg Ser Tyr Asp Leu Thr Gly
                165                 170                 175

Leu Lys Pro Gly Thr Glu Tyr Val Val Gln Ile Ile Gly Val Lys Gly
            180                 185                 190

Gly His Ile Ser Leu Pro Leu Ser Ala Ile Phe Thr Thr
            195                 200                 205

<210> SEQ ID NO 56
<211> LENGTH: 205
<212> TYPE: PRT
<213> ORGANISM: Artificial Sequence
<220> FEATURE:
<223> OTHER INFORMATION: bispecific EGFR/cMet binding molecule

<400> SEQUENCE: 56
```

```
Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Gly
                85                  90                  95

Gly Gly Gly Ser Gly Gly Gly Ser Gly Gly Gly Ser Gly Gly
                100                 105                 110

Gly Gly Ser Met Leu Pro Ala Pro Lys Asn Leu Val Val Ser Arg Val
            115                 120                 125

Thr Glu Asp Ser Ala Arg Leu Ser Trp Thr Ala Pro Asp Ala Ala Phe
    130                 135                 140

Asp Ser Phe Trp Ile Arg Tyr Phe Glu Phe Leu Gly Ser Gly Glu Ala
145                 150                 155                 160

Ile Val Leu Thr Val Pro Gly Ser Glu Arg Ser Tyr Asp Leu Thr Gly
                165                 170                 175

Leu Lys Pro Gly Thr Glu Tyr Val Val Gln Ile Ile Gly Val Lys Gly
            180                 185                 190

Gly His Ile Ser Leu Pro Leu Ser Ala Ile Phe Thr Thr
                195                 200                 205

<210> SEQ ID NO 57
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 57

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160
```

-continued

```
Tyr Asp Leu Thr Gly Leu Lys Pro Gly Thr Glu Tyr Val Val Asn Ile
            165                 170                 175
Met Gly Val Lys Gly Gly Lys Ile Ser Pro Pro Leu Ser Ala Ile Phe
        180                 185                 190
Thr Thr

<210> SEQ ID NO 58
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 58

Met Leu Pro Ala Pro Lys Asn Leu Val Val Ser Glu Val Thr Glu Asp
1               5                   10                  15
Ser Ala Arg Leu Ser Trp Asp Asp Pro Trp Ala Phe Tyr Glu Ser Phe
            20                  25                  30
Leu Ile Gln Tyr Gln Glu Ser Glu Lys Val Gly Glu Ala Ile Val Leu
        35                  40                  45
Thr Val Pro Gly Ser Glu Arg Ser Tyr Asp Leu Thr Gly Leu Lys Pro
    50                  55                  60
Gly Thr Glu Tyr Thr Val Ser Ile Tyr Gly Val His Asn Val Tyr Lys
65                  70                  75                  80
Asp Thr Asn Met Arg Gly Leu Pro Leu Ser Ala Ile Phe Thr Thr Ala
                85                  90                  95
Pro Ala Pro Ala Pro Ala Pro Ala Pro Leu Pro Ala Pro Lys Asn Leu
            100                 105                 110
Val Val Ser Arg Val Thr Glu Asp Ser Ala Arg Leu Ser Trp Thr Ala
        115                 120                 125
Pro Asp Ala Ala Phe Asp Ser Phe Trp Ile Arg Tyr Asp Glu Val Val
    130                 135                 140
Val Gly Gly Glu Ala Ile Val Leu Thr Val Pro Gly Ser Glu Arg Ser
145                 150                 155                 160
Tyr Asp Leu Thr Gly Leu Lys Pro Gly Thr Glu Tyr Tyr Val Asn Ile
                165                 170                 175
Leu Gly Val Lys Gly Gly Ser Ile Ser Val Pro Leu Ser Ala Ile Phe
            180                 185                 190
Thr Thr

<210> SEQ ID NO 59
<211> LENGTH: 195
<212> TYPE: PRT
<213> ORGANISM: Artificial Sequence
<220> FEATURE:
<223> OTHER INFORMATION: bispecific EGFR/cMet binding molecule

<400> SEQUENCE: 59

Met Leu Pro Ala Pro Lys Asn Leu Val Val Ser Glu Val Thr Glu Asp
1               5                   10                  15
Ser Ala Arg Leu Ser Trp Ala Asp Pro His Gly Phe Tyr Asp Ser Phe
            20                  25                  30
Leu Ile Gln Tyr Gln Glu Ser Glu Lys Val Gly Glu Ala Ile Val Leu
        35                  40                  45
Thr Val Pro Gly Ser Glu Arg Ser Tyr Asp Leu Thr Gly Leu Lys Pro
    50                  55                  60
```

```
Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Ile Phe Thr Thr Ala
                 85                  90                  95

Pro Ala Pro Ala Pro Ala Pro Ala Pro Met Leu Pro Ala Pro Lys Asn
            100                 105                 110

Leu Val Val Ser Arg Val Thr Glu Asp Ser Ala Arg Leu Ser Trp Thr
            115                 120                 125

Ala Pro Asp Ala Ala Phe Asp Ser Phe Trp Ile Arg Tyr Phe Glu Phe
        130                 135                 140

Leu Gly Ser Gly Glu Ala Ile Val Leu Thr Val Pro Gly Ser Glu Arg
145                 150                 155                 160

Ser Tyr Asp Leu Thr Gly Leu Lys Pro Gly Thr Glu Tyr Val Val Asn
                165                 170                 175

Ile Met Gly Val Lys Gly Gly Lys Ile Ser Pro Pro Leu Ser Ala Ile
                180                 185                 190

Phe Thr Thr
        195

<210> SEQ ID NO 60
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 60

Met Leu Pro Ala Pro Lys Asn Leu Val Val Ser Glu Val Thr Glu Asp
 1               5                  10                  15

Ser Ala Arg Leu Ser Trp Ala Asp Pro His Gly Phe Tyr Asp Ser Phe
                20                  25                  30

Leu Ile Gln Tyr Gln Glu Ser Glu Lys Val Gly Glu Ala Ile Val Leu
             35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Ile Phe Thr Thr Ala
                 85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Asp Glu Val Val
        130                 135                 140

Val Gly Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Tyr Val Asn Ile
                165                 170                 175

Leu Gly Val Lys Gly Gly Ser Ile Ser Val Pro Leu Ser Ala Ile Phe
                180                 185                 190

Thr Thr

<210> SEQ ID NO 61
<211> LENGTH: 194
<212> TYPE: PRT
```

<213> ORGANISM: Artificial Sequence
<220> FEATURE:
<223> OTHER INFORMATION: bispecific EGFR/cMet binding molecule

<400> SEQUENCE: 61

```
Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
        130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Lys Ile Ser Pro Pro Leu Ser Ala Ile Phe
            180                 185                 190

Thr Thr
```

<210> SEQ ID NO 62
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 62

```
Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Val
```

130                 135                 140
Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
                180                 185                 190

Thr Thr

<210> SEQ ID NO 63
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 63

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Val
        130                 135                 140

Ser Lys Gly Asp Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
                180                 185                 190

Thr Thr

<210> SEQ ID NO 64
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 64

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

```
Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Ile Arg Gly Leu Pro Leu Ser Ala Ile Phe Thr Thr Ala
                 85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
                115                 120                 125

Pro Asp Ala Ala Phe Asp Ser Phe Trp Ile Arg Tyr Phe Glu Phe Leu
130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
                180                 185                 190

Thr Thr

<210> SEQ ID NO 65
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 65

Met Leu Pro Ala Pro Lys Asn Leu Val Val Ser Glu Val Thr Glu Asp
 1               5                  10                  15

Ser Ala Arg Leu Ser Trp Asp Asp Pro His Ala Phe Tyr Glu Ser Phe
                20                  25                  30

Leu Ile Gln Tyr Gln Glu Ser Glu Lys Val Gly Glu Ala Ile Val Leu
                35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Ile Arg Gly Leu Pro Leu Ser Ala Ile Phe Thr Thr Ala
                 85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
                115                 120                 125

Pro Asp Ala Ala Phe Asp Ser Phe Trp Ile Arg Tyr Phe Glu Phe Leu
130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Lys Ile Ser Pro Pro Leu Ser Ala Ile Phe
                180                 185                 190

Thr Thr
```

-continued

```
<210> SEQ ID NO 66
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 66

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Val
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
                180                 185                 190

Thr Thr

<210> SEQ ID NO 67
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 67

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
```

```
                115                 120                 125
Pro Asp Ala Ala Phe Asp Ser Phe Trp Ile Arg Tyr Phe Glu Phe Val
        130                 135                 140

Ser Lys Gly Asp Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
            180                 185                 190

Thr Thr

<210> SEQ ID NO 68
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 68

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
            180                 185                 190

Thr Thr

<210> SEQ ID NO 69
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 69

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30
```

```
Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
     50                  55                  60

Gly Thr Glu Tyr Thr Val Ser Ile Tyr Gly Val His Asn Val Tyr Lys
 65                  70                  75                  80

Asp Thr Asn Ile Arg Gly Leu Pro Leu Ser Ala Ile Phe Thr Thr Ala
                 85                  90                  95

Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
            130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Lys Ile Ser Pro Pro Leu Ser Ala Ile Phe
            180                 185                 190

Thr Thr

<210> SEQ ID NO 70
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 70

Met Leu Pro Ala Pro Lys Asn Leu Val Val Ser Glu Val Thr Glu Asp
 1               5                  10                  15

Ser Ala Arg Leu Ser Trp Ala Asp Pro His Gly Phe Tyr Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
     50                  55                  60

Gly Thr Glu Tyr Thr Val Ser Ile Tyr Gly Val His Asn Val Tyr Lys
 65                  70                  75                  80

Asp Thr Asn Ile Arg Gly Leu Pro Leu Ser Ala Ile Phe Thr Thr Ala
                 85                  90                  95

Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Val
            130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
            180                 185                 190
```

Thr Thr

<210> SEQ ID NO 71
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 71

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Val
    130                 135                 140

Ser Lys Gly Asp Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
            180                 185                 190

Thr Thr

<210> SEQ ID NO 72
<211> LENGTH: 194
<212> TYPE: PRT
<213> ORGANISM: Artificial Sequence
<220> FEATURE:
<223> OTHER INFORMATION: bispecific EGFR/cMet binding molecule

<400> SEQUENCE: 72

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu

```
                100              105              110
Val Val Ser Arg Val Thr Glu Asp Ser Ala Arg Leu Ser Trp Thr Ala
            115                  120              125

Pro Asp Ala Ala Phe Asp Ser Phe Trp Ile Arg Tyr Phe Glu Phe Leu
130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Ser Ile Ser Pro Leu Ser Ala Ile Phe
                180                 185                 190

Thr Thr

<210> SEQ ID NO 73
<211> LENGTH: 1210
<212> TYPE: PRT
<213> ORGANISM: HOMO SAPIENS

<400> SEQUENCE: 73

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
```

-continued

```
                275                 280                 285
Ala Thr Cys Val Lys Lys Cys Pro Arg Asn Tyr Val Thr Asp His
    290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
                340                 345                 350
Ala Thr Asn Ile Lys His Phe Lys Asn Cys Thr Ser Ile Ser Gly Asp
                355                 360                 365
Leu His Ile Leu Pro Val Ala Phe Arg Gly Asp Ser Phe Thr His Thr
                370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
                420                 425                 430
His Gly Gln Phe Ser Leu Ala Val Val Ser Leu Asn Ile Thr Ser Leu
                435                 440                 445
Gly Leu Arg Ser Leu Lys Glu Ile Ser Asp Gly Asp Val Ile Ile Ser
                450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
                500                 505                 510
Glu Gly Cys Trp Gly Pro Glu Pro Arg Asp Cys Val Ser Cys Arg Asn
                515                 520                 525
Val Ser Arg Gly Arg Glu Cys Val Asp Lys Cys Asn Leu Leu Glu Gly
                530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
                580                 585                 590
Lys Thr Cys Pro Ala Gly Val Met Gly Glu Asn Asn Thr Leu Val Trp
                595                 600                 605
Lys Tyr Ala Asp Ala Gly His Val Cys His Leu Cys His Pro Asn Cys
                610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
                660                 665                 670
Ile Val Arg Lys Arg Thr Leu Arg Arg Leu Leu Gln Glu Arg Glu Leu
                675                 680                 685
Val Glu Pro Leu Thr Pro Ser Gly Glu Ala Pro Asn Gln Ala Leu Leu
                690                 695                 700
```

-continued

```
Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
                755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
                835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
                900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
                995                 1000                1005

Asp Val  Val Asp Ala Asp Glu  Tyr Leu Ile Pro Gln  Gln Gly Phe
    1010            1015                1020

Phe Ser  Ser Pro Ser Thr  Ser Arg Thr Pro Leu Leu  Ser Ser Leu
    1025            1030                1035

Ser Ala  Thr Ser Asn Asn Ser  Thr Val Ala Cys Ile  Asp Arg Asn
    1040                1045                1050

Gly Leu  Gln Ser Cys Pro  Ile Lys Glu Asp Ser Phe  Leu Gln Arg
    1055            1060                1065

Tyr Ser  Ser Asp Pro Thr Gly  Ala Leu Thr Glu Asp  Ser Ile Asp
    1070            1075                1080

Asp Thr  Phe Leu Pro Val Pro  Glu Tyr Ile Asn Gln  Ser Val Pro
    1085            1090                1095

Lys Arg  Pro Ala Gly Ser Val  Gln Asn Pro Val Tyr  His Asn Gln
    1100            1105                1110
```

-continued

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205            1210

<210> SEQ ID NO 74
<211> LENGTH: 53
<212> TYPE: PRT
<213> ORGANISM: HOMO SAPIENS

<400> SEQUENCE: 74

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 75
<211> LENGTH: 2201
<212> TYPE: PRT
<213> ORGANISM: Homo sapiens

<400> SEQUENCE: 75

Met Gly Ala Met Thr Gln Leu Leu Ala Gly Val Phe Leu Ala Phe Leu
1               5                   10                  15

Ala Leu Ala Thr Glu Gly Gly Val Leu Lys Lys Val Ile Arg His Lys
            20                  25                  30

Arg Gln Ser Gly Val Asn Ala Thr Leu Pro Glu Glu Asn Gln Pro Val
        35                  40                  45

Val Phe Asn His Val Tyr Asn Ile Lys Leu Pro Val Gly Ser Gln Cys
    50                  55                  60

Ser Val Asp Leu Glu Ser Ala Ser Gly Glu Lys Asp Leu Ala Pro Pro
65                  70                  75                  80

Ser Glu Pro Ser Glu Ser Phe Gln Glu His Thr Val Asp Gly Glu Asn
                85                  90                  95

Gln Ile Val Phe Thr His Arg Ile Asn Ile Pro Arg Arg Ala Cys Gly
            100                 105                 110

Cys Ala Ala Ala Pro Asp Val Lys Glu Leu Leu Ser Arg Leu Glu Glu
        115                 120                 125

Leu Glu Asn Leu Val Ser Ser Leu Arg Glu Gln Cys Thr Ala Gly Ala
    130                 135                 140

Gly Cys Cys Leu Gln Pro Ala Thr Gly Arg Leu Asp Thr Arg Pro Phe
145                 150                 155                 160

-continued

```
Cys Ser Gly Arg Gly Asn Phe Ser Thr Glu Gly Cys Gly Cys Val Cys
            165                 170                 175
Glu Pro Gly Trp Lys Gly Pro Asn Cys Ser Glu Pro Cys Pro Gly
        180                 185                 190
Asn Cys His Leu Arg Gly Arg Cys Ile Asp Gly Gln Cys Ile Cys Asp
            195                 200                 205
Asp Gly Phe Thr Gly Glu Asp Cys Ser Gln Leu Ala Cys Pro Ser Asp
        210                 215                 220
Cys Asn Asp Gln Gly Lys Cys Val Asn Gly Val Cys Ile Cys Phe Glu
225                 230                 235                 240
Gly Tyr Ala Gly Ala Asp Cys Ser Arg Glu Ile Cys Pro Val Pro Cys
                245                 250                 255
Ser Glu Glu His Gly Thr Cys Val Asp Gly Leu Cys Val Cys His Asp
            260                 265                 270
Gly Phe Ala Gly Asp Asp Cys Asn Lys Pro Leu Cys Leu Asn Asn Cys
        275                 280                 285
Tyr Asn Arg Gly Arg Cys Val Glu Asn Glu Cys Val Cys Asp Glu Gly
        290                 295                 300
Phe Thr Gly Glu Asp Cys Ser Glu Leu Ile Cys Pro Asn Asp Cys Phe
305                 310                 315                 320
Asp Arg Gly Arg Cys Ile Asn Gly Thr Cys Tyr Cys Glu Glu Gly Phe
                325                 330                 335
Thr Gly Glu Asp Cys Gly Lys Pro Thr Cys Pro His Ala Cys His Thr
            340                 345                 350
Gln Gly Arg Cys Glu Glu Gly Gln Cys Val Cys Asp Glu Gly Phe Ala
        355                 360                 365
Gly Val Asp Cys Ser Glu Lys Arg Cys Pro Ala Asp Cys His Asn Arg
    370                 375                 380
Gly Arg Cys Val Asp Gly Arg Cys Glu Cys Asp Asp Gly Phe Thr Gly
385                 390                 395                 400
Ala Asp Cys Gly Glu Leu Lys Cys Pro Asn Gly Cys Ser Gly His Gly
                405                 410                 415
Arg Cys Val Asn Gly Gln Cys Val Cys Asp Glu Gly Tyr Thr Gly Glu
            420                 425                 430
Asp Cys Ser Gln Leu Arg Cys Pro Asn Asp Cys His Ser Arg Gly Arg
        435                 440                 445
Cys Val Glu Gly Lys Cys Val Cys Glu Gln Gly Phe Lys Gly Tyr Asp
    450                 455                 460
Cys Ser Asp Met Ser Cys Pro Asn Asp Cys His Gln His Gly Arg Cys
465                 470                 475                 480
Val Asn Gly Met Cys Val Cys Asp Asp Gly Tyr Thr Gly Glu Asp Cys
                485                 490                 495
Arg Asp Arg Gln Cys Pro Arg Asp Cys Ser Asn Arg Gly Leu Cys Val
            500                 505                 510
Asp Gly Gln Cys Val Cys Glu Asp Gly Phe Thr Gly Pro Asp Cys Ala
        515                 520                 525
Glu Leu Ser Cys Pro Asn Asp Cys His Gly Gln Gly Arg Cys Val Asn
    530                 535                 540
Gly Gln Cys Val Cys His Glu Gly Phe Met Gly Lys Asp Cys Lys Glu
545                 550                 555                 560
Gln Arg Cys Pro Ser Asp Cys His Gly Gln Gly Arg Cys Val Asp Gly
                565                 570                 575
Gln Cys Ile Cys His Glu Gly Phe Thr Gly Leu Asp Cys Gly Gln His
```

-continued

```
            580                 585                 590
Ser Cys Pro Ser Asp Cys Asn Asn Leu Gly Gln Cys Val Ser Gly Arg
            595                 600                 605

Cys Ile Cys Asn Glu Gly Tyr Ser Gly Glu Asp Cys Ser Glu Val Ser
            610                 615                 620

Pro Pro Lys Asp Leu Val Val Thr Glu Val Thr Glu Thr Val Asn
625                 630                 635                 640

Leu Ala Trp Asp Asn Glu Met Arg Val Thr Glu Tyr Leu Val Val Tyr
                    645                 650                 655

Thr Pro Thr His Glu Gly Gly Leu Glu Met Gln Phe Arg Val Pro Gly
                    660                 665                 670

Asp Gln Thr Ser Thr Ile Ile Gln Glu Leu Glu Pro Gly Val Glu Tyr
            675                 680                 685

Phe Ile Arg Val Phe Ala Ile Leu Glu Asn Lys Lys Ser Ile Pro Val
            690                 695                 700

Ser Ala Arg Val Ala Thr Tyr Leu Pro Ala Pro Glu Gly Leu Lys Phe
705                 710                 715                 720

Lys Ser Ile Lys Glu Thr Ser Val Glu Val Glu Trp Asp Pro Leu Asp
                    725                 730                 735

Ile Ala Phe Glu Thr Trp Glu Ile Ile Phe Arg Asn Met Asn Lys Glu
                    740                 745                 750

Asp Glu Gly Glu Ile Thr Lys Ser Leu Arg Arg Pro Glu Thr Ser Tyr
            755                 760                 765

Arg Gln Thr Gly Leu Ala Pro Gly Gln Glu Tyr Glu Ile Ser Leu His
            770                 775                 780

Ile Val Lys Asn Asn Thr Arg Gly Pro Gly Leu Lys Arg Val Thr Thr
785                 790                 795                 800

Thr Arg Leu Asp Ala Pro Ser Gln Ile Glu Val Lys Asp Val Thr Asp
                    805                 810                 815

Thr Thr Ala Leu Ile Thr Trp Phe Lys Pro Leu Ala Glu Ile Asp Gly
                    820                 825                 830

Ile Glu Leu Thr Tyr Gly Ile Lys Asp Val Pro Gly Asp Arg Thr Thr
            835                 840                 845

Ile Asp Leu Thr Glu Asp Glu Asn Gln Tyr Ser Ile Gly Asn Leu Lys
            850                 855                 860

Pro Asp Thr Glu Tyr Glu Val Ser Leu Ile Ser Arg Arg Gly Asp Met
865                 870                 875                 880

Ser Ser Asn Pro Ala Lys Glu Thr Phe Thr Thr Gly Leu Asp Ala Pro
                    885                 890                 895

Arg Asn Leu Arg Arg Val Ser Gln Thr Asp Asn Ser Ile Thr Leu Glu
                    900                 905                 910

Trp Arg Asn Gly Lys Ala Ala Ile Asp Ser Tyr Arg Ile Lys Tyr Ala
            915                 920                 925

Pro Ile Ser Gly Gly Asp His Ala Glu Val Asp Val Pro Lys Ser Gln
            930                 935                 940

Gln Ala Thr Thr Lys Thr Thr Leu Thr Gly Leu Arg Pro Gly Thr Glu
945                 950                 955                 960

Tyr Gly Ile Gly Val Ser Ala Val Lys Glu Asp Lys Glu Ser Asn Pro
                    965                 970                 975

Ala Thr Ile Asn Ala Ala Thr Glu Leu Asp Thr Pro Lys Asp Leu Gln
                    980                 985                 990

Val Ser Glu Thr Ala Glu Thr Ser  Leu Thr Leu Leu Trp  Lys Thr Pro
            995                 1000                1005
```

```
Leu Ala Lys Phe Asp Arg Tyr Arg Leu Asn Tyr Ser Leu Pro Thr
        1010                1015                1020

Gly Gln Trp Val Gly Val Gln Leu Pro Arg Asn Thr Thr Ser Tyr
        1025                1030                1035

Val Leu Arg Gly Leu Glu Pro Gly Gln Glu Tyr Asn Val Leu Leu
        1040                1045                1050

Thr Ala Glu Lys Gly Arg His Lys Ser Lys Pro Ala Arg Val Lys
        1055                1060                1065

Ala Ser Thr Glu Gln Ala Pro Glu Leu Glu Asn Leu Thr Val Thr
        1070                1075                1080

Glu Val Gly Trp Asp Gly Leu Arg Leu Asn Trp Thr Ala Ala Asp
        1085                1090                1095

Gln Ala Tyr Glu His Phe Ile Ile Gln Val Gln Glu Ala Asn Lys
        1100                1105                1110

Val Glu Ala Ala Arg Asn Leu Thr Val Pro Gly Ser Leu Arg Ala
        1115                1120                1125

Val Asp Ile Pro Gly Leu Lys Ala Ala Thr Pro Tyr Thr Val Ser
        1130                1135                1140

Ile Tyr Gly Val Ile Gln Gly Tyr Arg Thr Pro Val Leu Ser Ala
        1145                1150                1155

Glu Ala Ser Thr Gly Glu Thr Pro Asn Leu Gly Glu Val Val Val
        1160                1165                1170

Ala Glu Val Gly Trp Asp Ala Leu Lys Leu Asn Trp Thr Ala Pro
        1175                1180                1185

Glu Gly Ala Tyr Glu Tyr Phe Phe Ile Gln Val Gln Glu Ala Asp
        1190                1195                1200

Thr Val Glu Ala Ala Gln Asn Leu Thr Val Pro Gly Gly Leu Arg
        1205                1210                1215

Ser Thr Asp Leu Pro Gly Leu Lys Ala Ala Thr His Tyr Thr Ile
        1220                1225                1230

Thr Ile Arg Gly Val Thr Gln Asp Phe Ser Thr Thr Pro Leu Ser
        1235                1240                1245

Val Glu Val Leu Thr Glu Val Pro Asp Met Gly Asn Leu Thr
        1250                1255                1260

Val Thr Glu Val Ser Trp Asp Ala Leu Arg Leu Asn Trp Thr Thr
        1265                1270                1275

Pro Asp Gly Thr Tyr Asp Gln Phe Thr Ile Gln Val Gln Glu Ala
        1280                1285                1290

Asp Gln Val Glu Glu Ala His Asn Leu Thr Val Pro Gly Ser Leu
        1295                1300                1305

Arg Ser Met Glu Ile Pro Gly Leu Arg Ala Gly Thr Pro Tyr Thr
        1310                1315                1320

Val Thr Leu His Gly Glu Val Arg Gly His Ser Thr Arg Pro Leu
        1325                1330                1335

Ala Val Glu Val Val Thr Glu Asp Leu Pro Gln Leu Gly Asp Leu
        1340                1345                1350

Ala Val Ser Glu Val Gly Trp Asp Gly Leu Arg Leu Asn Trp Thr
        1355                1360                1365

Ala Ala Asp Asn Ala Tyr Glu His Phe Val Ile Gln Val Gln Glu
        1370                1375                1380

Val Asn Lys Val Glu Ala Ala Gln Asn Leu Thr Leu Pro Gly Ser
        1385                1390                1395
```

```
Leu Arg Ala Val Asp Ile Pro Gly Leu Glu Ala Ala Thr Pro Tyr
    1400            1405                1410

Arg Val Ser Ile Tyr Gly Val Ile Arg Gly Tyr Arg Thr Pro Val
    1415            1420                1425

Leu Ser Ala Glu Ala Ser Thr Ala Lys Glu Pro Glu Ile Gly Asn
    1430            1435                1440

Leu Asn Val Ser Asp Ile Thr Pro Glu Ser Phe Asn Leu Ser Trp
    1445            1450                1455

Met Ala Thr Asp Gly Ile Phe Glu Thr Phe Thr Ile Glu Ile Ile
    1460            1465                1470

Asp Ser Asn Arg Leu Leu Glu Thr Val Glu Tyr Asn Ile Ser Gly
    1475            1480                1485

Ala Glu Arg Thr Ala His Ile Ser Gly Leu Pro Pro Ser Thr Asp
    1490            1495                1500

Phe Ile Val Tyr Leu Ser Gly Leu Ala Pro Ser Ile Arg Thr Lys
    1505            1510                1515

Thr Ile Ser Ala Thr Ala Thr Thr Glu Ala Leu Pro Leu Leu Glu
    1520            1525                1530

Asn Leu Thr Ile Ser Asp Ile Asn Pro Tyr Gly Phe Thr Val Ser
    1535            1540                1545

Trp Met Ala Ser Glu Asn Ala Phe Asp Ser Phe Leu Val Thr Val
    1550            1555                1560

Val Asp Ser Gly Lys Leu Leu Asp Pro Gln Glu Phe Thr Leu Ser
    1565            1570                1575

Gly Thr Gln Arg Lys Leu Glu Leu Arg Gly Leu Ile Thr Gly Ile
    1580            1585                1590

Gly Tyr Glu Val Met Val Ser Gly Phe Thr Gln Gly His Gln Thr
    1595            1600                1605

Lys Pro Leu Arg Ala Glu Ile Val Thr Glu Ala Glu Pro Glu Val
    1610            1615                1620

Asp Asn Leu Leu Val Ser Asp Ala Thr Pro Asp Gly Phe Arg Leu
    1625            1630                1635

Ser Trp Thr Ala Asp Glu Gly Val Phe Asp Asn Phe Val Leu Lys
    1640            1645                1650

Ile Arg Asp Thr Lys Lys Gln Ser Glu Pro Leu Glu Ile Thr Leu
    1655            1660                1665

Leu Ala Pro Glu Arg Thr Arg Asp Ile Thr Gly Leu Arg Glu Ala
    1670            1675                1680

Thr Glu Tyr Glu Ile Glu Leu Tyr Gly Ile Ser Lys Gly Arg Arg
    1685            1690                1695

Ser Gln Thr Val Ser Ala Ile Ala Thr Thr Ala Met Gly Ser Pro
    1700            1705                1710

Lys Glu Val Ile Phe Ser Asp Ile Thr Glu Asn Ser Ala Thr Val
    1715            1720                1725

Ser Trp Arg Ala Pro Thr Ala Gln Val Glu Ser Phe Arg Ile Thr
    1730            1735                1740

Tyr Val Pro Ile Thr Gly Gly Thr Pro Ser Met Val Thr Val Asp
    1745            1750                1755

Gly Thr Lys Thr Gln Thr Arg Leu Val Lys Leu Ile Pro Gly Val
    1760            1765                1770

Glu Tyr Leu Val Ser Ile Ile Ala Met Lys Gly Phe Glu Glu Ser
    1775            1780                1785

Glu Pro Val Ser Gly Ser Phe Thr Thr Ala Leu Asp Gly Pro Ser
```

-continued

```
              1790                1795                1800
Gly Leu Val Thr Ala Asn Ile Thr Asp Ser Glu Ala Leu Ala Arg
        1805                1810                1815
Trp Gln Pro Ala Ile Ala Thr Val Asp Ser Tyr Val Ile Ser Tyr
        1820                1825                1830
Thr Gly Glu Lys Val Pro Glu Ile Thr Arg Thr Val Ser Gly Asn
        1835                1840                1845
Thr Val Glu Tyr Ala Leu Thr Asp Leu Glu Pro Ala Thr Glu Tyr
        1850                1855                1860
Thr Leu Arg Ile Phe Ala Glu Lys Gly Pro Gln Lys Ser Ser Thr
        1865                1870                1875
Ile Thr Ala Lys Phe Thr Thr Asp Leu Asp Ser Pro Arg Asp Leu
        1880                1885                1890
Thr Ala Thr Glu Val Gln Ser Glu Thr Ala Leu Leu Thr Trp Arg
        1895                1900                1905
Pro Pro Arg Ala Ser Val Thr Gly Tyr Leu Leu Val Tyr Glu Ser
        1910                1915                1920
Val Asp Gly Thr Val Lys Glu Val Ile Val Gly Pro Asp Thr Thr
        1925                1930                1935
Ser Tyr Ser Leu Ala Asp Leu Ser Pro Ser Thr His Tyr Thr Ala
        1940                1945                1950
Lys Ile Gln Ala Leu Asn Gly Pro Leu Arg Ser Asn Met Ile Gln
        1955                1960                1965
Thr Ile Phe Thr Thr Ile Gly Leu Leu Tyr Pro Phe Pro Lys Asp
        1970                1975                1980
Cys Ser Gln Ala Met Leu Asn Gly Asp Thr Thr Ser Gly Leu Tyr
        1985                1990                1995
Thr Ile Tyr Leu Asn Gly Asp Lys Ala Glu Ala Leu Glu Val Phe
        2000                2005                2010
Cys Asp Met Thr Ser Asp Gly Gly Gly Trp Ile Val Phe Leu Arg
        2015                2020                2025
Arg Lys Asn Gly Arg Glu Asn Phe Tyr Gln Asn Trp Lys Ala Tyr
        2030                2035                2040
Ala Ala Gly Phe Gly Asp Arg Arg Glu Glu Phe Trp Leu Gly Leu
        2045                2050                2055
Asp Asn Leu Asn Lys Ile Thr Ala Gln Gly Gln Tyr Glu Leu Arg
        2060                2065                2070
Val Asp Leu Arg Asp His Gly Glu Thr Ala Phe Ala Val Tyr Asp
        2075                2080                2085
Lys Phe Ser Val Gly Asp Ala Lys Thr Arg Tyr Lys Leu Lys Val
        2090                2095                2100
Glu Gly Tyr Ser Gly Thr Ala Gly Asp Ser Met Ala Tyr His Asn
        2105                2110                2115
Gly Arg Ser Phe Ser Thr Phe Asp Lys Asp Thr Asp Ser Ala Ile
        2120                2125                2130
Thr Asn Cys Ala Leu Ser Tyr Lys Gly Ala Phe Trp Tyr Arg Asn
        2135                2140                2145
Cys His Arg Val Asn Leu Met Gly Arg Tyr Gly Asp Asn Asn His
        2150                2155                2160
Ser Gln Gly Val Asn Trp Phe His Trp Lys Gly His Glu His Ser
        2165                2170                2175
Ile Gln Phe Ala Glu Met Lys Leu Arg Pro Ser Asn Phe Arg Asn
        2180                2185                2190
```

Leu Glu Gly Arg Arg Lys Arg Ala
    2195                2200

<210> SEQ ID NO 76
<211> LENGTH: 89
<212> TYPE: PRT
<213> ORGANISM: Artificial Sequence
<220> FEATURE:
<223> OTHER INFORMATION: Fibcon FN3 domain

<400> SEQUENCE: 76

Leu Asp Ala Pro Thr Asp Leu Gln Val Thr Asn Val Thr Asp Thr Ser
1               5                   10                  15

Ile Thr Val Ser Trp Thr Pro Pro Ser Ala Thr Ile Thr Gly Tyr Arg
            20                  25                  30

Ile Thr Tyr Thr Pro Ser Asn Gly Pro Gly Glu Pro Lys Glu Leu Thr
        35                  40                  45

Val Pro Pro Ser Ser Thr Ser Val Thr Ile Thr Gly Leu Thr Pro Gly
    50                  55                  60

Val Glu Tyr Val Val Ser Leu Tyr Ala Leu Lys Asp Asn Gln Glu Ser
65                  70                  75                  80

Pro Pro Leu Val Gly Thr Gln Thr Thr
                85

<210> SEQ ID NO 77
<211> LENGTH: 94
<212> TYPE: PRT
<213> ORGANISM: Homo sapiens

<400> SEQUENCE: 77

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 78
<211> LENGTH: 4
<212> TYPE: PRT
<213> ORGANISM: Artificial Sequence
<220> FEATURE:
<223> OTHER INFORMATION: linker

<400> SEQUENCE: 78

Gly Ser Gly Ser
1

<210> SEQ ID NO 79
<211> LENGTH: 25
<212> TYPE: PRT
<213> ORGANISM: Artificial Sequence
<220> FEATURE:
<223> OTHER INFORMATION: linker

```
<400> SEQUENCE: 79

Gly Gly Gly Gly Ser Gly Gly Gly Ser Gly Gly Gly Ser Gly
1               5                   10                  15

Gly Gly Gly Ser Gly Gly Gly Ser
            20                  25

<210> SEQ ID NO 80
<211> LENGTH: 4
<212> TYPE: PRT
<213> ORGANISM: Artificial Sequence
<220> FEATURE:
<223> OTHER INFORMATION: linker

<400> SEQUENCE: 80

Ala Pro Ala Pro
1

<210> SEQ ID NO 81
<211> LENGTH: 10
<212> TYPE: PRT
<213> ORGANISM: Artificial Sequence
<220> FEATURE:
<223> OTHER INFORMATION: linker

<400> SEQUENCE: 81

Ala Pro Ala Pro Ala Pro Ala Pro Ala Pro
1               5                   10

<210> SEQ ID NO 82
<211> LENGTH: 20
<212> TYPE: PRT
<213> ORGANISM: Artificial Sequence
<220> FEATURE:
<223> OTHER INFORMATION: linker

<400> SEQUENCE: 82

Ala Pro Ala Pro Ala Pro Ala Pro Ala Pro Ala Pro Ala Pro Ala Pro
1               5                   10                  15

Ala Pro Ala Pro
            20

<210> SEQ ID NO 83
<211> LENGTH: 40
<212> TYPE: PRT
<213> ORGANISM: Artificial Sequence
<220> FEATURE:
<223> OTHER INFORMATION: linker

<400> SEQUENCE: 83

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro
                35                  40

<210> SEQ ID NO 84
<211> LENGTH: 29
<212> TYPE: PRT
<213> ORGANISM: Artificial Sequence
<220> FEATURE:
<223> OTHER INFORMATION: linker

<400> SEQUENCE: 84
```

```
Ala Glu Ala Ala Ala Lys Glu Ala Ala Lys Glu Ala Ala Lys
1               5                   10                  15

Glu Ala Ala Lys Glu Ala Ala Lys Ala Ala Ala
            20                  25
```

<210> SEQ ID NO 85
<211> LENGTH: 8
<212> TYPE: PRT
<213> ORGANISM: Artificial Sequence
<220> FEATURE:
<223> OTHER INFORMATION: tencon BC loop

<400> SEQUENCE: 85

```
Thr Ala Pro Asp Ala Ala Phe Asp
1               5
```

<210> SEQ ID NO 86
<211> LENGTH: 7
<212> TYPE: PRT
<213> ORGANISM: Artificial Sequence
<220> FEATURE:
<223> OTHER INFORMATION: tencon FG loop

<400> SEQUENCE: 86

```
Lys Gly Gly His Arg Ser Asn
1               5
```

<210> SEQ ID NO 87
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 87

```
Ala Asp Pro His Gly Phe Tyr Asp
1               5
```

<210> SEQ ID NO 88
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 88

```
Thr Tyr Asp Arg Asp Gly Tyr Asp
1               5
```

<210> SEQ ID NO 89
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 89

```
Trp Asp Pro Phe Ser Phe Tyr Asp
1               5
```

<210> SEQ ID NO 90
<211> LENGTH: 8
<212> TYPE: PRT
<213> ORGANISM: Artificial Sequence
<220> FEATURE:
<223> OTHER INFORMATION: EGFR binding FN3 domain BC loop

```
<400> SEQUENCE: 90

Asp Asp Pro Arg Gly Phe Tyr Glu
1               5

<210> SEQ ID NO 91
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 91

Thr Trp Pro Tyr Ala Asp Leu Asp
1               5

<210> SEQ ID NO 92
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 92

Gly Tyr Asn Gly Asp His Phe Asp
1               5

<210> SEQ ID NO 93
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 93

Asp Tyr Asp Leu Gly Val Tyr Asp
1               5

<210> SEQ ID NO 94
<211> LENGTH: 8
<212> TYPE: PRT
<213> ORGANISM: Artificial Sequence
<220> FEATURE:
<223> OTHER INFORMATION: EGFR binding FN3 domain BC loop

<400> SEQUENCE: 94

Asp Asp Pro Trp Asp Phe Tyr Glu
1               5

<210> SEQ ID NO 95
<211> LENGTH: 12
<212> TYPE: PRT
<213> ORGANISM: Artificial Sequence
<220> FEATURE:
<223> OTHER INFORMATION: EGFR binding FN3 domain FG loop

<400> SEQUENCE: 95

His Asn Val Tyr Lys Asp Thr Asn Met Arg Gly Leu
1               5                   10

<210> SEQ ID NO 96
<211> LENGTH: 11
<212> TYPE: PRT
<213> ORGANISM: Artificial Sequence
<220> FEATURE:
<223> OTHER INFORMATION: EGFR binding FN3 domain FG loop

<400> SEQUENCE: 96
```

Leu Gly Ser Tyr Val Phe Glu His Asp Val Met
1               5                   10

<210> SEQ ID NO 97
<211> LENGTH: 285
<212> TYPE: DNA
<213> ORGANISM: Artificial Sequence
<220> FEATURE:
<223> OTHER INFORMATION: EGFR binding FN3 domain from ECB97; P54AR4-
      83V22

<400> SEQUENCE: 97
atgttgccag cgccgaagaa cctggtagtt agcgaggtta ctgaggacag cgcgcgtctg      60
agctgggacg atccgtgggc gttctacgag agctttctga tccagtatca agagagcgag     120
aaagtcggtg aagcgattgt gctgaccgtc ccgggctccg agcgttccta cgacctgacc     180
ggtttgaagc cgggtaccga gtatacggtg agcatctacg gtgttcacaa tgtctataag     240
gacactaata tccgcggtct gcctctgagc gccattttca ccacc                     285

<210> SEQ ID NO 98
<211> LENGTH: 285
<212> TYPE: DNA
<213> ORGANISM: Artificial Sequence
<220> FEATURE:
<223> OTHER INFORMATION: EGFR binding FN3 domain from ECB15; P54AR4-
      83V2

<400> SEQUENCE: 98
atgctgccag ccctaagaa tctggtcgtg agcgaagtaa ccgaggacag cgcccgcctg       60
agctgggacg acccgtgggc gttctatgag tctttcctga ttcagtatca agaaagcgaa     120
aaagttggcg aagcgatcgt cctgaccgtc ccgggtagcg agcgctccta cgatctgacc     180
ggcctgaaac cgggtacgga gtacacggtg tccatttacg gtgttcacaa tgtgtataaa     240
gacaccaaca tgcgtggcct gccgctgtcg gcgattttca ccacc                     285

<210> SEQ ID NO 99
<211> LENGTH: 89
<212> TYPE: PRT
<213> ORGANISM: Artificial Sequence
<220> FEATURE:
<223> OTHER INFORMATION: tencon27 FN3 domain

<400> SEQUENCE: 99

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr
                85

<210> SEQ ID NO 100
<211> LENGTH: 89
<212> TYPE: PRT
<213> ORGANISM: Artificial Sequence

```
<220> FEATURE:
<223> OTHER INFORMATION: TCL14 library
<220> FEATURE:
<221> NAME/KEY: MISC_FEATURE
<222> LOCATION: (32)..(32)
<223> OTHER INFORMATION: Xaa is any amino acid
<220> FEATURE:
<221> NAME/KEY: MISC_FEATURE
<222> LOCATION: (34)..(34)
<223> OTHER INFORMATION: Xaa is any amino acid
<220> FEATURE:
<221> NAME/KEY: MISC_FEATURE
<222> LOCATION: (36)..(36)
<223> OTHER INFORMATION: Xaa is any amino acid
<220> FEATURE:
<221> NAME/KEY: MISC_FEATURE
<222> LOCATION: (38)..(38)
<223> OTHER INFORMATION: Xaa is any amino acid
<220> FEATURE:
<221> NAME/KEY: MISC_FEATURE
<222> LOCATION: (39)..(39)
<223> OTHER INFORMATION: Xaa is any amino acid
<220> FEATURE:
<221> NAME/KEY: MISC_FEATURE
<222> LOCATION: (40)..(40)
<223> OTHER INFORMATION: Xaa is any amino acid
<220> FEATURE:
<221> NAME/KEY: MISC_FEATURE
<222> LOCATION: (41)..(41)
<223> OTHER INFORMATION: Xaa is any amino acid
<220> FEATURE:
<221> NAME/KEY: MISC_FEATURE
<222> LOCATION: (68)..(68)
<223> OTHER INFORMATION: Xaa is any amino acid
<220> FEATURE:
<221> NAME/KEY: MISC_FEATURE
<222> LOCATION: (70)..(70)
<223> OTHER INFORMATION: Xaa is any amino acid
<220> FEATURE:
<221> NAME/KEY: MISC_FEATURE
<222> LOCATION: (72)..(72)
<223> OTHER INFORMATION: Xaa is any amino acid
<220> FEATURE:
<221> NAME/KEY: MISC_FEATURE
<222> LOCATION: (78)..(78)
<223> OTHER INFORMATION: Xaa is any amino acid
<220> FEATURE:
<221> NAME/KEY: MISC_FEATURE
<222> LOCATION: (79)..(79)
<223> OTHER INFORMATION: Xaa is any amino acid
<220> FEATURE:
<221> NAME/KEY: MISC_FEATURE
<222> LOCATION: (81)..(81)
<223> OTHER INFORMATION: Xaa is any amino acid

<400> SEQUENCE: 100

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Xaa Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Xaa Val Xaa Ile Xaa Gly Val Lys Gly Gly Xaa Xaa Ser
65                  70                  75                  80

Xaa Pro Leu Ser Ala Ile Phe Thr Thr
                85

<210> SEQ ID NO 101
<211> LENGTH: 1408
<212> TYPE: PRT
```

<213> ORGANISM: HOMO SAPIENS

<400> SEQUENCE: 101

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

-continued

```
Thr Leu Leu Arg Asn Ser Ser Gly Cys Glu Ala Arg Arg Asp Glu Tyr
                405                 410                 415
Arg Thr Glu Phe Thr Thr Ala Leu Gln Arg Val Asp Leu Phe Met Gly
            420                 425                 430
Gln Phe Ser Glu Val Leu Leu Thr Ser Ile Ser Thr Phe Ile Lys Gly
        435                 440                 445
Asp Leu Thr Ile Ala Asn Leu Gly Thr Ser Glu Gly Arg Phe Met Gln
    450                 455                 460
Val Val Val Ser Arg Ser Gly Pro Ser Thr Pro His Val Asn Phe Leu
465                 470                 475                 480
Leu Asp Ser His Pro Val Ser Pro Glu Val Ile Val Glu His Thr Leu
                485                 490                 495
Asn Gln Asn Gly Tyr Thr Leu Val Ile Thr Gly Lys Lys Ile Thr Lys
            500                 505                 510
Ile Pro Leu Asn Gly Leu Gly Cys Arg His Phe Gln Ser Cys Ser Gln
        515                 520                 525
Cys Leu Ser Ala Pro Pro Phe Val Gln Cys Gly Trp Cys His Asp Lys
    530                 535                 540
Cys Val Arg Ser Glu Glu Cys Leu Ser Gly Thr Trp Thr Gln Gln Ile
545                 550                 555                 560
Cys Leu Pro Ala Ile Tyr Lys Val Phe Pro Asn Ser Ala Pro Leu Glu
                565                 570                 575
Gly Gly Thr Arg Leu Thr Ile Cys Gly Trp Asp Phe Gly Phe Arg Arg
            580                 585                 590
Asn Asn Lys Phe Asp Leu Lys Lys Thr Arg Val Leu Leu Gly Asn Glu
        595                 600                 605
Ser Cys Thr Leu Thr Leu Ser Glu Ser Thr Met Asn Thr Leu Lys Cys
    610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
                645                 650                 655
Pro Val Ile Thr Ser Ile Ser Pro Lys Tyr Gly Pro Met Ala Gly Gly
            660                 665                 670
Thr Leu Leu Thr Leu Thr Gly Asn Tyr Leu Asn Ser Gly Asn Ser Arg
        675                 680                 685
His Ile Ser Ile Gly Gly Lys Thr Cys Thr Leu Lys Ser Val Ser Asn
    690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
                725                 730                 735
Ser Tyr Arg Glu Asp Pro Ile Val Tyr Glu Ile His Pro Thr Lys Ser
            740                 745                 750
Phe Ile Ser Thr Trp Trp Lys Glu Pro Leu Asn Ile Val Ser Phe Leu
        755                 760                 765
Phe Cys Phe Ala Ser Gly Gly Ser Thr Ile Thr Gly Val Gly Lys Asn
    770                 775                 780
Leu Asn Ser Val Ser Val Pro Arg Met Val Ile Asn Val His Glu Ala
785                 790                 795                 800
Gly Arg Asn Phe Thr Val Ala Cys Gln His Arg Ser Asn Ser Glu Ile
                805                 810                 815
Ile Cys Cys Thr Thr Pro Ser Leu Gln Gln Leu Asn Leu Gln Leu Pro
```

```
                    820                 825                 830
Leu Lys Thr Lys Ala Phe Phe Met Leu Asp Gly Ile Leu Ser Lys Tyr
            835                 840                 845
Phe Asp Leu Ile Tyr Val His Asn Pro Val Phe Lys Pro Phe Glu Lys
    850                 855                 860
Pro Val Met Ile Ser Met Gly Asn Glu Asn Val Leu Glu Ile Lys Gly
865                 870                 875                 880
Asn Asp Ile Asp Pro Glu Ala Val Lys Gly Glu Val Leu Lys Val Gly
                885                 890                 895
Asn Lys Ser Cys Glu Asn Ile His Leu His Ser Glu Ala Val Leu Cys
            900                 905                 910
Thr Val Pro Asn Asp Leu Leu Lys Leu Asn Ser Glu Leu Asn Ile Glu
        915                 920                 925
Trp Lys Gln Ala Ile Ser Ser Thr Val Leu Gly Lys Val Ile Val Gln
    930                 935                 940
Pro Asp Gln Asn Phe Thr Gly Leu Ile Ala Gly Val Val Ser Ile Ser
945                 950                 955                 960
Thr Ala Leu Leu Leu Leu Gly Phe Phe Leu Trp Leu Lys Lys Arg
                965                 970                 975
Lys Gln Ile Lys Asp Leu Gly Ser Glu Leu Val Arg Tyr Asp Ala Arg
            980                 985                 990
Val His Thr Pro His Leu Asp Arg  Leu Val Ser Ala Arg  Ser Val Ser
        995                 1000                1005
Pro Thr  Thr Glu Met Val Ser  Asn Glu Ser Val Asp  Tyr Arg Ala
   1010                 1015                1020
Thr Phe  Pro Glu Asp Gln Phe  Pro Asn Ser Ser Gln  Asn Gly Ser
   1025                 1030                1035
Cys Arg  Gln Val Gln Tyr Pro  Leu Thr Asp Met Ser  Pro Ile Leu
   1040                 1045                1050
Thr Ser  Gly Asp Ser Asp Ile  Ser Ser Pro Leu Leu  Gln Asn Thr
   1055                 1060                1065
Val His  Ile Asp Leu Ser Ala  Leu Asn Pro Glu Leu  Val Gln Ala
   1070                 1075                1080
Val Gln  His Val Val Ile Gly  Pro Ser Ser Leu Ile  Val His Phe
   1085                 1090                1095
Asn Glu  Val Ile Gly Arg Gly  His Phe Gly Cys Val  Tyr His Gly
   1100                 1105                1110
Thr Leu  Leu Asp Asn Asp Gly  Lys Lys Ile His Cys  Ala Val Lys
   1115                 1120                1125
Ser Leu  Asn Arg Ile Thr Asp  Ile Gly Glu Val Ser  Gln Phe Leu
   1130                 1135                1140
Thr Glu  Gly Ile Ile Met Lys  Asp Phe Ser His Pro  Asn Val Leu
   1145                 1150                1155
Ser Leu  Leu Gly Ile Cys Leu  Arg Ser Glu Gly Ser  Pro Leu Val
   1160                 1165                1170
Val Leu  Pro Tyr Met Lys His  Gly Asp Leu Arg Asn  Phe Ile Arg
   1175                 1180                1185
Asn Glu  Thr His Asn Pro Thr  Val Lys Asp Leu Ile  Gly Phe Gly
   1190                 1195                1200
Leu Gln  Val Ala Lys Gly Met  Lys Tyr Leu Ala Ser  Lys Lys Phe
   1205                 1210                1215
Val His  Arg Asp Leu Ala Ala  Arg Asn Cys Met Leu  Asp Glu Lys
   1220                 1225                1230
```

```
Phe Thr Val Lys Val Ala Asp Phe Gly Leu Ala Arg Asp Met Tyr
    1235                1240                1245

Asp Lys Glu Tyr Tyr Ser Val His Asn Lys Thr Gly Ala Lys Leu
    1250                1255                1260

Pro Val Lys Trp Met Ala Leu Glu Ser Leu Gln Thr Gln Lys Phe
    1265                1270                1275

Thr Thr Lys Ser Asp Val Trp Ser Phe Gly Val Leu Leu Trp Glu
    1280                1285                1290

Leu Met Thr Arg Gly Ala Pro Pro Tyr Pro Asp Val Asn Thr Phe
    1295                1300                1305

Asp Ile Thr Val Tyr Leu Leu Gln Gly Arg Arg Leu Leu Gln Pro
    1310                1315                1320

Glu Tyr Cys Pro Asp Pro Leu Tyr Glu Val Met Leu Lys Cys Trp
    1325                1330                1335

His Pro Lys Ala Glu Met Arg Pro Ser Phe Ser Glu Leu Val Ser
    1340                1345                1350

Arg Ile Ser Ala Ile Phe Ser Thr Phe Ile Gly Glu His Tyr Val
    1355                1360                1365

His Val Asn Ala Thr Tyr Val Asn Val Lys Cys Val Ala Pro Tyr
    1370                1375                1380

Pro Ser Leu Leu Ser Ser Glu Asp Asn Ala Asp Asp Glu Val Asp
    1385                1390                1395

Thr Arg Pro Ala Ser Phe Trp Glu Thr Ser
    1400                1405

<210> SEQ ID NO 102
<211> LENGTH: 697
<212> TYPE: PRT
<213> ORGANISM: HOMO SAPIENS

<400> SEQUENCE: 102

Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
                20                  25                  30

Val Asn Thr Ala Asp Gln Cys Ala Asn Arg Cys Thr Arg Asn Lys Gly
            35                  40                  45

Leu Pro Phe Thr Cys Lys Ala Phe Val Phe Asp Lys Ala Arg Lys Gln
        50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
            100                 105                 110

Lys Ser Gly Ile Lys Cys Gln Pro Trp Ser Ser Met Ile Pro His Glu
        115                 120                 125

His Ser Phe Leu Pro Ser Ser Tyr Arg Gly Lys Asp Leu Gln Glu Asn
    130                 135                 140

Tyr Cys Arg Asn Pro Arg Gly Glu Glu Gly Gly Pro Trp Cys Phe Thr
145                 150                 155                 160

Ser Asn Pro Glu Val Arg Tyr Glu Val Cys Asp Ile Pro Gln Cys Ser
                165                 170                 175

Glu Val Glu Cys Met Thr Cys Asn Gly Glu Ser Tyr Arg Gly Leu Met
```

-continued

```
                180                 185                 190
Asp His Thr Glu Ser Gly Lys Ile Cys Gln Arg Trp Asp His Gln Thr
                195                 200                 205
Pro His Arg His Lys Phe Leu Pro Glu Arg Tyr Pro Asp Lys Gly Phe
                210                 215                 220
Asp Asp Asn Tyr Cys Arg Asn Pro Asp Gly Gln Pro Arg Pro Trp Cys
225                 230                 235                 240
Tyr Thr Leu Asp Pro His Thr Arg Trp Glu Tyr Cys Ala Ile Lys Thr
                245                 250                 255
Cys Ala Asp Asn Thr Met Asn Asp Thr Asp Val Pro Leu Glu Thr Thr
                260                 265                 270
Glu Cys Ile Gln Gly Gln Gly Glu Gly Tyr Arg Gly Thr Val Asn Thr
                275                 280                 285
Ile Trp Asn Gly Ile Pro Cys Gln Arg Trp Asp Ser Gln Tyr Pro His
                290                 295                 300
Glu His Asp Met Thr Pro Glu Asn Phe Lys Cys Lys Asp Leu Arg Glu
305                 310                 315                 320
Asn Tyr Cys Arg Asn Pro Asp Gly Ser Glu Ser Pro Trp Cys Phe Thr
                325                 330                 335
Thr Asp Pro Asn Ile Arg Val Gly Tyr Cys Ser Gln Ile Pro Asn Cys
                340                 345                 350
Asp Met Ser His Gly Gln Asp Cys Tyr Arg Gly Asn Gly Lys Asn Tyr
                355                 360                 365
Met Gly Asn Leu Ser Gln Thr Arg Ser Gly Leu Thr Cys Ser Met Trp
                370                 375                 380
Asp Lys Asn Met Glu Asp Leu His Arg His Ile Phe Trp Glu Pro Asp
385                 390                 395                 400
Ala Ser Lys Leu Asn Glu Asn Tyr Cys Arg Asn Pro Asp Asp Asp Ala
                405                 410                 415
His Gly Pro Trp Cys Tyr Thr Gly Asn Pro Leu Ile Pro Trp Asp Tyr
                420                 425                 430
Cys Pro Ile Ser Arg Cys Glu Gly Asp Thr Thr Pro Thr Ile Val Asn
                435                 440                 445
Leu Asp His Pro Val Ile Ser Cys Ala Lys Thr Lys Gln Leu Arg Val
                450                 455                 460
Val Asn Gly Ile Pro Thr Arg Thr Asn Ile Gly Trp Met Val Ser Leu
465                 470                 475                 480
Arg Tyr Arg Asn Lys His Ile Cys Gly Gly Ser Leu Ile Lys Glu Ser
                485                 490                 495
Trp Val Leu Thr Ala Arg Gln Cys Phe Pro Ser Arg Asp Leu Lys Asp
                500                 505                 510
Tyr Glu Ala Trp Leu Gly Ile His Asp Val His Gly Arg Gly Asp Glu
                515                 520                 525
Lys Cys Lys Gln Val Leu Asn Val Ser Gln Leu Val Tyr Gly Pro Glu
                530                 535                 540
Gly Ser Asp Leu Val Leu Met Lys Leu Ala Arg Pro Ala Val Leu Asp
545                 550                 555                 560
Asp Phe Val Ser Thr Ile Asp Leu Pro Asn Tyr Gly Cys Thr Ile Pro
                565                 570                 575
Glu Lys Thr Ser Cys Ser Val Tyr Gly Trp Gly Tyr Thr Gly Leu Ile
                580                 585                 590
Asn Tyr Asp Gly Leu Leu Arg Val Ala His Leu Tyr Ile Met Gly Asn
                595                 600                 605
```

Glu Lys Cys Ser Gln His His Arg Gly Lys Val Thr Leu Asn Glu Ser
    610                 615                 620

Glu Ile Cys Ala Gly Ala Glu Lys Ile Gly Ser Gly Pro Cys Glu Gly
625                 630                 635                 640

Asp Tyr Gly Gly Pro Leu Val Cys Glu Gln His Lys Met Arg Met Val
                645                 650                 655

Leu Gly Val Ile Val Pro Gly Arg Gly Cys Ala Ile Pro Asn Arg Pro
            660                 665                 670

Gly Ile Phe Val Arg Val Ala Tyr Tyr Ala Lys Trp Ile His Lys Ile
        675                 680                 685

Ile Leu Thr Tyr Lys Val Pro Gln Ser
    690                 695

<210> SEQ ID NO 103
<211> LENGTH: 276
<212> TYPE: DNA
<213> ORGANISM: Artificial Sequence
<220> FEATURE:
<223> OTHER INFORMATION: c-Met binding FN3 domain

<400> SEQUENCE: 103
ctgccggctc cgaagaactt ggtggtgagc cgtgttaccg aagatagcgc acgcctgagc      60
tggacggcac cggatgcggc gttcgatagc ttctggattc gctatttga gtttctgggt     120 agcggtgagg caattgttct gacggtgccg ggctctgaac gctcctacga tttgaccggt     180
ctgaaaccgg gcaccgagta tgtggtgaac attctgagcg ttaagggcgg tagcatcagc     240
ccaccgctga gcgcgatctt cacgactggt ggttgc                              276

<210> SEQ ID NO 104
<211> LENGTH: 267
<212> TYPE: DNA
<213> ORGANISM: Artificial Sequence
<220> FEATURE:
<223> OTHER INFORMATION: c-Met binding FN3 domain

<400> SEQUENCE: 104
ctgccggcac cgaagaacct ggttgtcagc cgtgtgaccg aggatagcgc acgtttgagc      60
tggaccgctc cggatgcagc cttttgacagc ttctggattc gttactttga atttctgggt    120
agcggtgagg cgatcgttct gacggtgccg ggctctgaac gcagctatga tttgacgggc     180
ctgaagccgg gtactgagta cgtggttaac atcatgggcg ttaagggtgg taaaatcagc     240
ccgccattgt ccgcgatctt taccacg                                        267

<210> SEQ ID NO 105
<211> LENGTH: 5
<212> TYPE: PRT
<213> ORGANISM: Artificial Sequence
<220> FEATURE:
<223> OTHER INFORMATION: linker

<400> SEQUENCE: 105

Gly Gly Gly Gly Ser
1               5

<210> SEQ ID NO 106
<211> LENGTH: 194
<212> TYPE: PRT
<213> ORGANISM: Artificial Sequence
<220> FEATURE:
<223> OTHER INFORMATION: Bispecific EGFR/c-Met binding molecule

<400> SEQUENCE: 106

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
                100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
                180                 185                 190

Thr Thr

<210> SEQ ID NO 107
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 107

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr
                85                  90

<210> SEQ ID NO 108
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 108

Leu Pro Ala Pro Lys Asn Leu Val Val Ser Glu Val Thr Glu Asp Ser
1               5                   10                  15

Ala Arg Leu Ser Trp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr
                85                  90

<210> SEQ ID NO 109
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 109

Leu Pro Ala Pro Lys Asn Leu Val Val Ser Glu Val Thr Glu Asp Ser
1               5                   10                  15

Ala Arg Leu Ser Trp Asp Pro His Ala Phe Tyr Glu Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr
                85                  90

<210> SEQ ID NO 110
<211> LENGTH: 94
<212> TYPE: PRT
<213> ORGANISM: Artificial Sequence
<220> FEATURE:
<223> OTHER INFORMATION: EGFR binding FN3 domain

<400> SEQUENCE: 110

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr
                85                  90

<210> SEQ ID NO 111
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 111

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
                20                  25                  30

Ile Arg Tyr Phe Glu Phe Leu Gly Ser Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Asn Ile Leu Gly Val Lys Gly Lys Ile Ser
65                  70                  75                  80

Pro Pro Leu Ser Ala Ile Phe Thr Thr
                85

<210> SEQ ID NO 112
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 112

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
                20                  25                  30

Ile Arg Tyr Phe Glu Phe Val Gly Ser Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Asn Ile Leu Gly Val Lys Gly Gly Ser Ile Ser
65                  70                  75                  80

Pro Pro Leu Ser Ala Ile Phe Thr Thr
                85

<210> SEQ ID NO 113
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 113

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
                20                  25                  30

Ile Arg Tyr Phe Glu Phe Val Ser Lys Gly Asp Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Asn Ile Leu Gly Val Lys Gly Gly Ser Ile Ser
65                  70                  75                  80

Pro Pro Leu Ser Ala Ile Phe Thr Thr
                85

<210> SEQ ID NO 114
<211> LENGTH: 89
<212> TYPE: PRT
<213> ORGANISM: Artificial Sequence
<220> FEATURE:
<223> OTHER INFORMATION: c-Met binding FN3 domain

<400> SEQUENCE: 114

```
Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Trp
            20                  25                  30

Ile Arg Tyr Phe Glu Phe Leu Gly Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Leu Ser Val Lys Gly Gly Ser Ile Ser
65                  70                  75                  80

Pro Pro Leu Ser Ala Ile Phe Thr Thr
                85
```

<210> SEQ ID NO 115
<211> LENGTH: 591
<212> TYPE: DNA
<213> ORGANISM: Artificial Sequence
<220> FEATURE:
<223> OTHER INFORMATION: Bispecific EGFR/c-Met binding molecule

<400> SEQUENCE: 115

```
atgttgccag cgccgaagaa cctggtagtt agcgaggtta ctgaggacag cgcgcgtctg    60
agctgggacg atccgtgggc gttctacgag agctttctga tccagtatca agagagcgag   120
aaagtcggtg aagcgattgt gctgaccgtc ccgggctccg agcgttccta cgacctgacc   180
ggtttgaagc cgggtaccga gtatacggtg agcatctacg tgttcacaaa tgtctataag   240
gacactaata tccgcggtct gcctctgagc gccattttca ccaccgcacc ggcaccggct   300
ccggctcctg ccccgctgcc ggctccgaag aacttggtgg tgagccgtgt accgaagat   360 agcgcacgcc tgagctggac ggcaccggat gcggcgttcg atagcttctg gattcgctat   420
tttgagtttc tgggtagcgg tgaggcaatt gttctgacgg tgccgggctc tgaacgctcc   480
tacgatttga ccggtctgaa accgggcacc gagtatgtgg tgaacattct gagcgttaag   540
ggcggtagca tcagcccacc gctgagcgcg atcttcacga ctggtggttg c            591
```

<210> SEQ ID NO 116
<211> LENGTH: 582
<212> TYPE: DNA
<213> ORGANISM: Artificial Sequence
<220> FEATURE:
<223> OTHER INFORMATION: Bispecific EGFR/c-Met binding molecule

<400> SEQUENCE: 116

```
atgctgccag cccctaagaa tctggtcgtg agcgaagtaa ccgaggacag cgcccgcctg    60
agctgggacg acccgtgggc gttctatgag tctttcctga ttcagtatca agaaagcgaa   120
aaagttggcg aagcgatcgt cctgaccgtc ccgggtagcg agcgctccta cgatctgacc   180
ggcctgaaac cgggtacgga gtacacggtg tccatttacg tgttcacaaa tgtgtataaa   240
gacaccaaca tgcgtggcct gccgctgtcg gcgattttca ccaccgcgcc tgcgccagcg   300
cctgcaccgg ctccgctgcc ggcaccgaag aacctggttg tcagccgtgt gaccgaggat   360
```

```
agcgcacgtt tgagctggac cgctccggat gcagcctttg acagcttctg gattcgttac    420
tttgaatttc tgggtagcgg tgaggcgatc gttctgacgg tgccgggctc tgaacgcagc    480
tatgatttga cgggcctgaa gccgggtact gagtacgtgg ttaacatcat gggcgttaag    540
ggtggtaaaa tcagcccgcc attgtccgcg atctttacca cg                      582
```

<210> SEQ ID NO 117
<211> LENGTH: 51
<212> TYPE: PRT
<213> ORGANISM: Artificial Sequence
<220> FEATURE:
<223> OTHER INFORMATION: albumin binding domain

<400> SEQUENCE: 117

```
Thr Ile Asp Glu Trp Leu Leu Lys Glu Ala Lys Glu Lys Ala Ile Glu
1               5                   10                  15

Glu Leu Lys Lys Ala Gly Ile Thr Ser Asp Tyr Tyr Phe Asp Leu Ile
            20                  25                  30

Asn Lys Ala Lys Thr Val Glu Gly Val Asn Ala Leu Lys Asp Glu Ile
        35                  40                  45

Leu Lys Ala
    50
```

<210> SEQ ID NO 118
<211> LENGTH: 250
<212> TYPE: PRT
<213> ORGANISM: Artificial Sequence
<220> FEATURE:
<223> OTHER INFORMATION: Bispecific EGFR/c-Met binding molecule

<400> SEQUENCE: 118

```
Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Asp Glu Val Val
    130                 135                 140

Val Gly Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Tyr Val Asn Ile
                165                 170                 175

Leu Gly Val Lys Gly Gly Ser Ile Ser Val Pro Leu Ser Ala Ile Phe
            180                 185                 190

Thr Thr Ala Pro Ala Pro Ala Pro Ala Pro Ala Pro Leu Ala Glu Ala
        195                 200                 205
```

```
Lys Val Leu Ala Asn Arg Glu Leu Asp Lys Tyr Gly Val Ser Asp Tyr
            210                 215                 220

Tyr Lys Asn Leu Ile Asn Ala Lys Thr Val Glu Gly Val Lys Ala
225                 230                 235                 240

Leu Leu Asp Glu Ile Leu Ala Ala Leu Pro
                245                 250

<210> SEQ ID NO 119
<211> LENGTH: 250
<212> TYPE: PRT
<213> ORGANISM: Artificial Sequence
<220> FEATURE:
<223> OTHER INFORMATION: Bispecific EGFR/c-Met binding molecule

<400> SEQUENCE: 119

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Asp Glu Val Val
        130                 135                 140

Val Gly Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Tyr Val Asn Ile
                165                 170                 175

Leu Gly Val Lys Gly Gly Ser Ile Ser Val Pro Leu Ser Ala Ile Phe
            180                 185                 190

Thr Thr Ala Pro Ala Pro Ala Pro Ala Pro Leu Ala Glu Ala
        195                 200                 205

Lys Val Leu Ala Asn Arg Glu Leu Asp Lys Tyr Gly Val Ser Asp Tyr
            210                 215                 220

Tyr Lys Asn Leu Ile Asn Ala Lys Thr Val Glu Gly Val Lys Ala
225                 230                 235                 240

Leu Leu Asp Glu Ile Leu Ala Ala Leu Pro
                245                 250

<210> SEQ ID NO 120
<211> LENGTH: 250
<212> TYPE: PRT
<213> ORGANISM: Artificial Sequence
<220> FEATURE:
<223> OTHER INFORMATION: Bispecific EGFR/c-Met binding molecule

<400> SEQUENCE: 120

Met Leu Pro Ala Pro Lys Asn Leu Val Val Ser Glu Val Thr Glu Asp
```

```
  1               5                   10                  15
Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
        130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Gly Val Lys Gly Gly Lys Ile Ser Pro Pro Leu Ser Ala Ile Phe
            180                 185                 190

Thr Thr Ala Pro Ala Pro Ala Pro Ala Pro Leu Ala Glu Ala
        195                 200                 205

Lys Val Leu Ala Asn Arg Glu Leu Asp Lys Tyr Gly Val Ser Asp Tyr
    210                 215                 220

Tyr Lys Asn Leu Ile Asn Asn Ala Lys Thr Val Glu Gly Val Lys Ala
225                 230                 235                 240

Leu Leu Asp Glu Ile Leu Ala Ala Leu Pro
                245                 250

<210> SEQ ID NO 121
<211> LENGTH: 250
<212> TYPE: PRT
<213> ORGANISM: Artificial Sequence
<220> FEATURE:
<223> OTHER INFORMATION: Bispecific EGFR/c-Met binding molecule

<400> SEQUENCE: 121

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
```

```
            115                 120                 125
Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Gly Val Lys Gly Lys Ile Ser Pro Leu Ser Ala Ile Phe
            180                 185                 190

Thr Thr Ala Pro Ala Pro Ala Pro Ala Pro Leu Ala Glu Ala
            195                 200                 205

Lys Val Leu Ala Asn Arg Glu Leu Asp Lys Tyr Gly Val Ser Asp Tyr
    210                 215                 220

Tyr Lys Asn Leu Ile Asn Asn Ala Lys Thr Val Glu Gly Val Lys Ala
225                 230                 235                 240

Leu Leu Asp Glu Ile Leu Ala Ala Leu Pro
                245                 250

<210> SEQ ID NO 122
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 122

Met Leu Pro Ala Pro Lys Asn Leu Val Val Ser Glu Val Thr Glu Asp
1               5                   10                  15

Ser Leu Arg Leu Ser Trp Ala Asp Pro His Gly Phe Tyr Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 123
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 123

Met Leu Pro Ala Pro Lys Asn Leu Val Val Ser Glu Val Thr Glu Asp
1               5                   10                  15

Ser Leu Arg Leu Ser Trp Thr Tyr Asp Arg Asp Gly Tyr Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80
```

```
Asp Thr Asn Met Arg Gly Leu Pro Leu Ser Ala Glu Phe Thr Thr
                85                  90                  95

<210> SEQ ID NO 124
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 124

Met Leu Pro Ala Pro Lys Asn Leu Val Val Ser Glu Val Thr Glu Asp
1               5                   10                  15

Ser Leu Arg Leu Ser Trp Gly Tyr Asn Gly Asp His Phe Asp Ser Phe
                20                  25                  30

Leu Ile Gln Tyr Gln Glu Ser Glu Lys Val Gly Glu Ala Ile Asn Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 125
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 125

Met Leu Pro Ala Pro Lys Asn Leu Val Val Ser Glu Val Thr Glu Asp
1               5                   10                  15

Ser Leu Arg Leu Ser Trp Asp Asp Pro Arg Gly Phe Tyr Glu Ser Phe
                20                  25                  30

Leu Ile Gln Tyr Gln Glu Ser Glu Lys Val Gly Glu Ala Ile Asn Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 126
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 126

Met Leu Pro Ala Pro Lys Asn Leu Val Val Ser Glu Val Thr Glu Asp
1               5                   10                  15

Ser Leu Arg Leu Ser Trp Thr Trp Pro Tyr Ala Asp Leu Asp Ser Phe
                20                  25                  30

Leu Ile Gln Tyr Gln Glu Ser Glu Lys Val Gly Glu Ala Ile Asn Leu
            35                  40                  45

Thr Val Pro Gly Ser Glu Arg Ser Tyr Asp Leu Thr Gly Leu Lys Pro
```

```
                  50                  55                  60
Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Glu Phe Thr Thr
                 85                  90                  95

<210> SEQ ID NO 127
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 127

Met Leu Pro Ala Pro Lys Asn Leu Val Val Ser Glu Val Thr Glu Asp
  1               5                  10                  15

Ser Leu Arg Leu Ser Trp Gly Tyr Asn Gly Asp His Phe Asp Ser Phe
                 20                  25                  30

Leu Ile Gln Tyr Gln Glu Ser Glu Lys Val Gly Glu Ala Ile Asn Leu
             35                  40                  45

Thr Val Pro Gly Ser Glu Arg Ser Tyr Asp Leu Thr Gly Leu Lys Pro
         50                  55                  60

Gly Thr Glu Tyr Thr Val Ser Ile Tyr Gly Val His Asn Val Tyr Lys
 65                  70                  75                  80

Asp Thr Asn Met Arg Gly Leu Pro Leu Ser Ala Glu Phe Thr Thr
                 85                  90                  95

<210> SEQ ID NO 128
<211> LENGTH: 96
<212> TYPE: PRT
<213> ORGANISM: Artificial Sequence
<220> FEATURE:
<223> OTHER INFORMATION: EGFR binding FN3 domain

<400> SEQUENCE: 128

Met Leu Pro Ala Pro Lys Asn Leu Val Val Ser Glu Val Thr Glu Asp
  1               5                  10                  15

Ser Leu Arg Leu Ser Trp Asp Tyr Asp Leu Gly Val Tyr Phe Asp Ser
                 20                  25                  30

Phe Leu Ile Gln Tyr Gln Glu Ser Glu Lys Val Gly Glu Ala Ile Asn
             35                  40                  45

Leu Thr Val Pro Gly Ser Glu Arg Ser Tyr Asp Leu Thr Gly Leu Lys
         50                  55                  60

Pro Gly Thr Glu Tyr Thr Val Ser Ile Tyr Gly Val His Asn Val Tyr
 65                  70                  75                  80

Lys Asp Thr Asn Met Arg Gly Leu Pro Leu Ser Ala Glu Phe Thr Thr
                 85                  90                  95

<210> SEQ ID NO 129
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 129

Met Leu Pro Ala Pro Lys Asn Leu Val Val Ser Glu Val Thr Glu Asp
  1               5                  10                  15

Ser Leu Arg Leu Ser Trp Asp Asp Pro Trp Ala Phe Tyr Glu Ser Phe
                 20                  25                  30
```

```
Leu Ile Gln Tyr Gln Glu Ser Glu Lys Val Gly Glu Ala Ile Asn Leu
            35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 130
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 130

Met Leu Pro Ala Pro Lys Asn Leu Val Val Ser Glu Val Thr Glu Asp
1               5                   10                  15

Ser Leu Arg Leu Ser Trp Thr Ala Pro Asp Ala Ala Phe Asp Ser Phe
                20                  25                  30

Leu Ile Gln Tyr Gln Glu Ser Glu Lys Val Gly Glu Ala Ile Asn Leu
            35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Leu Gly Ser Tyr Val
65                  70                  75                  80

Phe Glu His Asp Val Met Leu Pro Leu Ser Ala Glu Phe Thr Thr
                85                  90                  95

<210> SEQ ID NO 131
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 131

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 132
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 132
```

Met Leu Pro Ala Pro Lys Asn Leu Val Val Ser Glu Val Thr Glu Asp
1               5                   10                  15

Ser Ala Arg Leu Ser Trp Thr Ala Pro Asp Ala Phe Asp Ser Phe
            20                  25                  30

Leu Ile Gln Tyr Gln Glu Ser Glu Lys Val Gly Glu Ala Ile Val Leu
                35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val Leu Gly Ser Tyr Val
65                  70                  75                  80

Phe Glu His Asp Val Met Leu Pro Leu Ser Ala Ile Phe Thr Thr
                85                  90                  95

<210> SEQ ID NO 133
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 133

Met Leu Pro Ala Pro Lys Asn Leu Val Val Ser Glu Val Thr Glu Asp
1               5                   10                  15

Ser Leu Arg Leu Ser Trp Thr Trp Pro Tyr Ala Asp Leu Asp Ser Phe
            20                  25                  30

Leu Ile Gln Tyr Gln Glu Ser Glu Lys Val Gly Glu Ala Ile Asn Leu
                35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Glu Phe Thr Thr
                85                  90                  95

<210> SEQ ID NO 134
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 134

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
            20                  25                  30

Leu Ile Gln Tyr Gln Glu Ser Lys Val Gly Glu Ala Ile Val Leu
                35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Met Arg Gly Leu Pro Leu Ser Ala Ile Phe Thr Thr
                85                  90                  95

<210> SEQ ID NO 135
<211> LENGTH: 95
<212> TYPE: PRT
<213> ORGANISM: Artificial Sequence

```
<220> FEATURE:
<223> OTHER INFORMATION: EGFR binding FN3 domain

<400> SEQUENCE: 135

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr
                85                  90                  95

<210> SEQ ID NO 136
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 136

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr
                85                  90                  95

<210> SEQ ID NO 137
<211> LENGTH: 95
<212> TYPE: PRT
<213> ORGANISM: Artificial Sequence
<220> FEATURE:
<223> OTHER INFORMATION: EGFR binding FN3 domain

<400> SEQUENCE: 137

Met Leu Pro Ala Pro Lys Asn Leu Val Val Ser Glu Val Thr Glu Asp
1               5                   10                  15

Ser Ala Arg Leu Ser Trp Ala Asp Pro His Gly Phe Tyr Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr
                85                  90                  95
```

<210> SEQ ID NO 138
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 138

```
Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly
                85                  90                  95

Gly Gly Ser Gly Gly Gly Gly Ser Gly Gly Gly Gly Ser Gly Gly Gly
            100                 105                 110

Gly Ser Met Leu Pro Ala Pro Lys Asn Leu Val Val Ser Arg Val Thr
        115                 120                 125

Glu Asp Ser Ala Arg Leu Ser Trp Thr Ala Pro Asp Ala Ala Phe Asp
    130                 135                 140

Ser Phe Trp Ile Arg Tyr Asp Glu Val Val Val Gly Gly Glu Ala Ile
145                 150                 155                 160

Val Leu Thr Val Pro Gly Ser Glu Arg Ser Tyr Asp Leu Thr Gly Leu
                165                 170                 175

Lys Pro Gly Thr Glu Tyr Tyr Val Asn Ile Leu Gly Val Lys Gly Gly
            180                 185                 190

Ser Ile Ser Val Pro Leu Ser Ala Ile Phe Thr Thr
        195                 200
```

<210> SEQ ID NO 139
<211> LENGTH: 203
<212> TYPE: PRT
<213> ORGANISM: Artificial Sequence
<220> FEATURE:
<223> OTHER INFORMATION: Bispecific EGFR/c-Met binding domain

<400> SEQUENCE: 139

```
Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly
                85                  90                  95

Gly Gly Ser Gly Gly Gly Gly Ser Gly Gly Gly Gly Ser Gly Gly Gly
            100                 105                 110
```

```
Gly Ser Leu Pro Ala Pro Lys Asn Leu Val Val Ser Arg Val Thr Glu
        115                 120                 125

Asp Ser Ala Arg Leu Ser Trp Thr Ala Pro Asp Ala Ala Phe Asp Ser
    130                 135                 140

Phe Trp Ile Arg Tyr Phe Glu Phe Leu Gly Ser Gly Glu Ala Ile Val
145                 150                 155                 160

Leu Thr Val Pro Gly Ser Glu Arg Ser Tyr Asp Leu Thr Gly Leu Lys
                165                 170                 175

Pro Gly Thr Glu Tyr Val Val Asn Ile Met Gly Val Lys Gly Gly Lys
            180                 185                 190

Ile Ser Pro Pro Leu Ser Ala Ile Phe Thr Thr
        195                 200

<210> SEQ ID NO 140
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 140

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly
                85                  90                  95

Gly Gly Ser Gly Gly Gly Gly Ser Gly Gly Gly Gly Ser Gly Gly Gly
            100                 105                 110

Gly Ser Met Leu Pro Ala Pro Lys Asn Leu Val Val Ser Arg Val Thr
        115                 120                 125

Glu Asp Ser Ala Arg Leu Ser Trp Thr Ala Pro Asp Ala Ala Phe Asp
    130                 135                 140

Ser Phe Trp Ile Arg Tyr Phe Glu Phe Leu Gly Ser Gly Glu Ala Ile
145                 150                 155                 160

Val Leu Thr Val Pro Gly Ser Glu Arg Ser Tyr Asp Leu Thr Gly Leu
                165                 170                 175

Lys Pro Gly Thr Glu Tyr Val Val Gln Ile Ile Gly Val Lys Gly Gly
            180                 185                 190

His Ile Ser Leu Pro Leu Ser Ala Ile Phe Thr Thr
        195                 200

<210> SEQ ID NO 141
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 141

Leu Pro Ala Pro Lys Asn Leu Val Val Ser Glu Val Thr Glu Asp Ser
```

```
                1               5                      10                      15
            Ala Arg Leu Ser Trp Asp Asp Pro Trp Ala Phe Tyr Glu Ser Phe Leu
                            20                      25                  30

Ile Gln Tyr Gln Glu Ser Glu Lys Val Gly Glu Ala Ile Val Leu Thr
                            35                      40                  45

Val Pro Gly Ser Glu Arg Ser Tyr Asp Leu Thr Gly Leu Lys Pro Gly
                        50                      55                  60

Thr Glu Tyr Thr Val Ser Ile Tyr Gly Val His Asn Val Tyr Lys Asp
            65                      70                  75                  80

Thr Asn Met Arg Gly Leu Pro Leu Ser Ala Ile Phe Thr Thr Gly Gly
                                85                  90                  95

Gly Gly Ser Gly Gly Gly Gly Ser Gly Gly Gly Ser Gly Gly
                            100                     105                 110

Gly Ser Met Leu Pro Ala Pro Lys Asn Leu Val Val Ser Arg Val Thr
                            115                     120                 125

Glu Asp Ser Ala Arg Leu Ser Trp Thr Ala Pro Asp Ala Ala Phe Asp
                        130                     135                 140

Ser Phe Phe Ile Arg Tyr Asp Glu Phe Leu Arg Ser Gly Glu Ala Ile
            145                     150                 155                 160

Val Leu Thr Val Pro Gly Ser Glu Arg Ser Tyr Asp Leu Thr Gly Leu
                                165                 170                 175

Lys Pro Gly Thr Glu Tyr Trp Val Thr Ile Leu Gly Val Lys Gly Gly
                            180                     185                 190

Leu Val Ser Thr Pro Leu Ser Ala Ile Phe Thr Thr
                        195                     200

<210> SEQ ID NO 142
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 142

Leu Pro Ala Pro Lys Asn Leu Val Val Ser Glu Val Thr Glu Asp Ser
            1               5                      10                      15

Ala Arg Leu Ser Trp Ala Asp Pro His Gly Phe Tyr Asp Ser Phe Leu
                            20                      25                  30

Ile Gln Tyr Gln Glu Ser Glu Lys Val Gly Glu Ala Ile Val Leu Thr
                            35                      40                  45

Val Pro Gly Ser Glu Arg Ser Tyr Asp Leu Thr Gly Leu Lys Pro Gly
                        50                      55                  60

Thr Glu Tyr Thr Val Ser Ile Tyr Gly Val His Asn Val Tyr Lys Asp
            65                      70                  75                  80

Thr Asn Met Arg Gly Leu Pro Leu Ser Ala Ile Phe Thr Thr Gly Gly
                                85                  90                  95

Gly Gly Ser Gly Gly Gly Gly Ser Gly Gly Gly Ser Gly Gly
                            100                     105                 110

Gly Ser Met Leu Pro Ala Pro Lys Asn Leu Val Val Ser Arg Val Thr
                            115                     120                 125

Glu Asp Ser Ala Arg Leu Ser Trp Thr Ala Pro Asp Ala Ala Phe Asp
                        130                     135                 140

Ser Phe Trp Ile Arg Tyr Phe Glu Phe Leu Gly Ser Gly Glu Ala Ile
            145                     150                 155                 160

Val Leu Thr Val Pro Gly Ser Glu Arg Ser Tyr Asp Leu Thr Gly Leu
```

```
                165                 170                 175

Lys Pro Gly Thr Glu Tyr Val Val Asn Ile Met Gly Val Lys Gly Gly
            180                 185                 190

Lys Ile Ser Pro Pro Leu Ser Ala Ile Phe Thr Thr
            195                 200

<210> SEQ ID NO 143
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 143

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly
                85                  90                  95

Gly Gly Ser Gly Gly Gly Gly Ser Gly Gly Gly Gly Ser Gly Gly Gly
            100                 105                 110

Gly Ser Met Leu Pro Ala Pro Lys Asn Leu Val Val Ser Arg Val Thr
            115                 120                 125

Glu Asp Ser Ala Arg Leu Ser Trp Thr Ala Pro Asp Ala Ala Phe Asp
            130                 135                 140

Ser Phe Trp Ile Arg Tyr Phe Glu Phe Leu Gly Ser Gly Glu Ala Ile
145                 150                 155                 160

Val Leu Thr Val Pro Gly Ser Glu Arg Ser Tyr Asp Leu Thr Gly Leu
                165                 170                 175

Lys Pro Gly Thr Glu Tyr Val Val Gln Ile Ile Gly Val Lys Gly Gly
            180                 185                 190

His Ile Ser Leu Pro Leu Ser Ala Ile Phe Thr Thr
            195                 200

<210> SEQ ID NO 144
<211> LENGTH: 204
<212> TYPE: PRT
<213> ORGANISM: Artificial Sequence
<220> FEATURE:
<223> OTHER INFORMATION: Bispecific EGFR/c-Met binding domain

<400> SEQUENCE: 144

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60
```

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Gly Gly
            85                  90                  95

Gly Gly Ser Gly Gly Gly Gly Ser Gly Gly Gly Gly Ser Gly Gly Gly
        100                 105                 110

Gly Ser Met Leu Pro Ala Pro Lys Asn Leu Val Val Ser Arg Val Thr
        115                 120                 125

Glu Asp Ser Ala Arg Leu Ser Trp Thr Ala Pro Asp Ala Ala Phe Asp
    130                 135                 140

Ser Phe Trp Ile Arg Tyr Phe Glu Phe Leu Gly Ser Gly Glu Ala Ile
145                 150                 155                 160

Val Leu Thr Val Pro Gly Ser Glu Arg Ser Tyr Asp Leu Thr Gly Leu
                165                 170                 175

Lys Pro Gly Thr Glu Tyr Val Val Gln Ile Ile Gly Val Lys Gly Gly
            180                 185                 190

His Ile Ser Leu Pro Leu Ser Ala Ile Phe Thr Thr
            195                 200

<210> SEQ ID NO 145
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 145

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
            85                  90                  95

Ala Pro Ala Pro Ala Pro Ala Pro Leu Pro Ala Pro Lys Asn Leu Val
        100                 105                 110

Val Ser Arg Val Thr Glu Asp Ser Ala Arg Leu Ser Trp Thr Ala Pro
    115                 120                 125

Asp Ala Ala Phe Asp Ser Phe Trp Ile Arg Tyr Phe Glu Phe Leu Gly
130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Met
            165                 170                 175

Gly Val Lys Gly Gly Lys Ile Ser Pro Pro Leu Ser Ala Ile Phe Thr
        180                 185                 190

Thr

<210> SEQ ID NO 146
<211> LENGTH: 193
<212> TYPE: PRT

-continued

<213> ORGANISM: Artificial Sequence
<220> FEATURE:
<223> OTHER INFORMATION: Bispecific EGFR/c-Met binding domain

<400> SEQUENCE: 146

```
Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Asp Glu Val Val Val
    130                 135                 140

Gly Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Tyr Val Asn Ile Leu
                165                 170                 175

Gly Val Lys Gly Gly Ser Ile Ser Val Pro Leu Ser Ala Ile Phe Thr
                180                 185                 190

Thr
```

<210> SEQ ID NO 147
<211> LENGTH: 194
<212> TYPE: PRT
<213> ORGANISM: Artificial Sequence
<220> FEATURE:
<223> OTHER INFORMATION: Bispecific EGFR/c-Met binding domain

<400> SEQUENCE: 147

```
Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Ala Pro Met Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Leu
```

```
                130                 135                 140
Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Met Gly Val Lys Gly Gly Lys Ile Ser Pro Pro Leu Ser Ala Ile Phe
                180                 185                 190

Thr Thr

<210> SEQ ID NO 148
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 148

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
                20                  25                  30

Ile Gln Tyr Gln Glu Ser Glu Lys Val Gly Glu Ala Ile Val Leu Thr
                35                  40                  45

Val Pro Gly Ser Glu Arg Ser Tyr Asp Leu Thr Gly Leu Lys Pro Gly
50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
                115                 120                 125

Asp Ala Ala Phe Asp Ser Phe Trp Ile Arg Tyr Asp Glu Val Val Val
                130                 135                 140

Gly Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Tyr Val Asn Ile Leu
                165                 170                 175

Gly Val Lys Gly Gly Ser Ile Ser Val Pro Leu Ser Ala Ile Phe Thr
                180                 185                 190

Thr

<210> SEQ ID NO 149
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 149

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
                20                  25                  30

Ile Gln Tyr Gln Glu Ser Glu Lys Val Gly Glu Ala Ile Val Leu Thr
                35                  40                  45
```

```
Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
            130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Lys Ile Ser Pro Pro Leu Ser Ala Ile Phe Thr
            180                 185                 190

Thr
```

<210> SEQ ID NO 150  
<211> LENGTH: 193  
<212> TYPE: PRT  
<213> ORGANISM: Artificial Sequence  
<220> FEATURE:  
<223> OTHER INFORMATION: Bispecific EGFR/c-Met binding domain

<400> SEQUENCE: 150

```
Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Val Gly
            130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Ser Ile Ser Pro Pro Leu Ser Ala Ile Phe Thr
            180                 185                 190

Thr
```

```
<210> SEQ ID NO 151
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 151

Leu Pro Ala Pro Lys Asn Leu Val Val Ser Glu Val Thr Glu Asp Ser
1               5                   10                  15

Ala Arg Leu Ser Trp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Ala Pro
            85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Val Ser
        130                 135                 140

Lys Gly Asp Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Ser Ile Ser Pro Pro Leu Ser Ala Ile Phe Thr
            180                 185                 190

Thr

<210> SEQ ID NO 152
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 152

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
            85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
```

```
                115                 120                 125
Asp Ala Ala Phe Asp Ser Phe Trp Ile Arg Tyr Phe Glu Phe Leu Gly
        130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Ser Val Lys Gly Gly Ser Ile Ser Pro Pro Leu Ser Ala Ile Phe Thr
            180                 185                 190

Thr

<210> SEQ ID NO 153
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 153

Leu Pro Ala Pro Lys Asn Leu Val Val Ser Glu Val Thr Glu Asp Ser
1               5                   10                  15

Ala Arg Leu Ser Trp Asp Asp Pro His Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
        130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Lys Ile Ser Pro Pro Leu Ser Ala Ile Phe Thr
            180                 185                 190

Thr

<210> SEQ ID NO 154
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 154

Leu Pro Ala Pro Lys Asn Leu Val Val Ser Glu Val Thr Glu Asp Ser
1               5                   10                  15

Ala Arg Leu Ser Trp Asp Asp Pro His Ala Phe Tyr Glu Ser Phe Leu
            20                  25                  30
```

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val His Asn Val Tyr Lys Asp
 65                  70                  75                  80

Thr Asn Ile Arg Gly Leu Pro Leu Ser Ala Ile Phe Thr Thr Ala Pro
                 85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
                115                 120                 125

Asp Ala Ala Phe Asp Ser Phe Trp Ile Arg Tyr Phe Glu Phe Val Gly
                130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Ser Ile Ser Pro Pro Leu Ser Ala Ile Phe Thr
                180                 185                 190

Thr

<210> SEQ ID NO 155
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 155

Leu Pro Ala Pro Lys Asn Leu Val Val Ser Glu Val Thr Glu Asp Ser
  1               5                  10                  15

Ala Arg Leu Ser Trp Asp Asp Pro His Ala Phe Tyr Glu Ser Phe Leu
                 20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val His Asn Val Tyr Lys Asp
 65                  70                  75                  80

Thr Asn Ile Arg Gly Leu Pro Leu Ser Ala Ile Phe Thr Thr Ala Pro
                 85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
                115                 120                 125

Asp Ala Ala Phe Asp Ser Phe Trp Ile Arg Tyr Phe Glu Phe Val Ser
                130                 135                 140

Lys Gly Asp Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Ser Ile Ser Pro Pro Leu Ser Ala Ile Phe Thr
                180                 185                 190

Thr

<210> SEQ ID NO 156
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 156

Leu Pro Ala Pro Lys Asn Leu Val Val Ser Glu Val Thr Glu Asp Ser
1               5                   10                  15

Ala Arg Leu Ser Trp Asp Asp Pro His Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Leu Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Ser Val Lys Gly Gly Ser Ile Ser Pro Pro Leu Ser Ala Ile Phe Thr
            180                 185                 190

Thr

<210> SEQ ID NO 157
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 157

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val

```
                    100                 105                 110
Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
        130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Lys Ile Ser Pro Pro Leu Ser Ala Ile Phe Thr
            180                 185                 190

Thr

<210> SEQ ID NO 158
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 158

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Val Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Ser Ile Ser Pro Pro Leu Ser Ala Ile Phe Thr
            180                 185                 190

Thr

<210> SEQ ID NO 159
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 159

Leu Pro Ala Pro Lys Asn Leu Val Val Ser Glu Val Thr Glu Asp Ser
1               5                   10                  15
```

```
Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val His Asn Val Tyr Lys Asp
 65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Val Ser
            130                 135                 140

Lys Gly Asp Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Gly Val Lys Gly Gly Ser Ile Ser Pro Pro Leu Ser Ala Ile Phe Thr
            180                 185                 190

Thr
```

<210> SEQ ID NO 160
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 160

```
Leu Pro Ala Pro Lys Asn Leu Val Val Ser Glu Val Thr Glu Asp Ser
 1               5                  10                  15

Ala Arg Leu Ser Trp Ala Asp Pro His Gly Phe Tyr Asp Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val His Asn Val Tyr Lys Asp
 65                  70                  75                  80

Thr Asn Ile Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
            130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175
```

Ser Val Lys Gly Gly Ser Ile Ser Pro Pro Leu Ser Ala Ile Phe Thr
            180                 185                 190

Thr

<210> SEQ ID NO 161
<211> LENGTH: 193
<212> TYPE: PRT
<213> ORGANISM: Artificial Sequence
<220> FEATURE:
<223> OTHER INFORMATION: Bispecific EGFR/c-Met binding domain

<400> SEQUENCE: 161

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Ile Arg Gly Leu Pro Leu Ser Ala Ile Phe Thr Thr Ala Pro
                85                  90                  95

Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
        130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Leu
                165                 170                 175

Ser Val Lys Gly Gly Ser Ile Ser Pro Pro Leu Ser Ala Ile Phe Thr
            180                 185                 190

Thr

<210> SEQ ID NO 162
<211> LENGTH: 249
<212> TYPE: PRT
<213> ORGANISM: Artificial Sequence
<220> FEATURE:
<223> OTHER INFORMATION: Bispecific EGFR/c-Met binding domain

<400> SEQUENCE: 162

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro

```
                    85                  90                  95
Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
                115                 120                 125

Asp Ala Ala Phe Asp Ser Phe Trp Ile Arg Tyr Asp Glu Val Val Val
            130                 135                 140

Gly Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Tyr Val Asn Ile Leu
                165                 170                 175

Gly Val Lys Gly Gly Ser Ile Ser Val Pro Leu Ser Ala Ile Phe Thr
                180                 185                 190

Thr Ala Pro Ala Pro Ala Pro Ala Pro Leu Ala Glu Ala Lys
                195                 200                 205

Val Leu Ala Asn Arg Glu Leu Asp Lys Tyr Gly Val Ser Asp Tyr Tyr
                210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245

<210> SEQ ID NO 163
<211> LENGTH: 249
<212> TYPE: PRT
<213> ORGANISM: Artificial Sequence
<220> FEATURE:
<223> OTHER INFORMATION: Bispecific EGFR/c-Met binding domain

<400> SEQUENCE: 163

Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Asp Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
                100                 105                 110

Val Ser Arg Val Thr Glu Asp Ser Ala Arg Leu Ser Trp Thr Ala Pro
                115                 120                 125

Asp Ala Ala Phe Asp Ser Phe Trp Ile Arg Tyr Asp Glu Val Val Val
            130                 135                 140

Gly Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Tyr Val Asn Ile Leu
                165                 170                 175

Gly Val Lys Gly Gly Ser Ile Ser Val Pro Leu Ser Ala Ile Phe Thr
                180                 185                 190

Thr Ala Pro Ala Pro Ala Pro Ala Pro Ala Pro Leu Ala Glu Ala Lys
```

```
                  195                 200                 205

Val Leu Ala Asn Arg Glu Leu Asp Lys Tyr Gly Val Ser Asp Tyr Tyr
    210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245

<210> SEQ ID NO 164
<211> LENGTH: 249
<212> TYPE: PRT
<213> ORGANISM: Artificial Sequence
<220> FEATURE:
<223> OTHER INFORMATION: Bispecific EGFR/c-Met binding domain

<400> SEQUENCE: 164

Leu Pro Ala Pro Lys Asn Leu Val Val Ser Glu Val Thr Glu Asp Ser
1               5                   10                  15

Ala Arg Leu Ser Trp Asp Asp Pro Trp Ala Phe Tyr Glu Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
        115                 120                 125

Asp Ala Ala Phe Asp Ser Phe Trp Ile Arg Tyr Phe Glu Phe Leu Gly
    130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Met
                165                 170                 175

Gly Val Lys Gly Gly Lys Ile Ser Pro Pro Leu Ser Ala Ile Phe Thr
            180                 185                 190

Thr Ala Pro Ala Pro Ala Pro Ala Pro Ala Pro Leu Ala Glu Ala Lys
        195                 200                 205

Val Leu Ala Asn Arg Glu Leu Asp Lys Tyr Gly Val Ser Asp Tyr Tyr
    210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245

<210> SEQ ID NO 165
<211> LENGTH: 249
<212> TYPE: PRT
<213> ORGANISM: Artificial Sequence
<220> FEATURE:
<223> OTHER INFORMATION: Bispecific EGFR/c-Met binding domain

<400> SEQUENCE: 165
```

```
Leu Pro Ala Pro Lys Asn Leu Val Val Ser Glu Val Thr Glu Asp Ser
1               5                   10                  15

Ala Arg Leu Ser Trp Ala Asp Pro His Gly Phe Tyr Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
50                  55                  60

Thr Glu Tyr Thr Val Ser Ile Tyr Gly Val His Asn Val Tyr Lys Asp
65                  70                  75                  80

Thr Asn Met Arg Gly Leu Pro Leu Ser Ala Ile Phe Thr Thr Ala Pro
                85                  90                  95

Ala Pro Ala Pro Ala Pro Ala Pro Leu Pro Ala Pro Lys Asn Leu Val
            100                 105                 110

Val Ser Arg Val Thr Glu Asp Ser Ala Arg Leu Ser Trp Thr Ala Pro
            115                 120                 125

Asp Ala Ala Phe Asp Ser Phe Trp Ile Arg Tyr Phe Glu Phe Leu Gly
            130                 135                 140

Ser Gly Glu Ala Ile Val Leu Thr Val Pro Gly Ser Glu Arg Ser Tyr
145                 150                 155                 160

Asp Leu Thr Gly Leu Lys Pro Gly Thr Glu Tyr Val Val Asn Ile Met
            165                 170                 175

Gly Val Lys Gly Gly Lys Ile Ser Pro Pro Leu Ser Ala Ile Phe Thr
            180                 185                 190

Thr Ala Pro Ala Pro Ala Pro Ala Pro Ala Pro Leu Ala Glu Ala Lys
            195                 200                 205

Val Leu Ala Asn Arg Glu Leu Asp Lys Tyr Gly Val Ser Asp Tyr Tyr
210                 215                 220

Lys Asn Leu Ile Asn Asn Ala Lys Thr Val Glu Gly Val Lys Ala Leu
225                 230                 235                 240

Leu Asp Glu Ile Leu Ala Ala Leu Pro
                245
```

<210> SEQ ID NO 166
<211> LENGTH: 588
<212> TYPE: DNA
<213> ORGANISM: Artificial Sequence
<220> FEATURE:
<223> OTHER INFORMATION: Bispecific EGFR/c-Met binding domain

<400> SEQUENCE: 166

```
ttgccagcgc cgaagaacct ggtagttagc gaggttactg aggacagcgc gcgtctgagc      60
tgggacgatc cgtgggcgtt ctacgagagc tttctgatcc agtatcaaga gagcgagaaa     120
gtcggtgaag cgattgtgct gaccgtcccg ggctccgagc gttcctacga cctgaccggt     180
ttgaagccgg gtaccgagta tacggtgagc atctacggtg ttcacaatgt ctataaggac     240
actaatatcc gcggtctgcc tctgagcgcc attttcacca ccgcaccggc accggctccg     300
gctcctgccc cgctgccggc tccgaagaac ttggtggtga ccgtgttac gaagatagc      360
gcacgcctga ctggacggc accgatgcg gcgttcgata gcttctggat tcgctatttt      420
gagtttctgg gtagcggtga ggcaattgtt ctgacggtgc cgggctctga acgctcctac     480
gatttgaccg gtctgaaacc gggcaccgag tatgtggtga acattctgag cgttaagggc     540
ggtagcatca gcccaccgct gagcgcgatc ttcacgactg gtggttgc                  588
```

<210> SEQ ID NO 167
<211> LENGTH: 579
<212> TYPE: DNA
<213> ORGANISM: Artificial Sequence
<220> FEATURE:
<223> OTHER INFORMATION: Bispecific EGFR/c-Met binding domain

<400> SEQUENCE: 167

```
ctgccagccc ctaagaatct ggtcgtgagc gaagtaaccg aggacagcgc ccgcctgagc    60
tgggacgacc cgtgggcgtt ctatgagtct ttcctgattc agtatcaaga aagcgaaaaa   120
gttggcgaag cgatcgtcct gaccgtcccg ggtagcgagc gctcctacga tctgaccggc   180
ctgaaaccgg gtacggagta cacggtgtcc atttacggtg ttcacaatgt gtataaagac   240
accaacatgc gtggcctgcc gctgtcggcg attttcacca ccgcgcctgc gccagcgcct   300
gcaccggctc cgctgccggc accgaagaac ctggttgtca gccgtgtgac cgaggatagc   360
gcacgtttga gctggaccgc tccggatgca gcctttgaca gcttctggat tcgttacttt   420
gaatttctgg gtagcggtga ggcgatcgtt ctgacggtgc cgggctctga acgcagctat   480
gatttgacgg gcctgaagcc gggtactgag tacgtggtta acatcatggg cgttaagggt   540
ggtaaaatca gcccgccatt gtccgcgatc tttaccacg                          579
```

<210> SEQ ID NO 168
<211> LENGTH: 282
<212> TYPE: DNA
<213> ORGANISM: Artificial Sequence
<220> FEATURE:
<223> OTHER INFORMATION: EGFR binding FN3 domain from ECB97

<400> SEQUENCE: 168

```
ttgccagcgc cgaagaacct ggtagttagc gaggttactg aggacagcgc gcgtctgagc    60
tgggacgatc cgtgggcgtt ctacgagagc tttctgatcc agtatcaaga gagcgagaaa   120
gtcggtgaag cgattgtgct gaccgtcccg ggctccgagc gttcctacga cctgaccggt   180
ttgaagccgg gtaccgagta tacggtgagc atctacggtg ttcacaatgt ctataaggac   240
actaatatcc gcggtctgcc tctgagcgcc attttcacca cc                      282
```

<210> SEQ ID NO 169
<211> LENGTH: 282
<212> TYPE: DNA
<213> ORGANISM: Artificial Sequence
<220> FEATURE:
<223> OTHER INFORMATION: EGFR binding FN3 domain from ECB15

<400> SEQUENCE: 169

```
ctgccagccc ctaagaatct ggtcgtgagc gaagtaaccg aggacagcgc ccgcctgagc    60
tgggacgacc cgtgggcgtt ctatgagtct ttcctgattc agtatcaaga aagcgaaaaa   120
gttggcgaag cgatcgtcct gaccgtcccg ggtagcgagc gctcctacga tctgaccggc   180
ctgaaaccgg gtacggagta cacggtgtcc atttacggtg ttcacaatgt gtataaagac   240
accaacatgc gtggcctgcc gctgtcggcg attttcacca cc                      282
```

<210> SEQ ID NO 170
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 170

```
Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Lys Ile Ser Pro Pro Leu Ser Ala Ile Phe
                180                 185                 190

Thr Thr Cys
        195

<210> SEQ ID NO 171
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 171

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Val
    130                 135                 140

Gly Ser Gly Glu Ala Ile Val Leu Thr Val Pro Gly Ser Glu Arg Ser
145                 150                 155                 160
```

Tyr Asp Leu Thr Gly Leu Lys Pro Gly Thr Glu Tyr Val Val Asn Ile
            165                 170                 175

Leu Gly Val Lys Gly Gly Ser Ile Ser Pro Pro Leu Ser Ala Ile Phe
            180                 185                 190

Thr Thr Cys
        195

<210> SEQ ID NO 172
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 172

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Val
    130                 135                 140

Ser Lys Gly Asp Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
            180                 185                 190

Thr Thr Cys
        195

<210> SEQ ID NO 173
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 173

Met Leu Pro Ala Pro Lys Asn Leu Val Val Ser Glu Val Thr Glu Asp
1               5                   10                  15

Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

```
Gly Thr Glu Tyr Thr Val Ser Ile Tyr Gly Val His Asn Val Tyr Lys
 65                  70                  75                  80

Asp Thr Asn Ile Arg Gly Leu Pro Leu Ser Ala Ile Phe Thr Thr Ala
                 85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Gly Ser Ile Ser Pro Pro Leu Ser Ala Ile Phe
            180                 185                 190

Thr Thr Cys
        195

<210> SEQ ID NO 174
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 174

Met Leu Pro Ala Pro Lys Asn Leu Val Val Ser Glu Val Thr Glu Asp
  1               5                  10                  15

Ser Ala Arg Leu Ser Trp Asp Asp Pro His Ala Phe Tyr Glu Ser Phe
                 20                  25                  30

Leu Ile Gln Tyr Gln Glu Ser Glu Lys Val Gly Glu Ala Ile Val Leu
             35                  40                  45

Thr Val Pro Gly Ser Glu Arg Ser Tyr Asp Leu Thr Gly Leu Lys Pro
 50                  55                  60

Gly Thr Glu Tyr Thr Val Ser Ile Tyr Gly Val His Asn Val Tyr Lys
 65                  70                  75                  80

Asp Thr Asn Ile Arg Gly Leu Pro Leu Ser Ala Ile Phe Thr Thr Ala
                 85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Lys Ile Ser Pro Pro Leu Ser Ala Ile Phe
            180                 185                 190

Thr Thr Cys
        195

<210> SEQ ID NO 175
```

```
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 175

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
        115                 120                 125

Pro Asp Ala Ala Phe Asp Ser Phe Trp Ile Arg Tyr Phe Glu Phe Val
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Gly Val Lys Gly Gly Ser Ile Ser Pro Pro Leu Ser Ala Ile Phe
                180                 185                 190

Thr Thr Cys
        195

<210> SEQ ID NO 176
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 176

Met Leu Pro Ala Pro Lys Asn Leu Val Val Ser Glu Val Thr Glu Asp
1               5                   10                  15

Ser Ala Arg Leu Ser Trp Asp Asp Pro His Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
```

```
                115              120             125
Pro Asp Ala Ala Phe Asp Ser Phe Trp Ile Arg Tyr Phe Glu Phe Val
            130             135             140

Ser Lys Gly Asp Ala Ile Val Leu Thr Val Pro Gly Ser Glu Arg Ser
145             150             155             160

Tyr Asp Leu Thr Gly Leu Lys Pro Gly Thr Glu Tyr Val Val Asn Ile
                165             170             175

Leu Gly Val Lys Gly Gly Ser Ile Ser Pro Pro Leu Ser Ala Ile Phe
            180             185             190

Thr Thr Cys
        195

<210> SEQ ID NO 177
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 177

Met Leu Pro Ala Pro Lys Asn Leu Val Val Ser Glu Val Thr Glu Asp
1               5               10              15

Ser Ala Arg Leu Ser Trp Asp Asp Pro His Ala Phe Tyr Glu Ser Phe
            20              25              30

Leu Ile Gln Tyr Gln Glu Ser Glu Lys Val Gly Glu Ala Ile Val Leu
        35              40              45

Thr Val Pro Gly Ser Glu Arg Ser Tyr Asp Leu Thr Gly Leu Lys Pro
50              55              60

Gly Thr Glu Tyr Thr Val Ser Ile Tyr Gly Val His Asn Val Tyr Lys
65              70              75              80

Asp Thr Asn Ile Arg Gly Leu Pro Leu Ser Ala Ile Phe Thr Thr Ala
            85              90              95

Pro Ala Pro Ala Pro Ala Pro Ala Pro Leu Pro Ala Pro Lys Asn Leu
            100             105             110

Val Val Ser Arg Val Thr Glu Asp Ser Ala Arg Leu Ser Trp Thr Ala
            115             120             125

Pro Asp Ala Ala Phe Asp Ser Phe Trp Ile Arg Tyr Phe Glu Phe Leu
            130             135             140

Gly Ser Gly Glu Ala Ile Val Leu Thr Val Pro Gly Ser Glu Arg Ser
145             150             155             160

Tyr Asp Leu Thr Gly Leu Lys Pro Gly Thr Glu Tyr Val Val Asn Ile
                165             170             175

Leu Ser Val Lys Gly Gly Ser Ile Ser Pro Pro Leu Ser Ala Ile Phe
            180             185             190

Thr Thr Cys
        195

<210> SEQ ID NO 178
<211> LENGTH: 195
<212> TYPE: PRT
<213> ORGANISM: Artificial Sequence
<220> FEATURE:
<223> OTHER INFORMATION: Bispecific EGFR/c-Met binding molecule

<400> SEQUENCE: 178

Met Leu Pro Ala Pro Lys Asn Leu Val Val Ser Glu Val Thr Glu Asp
1               5               10              15
```

```
Ser Ala Arg Leu Ser Trp Asp Asp Pro Trp Ala Phe Tyr Glu Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Ile Arg Gly Leu Pro Leu Ser Ala Ile Phe Thr Thr Ala
                85                  90                  95

Pro Ala Pro Ala Pro Ala Pro Leu Pro Ala Pro Lys Asn Leu
            100                 105                 110

Val Val Ser Arg Val Thr Glu Asp Ser Ala Arg Leu Ser Trp Thr Ala
            115                 120                 125

Pro Asp Ala Ala Phe Asp Ser Phe Trp Ile Arg Tyr Phe Glu Phe Leu
    130                 135                 140

Gly Ser Gly Glu Ala Ile Val Leu Thr Val Pro Gly Ser Glu Arg Ser
145                 150                 155                 160

Tyr Asp Leu Thr Gly Leu Lys Pro Gly Thr Glu Tyr Val Val Asn Ile
                165                 170                 175

Leu Ser Val Lys Gly Ser Ile Ser Pro Pro Leu Ser Ala Ile Phe
            180                 185                 190

Thr Thr Cys
        195

<210> SEQ ID NO 179
<211> LENGTH: 12
<212> TYPE: PRT
<213> ORGANISM: Artificial Sequence
<220> FEATURE:
<223> OTHER INFORMATION: Consensus FG loop of EGFR bindiing FN3 domain
<220> FEATURE:
<221> NAME/KEY: VARIANT
<222> LOCATION: (9)..(9)
<223> OTHER INFORMATION: Xaa may be Met or Ile

<400> SEQUENCE: 179

His Asn Val Tyr Lys Asp Thr Asn Xaa Arg Gly Leu
1               5                   10

<210> SEQ ID NO 180
<211> LENGTH: 12
<212> TYPE: PRT
<213> ORGANISM: Artificial Sequence
<220> FEATURE:
<223> OTHER INFORMATION: GF loop of EGFR binding FN3 domain

<400> SEQUENCE: 180

Leu Gly Ser Tyr Val Phe Glu His Asp Val Met Leu
1               5                   10

<210> SEQ ID NO 181
<211> LENGTH: 8
<212> TYPE: PRT
<213> ORGANISM: Artificial Sequence
<220> FEATURE:
<223> OTHER INFORMATION: Consensus BC loop of EGFR binding FN3 domain
<220> FEATURE:
<221> NAME/KEY: VARIANT
<222> LOCATION: (1)..(1)
<223> OTHER INFORMATION: Xaa may be Ala, Thr, Gly or Asp
<220> FEATURE:
<221> NAME/KEY: VARIANT
```

```
<222> LOCATION: (2)..(2)
<223> OTHER INFORMATION: Xaa may be Ala, Asp, Tyr or Trp
<220> FEATURE:
<221> NAME/KEY: VARIANT
<222> LOCATION: (3)..(3)
<223> OTHER INFORMATION: Xaa may be Pro, Asp or Asn
<220> FEATURE:
<221> NAME/KEY: VARIANT
<222> LOCATION: (4)..(4)
<223> OTHER INFORMATION: Xaa may be Leu or absent
<220> FEATURE:
<221> NAME/KEY: VARIANT
<222> LOCATION: (5)..(5)
<223> OTHER INFORMATION: Xaa may be Asp, His, Arg, Gly, Tyr or Trp
<220> FEATURE:
<221> NAME/KEY: VARIANT
<222> LOCATION: (6)..(6)
<223> OTHER INFORMATION: Xaa may be Glu, Asp or Ala
<220> FEATURE:
<221> NAME/KEY: VARIANT
<222> LOCATION: (7)..(7)
<223> OTHER INFORMATION: Xaa may be Ala, Phe, Gly, His or Asp
<220> FEATURE:
<221> NAME/KEY: VARIANT
<222> LOCATION: (8)..(8)
<223> OTHER INFORMATION: Xaa may be Tyr, Phe or Leu

<400> SEQUENCE: 181

Xaa Xaa Xaa Xaa Xaa Xaa Xaa Xaa
1               5

<210> SEQ ID NO 182
<211> LENGTH: 95
<212> TYPE: PRT
<213> ORGANISM: Artificial Sequence
<220> FEATURE:
<223> OTHER INFORMATION: EGFR binding FN3 domain consensus sequence
<220> FEATURE:
<221> NAME/KEY: VARIANT
<222> LOCATION: (22)..(22)
<223> OTHER INFORMATION: Xaa may be Ala, Thr, Gly or Asp
<220> FEATURE:
<221> NAME/KEY: VARIANT
<222> LOCATION: (23)..(23)
<223> OTHER INFORMATION: Xaa may be Ala, Asp, Tyr or Trp
<220> FEATURE:
<221> NAME/KEY: VARIANT
<222> LOCATION: (24)..(24)
<223> OTHER INFORMATION: Xaa may be Pro, Asp or Asn
<220> FEATURE:
<221> NAME/KEY: VARIANT
<222> LOCATION: (25)..(25)
<223> OTHER INFORMATION: Xaa may be Leu or absent
<220> FEATURE:
<221> NAME/KEY: VARIANT
<222> LOCATION: (26)..(26)
<223> OTHER INFORMATION: Xaa may be Asp, His, Arg, Gly, Tyr or Trp
<220> FEATURE:
<221> NAME/KEY: VARIANT
<222> LOCATION: (27)..(27)
<223> OTHER INFORMATION: Xaa may be Gly, Asp or Ala
<220> FEATURE:
<221> NAME/KEY: VARIANT
<222> LOCATION: (28)..(28)
<223> OTHER INFORMATION: Xaa may be Ala, Phe, Gly, His or Asp
<220> FEATURE:
<221> NAME/KEY: VARIANT
<222> LOCATION: (29)..(29)
<223> OTHER INFORMATION: Xaa may be Tyr, Phe or Leu
<220> FEATURE:
<221> NAME/KEY: VARIANT
<222> LOCATION: (84)..(84)
<223> OTHER INFORMATION: Xaa may be Met or Ile

<400> SEQUENCE: 182

Leu Pro Ala Pro Lys Asn Leu Val Val Ser Glu Val Thr Glu Asp Ser
```

```
                 1               5                  10                 15
Leu Arg Leu Ser Trp Xaa Xaa Xaa Xaa Xaa Xaa Xaa Asp Ser Phe
                20                  25                 30

Leu Ile Gln Tyr Gln Glu Ser Glu Lys Val Gly Glu Ala Ile Asn Leu
                35                  40                 45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Asn Val Tyr Lys
65                  70                  75                  80

Asp Thr Asn Xaa Arg Gly Leu Pro Leu Ser Ala Glu Phe Thr Thr
                85                  90                  95
```

<210> SEQ ID NO 183
<211> LENGTH: 95
<212> TYPE: PRT
<213> ORGANISM: Artificial Sequence
<220> FEATURE:
<223> OTHER INFORMATION: EGFR binding FN3 domain consensus sequence
<220> FEATURE:
<221> NAME/KEY: VARIANT
<222> LOCATION: (22)..(22)
<223> OTHER INFORMATION: Xaa may be Ala, Thr, Gly or Asp
<220> FEATURE:
<221> NAME/KEY: VARIANT
<222> LOCATION: (23)..(23)
<223> OTHER INFORMATION: Xaa may be Ala, Asp, Tyr or Trp
<220> FEATURE:
<221> NAME/KEY: VARIANT
<222> LOCATION: (24)..(24)
<223> OTHER INFORMATION: Xaa may be Pro, Asp or Asn
<220> FEATURE:
<221> NAME/KEY: VARIANT
<222> LOCATION: (25)..(25)
<223> OTHER INFORMATION: Xaa may be Leu or absent
<220> FEATURE:
<221> NAME/KEY: VARIANT
<222> LOCATION: (26)..(26)
<223> OTHER INFORMATION: Xaa may be Asp, His, Arg, Gly, Tyr or Trp
<220> FEATURE:
<221> NAME/KEY: VARIANT
<222> LOCATION: (27)..(27)
<223> OTHER INFORMATION: Xaa may be Gly, Asp or Ala
<220> FEATURE:
<221> NAME/KEY: VARIANT
<222> LOCATION: (28)..(28)
<223> OTHER INFORMATION: Xaa may be Ala, Phe, Gly, His or Asp
<220> FEATURE:
<221> NAME/KEY: VARIANT
<222> LOCATION: (29)..(29)
<223> OTHER INFORMATION: Xaa may be Tyr, Phe or Leu

<400> SEQUENCE: 183

```
Leu Pro Ala Pro Lys Asn Leu Val Val Ser Glu Val Thr Glu Asp Ser
1               5                   10                  15

Leu Arg Leu Ser Trp Xaa Xaa Xaa Xaa Xaa Xaa Xaa Asp Ser Phe
                20                  25                 30

Leu Ile Gln Tyr Gln Glu Ser Glu Lys Val Gly Glu Ala Ile Asn Leu
                35                  40                 45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Leu Gly Ser Tyr Val
65                  70                  75                  80

Phe Glu His Asp Val Met Leu Pro Leu Ser Ala Glu Phe Thr Thr
                85                  90                  95
```

<210> SEQ ID NO 184

```
<211> LENGTH: 15
<212> TYPE: PRT
<213> ORGANISM: Artificial Sequence
<220> FEATURE:
<223> OTHER INFORMATION: c-Met binding FN3 domain C strand and CD loop
      consensus sequence
<220> FEATURE:
<221> NAME/KEY: VARIANT
<222> LOCATION: (4)..(4)
<223> OTHER INFORMATION: Xaa is Trp, Phe or Val
<220> FEATURE:
<221> NAME/KEY: VARIANT
<222> LOCATION: (8)..(8)
<223> OTHER INFORMATION: Xaa is Asp, Phe or Leu
<220> FEATURE:
<221> NAME/KEY: VARIANT
<222> LOCATION: (10)..(10)
<223> OTHER INFORMATION: Xaa is Val, Phe or Leu
<220> FEATURE:
<221> NAME/KEY: VARIANT
<222> LOCATION: (11)..(11)
<223> OTHER INFORMATION: Xaa is Val, Leu or Thr
<220> FEATURE:
<221> NAME/KEY: VARIANT
<222> LOCATION: (12)..(12)
<223> OTHER INFORMATION: Xaa is Val, Arg, Gly, Leu, Thr or Ser
<220> FEATURE:
<221> NAME/KEY: VARIANT
<222> LOCATION: (13)..(13)
<223> OTHER INFORMATION: Xaa is Gly, Ser, Ala, Thr or Lys
<220> FEATURE:
<221> NAME/KEY: VARIANT
<222> LOCATION: (15)..(15)
<223> OTHER INFORMATION: Xaa is Glu or Asp

<400> SEQUENCE: 184

Asp Ser Phe Xaa Ile Arg Tyr Xaa Glu Xaa Xaa Xaa Xaa Gly Xaa
1               5                   10                  15

<210> SEQ ID NO 185
<211> LENGTH: 17
<212> TYPE: PRT
<213> ORGANISM: Artificial Sequence
<220> FEATURE:
<223> OTHER INFORMATION: c-Met binding FN3 domain F strand and FG loop
      consensus sequence
<220> FEATURE:
<221> NAME/KEY: VARIANT
<222> LOCATION: (4)..(4)
<223> OTHER INFORMATION: Xaa is Tyr, Trp, Ile, Val, Gly or Ala
<220> FEATURE:
<221> NAME/KEY: VARIANT
<222> LOCATION: (6)..(6)
<223> OTHER INFORMATION: Xaa is Asn, Thr, Qln or Gly
<220> FEATURE:
<221> NAME/KEY: VARIANT
<222> LOCATION: (8)..(8)
<223> OTHER INFORMATION: Xaa is Leu, Met, Asn or Ile
<220> FEATURE:
<221> NAME/KEY: VARIANT
<222> LOCATION: (9)..(9)
<223> OTHER INFORMATION: Xaa is Gly or Ser
<220> FEATURE:
<221> NAME/KEY: VARIANT
<222> LOCATION: (14)..(14)
<223> OTHER INFORMATION: Xaa is Ser, Leu, Gly, Tyr, Thr, Arg, His or Lys
<220> FEATURE:
<221> NAME/KEY: VARIANT
<222> LOCATION: (15)..(15)
<223> OTHER INFORMATION: Xaa is Ile, Val or Leu
<220> FEATURE:
<221> NAME/KEY: VARIANT
<222> LOCATION: (17)..(17)
<223> OTHER INFORMATION: Xaa is Val, Thr, His, Ile, Pro, Tyr or Leu

<400> SEQUENCE: 185
```

```
Thr Glu Tyr Xaa Val Xaa Ile Xaa Xaa Val Lys Gly Gly Xaa Xaa Ser
 1               5                  10                  15

Xaa

<210> SEQ ID NO 186
<211> LENGTH: 89
<212> TYPE: PRT
<213> ORGANISM: Artificial Sequence
<220> FEATURE:
<223> OTHER INFORMATION: c-Met binding FN3 domain consensus sequence
<220> FEATURE:
<221> NAME/KEY: VARIANT
<222> LOCATION: (32)..(32)
<223> OTHER INFORMATION: Xaa is Trp, Phe or Val
<220> FEATURE:
<221> NAME/KEY: VARIANT
<222> LOCATION: (36)..(36)
<223> OTHER INFORMATION: Xaa is Asp, Phe or Leu
<220> FEATURE:
<221> NAME/KEY: VARIANT
<222> LOCATION: (38)..(38)
<223> OTHER INFORMATION: Xaa is Val, Phe or Leu
<220> FEATURE:
<221> NAME/KEY: VARIANT
<222> LOCATION: (39)..(39)
<223> OTHER INFORMATION: Xaa is Val, Leu or Thr
<220> FEATURE:
<221> NAME/KEY: VARIANT
<222> LOCATION: (40)..(40)
<223> OTHER INFORMATION: Xaa is Val, Arg, Gly, Leu, Thr or Ser
<220> FEATURE:
<221> NAME/KEY: VARIANT
<222> LOCATION: (41)..(41)
<223> OTHER INFORMATION: Xaa is Gly, Ser, Ala, Thr or Lys
<220> FEATURE:
<221> NAME/KEY: VARIANT
<222> LOCATION: (43)..(43)
<223> OTHER INFORMATION: Xaa is Glu or Asp
<220> FEATURE:
<221> NAME/KEY: VARIANT
<222> LOCATION: (68)..(68)
<223> OTHER INFORMATION: Xaa is Tyr, Trp, Ile, Val, Gly or Ala
<220> FEATURE:
<221> NAME/KEY: VARIANT
<222> LOCATION: (70)..(70)
<223> OTHER INFORMATION: Xaa is Asn, Thr, Qln or Gly
<220> FEATURE:
<221> NAME/KEY: VARIANT
<222> LOCATION: (72)..(72)
<223> OTHER INFORMATION: Xaa is Leu, Met, Asn or Ile
<220> FEATURE:
<221> NAME/KEY: VARIANT
<222> LOCATION: (73)..(73)
<223> OTHER INFORMATION: Xaa is Gly or Ser
<220> FEATURE:
<221> NAME/KEY: VARIANT
<222> LOCATION: (78)..(78)
<223> OTHER INFORMATION: Xaa is Ser, Leu, Gly, Tyr, Thr, Arg, His or Lys
<220> FEATURE:
<221> NAME/KEY: VARIANT
<222> LOCATION: (79)..(79)
<223> OTHER INFORMATION: Xaa is Ile, Val or Leu
<220> FEATURE:
<221> NAME/KEY: VARIANT
<222> LOCATION: (81)..(81)
<223> OTHER INFORMATION: Xaa is Val, Thr, His, Ile, Pro, Tyr or Leu

<400> SEQUENCE: 186

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Xaa
                20                  25                  30

Ile Arg Tyr Xaa Glu Xaa Xaa Xaa Xaa Gly Xaa Ala Ile Val Leu Thr
            35                  40                  45
```

```
Val Pro Gly Ser Glu Arg Ser Tyr Asp Leu Thr Gly Leu Lys Pro Gly
    50                  55                  60

Thr Glu Tyr Xaa Val Xaa Ile Xaa Xaa Val Lys Gly Gly Xaa Xaa Ser
 65                  70                  75                  80

Xaa Pro Leu Ser Ala Glu Phe Thr Thr
                85

<210> SEQ ID NO 187
<211> LENGTH: 94
<212> TYPE: PRT
<213> ORGANISM: Artificial Sequence
<220> FEATURE:
<223> OTHER INFORMATION: EGFR consensus FN3 domain of bispecific
      EGFR/c-Met molecule
<220> FEATURE:
<221> NAME/KEY: VARIANT
<222> LOCATION: (11)..(11)
<223> OTHER INFORMATION: Xaa is Glu, Asn or Arg
<220> FEATURE:
<221> NAME/KEY: VARIANT
<222> LOCATION: (14)..(14)
<223> OTHER INFORMATION: Xaa is Glu or Pro
<220> FEATURE:
<221> NAME/KEY: VARIANT
<222> LOCATION: (17)..(17)
<223> OTHER INFORMATION: Xaa is Leu or Ala
<220> FEATURE:
<221> NAME/KEY: VARIANT
<222> LOCATION: (25)..(25)
<223> OTHER INFORMATION: Xaa is His or Trp
<220> FEATURE:
<221> NAME/KEY: VARIANT
<222> LOCATION: (29)..(29)
<223> OTHER INFORMATION: Xaa is Glu or Asp
<220> FEATURE:
<221> NAME/KEY: VARIANT
<222> LOCATION: (37)..(37)
<223> OTHER INFORMATION: Xaa is Glu or Pro
<220> FEATURE:
<221> NAME/KEY: VARIANT
<222> LOCATION: (46)..(46)
<223> OTHER INFORMATION: Xaa is Asn or Val
<220> FEATURE:
<221> NAME/KEY: VARIANT
<222> LOCATION: (73)..(73)
<223> OTHER INFORMATION: Xaa is Gly or Tyr
<220> FEATURE:
<221> NAME/KEY: VARIANT
<222> LOCATION: (83)..(83)
<223> OTHER INFORMATION: Xaa is Met or Ile
<220> FEATURE:
<221> NAME/KEY: VARIANT
<222> LOCATION: (91)..(91)
<223> OTHER INFORMATION: Xaa is Glu or Ile

<400> SEQUENCE: 187

Leu Pro Ala Pro Lys Asn Leu Val Val Ser Xaa Val Thr Xaa Asp Ser
  1               5                  10                  15

Xaa Arg Leu Ser Trp Asp Asp Pro Xaa Ala Phe Tyr Xaa Ser Phe Leu
                 20                  25                  30

Ile Gln Tyr Gln Xaa Ser Glu Lys Val Gly Glu Ala Ile Xaa Leu Thr
             35                  40                  45

Val Pro Gly Ser Glu Arg Ser Tyr Asp Leu Thr Gly Leu Lys Pro Gly
     50                  55                  60

Thr Glu Tyr Thr Val Ser Ile Tyr Xaa Val His Asn Val Tyr Lys Asp
 65                  70                  75                  80

Thr Asn Xaa Arg Gly Leu Pro Leu Ser Ala Xaa Phe Thr Thr
                85                  90
```

```
<210> SEQ ID NO 188
<211> LENGTH: 89
<212> TYPE: PRT
<213> ORGANISM: Artificial Sequence
<220> FEATURE:
<223> OTHER INFORMATION: c-Met consensus FN3 domain of bispecific
      EGFR/c-Met molecule
<220> FEATURE:
<221> NAME/KEY: VARIANT
<222> LOCATION: (11)..(11)
<223> OTHER INFORMATION: Xaa is Glu, Asn or Arg
<220> FEATURE:
<221> NAME/KEY: VARIANT
<222> LOCATION: (14)..(14)
<223> OTHER INFORMATION: Xaa is Glu or Pro
<220> FEATURE:
<221> NAME/KEY: VARIANT
<222> LOCATION: (17)..(17)
<223> OTHER INFORMATION: Xaa is Leu or Ala
<220> FEATURE:
<221> NAME/KEY: VARIANT
<222> LOCATION: (37)..(37)
<223> OTHER INFORMATION: Xaa is Glu or Pro
<220> FEATURE:
<221> NAME/KEY: VARIANT
<222> LOCATION: (39)..(39)
<223> OTHER INFORMATION: Xaa is Val or Leu
<220> FEATURE:
<221> NAME/KEY: VARIANT
<222> LOCATION: (40)..(40)
<223> OTHER INFORMATION: Xaa is Gly or Ser
<220> FEATURE:
<221> NAME/KEY: VARIANT
<222> LOCATION: (41)..(41)
<223> OTHER INFORMATION: Xaa is Ser or Lys
<220> FEATURE:
<221> NAME/KEY: VARIANT
<222> LOCATION: (43)..(43)
<223> OTHER INFORMATION: Xaa is Glu or Asp
<220> FEATURE:
<221> NAME/KEY: VARIANT
<222> LOCATION: (46)..(46)
<223> OTHER INFORMATION: Xaa is Asn or Val
<220> FEATURE:
<221> NAME/KEY: VARIANT
<222> LOCATION: (72)..(72)
<223> OTHER INFORMATION: Xaa is Leu or Met
<220> FEATURE:
<221> NAME/KEY: VARIANT
<222> LOCATION: (73)..(73)
<223> OTHER INFORMATION: Xaa is Gly or Ser
<220> FEATURE:
<221> NAME/KEY: VARIANT
<222> LOCATION: (78)..(78)
<223> OTHER INFORMATION: Xaa is Ser or Lys
<220> FEATURE:
<221> NAME/KEY: VARIANT
<222> LOCATION: (86)..(86)
<223> OTHER INFORMATION: Xaa is Glu or Ile

<400> SEQUENCE: 188

Leu Pro Ala Pro Lys Asn Leu Val Val Ser Xaa Val Thr Xaa Asp Ser
1               5                   10                  15

Xaa Arg Leu Ser Trp Thr Ala Pro Asp Ala Ala Phe Asp Ser Phe Trp
            20                  25                  30

Ile Arg Tyr Phe Xaa Phe Xaa Xaa Xaa Gly Xaa Ala Ile Xaa Leu Thr
        35                  40                  45

Val Pro Gly Ser Glu Arg Ser Tyr Asp Leu Thr Gly Leu Lys Pro Gly
    50                  55                  60

Thr Glu Tyr Val Val Asn Ile Xaa Xaa Val Lys Gly Gly Xaa Ile Ser
65                  70                  75                  80

Pro Pro Leu Ser Ala Xaa Phe Thr Thr
```

<210> SEQ ID NO 189
<211> LENGTH: 125
<212> TYPE: PRT
<213> ORGANISM: Homo Sapiens

<400> SEQUENCE: 189

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser
        115                 120                 125

<210> SEQ ID NO 190
<211> LENGTH: 107
<212> TYPE: PRT
<213> ORGANISM: Homo Sapiens

<400> SEQUENCE: 190

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 191
<211> LENGTH: 121
<212> TYPE: PRT
<213> ORGANISM: Homo Sapiens

<400> SEQUENCE: 191

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Asn Ile Lys Lys Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Gly Trp Gly Trp Gly Trp Tyr Phe Asp Leu Trp Gly
            100                 105                 110

Arg Gly Thr Leu Val Thr Val Ser Ser
        115                 120

<210> SEQ ID NO 192
<211> LENGTH: 107
<212> TYPE: PRT
<213> ORGANISM: Homo Sapiens

<400> SEQUENCE: 192

Glu Ile Val Leu Thr Gln Ser Pro Ala Thr Leu Ser Leu Ser Pro Gly
 1                5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Phe Gly Gln Gly Thr Lys Val Glu Ile Lys
            100                 105

<210> SEQ ID NO 193
<211> LENGTH: 119
<212> TYPE: PRT
<213> ORGANISM: Homo Sapiens

<400> SEQUENCE: 193

Gln Val Gln Leu Val Gln Ser Gly Ala Glu Val Lys Lys Pro Gly Ala
 1                5                  10                  15

Ser Val Lys Val Ser Cys Glu Thr Ser Gly Tyr Thr Phe Thr Ser Tyr
             20                  25                  30

Gly Ile Ser Trp Val Arg Gln Ala Pro Gly His Gly Leu Glu Trp Met
         35                  40                  45

Gly Trp Ile Ser Ala Tyr Asn Gly Tyr Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Leu Arg Gly Thr Asn Tyr Phe Asp Tyr Trp Gly Gln Gly
            100                 105                 110

Thr Leu Val Thr Val Ser Ser
        115

<210> SEQ ID NO 194

```
<211> LENGTH: 107
<212> TYPE: PRT
<213> ORGANISM: Homo Sapiens

<400> SEQUENCE: 194

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Phe Gln His Lys Pro Gly Lys Ala Pro Lys Leu Leu Ile
        35                  40                  45

Tyr Ala Ala Ser Ser Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 195
<211> LENGTH: 125
<212> TYPE: PRT
<213> ORGANISM: Homo Sapiens

<400> SEQUENCE: 195

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Thr Ile Ser Asp Asp Gly Ser Tyr Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Glu Gly Leu Tyr Tyr Tyr Gly Ser Gly Ser Tyr Tyr Asn Gln
            100                 105                 110

Asp Tyr Trp Gly Gln Gly Thr Leu Val Thr Val Ser Ser
        115                 120                 125

<210> SEQ ID NO 196
<211> LENGTH: 106
<212> TYPE: PRT
<213> ORGANISM: Homo Sapiens

<400> SEQUENCE: 196

Gln Leu Thr Gln Ser Pro Ser Ser Leu Ser Ala Ser Val Gly Asp Arg
1               5                   10                  15

Val Thr Ile Thr Cys Arg Ala Ser Gln Gly Leu Ser Ser Ala Leu Ala
            20                  25                  30

Trp Tyr Arg Gln Lys Pro Gly Lys Ala Pro Lys Leu Leu Ile Tyr Asp
        35                  40                  45

Ala Ser Ser Leu Glu Ser Gly Val Pro Ser Arg Phe Ser Gly Ser Gly
    50                  55                  60
```

Ser Gly Thr Asp Phe Thr Leu Thr Ile Ser Ser Leu Gln Pro Glu Asp
65                  70                  75                  80

Phe Ala Thr Tyr Tyr Cys Gln Gln Phe Thr Ser Tyr Pro Gln Ile Thr
                85                  90                  95

Phe Gly Gln Gly Thr Arg Leu Glu Ile Lys
            100                 105

<210> SEQ ID NO 197
<211> LENGTH: 457
<212> TYPE: PRT
<213> ORGANISM: Homo Sapiens

<400> SEQUENCE: 197

Gln Val Gln Leu Val Gln Ser Gly Ala Glu Val Lys Pro Gly Ala
1               5                   10                  15

Ser Val Lys Val Ser Cys Gln Ala Ser Gly Tyr Arg Phe Ser Asn Phe
                20                  25                  30

Val Ile His Trp Val Arg Gln Ala Pro Gly Gln Arg Phe Glu Trp Met
                35                  40                  45

Gly Trp Ile Asn Pro Tyr Asn Gly Asn Lys Glu Phe Ser Ala Lys Phe
            50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95

Ala Arg Val Gly Pro Tyr Ser Trp Asp Ser Pro Gln Asp Asn Tyr
                100                 105                 110

Tyr Met Asp Val Trp Gly Lys Gly Thr Thr Val Ile Val Ser Ser Ala
            115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Leu Gly Thr Gln Thr Tyr
            195                 200                 205

Ile Cys Asn Val Asn His Lys Pro Ser Asn Thr Lys Val Asp Lys Arg
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
                260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

```
Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Leu Leu
            405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 198
<211> LENGTH: 457
<212> TYPE: PRT
<213> ORGANISM: Homo Sapiens

<400> SEQUENCE: 198

Gln Val Gln Leu Val Gln Ser Gly Ala Glu Val Lys Lys Pro Gly Ala
1               5                   10                  15

Ser Val Lys Val Ser Cys Gln Ala Ser Gly Tyr Arg Phe Ser Asn Phe
            20                  25                  30

Val Ile His Trp Val Arg Gln Ala Pro Gly Gln Arg Phe Glu Trp Met
        35                  40                  45

Gly Trp Ile Asn Pro Tyr Asn Gly Asn Lys Glu Phe Ser Ala Lys Phe
    50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95

Ala Arg Val Gly Pro Tyr Ser Trp Asp Asp Ser Pro Gln Asp Asn Tyr
            100                 105                 110

Tyr Met Asp Val Trp Gly Lys Gly Thr Thr Val Ile Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
```

```
                       245                 250                 255
Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
            290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
            355                 360                 365

Thr Lys Asn Gln Val Ser Leu Thr Cys Leu Val Lys Gly Phe Tyr Pro
            370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Arg Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
            450                 455

<210> SEQ ID NO 199
<211> LENGTH: 455
<212> TYPE: PRT
<213> ORGANISM: Homo Sapiens

<400> SEQUENCE: 199

Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160
```

-continued

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
        180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Arg Val Glu
        210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 200
<211> LENGTH: 214
<212> TYPE: PRT
<213> ORGANISM: Homo Sapiens

<400> SEQUENCE: 200

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

-continued

```
Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 201
<211> LENGTH: 449
<212> TYPE: PRT
<213> ORGANISM: Homo Sapiens

<400> SEQUENCE: 201

Gln Val Gln Leu Val Gln Ser Gly Ala Glu Val Lys Lys Pro Gly Ala
1               5                   10                  15

Ser Val Lys Val Ser Cys Glu Thr Ser Gly Tyr Thr Phe Thr Ser Tyr
                20                  25                  30

Gly Ile Ser Trp Val Arg Gln Ala Pro Gly His Gly Leu Glu Trp Met
            35                  40                  45

Gly Trp Ile Ser Ala Tyr Asn Gly Tyr Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Arg Gly Thr Asn Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
```

```
               225                 230                 235                 240
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 202
<211> LENGTH: 214
<212> TYPE: PRT
<213> ORGANISM: Homo Sapiens

<400> SEQUENCE: 202

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Phe Gln His Lys Pro Gly Lys Ala Pro Lys Leu Leu Ile
        35                  40                  45

Tyr Ala Ala Ser Ser Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
                    195                 200                 205

Phe Asn Arg Gly Glu Cys
                    210

<210> SEQ ID NO 203
<211> LENGTH: 330
<212> TYPE: PRT
<213> ORGANISM: Homo Sapiens

<400> SEQUENCE: 203

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                    20                  25                  30

Phe Pro Glu Pro Val Thr Val Ser Trp Asn Ser Gly Ala Leu Thr Ser
                    35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                    100                 105                 110

Pro Ala Pro Glu Leu Leu Gly Gly Pro Ser Val Phe Leu Phe Pro Pro
                    115                 120                 125

Lys Pro Lys Asp Thr Leu Met Ile Ser Arg Thr Pro Glu Val Thr Cys
                    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                    165                 170                 175

Glu Gln Tyr Asn Ser Thr Tyr Arg Val Val Ser Val Leu Thr Val Leu
                    180                 185                 190

His Gln Asp Trp Leu Asn Gly Lys Glu Tyr Lys Cys Lys Val Ser Asn
                    195                 200                 205

Lys Ala Leu Pro Ala Pro Ile Glu Lys Thr Ile Ser Lys Ala Lys Gly
                    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                    260                 265                 270

Asn Tyr Lys Thr Thr Pro Pro Val Leu Asp Ser Asp Gly Ser Phe Phe
                    275                 280                 285

Leu Tyr Ser Arg Leu Thr Val Asp Lys Ser Arg Trp Gln Gln Gly Asn
                    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 204
<211> LENGTH: 330
<212> TYPE: PRT
<213> ORGANISM: Homo Sapiens

<400> SEQUENCE: 204

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 205
```

<211> LENGTH: 1368
<212> TYPE: DNA
<213> ORGANISM: Homo Sapiens

<400> SEQUENCE: 205

```
caggtgcagc tggtcgagag cggcggaggg gtggtgcagc ccggcagaag cctgaggctg    60
tcctgcgccg ccagcggctt caccttcagc acctacggca tgcactgggt gcggcaggcc   120
ccaggcaagg gcctggagtg ggtggccgtg atctgggacg acggcagcta caagtactac   180
ggcgacagcg tgaagggcag gttcaccatc agcagggaca acagcaagaa cacccctgtac  240
ctgcagatga acagcctgag ggccgaggac accgccgtgt actactgcgc cagggacggc   300
atcaccatgg tgcggggcgt gatgaaggac tacttcgact actggggcca gggcaccctg   360
gtgaccgtga gcgcccag caccaagggc ccaagcgtgt tcccctggc ccccagcagc      420
aagagcacca gcggcggcac agccgccctg ggctgcctgg tgaaggacta cttccccgag   480
ccagtgaccg tgtcctggaa ctctggcgcc ctgacctccg gcgtgcacac cttccccgcc   540
gtgctgcaga gcagcggcct gtacagcctg agcagcgtgg tgaccgtgcc cagcagcagc   600
ctgggcaccc agacctacat ctgcaacgtg aaccacaagc ccagcaacac caaggtggac   660
aagagagtgg agcccaagag ctgcgacaag acccacacct gcccccctg cccagccca    720
gagctgctgg gcggacccag cgtgttcctg ttcccccca gcccaagga caccctgatg    780
atcagcagga cccccgaggt gacctgcgtg gtggtggacg tgagccacga ggacccagag   840
gtgaagttca actggtacgt ggacggcgtg gaggtgcaca acgccaagac caagcccaga   900
gaggagcagt acaacagcac ctacagggtg gtgtccgtgc tgaccgtgct gcaccaggac   960
tggctgaacg gcaaggaata caagtgcaag gtctccaaca aggccctgcc agcccccatc  1020
gaaaagacca tcagcaaggc caagggccag ccacgggagc cccaggtgta caccctgccc  1080
cccagccggg aggagatgac caagaaccag gtgtccctga cctgtctggt gaagggcttc  1140
taccccagcg acatcgccgt ggagtgggag agcaacggcc agcccgagaa caactacaag  1200
accaccccc cagtgctgga cagcgacggc agcttcctcc tgtacagcaa gctgaccgtg  1260
gacaagtcca ggtggcagca gggcaacgtg ttcagctgca gcgtgatgca cgaggccctg  1320
cacaaccact acacccagaa gtccctgagc ctgagccccg gcaaatga            1368
```

<210> SEQ ID NO 206
<211> LENGTH: 642
<212> TYPE: DNA
<213> ORGANISM: Homo Sapiens

<400> SEQUENCE: 206

```
atccagctga cccagagccc cagcagcctg agcgccagcg tgggcgaccg ggtgaccatc    60
acctgccggg ccagccagga catcagcagc gccctggtct ggtatcagca gaagcccggc   120
aaggccccca gctgctgat ctacgacgcc agctccctgg aaagcggcgt gcccagccgg   180
ttcagcggca gcgagagcgg caccgacttc accctgacca tcagcagcct gcagcccgag   240
gacttcgcca cctactactg ccagcagttc aacagctacc ccctgacctt ggcggcgga   300
acaaaggtgg agatcaagcg tacggtggcc gctcccagcg tgttcatctt cccccccagc   360
gacgagcagc tgaagagcgg caccgccagc gtggtgtgcc tgctgaacaa cttctacccc   420
cgggaggcca aggtgcagtg gaaggtggac aacgccctgc agagcggcaa cagccaggag   480
agcgtcaccg agcaggacag caaggactcc acctacagcc tgagcagcac cctgaccctg   540
tccaaggccg actacgagaa gcacaaggtg tacgcctgcg aggtgaccca ccagggcctg   600
```

```
tccagccccg tgaccaagag cttcaacagg ggcgagtgct ga              642
```

<210> SEQ ID NO 207
<211> LENGTH: 1350
<212> TYPE: DNA
<213> ORGANISM: Homo Sapiens

<400> SEQUENCE: 207

```
caggttcagc tggtgcagtc tggagctgag gtgaagaagc ctggggcctc agtgaaggtc    60
tcctgcgaga cttctggtta caccttacc agctatggta tcagctgggt gcgacaggcc   120
cctggacacg gcttgagtg gatgggatgg atcagcgctt acaatggtta cacaaactat   180
gcacagaagc tccagggcag ggtcaccatg accacagaca catccacgag cacagcctac   240
atggagctga ggagcctgag atctgacgac acggccgtgt attactgtgc gagagatctg   300
agaggaacta actactttga ctactgggc cagggaaccc tggtcaccgt ctcctcagcc   360
tccaccaagg gcccaagcgt gttccctctg gccccagca gcaagagcac atctggcgga   420
acagccgccc tgggctgcct ggtgaaagac tacttccccg agccgtgac cgtgtcctgg   480
aactctggcg ccctgaccag cggcgtgcac acctttccag ccgtgctgca gagcagcggc   540
ctgtacagcc tgtccagcgt ggtgaccgtg cccagcagct ccctgggcac ccagacctac   600
atctgcaacg tgaaccacaa gcccagcaac accaaggtgg acaagcgggt ggaacccaag   660
agctgcgaca gacccacac ctgtccccc tgccctgccc tgaactgct gggcggaccc    720
tccgtgttcc tgttccccc aaagcccaag gacaccctga tgatcagccg gacccccgaa   780
gtgacctgcg tggtggtgga cgtgtcccac gaggaccctg aagtgaagtt caattggtac   840
gtggacggcg tggaagtgca caacgccaag accaagccca gagaggaaca gtacaacagc   900
acctaccggg tggtgtccgt gctgacagtg ctgcaccagg actggctgaa cggcaaagag   960
tacaagtgca aggtctccaa caaggccctg cctgctccca tcgagaaaac catcagcaag  1020
gccaagggcc agccccgcga gcctcaggtg tacacactgc ctcccagccg ggaagagatg  1080
accaagaacc aggtgtccct gacctgtctg gtgaaaggct tctacccag cgatatcgcc  1140
gtggaatggg agagcaacgg acagcccgag aacaactaca agaccacccc cctgtgctg   1200
gacagcgacg gctccttctt cctgtactct cggctgaccg tggacaagag ccggtggcag  1260
cagggaaacg tgttcagctg cagcgtgatg cacgaggccc tgcacaacca ctacacccag  1320
aagtccctga gcctgagccc cgggaagtga                                   1350
```

<210> SEQ ID NO 208
<211> LENGTH: 645
<212> TYPE: DNA
<213> ORGANISM: Homo Sapiens

<400> SEQUENCE: 208

```
gacatccaga tgacccagtc cccctcctcc gtgtccgcct ctgtgggcga cagagtgacc    60
atcacctgtc gggcctccca gggcatctcc aactggctgg cctggttcca gcacaagccc   120
ggcaaggccc ccaagctgct gatctacgcc gcctcctccc tgctgtccgg cgtgccctcc   180
agattctccg gctctggctc cggcaccgac ttcaccctga ccatctccag cctgcagccc   240
gaggacttcg ccacctacta ctgccagcag gccaactcct tccccatcac cttcggccag   300
ggcacccggc tggaaatcaa gcgtacggtg gccgctccca gcgtgttcat cttcccccc    360
agcgacgagc agctgaagag cggcaccgcc agcgtggtgt gcctgctgaa caacttctac   420
```

```
cccgggagg  ccaaggtgca  gtggaaggtg  gacaacgccc  tgcagagcgg  caacagccag      480
gagagcgtca  ccgagcagga  cagcaaggac  tccacctaca  gcctgagcag  cacccctgacc     540 ctgtccaagg  ccgactacga  gaagcacaag  gtgtacgcct  gcgaggtgac  ccaccagggc     600
ctgtccagcc  ccgtgaccaa  gagcttcaac  aggggcgagt  gctga                     645
```

<210> SEQ ID NO 209
<211> LENGTH: 215
<212> TYPE: PRT
<213> ORGANISM: Homo Sapiens

<400> SEQUENCE: 209

```
Glu Ile Val Leu Thr Gln Ser Pro Gly Thr Leu Ser Leu Ser Pro Gly
1               5                   10                  15

Glu Arg Ala Thr Phe Ser Cys Arg Ser Ser His Ser Ile Arg Ser Arg
            20                  25                  30

Arg Val Ala Trp Tyr Gln His Lys Pro Gly Gln Ala Pro Arg Leu Val
        35                  40                  45

Ile His Gly Val Ser Asn Arg Ala Ser Gly Ile Ser Asp Arg Phe Ser
    50                  55                  60

Gly Ser Gly Ser Gly Thr Asp Phe Thr Leu Thr Ile Thr Arg Val Glu
65                  70                  75                  80

Pro Glu Asp Phe Ala Leu Tyr Tyr Cys Gln Val Tyr Gly Ala Ser Ser
                85                  90                  95

Tyr Thr Phe Gly Gln Gly Thr Lys Leu Glu Arg Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 210
<211> LENGTH: 5
<212> TYPE: PRT
<213> ORGANISM: Homo Sapiens

<400> SEQUENCE: 210

```
Thr Tyr Gly Met His
1               5
```

<210> SEQ ID NO 211
<211> LENGTH: 17
<212> TYPE: PRT
<213> ORGANISM: Homo Sapiens

<400> SEQUENCE: 211

```
Val Ile Trp Asp Asp Gly Ser Tyr Lys Tyr Tyr Gly Asp Ser Val Lys
1               5                   10                  15
```

Gly

<210> SEQ ID NO 212
<211> LENGTH: 16
<212> TYPE: PRT
<213> ORGANISM: Homo Sapiens

<400> SEQUENCE: 212

Asp Gly Ile Thr Met Val Arg Gly Val Met Lys Asp Tyr Phe Asp Tyr
1               5                   10                  15

<210> SEQ ID NO 213
<211> LENGTH: 11
<212> TYPE: PRT
<213> ORGANISM: Homo Sapiens

<400> SEQUENCE: 213

Arg Ala Ser Gln Asp Ile Ser Ser Ala Leu Val
1               5                   10

<210> SEQ ID NO 214
<211> LENGTH: 7
<212> TYPE: PRT
<213> ORGANISM: Homo Sapiens

<400> SEQUENCE: 214

Asp Ala Ser Ser Leu Glu Ser
1               5

<210> SEQ ID NO 215
<211> LENGTH: 9
<212> TYPE: PRT
<213> ORGANISM: Homo Sapiens

<400> SEQUENCE: 215

Gln Gln Phe Asn Ser Tyr Pro Leu Thr
1               5

<210> SEQ ID NO 216
<211> LENGTH: 5
<212> TYPE: PRT
<213> ORGANISM: Homo Sapiens

<400> SEQUENCE: 216

Ser Tyr Gly Ile Ser
1               5

<210> SEQ ID NO 217
<211> LENGTH: 17
<212> TYPE: PRT
<213> ORGANISM: Homo Sapiens

<400> SEQUENCE: 217

Trp Ile Ser Ala Tyr Asn Gly Tyr Thr Asn Tyr Ala Gln Lys Leu Gln
1               5                   10                  15

Gly

<210> SEQ ID NO 218
<211> LENGTH: 10
<212> TYPE: PRT
<213> ORGANISM: Homo Sapiens

<400> SEQUENCE: 218

Asp Leu Arg Gly Thr Asn Tyr Phe Asp Tyr
1               5                   10

<210> SEQ ID NO 219
<211> LENGTH: 11
<212> TYPE: PRT
<213> ORGANISM: Homo Sapiens

<400> SEQUENCE: 219

Arg Ala Ser Gln Gly Ile Ser Asn Trp Leu Ala
1               5                   10

<210> SEQ ID NO 220
<211> LENGTH: 7
<212> TYPE: PRT
<213> ORGANISM: Homo Sapiens

<400> SEQUENCE: 220

Ala Ala Ser Ser Leu Leu Ser
1               5

<210> SEQ ID NO 221
<211> LENGTH: 9
<212> TYPE: PRT
<213> ORGANISM: Homo Sapiens

<400> SEQUENCE: 221

Gln Gln Ala Asn Ser Phe Pro Ile Thr
1               5

<210> SEQ ID NO 222
<211> LENGTH: 5
<212> TYPE: PRT
<213> ORGANISM: Homo Sapiens

<400> SEQUENCE: 222

Ser Tyr Trp Met Asn
1               5

<210> SEQ ID NO 223
<211> LENGTH: 17
<212> TYPE: PRT
<213> ORGANISM: Homo Sapiens

<400> SEQUENCE: 223

Asn Ile Lys Lys Asp Gly Ser Glu Lys Tyr Tyr Val Asp Ser Val Lys
1               5                   10                  15

Gly

<210> SEQ ID NO 224
<211> LENGTH: 12
<212> TYPE: PRT
<213> ORGANISM: Homo Sapiens

<400> SEQUENCE: 224

Asp Leu Gly Trp Gly Trp Gly Trp Tyr Phe Asp Leu
1               5                   10

<210> SEQ ID NO 225
<211> LENGTH: 11
<212> TYPE: PRT
<213> ORGANISM: Homo Sapiens

<400> SEQUENCE: 225

```
Arg Ala Ser Gln Ser Val Ser Ser Tyr Leu Ala
1               5                   10

<210> SEQ ID NO 226
<211> LENGTH: 7
<212> TYPE: PRT
<213> ORGANISM: Homo Sapiens

<400> SEQUENCE: 226

Asp Ala Ser Asn Arg Ala Thr
1               5

<210> SEQ ID NO 227
<211> LENGTH: 9
<212> TYPE: PRT
<213> ORGANISM: Homo Sapiens

<400> SEQUENCE: 227

Gln Gln Arg Ser Asn Trp Pro Pro Thr
1               5

<210> SEQ ID NO 228
<211> LENGTH: 5
<212> TYPE: PRT
<213> ORGANISM: Homo Sapiens

<400> SEQUENCE: 228

Asp Tyr Tyr Met Tyr
1               5

<210> SEQ ID NO 229
<211> LENGTH: 17
<212> TYPE: PRT
<213> ORGANISM: Homo Sapiens

<400> SEQUENCE: 229

Thr Ile Ser Asp Asp Gly Ser Tyr Thr Tyr Tyr Pro Asp Ser Val Lys
1               5                   10                  15

Gly

<210> SEQ ID NO 230
<211> LENGTH: 16
<212> TYPE: PRT
<213> ORGANISM: Homo Sapiens

<400> SEQUENCE: 230

Glu Gly Leu Tyr Tyr Tyr Gly Ser Gly Ser Tyr Tyr Asn Gln Asp Tyr
1               5                   10                  15

<210> SEQ ID NO 231
<211> LENGTH: 11
<212> TYPE: PRT
<213> ORGANISM: Homo Sapiens

<400> SEQUENCE: 231

Arg Ala Ser Gln Gly Leu Ser Ser Ala Leu Ala
1               5                   10

<210> SEQ ID NO 232
<211> LENGTH: 7
<212> TYPE: PRT
<213> ORGANISM: Homo Sapiens

<400> SEQUENCE: 232
```

Asp Ala Ser Ser Leu Glu Ser
1               5

<210> SEQ ID NO 233
<211> LENGTH: 10
<212> TYPE: PRT
<213> ORGANISM: Homo Sapiens

<400> SEQUENCE: 233

Gln Gln Phe Thr Ser Tyr Pro Gln Ile Thr
1               5                   10

<210> SEQ ID NO 234
<211> LENGTH: 451
<212> TYPE: PRT
<213> ORGANISM: Homo Sapiens

<400> SEQUENCE: 234

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Asn Ile Lys Lys Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Trp Gly Trp Gly Trp Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Leu Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 235
<211> LENGTH: 214
<212> TYPE: PRT
<213> ORGANISM: Homo Sapiens

<400> SEQUENCE: 235

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 236
<211> LENGTH: 455
<212> TYPE: PRT
<213> ORGANISM: Homo Sapiens

<400> SEQUENCE: 236
```

| | | | | | | | | | | | | | | | |
|---|---|---|---|---|---|---|---|---|---|---|---|---|---|---|---|
|Glu|Val|Gln|Leu|Val|Glu|Ser|Gly|Gly|Gly|Leu|Val|Lys|Pro|Gly|Gly|
|1| | | |5| | | | |10| | | | |15| |

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Thr Ile Ser Asp Asp Gly Ser Tyr Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Glu Gly Leu Tyr Tyr Tyr Gly Ser Gly Ser Tyr Tyr Asn Gln
            100                 105                 110

Asp Tyr Trp Gly Gln Gly Thr Leu Val Thr Val Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp

```
                370                 375                 380
Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450                 455

<210> SEQ ID NO 237
<211> LENGTH: 213
<212> TYPE: PRT
<213> ORGANISM: Homo Sapiens

<400> SEQUENCE: 237

Gln Leu Thr Gln Ser Pro Ser Leu Ser Ala Ser Val Gly Asp Arg
1               5                   10                  15

Val Thr Ile Thr Cys Arg Ala Ser Gln Gly Leu Ser Ser Ala Leu Ala
                20                  25                  30

Trp Tyr Arg Gln Lys Pro Gly Lys Ala Pro Lys Leu Leu Ile Tyr Asp
            35                  40                  45

Ala Ser Ser Leu Glu Ser Gly Val Pro Ser Arg Phe Ser Gly Ser Gly
        50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Phe Thr Ser Tyr Pro Gln Ile Thr
                85                  90                  95

Phe Gly Gln Gly Thr Arg Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 238
<211> LENGTH: 15
<212> TYPE: PRT
<213> ORGANISM: Homo Sapiens

<400> SEQUENCE: 238

Pro Glu Phe Arg Asp Ser Tyr Pro Ile Lys Tyr Val His Ala Phe
1               5                   10                  15
```

```
<210> SEQ ID NO 239
<211> LENGTH: 16
<212> TYPE: PRT
<213> ORGANISM: Homo Sapiens

<400> SEQUENCE: 239

Phe Ala Gln Ser Lys Pro Asp Ser Ala Glu Pro Met Asp Arg Ser Ala
1               5                   10                  15

<210> SEQ ID NO 240
<211> LENGTH: 16
<212> TYPE: PRT
<213> ORGANISM: Homo Sapiens

<400> SEQUENCE: 240

Pro Gly Ala Gln Leu Ala Arg Gln Ile Gly Ala Ser Leu Asn Asp Asp
1               5                   10                  15
```